US009562096B2

(12) United States Patent
Isumi et al.

(10) Patent No.: US 9,562,096 B2
(45) Date of Patent: *Feb. 7, 2017

(54) ANTI-ROBO4 ANTIBODY

(71) Applicant: DAIICHI SANKYO COMPANY, LIMITED, Tokyo (JP)

(72) Inventors: Yoshitaka Isumi, Tokyo (JP); Toshiyuki Sato, Tokyo (JP); Jun Hasegawa, Tokyo (JP); Tatsuya Inoue, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/966,292

(22) Filed: Dec. 11, 2015

(65) Prior Publication Data

US 2016/0108120 A1 Apr. 21, 2016

Related U.S. Application Data

(63) Continuation of application No. 14/397,210, filed as application No. PCT/IB2013/053312 on Apr. 26, 2013.

(30) Foreign Application Priority Data

Apr. 27, 2012 (JP) ................. 2012-103929
Jan. 24, 2013 (JP) ................. 2013-011042

(51) Int. Cl.
*C07K 16/00* (2006.01)
*A61K 39/395* (2006.01)
*C07K 16/28* (2006.01)
*A61K 39/00* (2006.01)

(52) U.S. Cl.
CPC ........... *C07K 16/28* (2013.01); *A61K 39/3955* (2013.01); *C07K 16/2803* (2013.01); *A61K 2039/505* (2013.01); *C07K 2317/24* (2013.01); *C07K 2317/33* (2013.01); *C07K 2317/565* (2013.01); *C07K 2317/70* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2004/0198959 A1 10/2004 Komatsu et al.
2008/0019963 A1 1/2008 Bicknell et al.
2011/0059013 A1 3/2011 Koch et al.

FOREIGN PATENT DOCUMENTS

| EP | 1565491 | 3/2010 |
|---|---|---|
| JP | 2010-518115 | 5/2010 |
| JP | 2012-050442 | 3/2012 |
| WO | WO 02/36771 | 5/2002 |
| WO | WO 2004/003163 | 1/2004 |
| WO | WO 2004/046191 | 6/2004 |
| WO | WO 2008/073441 | 6/2008 |
| WO | WO 2008/100805 | 8/2008 |

OTHER PUBLICATIONS

Koch et al. Robo4 Maintains Vessel Integrity and Inhibits Angiogenesis by Interacting with UNC5B. Developmental Cell 20, 33-46, Jan. 18, 2011.*
Written Opinion in International Application No. PCT/IB2013/053312, Sep. 16, 2013, pp. 1-7.
Guijarro-Muñoz, I., et al., "The axonal repellent Slit2 inhibits pericyte migration: Potential implications in angiogenesis," *Experimental Cell Research*, 2012, vol. 318, pp. 371-378.
Koch, A.W., et al., "Robo4 Maintains Vessel Integrity and Inhibits Angiogenesis by Interacting with UNC5B," *Developmental Cell*, Jan. 18, 2011, vol. 20, pp. 33-46.
Park. K.W., et al., "Robo4 is a vascular-specific receptor that inhibits endothelial migration," *Developmental Biology*, 2003, vol. 261, pp. 251-267.
Gröne, J. et al. "Robo1/Robo4: Differential expression of angiogenic markers in colorectal cancer" *Oncology Reports*, 2006, pp. 1437-1443, vol. 15.
Huang, L. et al. "Expression of Robo4 in the fibrovascular membranes from patients with proliferative diabetic retinopathy and its role in RF/6A and RPE cells" *Molecular Vision*, May 29, 2009, pp. 1057-1069, vol. 15.
Huminiecki, L. et al. "Magic Roundabout is a New Member of the Roundabout Receptor Family That is Endothelial Specific and Expressed at Sites of Active Angiogenesis" *Genomics*, Apr. 2002, pp. 547-552, vol. 79, No. 4.
Jones, C. A. et al. "Robo4 stabilizes the vascular network by inhibiting pathologic angiogenesis and endothelial hyperpermeability" *Nature Medicine*, Apr. 2008, pp. 1-13, vol. 14, No. 4.
Kaur, S. et al. "Silencing of directional migration in roundabout4 knockdown endothelial cells" *BMC Cell Biology*, Nov. 3, 2008, pp. 61-72, vol. 9, No. 61.
London, N. R. et al. "Targeting Robo4-Dependent Slit Signaling to Survive the Cytokine Storm in Sepsis and Influenza" *Science Translational Medicine*, Mar. 17, 2010, pp. 1-11, vol. 2, No. 23, 23ra19.

(Continued)

*Primary Examiner* — Maher Haddad
(74) *Attorney, Agent, or Firm* — Saliwanchik, Lloyd & Eisenschenk

(57) ABSTRACT

Problem to be Solved
The present invention relates to an antibody having an anti-angiogenesis activity. More specifically, the present invention relates to an antibody against ROBO4 and a pharmaceutical composition containing the antibody. An object of the present invention is to provide an anti-ROBO4 antibody having an anti-angiogenesis effect, a pharmaceutical composition or the like comprising the antibody, a method for suppressing angiogenesis using the antibody, etc. Another object of the present invention is to provide a method for producing the antibody. The antibody of the present invention activates the downstream signal of ROBO4 and has a suppressive activity against cell migration induced by VEGF or bFGF. The antibody of the present invention also exhibits an anti-angiogenesis effect in in-vivo models.

38 Claims, 31 Drawing Sheets

(56) References Cited

OTHER PUBLICATIONS

Marlow, R. et al. "Vascular Robo4 restricts proangiogenic VEGF signaling in breast" *Proceedings of the National Academy of Sciences,* Jun. 8, 2010, pp. 10520-10525, vol. 107, No. 23.
R&D Systems "Monoclonal Anti-human ROBO4 Antibody" *R&D Systems, Inc.,* Mar. 24, 2005, p. 1, Clone 265703, Catalog No. MAB2454.
R&D Systems "Monoclonal Anti-human ROBO4 Antibody" *R&D Systems, Inc.,* Sep. 24, 2008, p. 1, Clone 265721, Catalog No. MAB24541.
Seth, P. et al. "Magic roundabout, a tumor endothelial marker: Expression and signaling" *Biochemical and Biophysical Research Communications,* 2005, pp. 533-541, vol. 332.
Sheldon, H. et al. "Active involvement of Robot and Robo4 in filopodia formation and endothelial cell motility mediated via WASP and other actin nucleation-promoting factors" *FASEB J.,* Feb. 2009, pp. 1-15, vol. 23, No. 2.
Suchting, S. et al. "Soluble Robo4 receptor inhibits in vivo angiogenesis and endothelial cell migration" *The FASEB Journal,* Oct. 14, 2004, pp. 1-17.
Jones, C. A. et al. "Slit2—Robo4 signaling promotes vascular stability by blocking Arf6 activity" *Nature Cell Biology,* Nov. 2009, pp. 1-17, vol. 11, No. 11.
Chen, H. et al. "Slit-Robo Signaling in Ocular Angiogenesis" *Retinal Degenerative Diseases, Advances in Medicine and Biology,* 2010, pp. 457-463.
Legg, J. A. et al. "Slits and Roundabouts in cancer, tumour angiogenesis and endothelial cell migration" *Angiogenesis,* 2008, pp. 13-21, vol. 11.
London, N. R. et al. "Emerging mechanisms of vascular stabilization" *Journal of Thrombosis and Haemostasis,* 2009, pp. 57-60, vol. 7, Suppl. 1.
Shibata, F. et al. "Roundabout 4 is Expressed on Hematopoietic Stem Cells and Potentially Involved in the Niche-Mediated Regulation of the Side Population Phenotype" *Stem Cells,* 2009, pp. 183-190, vol. 27.
Verissimo, A. R. et al. "Functionally defining the endothelial transcriptome, from Robo4 to ECSCR" *Biochemical Society Transactions,* 2009, pp. 1214-1217, vol. 37, Part 6.

* cited by examiner

Figure 1 Reporter activity
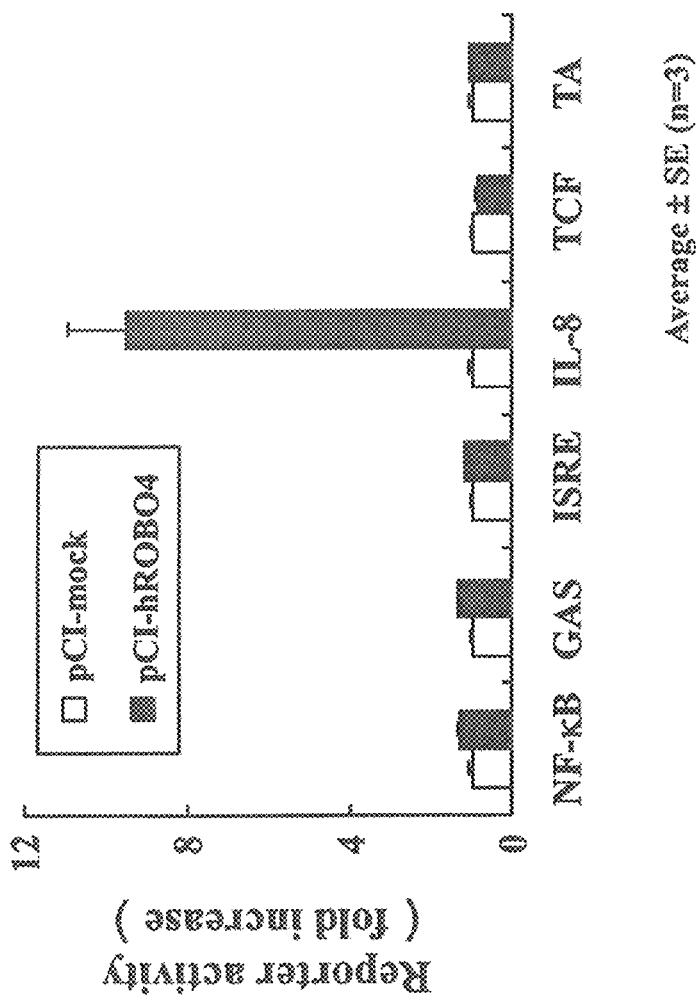
Figure 2 IL-8 promoter activity

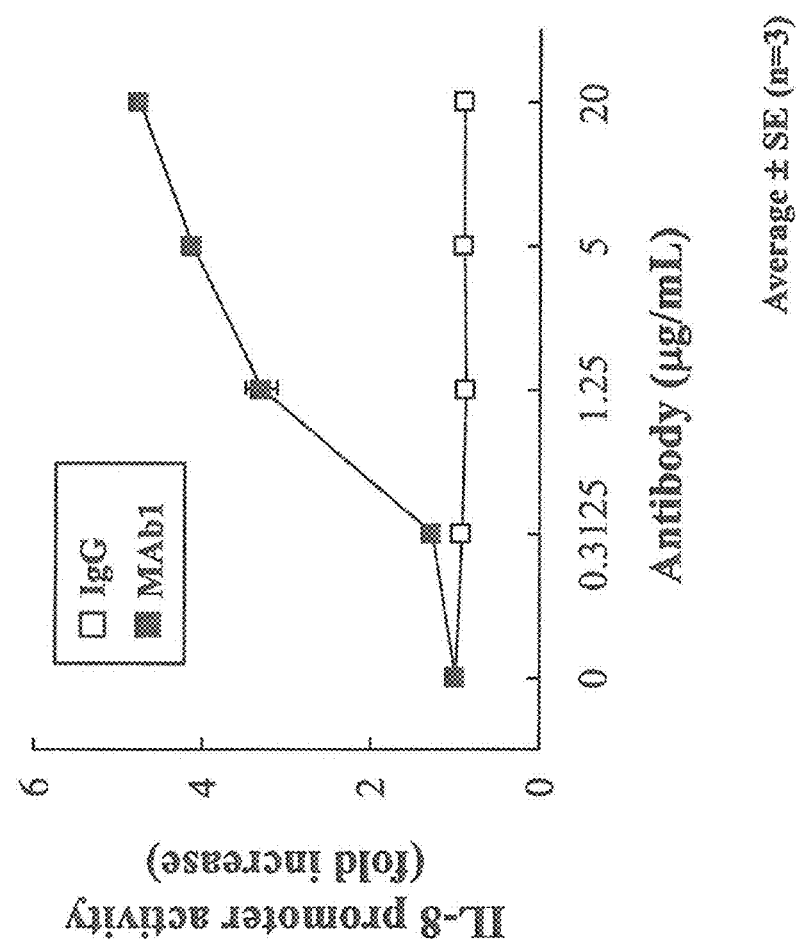

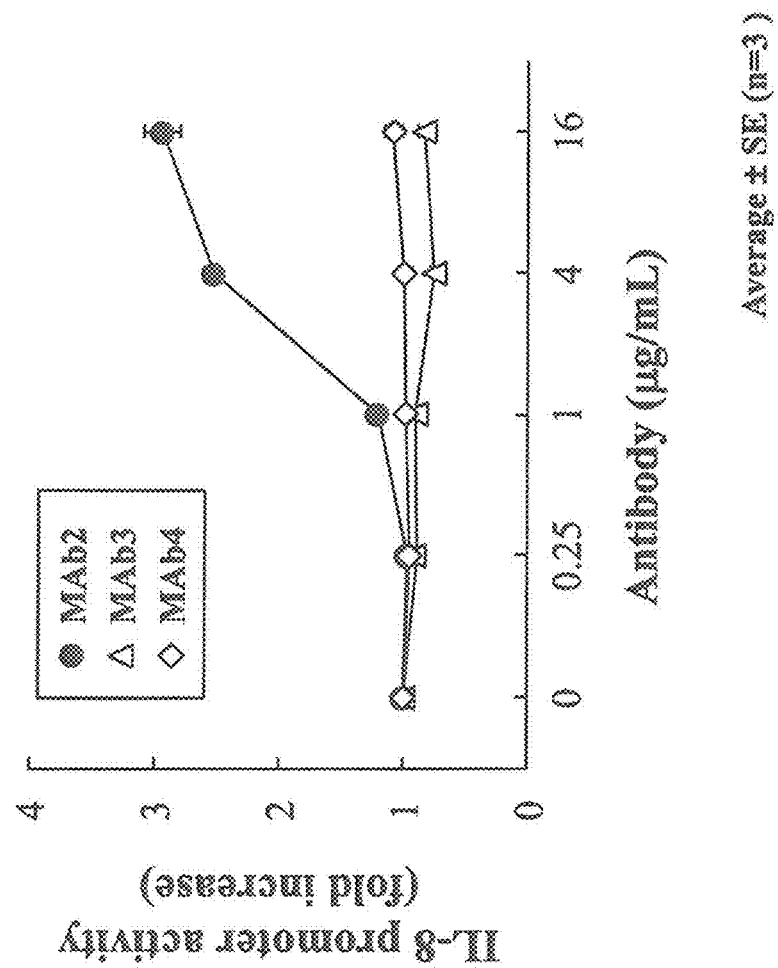
Figure 4 IL-8 promoter activity

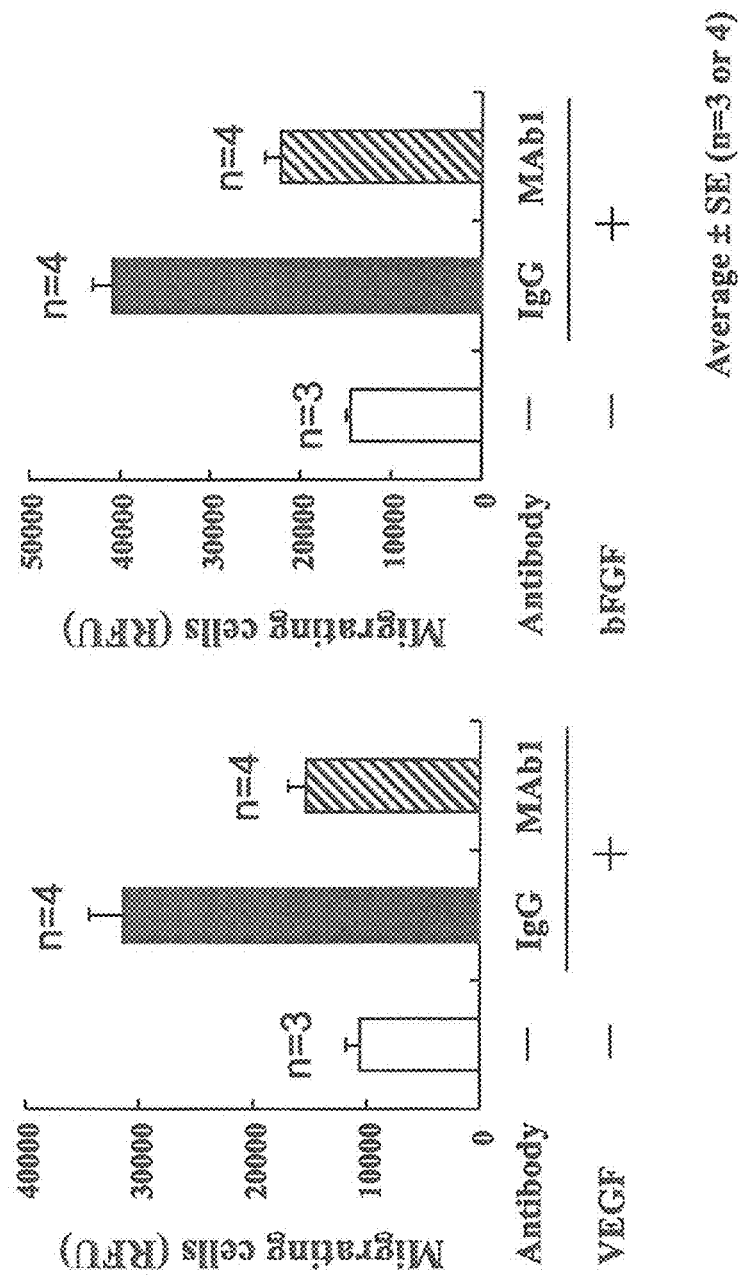
Figure 5 The migratory capacity of HUVEC

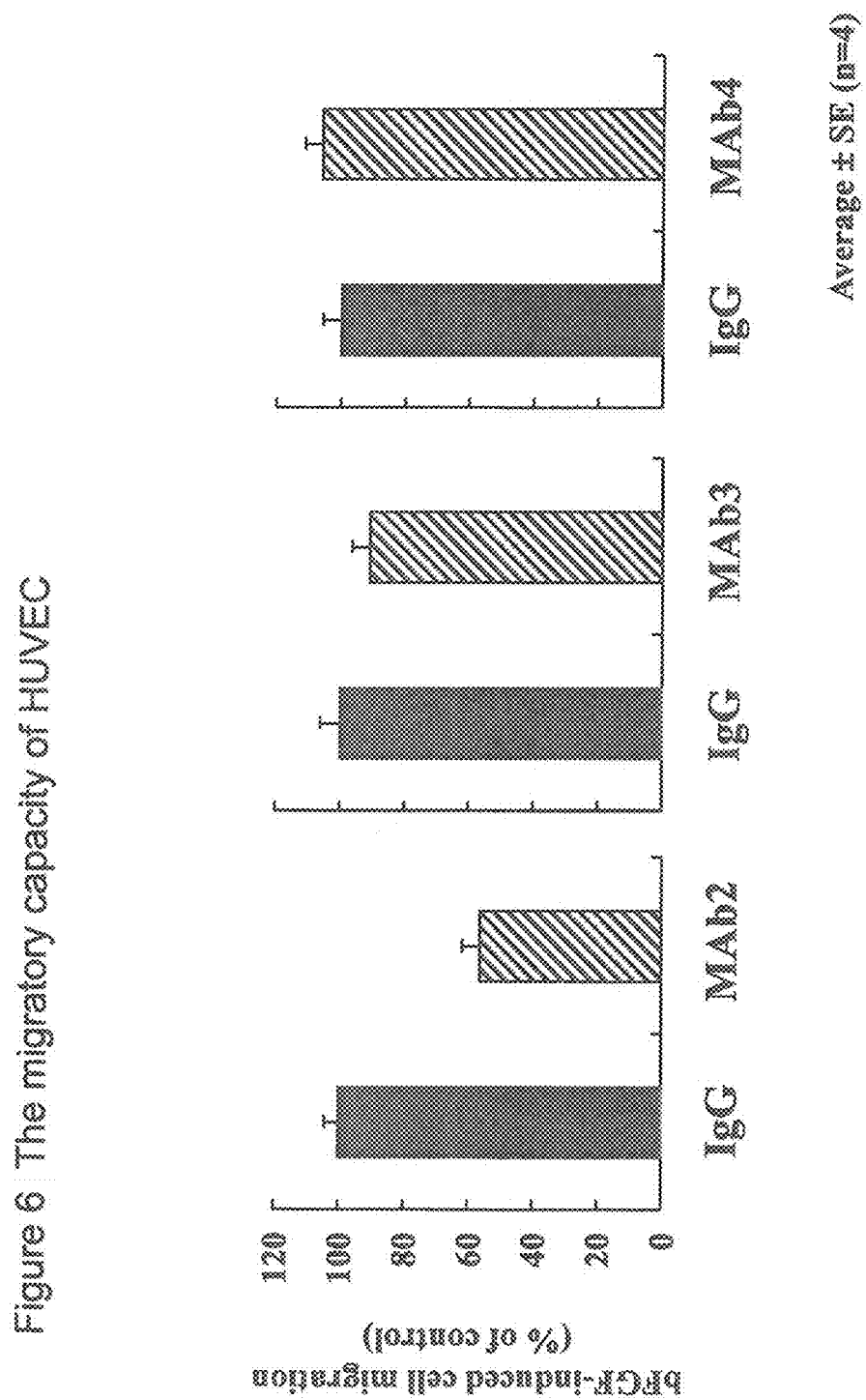

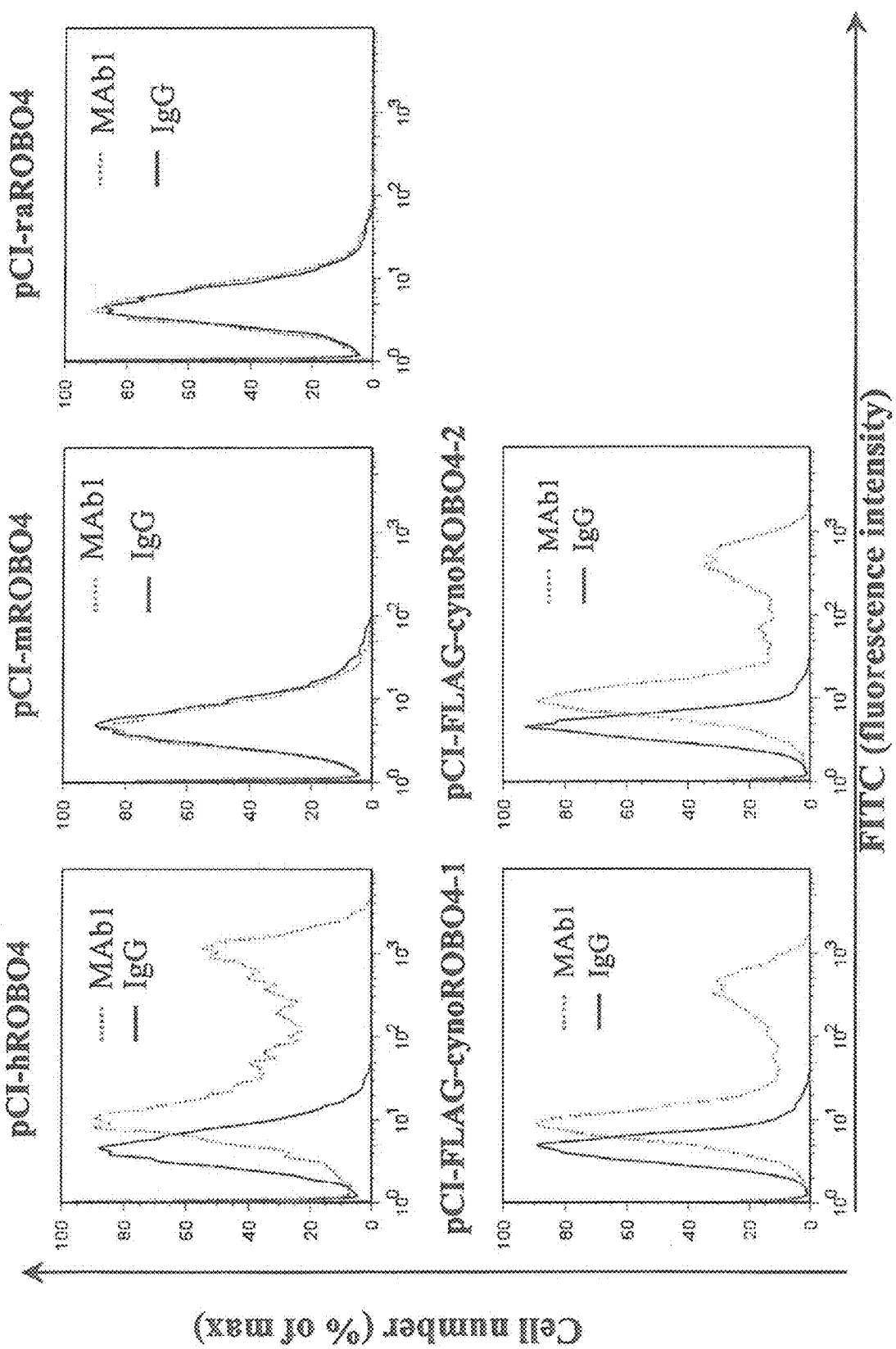
Figure 7 The binding activity

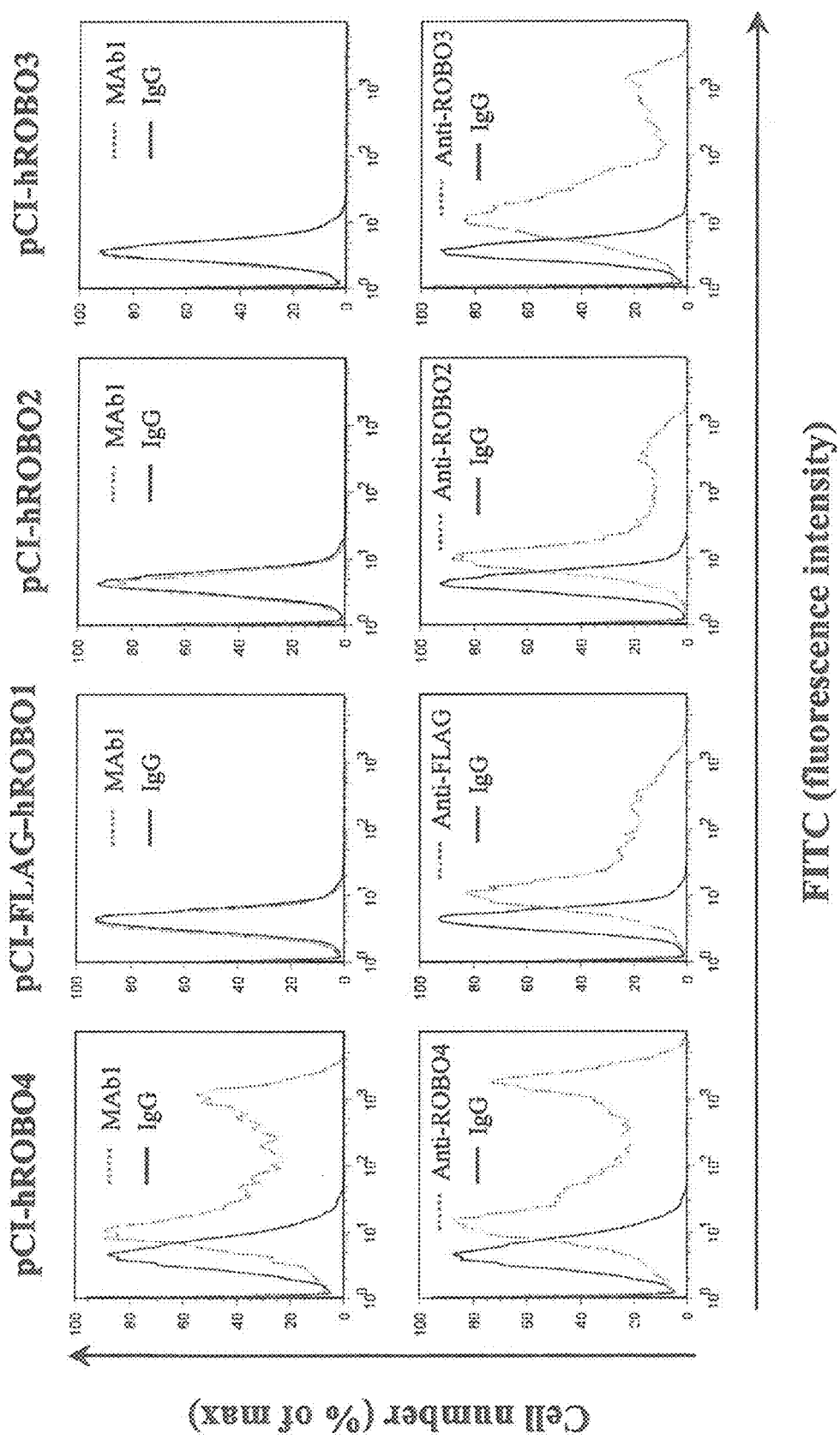
Figure 8 The binding activity

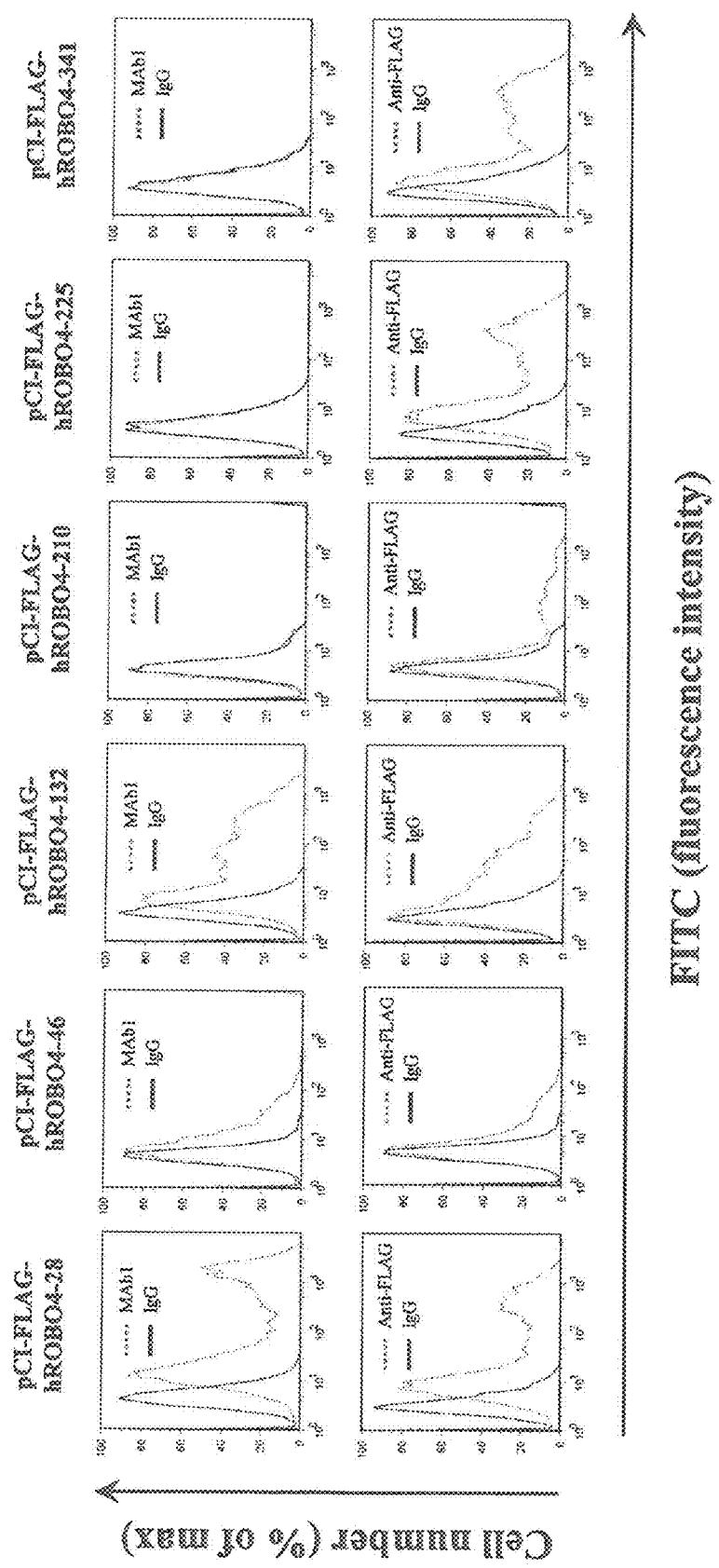

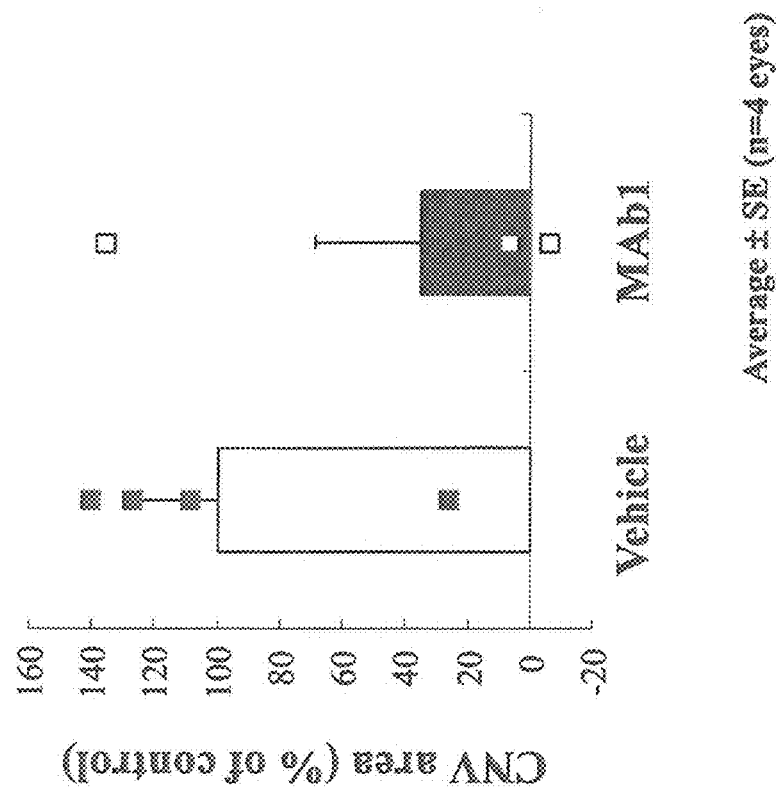
Figure 10 In vivo efficacy of MAb1

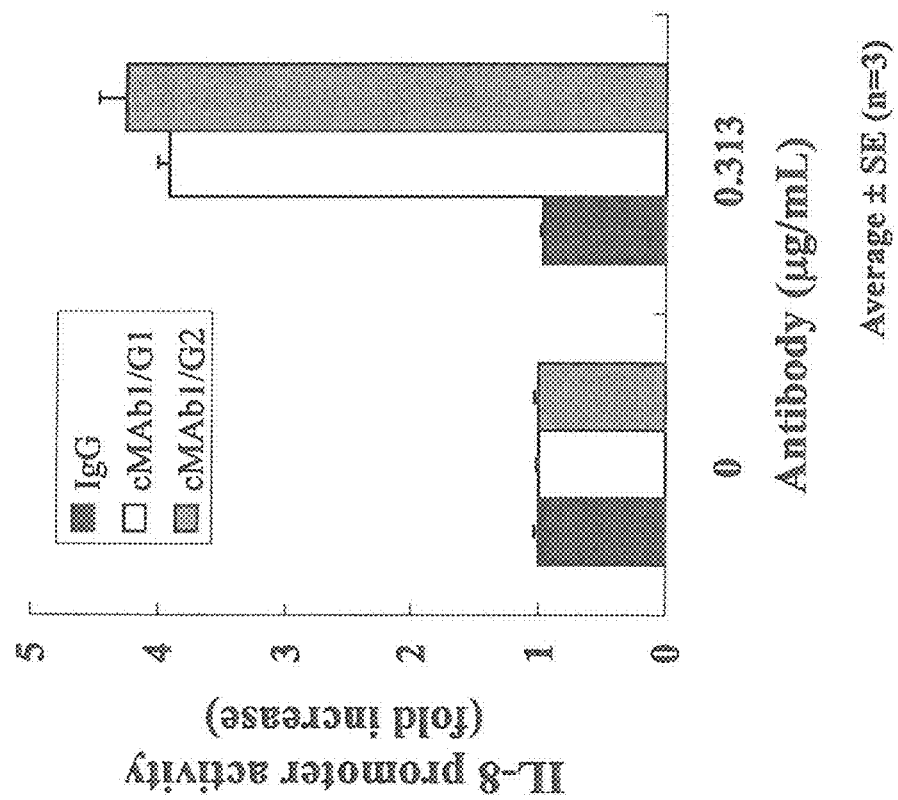
Figure 11 IL-8 promoter activity

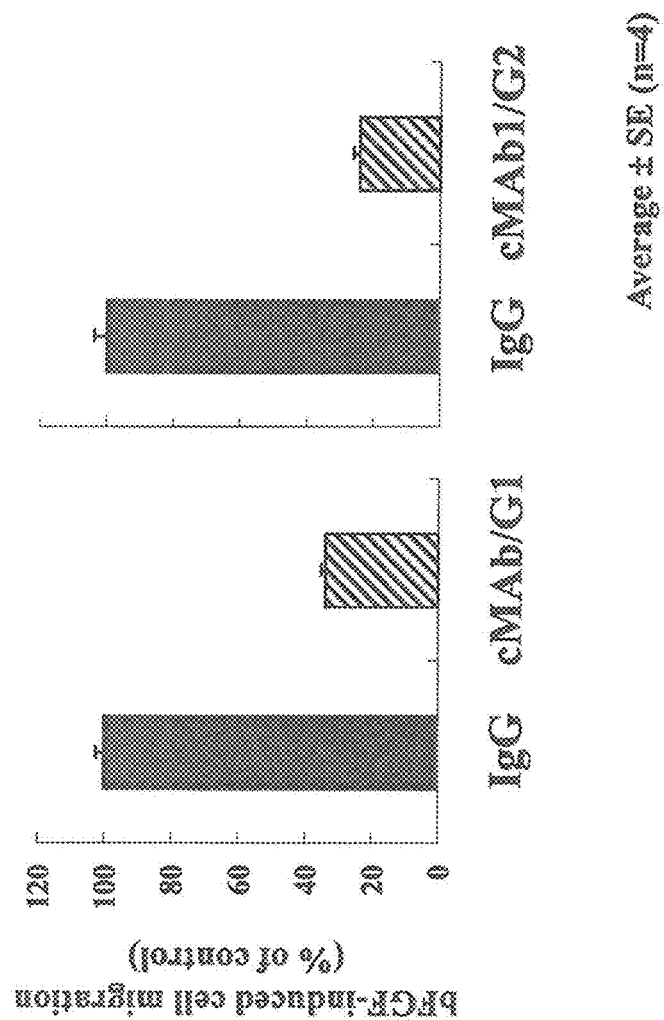
Figure 12 The migratory capacity of HUVEC

Figure 13  cDNA encoding full-length human ROBO4 (SEQ ID NO: 1)

atgggctctggaggagacagcctcctgggggcaggggttccctgcctctgctgtcctgctcatcatgggaggcatggctcag
gactccccgccccagatcctagtccaccccaggaccagctgttccagggccctggccctgccaggatgagctgccaagcctca
ggccagccacctcccaccatccgctggttgctgaatgggcagccctgagcatggtgccccagacccacaccacctcctgcctg
atgggacccttctgctgctacagcccctgcccggggacatgccacgatggccaggcctgtccacagacctgggtgtctaca
catgtgaggccagcaaccggcttggcacggcagtcagcagaggcgctcggctgtctgtggctgtcctccggggaggatttccag
atccagcctcgggacatggtggctgtggtgggtgagcagtttactctggaatgtgggccgccctggggccacccagagccac
agtctcatggtggaaagatgggaaacccctggccctccagcccgaaggcacacagtgtccggggggtccctgctgatggca
agagcagagaagagtgacgaagggacctacatgtgtgtggccaccaacagcgcaggacataggagagccgcgcagccc
gggtttccatccaggagccccaggactacacggagcctgtggagcttctggctgtgcgaattcagctggaaaatgtgacactg
ctgaacccggatcctgcagagggccccaagcctagaccggcggtgtggctcagctggaaggtcagtggccctgctgcgcctgc
ccaatcttacacggccttgttcaggacccagactgccccggggaggccagggagctccgtgggcagaggagctgctggccggct
ggcagagcgcagagcttggaggcctccactggggccaagactacgagttcaaagtgagaccatcctctggccgggctcgagg
ccctgacagcaacgtgctgctcctgaggctgccggaaaaagtgcccagtgccccacctcaggaagtgactctaaagcctggca
atggcactgtctttgtgagctgggtcccaccacctgctgaaaaccacaatggcatcatccgtggctaccaggtctggagcctgg
gcaacacatcactgccaccagccaactggactgtagttggtgagcagacccagctggaaatcgccacccatatgccaggctcc
tactgcgtgcaagtggctgcagtcactggtgctggagctggggagcccagtagacctgtctgcctccttttagagcaggccatg
gagcgagccacccaagaacccagtgagcatggtccctggaccctggagcagctgagggctaccttgaagcggctgaggtca
ttgccacctgcggtgttgcactctggctgctgcttctgggcacggccgtgtgtatccaccgccggcgccgagctagggtgcacct
gggcccaggtctgtacagatataccagtgaggatgccatcctaaaacacaggatggatcacagtgactcccagtggttggca
gacacttggcgttccacctctggctctcgggacctgagcagcagcagcagcctcagcagtcggctgggggcggatgcccggga
cccactagactgtcgtcgctccttgctctcctgggactcccgaagccccggcgtgcccctgcttccagacaccagcactttttatg
gctccctcatcgctgagctgccctccagtacccccagccaggccaagtcccaggtccagctgtcaggcgcctcccaccccagct
ggcccagctctccagcccctgttccagctcagacagcctctgcagccgcaggggactctcttctccccgcttgtctctggcccctgc
agaggcttggaaggccaaaaagaagcaggagctgcagcatgccaacagttccccactgctccggggcagccactccttgga
gctccgggcctgtgagttaggaaatagaggttccaagaacctttcccaaagcccaggagctgtgccccaagctctggttgcct
ggcgggccctgggaccgaaactcctcagctcctcaaatgagctggttactcgtcatctcctccagcaccctctttcctcatgaa
actccccccaactcagagtcaacagacccagcctccgtggcaccacaggctccctcctccatcctgctgccagcagccccatcc
ccatccttagcccctgcagtcccctagccccaggcctcttccctctctggcccagcccagcttccagtcgcctgtccagctcctc
actgtcatccctggggaggatcaagacagcgtgctgacccctgaggaggtagccctgtgcttggaactcagtgagggtgag
gagactcccaggaacagcgtctctccatgccaagggctccttcaccccccaccacctatgggtacatcagcgtcccaacagcc
tcagagttcacggacatgggcaggactggaggagggtgggcccaaggggggagtcttgctgtgcccacctcggccctgcc
tcaccccaccccagcgagggctccttagccaatggttggggctcagcctctgaggacaatgccgccagcgcagagccagc
cttgtcagctcctccgatggctccttcctcgctgatgctcactttgccgggccctggcagtggctgtggatagctttggtttcggt
ctagagcccaggggaggcagactgcgtcttcatagatgcctcatcacctccctcccacgggatgagatcttcctgaccccaac
ctctccctgccctgtgggagtggaggccagactggttggaagacatggaggtcagccacacccagcggctgggaaggggg Figure 13 (continued)
atgcctccctggcccctgactctcagatctcttcccagagaagtcagctccactgtcgtatgcccaaggctggtgcttctcctgt
agattactcd tga
stop codon Figure 14 The full-length amino acid sequence of human ROBO4 (SEQ ID NO: 2)
MGSGGDSLLGGRGSLPLLLLLIMGGMAQDSPPQILVHPQDQLFQGPGPARMSCQAS
GQPPPTIRWLLNGQPLSMVPPDPHHLLPDGTLLLLQPPARGHAHDGQALSTDLGVY
TCEASNRLGTAVSRGARLSVAVLREDFQIQPRDMVAVGEQFTLECGPPWGHPEPTV
SWWKDGKPLALQPGRHTVSGGSLLMARAEKSDEGTYMCVATNSAGHRESRAARVS
IQEPQDYTEPVELLAVRIQLENVTLLNPDPAEGPKPRPAVWLSWKVSGPAAPAQSYT
ALFRTQTAPGGQGAPWAEELLAGWQSAELGGLHWGQDYEFKVRPSSGRARGPDSN
VLLLRLPEKVPSAPPQEVTLKPGNGTVFVSWVPPPAENHNGIIRGYQVWSLGNTSLP
PANWTVVGEQTQLEIATHMPGSYCVQVAAVTGAGAGEPSRPVCLLLEQAMERATQE
PSEHGPWTLEQLRATLKRPEVIATCGVALWLLLLGTAVCIHRRRRARVHLGPGLYRY
TSEDAILKHRMDHSDSQWLADTWRSTSGSRDLSSSSSLSSRLGADARDPLDCRRSL
LSWDSRSPGVPLLPDTSTFYGSLIAELPSSTPARPSPQVPAVRRLPPQLAQLSSPCSSS
DSLCSRRGLSSPRLSLAPAEAWKAKKKQELQHANSSPLLRGSHSLELRACELGNRG
SKNLSQSPGAVPQALVAWRALGPKLLSSSNELVTRHLPPAPLFPHETPPTQSQQTQP
PVAPQAPSSILLPAAPIPILSPCSPPSPQASSLSGPSPASSRLSSSSLSSLGEDQDSVLTP
EEVALCLELSEGEETPRNSVSPMPRAPSPPTTYGYISVPTASEFTDMGRTGGGVGPK
GGVLLCPPRPCLTPTPSEGSLANGWGSASEDNAASARASLVSSSDGSFLADAHFARA
LAVAVDSFGFGLEPREADCVFIDASSPPSPRDEIFLTPNLSLPLWEWRPDWLEDMEV
SHTQRLGRGMPPWPPDSQISSQRSQLHCRMPKAGASPVDYS Figure 15 The nucleotide sequence of cDNA encoding the heavy chain variable region
of MAb1 (SEQ ID NO: 30)
gaagtgcagctggtggagtctgggggaggcttagtgaagcctggagggtccctgaaactctcctgtgcagcctctggattcactttca
gtacctatgccatgtcttgggttcgccagactccggagaagaggctggagtgggtcgcaaccattagtaatggtggtacttacacct
actatccagacagtgtgaagggtcgattcaccatctccagagacaatgccgagaacaccctgtacctgcaaatgagcagtctgagg
tctgaggacacggccatgtatttctgtgcaagactaatctactatgattaccttgactactggggccacggcaccactctcacagtctc
ctca Figure 16 The amino acid sequence of the MAb1 heavy chain variable region (SEQ ID
NO: 31)
EVQLVESGGGLVKPGGSLKLSCAASGFTFSTYAMSWVRQTPEKRLEWVATISNGGTYTY Figure 16 (continued)
YPDSVKGRFTISRDNAENTLYLQMSSLRSEDTAMYFCARLIYYDYLDYWGHGTTLTVSS Figure 17 The nucleotide sequence of cDNA encoding the light chain variable region of MAb1 (SEQ ID NO: 32)

gatgctgtgatgacccaaactccactctccctgcctgtcagtcttggagatcaagcctccatctcttgcaggtctagtcagagccttga
aaacagtaatggaaacacctatttgaactggtacttccagaaaccaggccagtctccacagctcctgatctacagggtttccaaccg
attttctggggtcctagacaggttcagtggtagtggatcagggacagatttcacactgaaaatcagcagagtggaggctgaagatt
tcggagtttatttctgcctccaagttactcatgtcccgtggacgttcggtggaggcaccaagctggaaatcaaacgggct Figure 18 The amino acid sequence of the MAb1 light chain variable region (SEQ ID NO: 33)

DAVMTQTPLSLPVSLGDQASISCRSSQSLENSNGNTYLNWYFQKPGQSPQLLIYRVS
NRFSGVLDRFSGSGSGTDFTLKISRVEAEDFGVYFCLQVTHVPWTFGGGTKLEIKRA

Figure 19 Figure 19 shows the nucleotide sequence of cDNA encoding the light chain of cMAb1 (SEQ ID NO: 37)

atggtgctgcagacccaggtgttcatctccctgctgctgtggatctccggcgcgtacggcgatgctgtgatgacccaaactccactctc
cctgcctgtcagtcttggagatcaagcctccatctcttgcaggtctagtcagagccttgaaaacagtaatggaaacacctatttgaac
tggtacttccagaaaccaggccagtctccacagctcctgatctacagggtttccaaccgattttctggggtcctagacaggttcagtgg
tagtggatcagggacagatttcacactgaaaatcagcagagtggaggctgaagatttcggagtttatttctgcctccaagttactca
tgtcccgtggacgttcggtggaggcaccaagctggaaatcaaacgggctgtggccgccccctccgtgttcatcttccccccctccgacg
agcagctgaagtccggcaccgcctccgtggtgtgcctgctgaataacttctaccccagagaggccaaggtgcagtggaaggtggac
aacgccctgcagtccgggaactcccaggagagcgtgaccgagcaggacagcaaggacagcacctacagcctgagcagcaccctga
ccctgagcaaagccgactacgagaagcacaaggtgtacgcctgcgaggtgacccaccagggcctgagctccccgtcaccaagagc
ttcaacagggggagtgt
Secretory signal sequence(1-60), Variable region(61-402), Constant region(403-717)

Figure 20 The amino acid sequence of the cMAb1 light chain (SEQ ID NO: 38)
MVLQTQVFISLLLWISGAYGDAVMTQTPLSLPVSLGDQASISCRSSQSLENSNGNTYLNW
YFQKPGQSPQLLIYRVSNRFSGVLDRFSGSGSGTDFTLKISRVEAEDFGVYFCLQVTHVP
WTFGGGTKLEIKRAVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGE
C
Secretory signal sequence(1-20), Variable region(21-134), Constant region(135-239)

Figure 21 The nucleotide sequence of cDNA encoding the heavy chain of cMAb1-1 (SEQ ID NO: 39)

atgaaacacctgtggttcttcctcctgctggtggcagctcccagatgggtgctgagcgaagtgcagctggtggagtctggggg
aggcttagtgaagcctggagggtccctgaaactctcctgtgcagcctctggattcactttcagtacctatgccatgtcttgggttc
gccagactccggagaagaggctggagtgggtcgcaaccattagtaatggtggtacttacacctactatccagacagtgtgaa
gggtcgattcaccatctccagagacaatgccgagaacaccctgtacctgcaaatgagcagtctgaggtctgaggacacggcc
atgtatttctgtgcaagactaatctactatgattaccttgactactggggccacggcaccactctcacagtcagctcagcctcca
ccaagggcccaagcgtcttcccctggcacctcctccaagagcacctctggcggcacagccgccctgggctgcctggtcaagg
actacttccccgaacccgtgaccgtgagctggaactcaggcgccctgaccagcggcgtgcacaccttccccgctgtcctgcagtc
ctcaggactctactccctcagcagcgtggtgaccgtgccctccagcagcttgggcacccagacctacatctgcaacgtgaatca
caagcccagcaacaccaaggtggacaagagagttgagcccaaatcttgtgacaaaactcacacatgcccaccctgcccagca
cctgaactcctggggggacccagtcttcctcttccccccaaaacccaaggacaccctcatgatctcccggacccctgaggtca
catgcgtggtggtggacgtgagccacgaagaccctgaggtcaagttcaactggtacgtggacggcgtggaggtgcataatgc
caagacaaagccccgggaggagcagtacaacagcacgtaccgggtggtcagcgtcctcaccgtcctgcaccaggactggctg
aatggcaaggagtacaagtgcaaggtctccaacaaagccctcccagcccccatcgagaaaaccatctccaaagccaaaggc
cagccccgggaaccacaggtgtacaccctgcccccatcccgggaggagatgaccaagaaccaggtcagcctgacctgcctgg
tcaaaggcttctatcccagcgacatcgccgtggagtgggagagcaatgggcagccggagaacaactacaagaccacccctcc
cgtgctggactccgacggctccttcttcctctacagcaagctcaccgtggacaagagcaggtggcagcagggcaacgtcttctc
atgctccgtgatgcatgaggctctgcacaaccactacacccagaagagcctctccctgtctccgggcaaa Secretory signal sequence(1-57), Variable region(58-411), Constant region(412-1401)

Figure 22 The amino acid sequence of the cMAb1-1 heavy chain (SEQ ID NO: 40)
MKHLWFFLLLVAAPRWVLSEVQLVESGGGLVKPGGSLKLSCAASGFTFSTYAMSWV
RQTPEKRLEWVATISNGGTYTYYPDSVKGRFTISRDNAENTLYLQMSSLRSEDTAMY
FCARLIYYDYLDYWGHGTTLTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSN
TKVDKRVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEAL
HNHYTQKSLSLSPGK Secretory signal sequence(1-19), Variable region(20-137), Constant region(138-467)

Figure 23 The nucleotide sequence of cDNA encoding the heavy chain of cMAb1-2 (SEQ ID NO: 41)

atgaaacacctgtggttcttcctcctgctggtggcagctcccagatgggtgctgagcgaagtgcagctggtggagtctgggggaggc
ttagtgaagcctggagggtccctgaaactctcctgtgcagcctctggattcactttcagtacctatgccatgtcttggttcgccagact
ccggagaagaggctggagtgggtcgcaaccattagtaatggtggtacttacacctactatccagacagtgtgaagggtcgattcac
catctccagagacaatgccgagaacaccctgtacctgcaaatgagcagtctgaggtctgaggacacggccatgtatttctgtgcaag
actaatctactatgattaccttgactactggggccacggcaccactctcacagtcagctcagccagcaccaagggcccttccgtgttcc
ctctggccccttgtagccgttccaccagcgagtccaccgccgcccttggctgtctggtgaaggactacttccctgagcctgtgaccgtga
gctggaactccggagcccttaccagcggcgtgcacaccttcctgccgtgctgcagtccagcggcctttactccctgagctccgtggtg
accgtgcctagctccaacttcggcacccaaacctacacctgtaacgtggaccacaagcctagcaacaccaaggtggacaagaccgt
ggagcgtaagtgttgtgtggagtgtcctccttgtcctgcccctactgtggccggaccttccgtgttcctttccctcctaagcctaaggac
accctgatgatcagccgtaccctgaggtgacctgtgtggtggtggacgtgtcccacgaggaccctgaggtgcagttcaactggtac
gtggacggcgtggaggtgcacaacgccaagaccaagcctcgtgaggagcaattcaacagcaccttccgtgtggtgtccgtgcttacc
gtggtgcaccaagactggctgaacggcaaggagtacaagtgtaaggtgagcaacaagggcacttcctgccctatcgagaagacca
tctccaagaccaagggccaacctcgtgagcctcaagtgtacacccttcctcctagccgtgaggagatgaccaagaaccaagtgtccc
ttacctgtctggtgaagggcttctaccctagcgacatcgccgtggagtgggagtccaacggacaacctgagaacaactacaagacc
acccctcctatgcttgacagcgacggctccttcttcctgtacagcaagctgaccgtggacaagtcccgttggcaacaaggcaacgtgtt
cagctgttccgtgatgcacgaggccctgcacaaccactacacccaaaagagcctttccctgagccctggaaag Secretory signal sequence(1-57), Variable region(58-411), Constant region(412-1389)

Figure 24 The amino acid sequence of the cMAb1-2 heavy chain (SEQ ID NO: 42)

MKHLWFFLLLVAAPRWVLSEVQLVESGGGLVKPGGSLKLSCAASGFTFSTYAMSWV
RQTPEKRLEWVATISNGGTYTYYPDSVKGRFTISRDNAENTLYLQMSSLRSEDTAMY
FCARLIYYDYLDYWGHGTTLTVSSASTKGPSVFPLAPCSRSTSESTAALGCLVKDYFP
EPVTVSWNSGALTSGVHTFPAVLQSSGLYSLSSVVTVPSSNFGTQTYTCNVDHKPSN
TKVDKTVERKCCVECPPCPAPPVAGPSVFLFPPKPKDTLMISRTPEVTCVVVDVSHE
DPEVQFNWYVDGVEVHNAKTKPREEQFNSTFRVVSVLTVVHQDWLNGKEYKCKV
SNKGLPAPIEKTISKTKGQPREPQVYTLPPSREEMTKNQVSLTCLVKGFYPSDIAVE
WESNGQPENNYKTTPPMLDSDGSFFLYSKLTVDKSRWQQGNVFSCSVMHEALHN
HYTQKSLSLSPGK

Secretory signal sequence(1-19), Variable region(20-137), Constant region(138-463)

Figure 25 The amino acid sequence of the heavy chain CDRH1 of MAb1 (SEQ ID NO: 44)
TYAMS Figure 26 The amino acid sequence of the heavy chain CDRH2 of MAb1 (SEQ ID NO: 46)
TISNGGTYTYYPDSVKG Figure 27 The amino acid sequence of the heavy chain CDRH3 of MAb1 (SEQ ID NO: 48)
LIYYDYLDY Figure 28 The amino acid sequence of the light chain CDRL1 of MAb1 (SEQ ID NO: 50)
RSSQSLENSNGNTYLN Figure 29 The amino acid sequence of the light chain CDRL2 of MAb1 (SEQ ID NO: 52)
RVSNRFS Figure 30 The amino acid sequence of the light chain CDRL3 of MAb1 (SEQ ID NO: 54)
LQVTHVPWT Figure 31 The nucleotide sequence of cDNA encoding a hMAb1-H1-type heavy chain (SEQ ID NO: 55).

atgaaacacctgtggttcttcctcctgctggtggcagctcccagatgggtgctgagcgaggtgcagctggtggaaagcg
gcggaggcctggtgcagcctggcggctctctgagactgagctgtgccgccagcggcttcaccttcagcacctacgccatg
agctgggtccgacaggcccctggcaagggactggaatgggtggcaaccatcagcaacggcggcacctacacctactac
cccgacagcgtgaagggccggttcaccatcagccgggacaacgccaagaacaccctgtacctgcagatgaacagcctg
cgggccgaggacaccgccgtgtactactgcgccagactgatctactacgactacctggactactggggccagggcacc
tggtcaccgtcagctcagccagcaccaagggcccttccgtgttccctctggcccttgtagccgttccaccagcgagtccac
cgccgcccttggctgtctggtgaaggactacttccctgagcctgtgaccgtgagctggaactccggagcccttaccagcg
gcgtgcacacctcccctgccgtgctgcagtccagcggcctttactccctgagctccgtggtgaccgtgcctagctccaactt
cggcacccaaacctacacctgtaacgtggaccacaagcctagcaacaccaaggtggacaagaccgtggagcgtaagt
gttgtgtggagtgtcctccttgtcctgccctcctgtggccggaccttccgtgttccttttccctcctaagcctaaggacaccc
tgatgatcagccgtacccctgaggtgacctgtgtggtggtggacgtgtcccacgaggaccctgaggtgcagttcaactg
gtacgtggacggcgtggaggtgcacaacgccaagaccaagcctcgtgaggagcaattcaacagcaccttccgtgtggt
gtccgtgcttaccgtggtgcaccaagactggctgaacggcaaggagtacaagtgtaaggtgagcaacaagggacttcc
tgcccctatcgagaagaccatctccaagaccaagggccaacctcgtgagcctcaagtgtacacccttcctcctagccgtg
aggagatgaccaagaaccaagtgtcccttacctgtctggtgaagggcttctaccctagcgacatcgccgtggagtggga
gtccaacggacaacctgagaacaactacaagaccaccctcctatgcttgacagcgacggctccttcttcctgtacagca
agctgaccgtggacaagtccgttggcaacaaggcaacgtgttcagctgttccgtgatgcacgaggccctgcacaacca
ctacacccaaaagagcctttccctgagccctggaaag Secretory signal sequence(1-57), Variable region (58-411), Constant region(412-1389)

Figure 32 The amino acid sequence of the hMAb1-H1-type heavy chain (SEQ ID NO: 56)

MKHLWFFLLLVAAPRWVLSEVQLVESGGGLVQPGGSLRLSCAASGFTFSTYAMS
WVRQAPGKGLEWVATISNGGTYTYYPDSVKGRFTISRDNAKNTLYLQMNSLRA
EDTAVYYCARLIYYDYLDYWGQGTLVTVSSASTKGPSVFPLAPCSRSTSESTAAL
GCLVKDYFPEPVTVSWNSGALTSGVHTFPAVLQSSGLYSLSSVVTVPSSNFGTQT
YTCNVDHKPSNTKVDKTVERKCCVECPPCPAPPVAGPSVFLFPPKPKDTLMISR
TPEVTCVVVDVSHEDPEVQFNWYVDGVEVHNAKTKPREEQFNSTFRVVSVLTV
VHQDWLNGKEYKCKVSNKGLPAPIEKTISKTKGQPREPQVYTLPPSREEMTKN
QVSLTCLVKGFYPSDIAVEWESNGQPENNYKTTPPMLDSDGSFFLYSKLTVDKS
RWQQGNVFSCSVMHEALHNHYTQKSLSLSPGK

Secretory signal sequence(1-19), Variable region(20-137), Constant region(138-463)

Figure 33 The nucleotide sequence of cDNA encoding a hMAb1-H2-type heavy chain (SEQ ID NO: 57).

atgaaacacctgtggttcttcctcctgctggtggcagctccagatgggtgctgagcgaggtgcagctggtggaaagcg
gcggaggcctggtgcagcctggcggctctctgagactgagctgtgccgccagcggcttcaccttcagcacctacgccatg
agctgggtccgacaggcccctggcaagggactggaatgggtggcaaccatcagccaaggcggcacctacacctactac
cccgacagcgtgaagggccggttcaccatcagccgggacaacgccaagaacaccctgtacctgcagatgaacagcctg
cgggccgaggacaccgccgtgtactactgcgccagactgatctactacgactacctggactactggggccagggcaccc
tggtcaccgtcagctcagccagcaccaagggcccttccgtgttccctctggcccttgtagccgttccaccagcgagtccac
cgccgccttggctgtctggtgaaggactacttccctgagcctgtgaccgtgagctggaactccggagcccttaccagcg
gcgtgcacaccttcctgccgtgctgcagtccagcggcctttactccctgagctccgtggtgaccgtgcctagctccaactt
cggcacccaaacctacacctgtaacgtggaccacaagcctagcaacaccaaggtggacaagaccgtggagcgtaagt
gttgtgtggagtgtcctccttgtcctgcccctcctgtggccggaccttccgtgttccttttccctcctaagcctaaggacaccc
tgatgatcagccgtaccctgaggtgacctgtgtggtggtggacgtgtcccacgaggacccctgaggtgcagttcaactg
gtacgtggacggcgtggaggtgcacaacgccaagaccaagcctcgtgaggagcaattcaacagcaccttccgtgtggt
gtccgtgcttaccgtggtgcaccaagactggctgaacggcaaggagtacaagtgtaaggtgagcaacaagggacttcc
tgcccctatcgagaagaccatctccaagaccaagggccaacctcgtgagcctcaagtgtacaccttcctcctagccgtg
aggagatgaccaagaaccaagtgtcccttacctgtctggtgaagggcttctaccctagcgacatcgccgtggagtggga
gtccaacggacaacctgagaacaactacaagaccacccctcctatgcttgacagcgacggctccttcttcctgtacagca
agctgaccgtggacaagtcccgttggcaacaaggcaacgtgttcagctgttccgtgatgcacgaggccctgcacaacca
ctacacccaaaagagcctttccctgagccctggaaag Secretory signal sequence(1-57), Variable region(58-411), Constant region(412-1389)

Figure 34 The amino acid sequence of the hMAb1-H2-type heavy chain (SEQ ID NO: 58).

MKHLWFFLLLVAAPRWVLSEVQLVESGGGLVQPGGSLRLSCAASGFTFSTYAMS
WVRQAPGKGLEWVATISQGGTYTYYPDSVKGRFTISRDNAKNTLYLQMNSLRA
EDTAVYYCARLIYYDYLDYWGQGTLVTVSSASTKGPSVFPLAPCSRSTSESTAAL
GCLVKDYFPEPVTVSWNSGALTSGVHTFPAVLQSSGLYSLSSVVTVPSSNFGTQT
YTCNVDHKPSNTKVDKTVERKCCVECPPCPAPPVAGPSVFLFPPKPKDTLMISR
TPEVTCVVVDVSHEDPEVQFNWYVDGVEVHNAKTKPREEQFNSTFRVVSVLTV
VHQDWLNGKEYKCKVSNKGLPAPIEKTISKTKGQPREPQVYTLPPSREEMTKN
QVSLTCLVKGFYPSDIAVEWESNGQPENNYKTTPPMLDSDGSFFLYSKLTVDKS
RWQQGNVFSCSVMHEALHNHYTQKSLSLSPGK

Secretory signal sequence(1-19), Variable region(20-137), Constant region(138-463)

Figure 35 The nucleotide sequence of cDNA encoding a hMAb1-H3-type heavy chain (SEQ ID NO: 59)

atgaaacacctgtggttcttcctcctgctggtggcagctcccagatgggtgctgagcgaggtgcagctggtggaaagcg
gcggaggcctggtgcagcctggcggctctctgagactgagctgtgccgccagcggcttcaccttcagcacctacgccatg
agctgggtccgacaggcccctggcaagcggctggaatgggtggcaaccatcagcaacggcggcacctacacctactac
ccgacagcgtgaagggccggttcaccatcagccgggacaacgccaagaacaccctgtacctgcagatgaacagcctg
cgggccgaggacaccgccgtgtactactgcgccagactgatctactacgactacctggactactggggccagggcacc
tggtcaccgtcagctcagccagcaccaagggccctccgtgttcctctggccccttgtagccgttcaccagcgagtccac
cgccgcccttggctgtctggtgaaggactacttccctgagcctgtgaccgtgagctggaactccggagcccttaccagcg
gcgtgcacaccttccctgccgtgctgcagtccagcggcctttactccctgagctccgtggtgaccgtgcctagctccaactt
cggcacccaaacctacacctgtaacgtggaccacaagcctagcaacaccaaggtggacaagaccgtggagcgtaagt
gttgtgtggagtgtcctccttgtcctgccctcctgtggccggaccttccgtgttccttttcctcctaagcctaaggacaccc
tgatgatcagccgtaccctgaggtgacctgtgtggtggtggacgtgtccacgaggacctgaggtgcagttcaactg
gtacgtggacggcgtggaggtgcacaacgccaagaccaagcctcgtgaggagcaattcaacagcaccttccgtgtggt
gtccgtgcttaccgtggtgcaccaagactggctgaacggcaaggagtacaagtgtaaggtgagcaacaagggacttcc
tgcccctatcgagaagaccatctccaagaccaaggggccaacctcgtgagcctcaagtgtacacccttcctcctagccgtg
aggagatgaccaagaaccaagtgtcccttacctgtctggtgaagggcttctaccctagcgacatcgccgtggagtggga
gtccaacggacaacctgagaacaactacaagaccacccctcctatgcttgacagcgacggctccttcttcctgtacagca
agctgaccgtggacaagtcccgttggcaacaaggcaacgtgttcagctgttccgtgatgcacgaggccctgcacaacca
ctacacccaaaagagcctttccctgagccctggaaag Secretory signal sequence(1-57),Variable region(58-411),Constant region(412-1389)

Figure 36 The amino acid sequence of the hMAb1-H3-type heavy chain (SEQ ID NO: 60)

MKHLWFFLLLVAAPRWVLSEVQLVESGGGLVQPGGSLRLSCAASGFTFSTYAMS
WVRQAPGKRLEWVATISNGGTYTYYPDSVKGRFTISRDNAKNTLYLQMNSLRA
EDTAVYYCARLIYYDYLDYWGQGTLVTVSSASTKGPSVFPLAPCSRSTSESTAAL
GCLVKDYFPEPVTVSWNSGALTSGVHTFPAVLQSSGLYSLSSVVTVPSSNFGTQT
YTCNVDHKPSNTKVDKTVERKCCVECPPCPAPPVAGPSVFLFPPKPKDTLMISR
TPEVTCVVVDVSHEDPEVQFNWYVDGVEVHNAKTKPREEQFNSTFRVVSVLTV
VHQDWLNGKEYKCKVSNKGLPAPIEKTISKTKGQPREPQVYTLPPSREEMTKN
QVSLTCLVKGFYPSDIAVEWESNGQPENNYKTTPPMLDSDGSFFLYSKLTVDKS
RWQQGNVFSCSVMHEALHNHYTQKSLSLSPGK

Secretory signal sequence(1-19), Variable region(20-137), Constant region(138-463)

Figure 37 The nucleotide sequence of cDNA encoding a hMAb1-H4-type heavy chain (SEQ ID NO: 61)

atgaaacacctgtggttcttcctcctgctggtggcagctcccagatgggtgctgagcgaggtgcagctggtggaaagcg
gcggaggcctggtgcagcctggcggctctctgagactgagctgtgccgccagcggcttcaccttcagcacctacgccatg
agctgggtccgacaggcccctggcaagcggctggaatgggtggcaaccatcagccaaggcggcacctacacctactac
ccgacagcgtgaagggccggttcaccatcagcgggacaacgccaagaacaccctgtacctgcagatgaacagcctg
cgggccgaggacaccgccgtgtactactgcgccagactgatctactacgactacctggactactggggccagggcaccc
tggtcaccgtcagctcagccagcaccaaggggcccttccgtgttccctctggccccttgtagccgttccaccagcgagtccac
cgccgcccttggctgtctggtgaaggactacttccctgagcctgtgaccgtgagctggaactccggagcccttaccagcg
gcgtgcacaccttccctgccgtgctgcagtccagcggcctttactccctgagctccgtggtgaccgtgcctagctccaactt
cggcacccaaacctacacctgtaacgtggaccacaagcctagcaacaccaaggtggacaagaccgtggagcgtaagt
gttgtgtggagtgtcctccttgtcctgccctcctgtggccggaccttccgtgttcctttcctcctaagcctaaggacaccc
tgatgatcagccgtaccctgaggtgacctgtgtggtggtggacgtgtcccacgaggaccctgaggtgcagttcaactg
gtacgtggacggcgtggaggtgcacaacgccaagaccaagcctcgtgaggagcaattcaacagcaccttccgtgtggt
gtccgtgcttaccgtggtgcaccaagactggctgaacggcaaggagtacaagtgtaaggtgagcaacaagggacttcc
tgccctatcgagaagaccatctccaagaccaagggccaacctcgtgagcctcaagtgtacacccttcctcctagccgtg
aggagatgaccaagaaccaagtgtcccttacctgtctggtgaagggcttctaccctagcgacatcgccgtggagtggga
gtccaacggacaacctgagaacaactacaagaccaccctctatgcttgacagcgacggctccttcttcctgtacagca
agctgaccgtggacaagtcccgttggcaacaaggcaacgtgttcagctgttccgtgatgcacgaggccctgcacaacca
ctacacccaaaagagcctttccctgagccctggaaag Secretory signal sequence(1-57), Variable region(58-411), Constant region(412-1389)

Figure 38 The amino acid sequence of the hMAb1-H4-type heavy chain (SEQ ID NO: 62)

MKHLWFFLLLVAAPRWVLSEVQLVESGGGLVQPGGSLRLSCAASGFTFSTYAMS
WVRQAPGKRLEWVATISQGGTYTYYPDSVKGRFTISRDNAKNTLYLQMNSLRA
EDTAVYYCARLIYYDYLDYWGQGTLVTVSSASTKGPSVFPLAPCSRSTSESTAAL
GCLVKDYFPEPVTVSWNSGALTSGVHTFPAVLQSSGLYSLSSVVTVPSSNFGTQT
YTCNVDHKPSNTKVDKTVERKCCVECPPCPAPPVAGPSVFLFPPKPKDTLMISR
TPEVTCVVVDVSHEDPEVQFNWYVDGVEVHNAKTKPREEQFNSTFRVVSVLTV
VHQDWLNGKEYKCKVSNKGLPAPIEKTISKTKGQPREPQVYTLPPSREEMTKN
QVSLTCLVKGFYPSDIAVEWESNGQPENNYKTTPPMLDSDGSFFLYSKLTVDKS
RWQQGNVFSCSVMHEALHNHYTQKSLSLSPGK

Secretory signal sequence(1-19), Variable region(20-137), Constant region(138-463)

Figure 39 The nucleotide sequence of cDNA encoding a hMAb1-L1-type light chain (SEQ ID NO: 63)

atggtgctgcagacccaggtgttcatctccctgctgctgtggatctccggcgcgtacggcgacatcgtgatgacccagag
ccccctgagcctgcccgtgacactgggcgagcctgccagcatcagctgcagaagcagccagagcctggaaaacagcaa
cggcaacacctacctgaactggtatctgcagaagcccggccagtcccccagctgctgatctaccgggtgtccaaccggt
tcagcggcgtgcccgacagattcagcggcagcggctccggcaccgacttcaccctgaagatcagccgggtggaagccg
aggacgtgggcgtgtactactgtctgcaggtcacacacgtgccctggaccttcggccctggcaccaaggtggacatcaa
gcgtacggtggccgcccctccgtgttcatcttccccccctccgacgagcagctgaagtccggcaccgcctccgtggtgtgc
ctgctgaataacttctacccagagaggccaaggtgcagtggaaggtggacaacgccctgcagtccgggaactcccag
gagagcgtgaccgagcaggacagcaaggacagcacctacagcctgagcagcaccctgaccctgagcaaagccgacta
cgagaagcacaaggtgtacgcctgcgaggtgacccaccagggcctgagctcccccgtcaccaagagcttcaacagggg
ggagtgt Secretory signal sequence(1-60), Variable region(61-402), Constant region(403-717)

Figure 40 The amino acid sequence of the hMAb1-L1-type light chain (SEQ ID NO: 64)
MVLQTQVFISLLLWISGAYGDIVMTQSPLSLPVTLGEPASISCRSSQSLENSNGNT
YLNWYLQKPGQSPQLLIYRVSNRFSGVPDRFSGSGSGTDFTLKISRVEAEDVGV
YYCLQVTHVPWTFGPGTKVDIKRTVAAPSVFIFPPSDEQLKSGTASVVCLLNNFY
PREAKVQWKVDNALQSGNSQESVTEQDSKDSTYSLSSTLTLSKADYEKHKVYA
CEVTHQGLSSPVTKSFNRGEC Secretory signal sequence(1-20), Variable region(21-134), Constant region(135-239)

Figure 41 The nucleotide sequence of cDNA encoding a hMAb1-L2-type light chain (SEQ ID NO: 65)

atggtgctgcagacccaggtgttcatctcccctgctgctgtggatctccggcgcgtacggcgacatcgtgatgacccagag
ccccctgagcctgcccgtgacactgggcgagcctgccagcatcagctgcagaagcagccagagcctggaaaacgagaa
caagaacctgtacctgaactggtatctgcagaagcccggccagtcccccagctgctgatctaccgggtgtccaaccggt
tcagcggcgtgcccgacagattcagcggcagcggctccggcaccgacttcaccctgaagatcagccgggtggaagccg
aggacgtgggcgtgtactactgtctgcaggtcacacacgtgccctggaccttcggccctggcaccaaggtggacatcaa
gcgtacggtggccgccccctccgtgttcatcttcccccctccgacgagcagctgaagtccggcaccgcctccgtggtgtgc
ctgctgaataacttctaccccagagaggccaaggtgcagtggaaggtggacaacgccctgcagtccgggaactccag
gagagcgtgaccgagcaggacagcaaggacagcacctacagcctgagcagcaccctgaccctgagcaaagccgacta
cgagaagcacaaggtgtacgcctgcgaggtgacccaccagggcctgagctcccccgtcaccaagagcttcaacaggggg
ggagtgt Secretory signal sequence(1-60), Variable region(61-402), Constant region(403-717)

Figure 42 The amino acid sequence of the hMAb1-L2-type light chain (SEQ ID NO: 66)

MVLQTQVFISLLLWISGAYGDIVMTQSPLSLPVTLGEPASISCRSSQSLENENKNL
YLNWYLQKPGQSPQLLIYRVSNRFSGVPDRFSGSGSGTDPTLKISRVEAEDVGV
YYCLQVTHVPWTFGPGTKVDIKRTVAAPSVFIFPPSDEQLKSGTASVVCLLNNFY
PREAKVQWKVDNALQSGNSQESVTEQDSKDSTYSLSSTLTLSKADYEKHKVYA
CEVTHQGLSSPVTKSFNRGEC

Secretory signal sequence(1-20), Variable region(21-134), Constant region(135-239)

Figure 43 The amino acid sequence of CDRH1 of the hMAb1-H2- or hMAb1-H4-type heavy chain (SEQ ID NO: 67).
TYAMS Figure 44 The amino acid sequence of CDRH2 of the hMAb1-H2- or hMAb1-H4-type heavy chain (SEQ ID NO: 68)
TISQGGTYTYYPDSVKG Figure 45 The amino acid sequence of CDRH3 of the hMAb1-H2- or hMAb1-H4-type heavy chain (SEQ ID NO: 69)
LIYYDYLDY Figure 46 The amino acid sequence of CDRL1 of the hMAb1-L2-type light chain (SEQ ID NO: 70)
RSSQSLENENKNLYLN Figure 47 The amino acid sequence of CDRL2 of the hMAb1-L2-type light chain (SEQ ID NO: 71)
RVSNRFS Figure 48 The amino acid sequence of CDRL3 of the hMAb1-L2-type light chain (SEQ ID NO: 72).
LQVTHVPWT

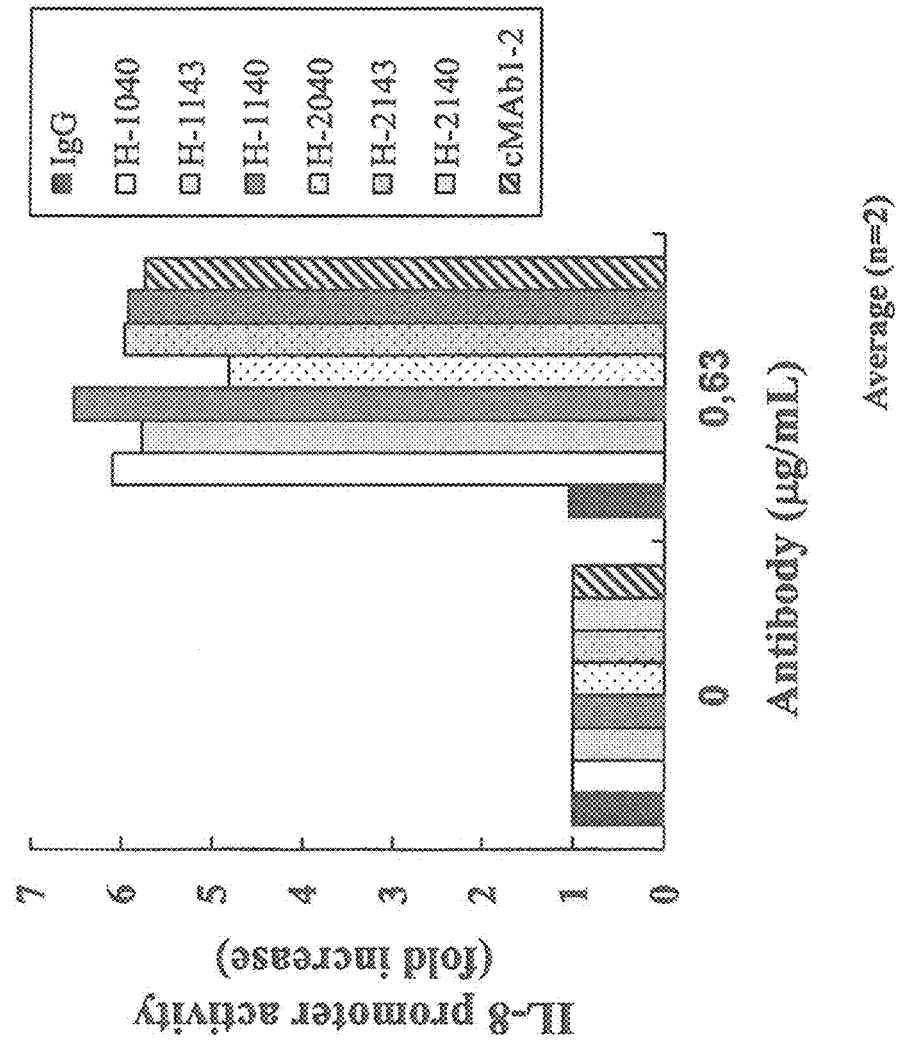
Figure 49  IL-8 promoter activity assay

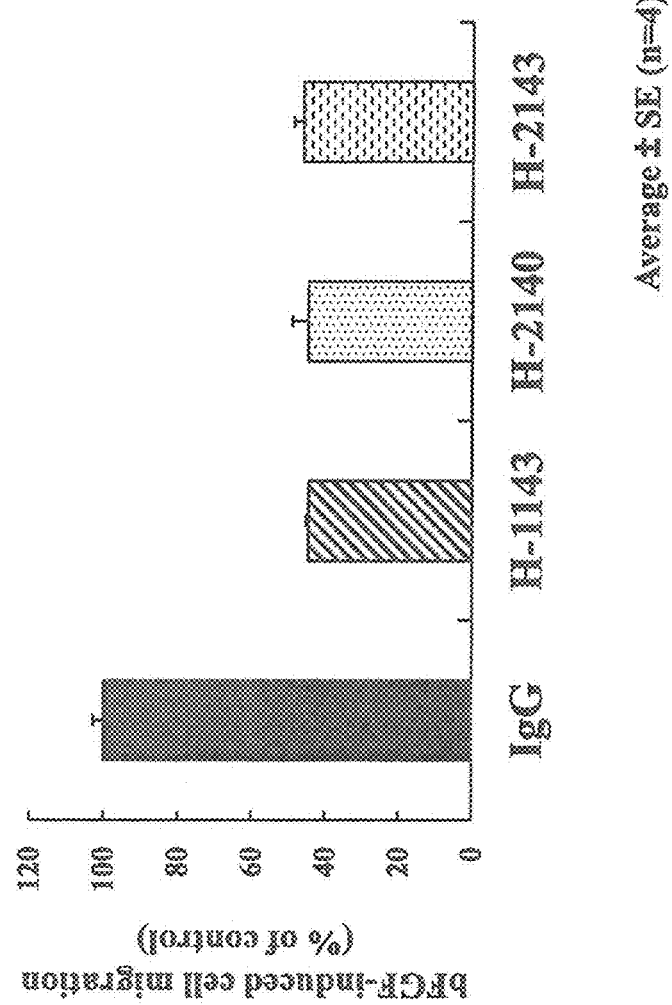
Figure 50  bFGF-induced HUVEC migration assay

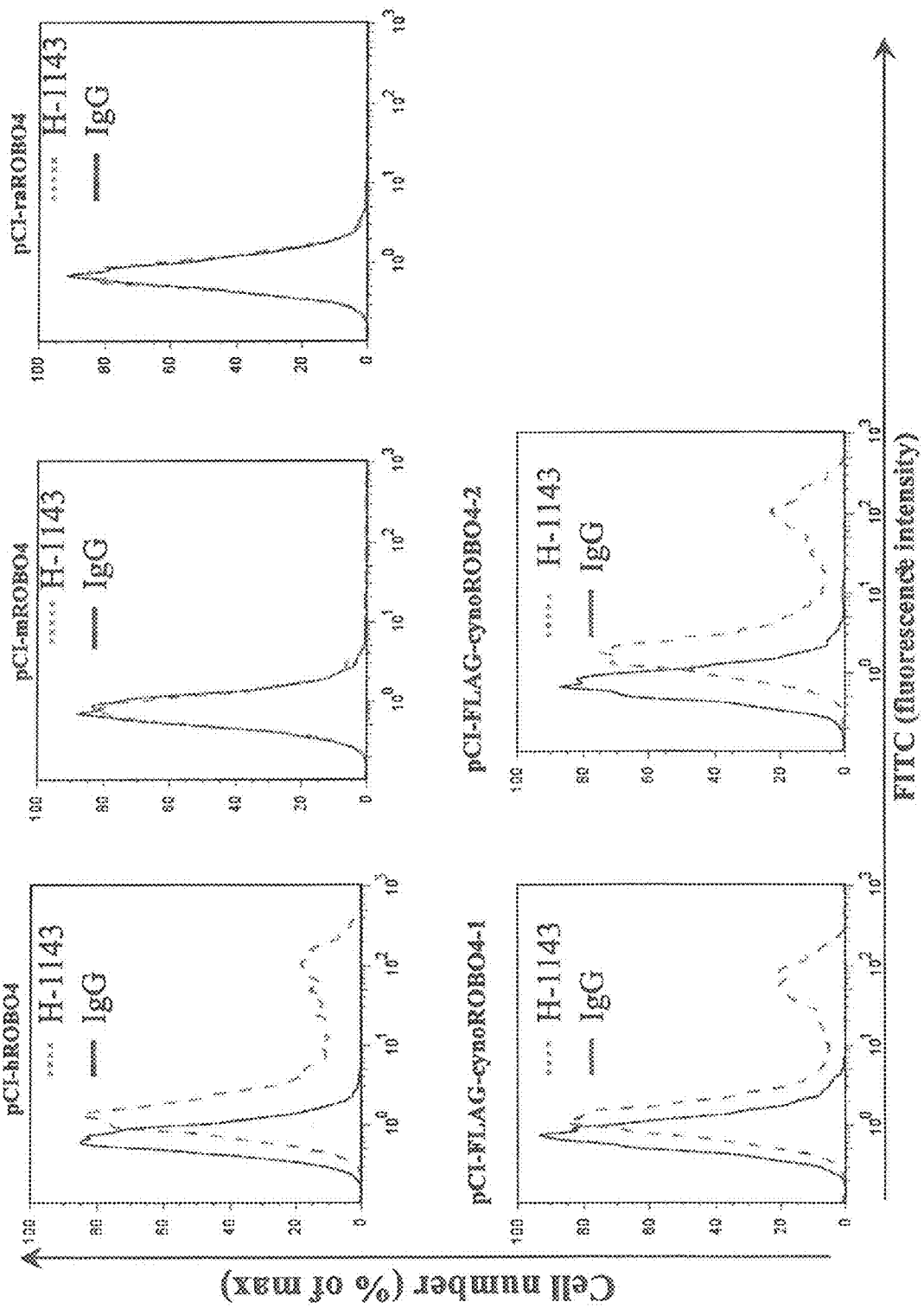
Figure 51 The cross-species reactivity of H-1143

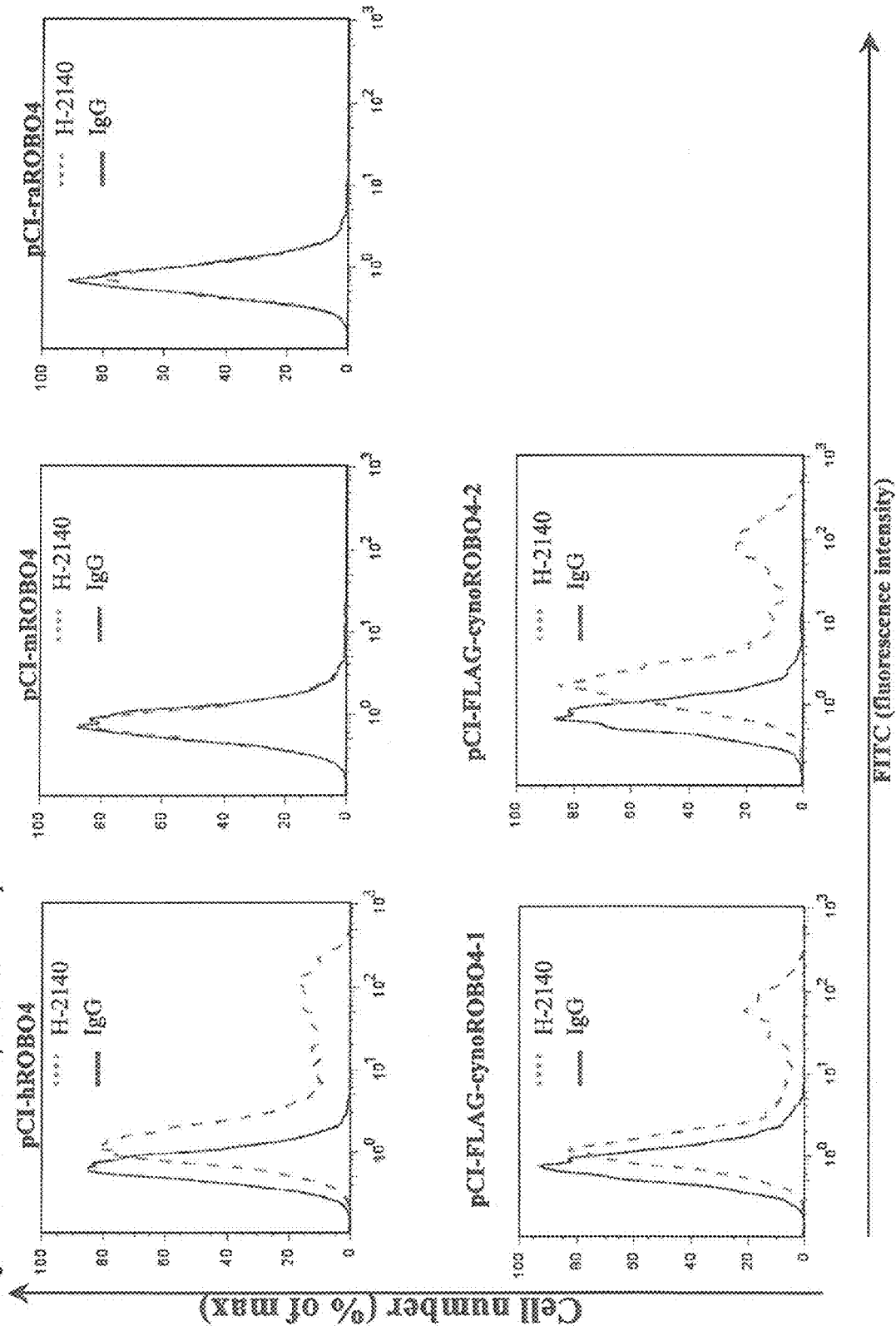
Figure 52 The cross-species reactivity of H-2140

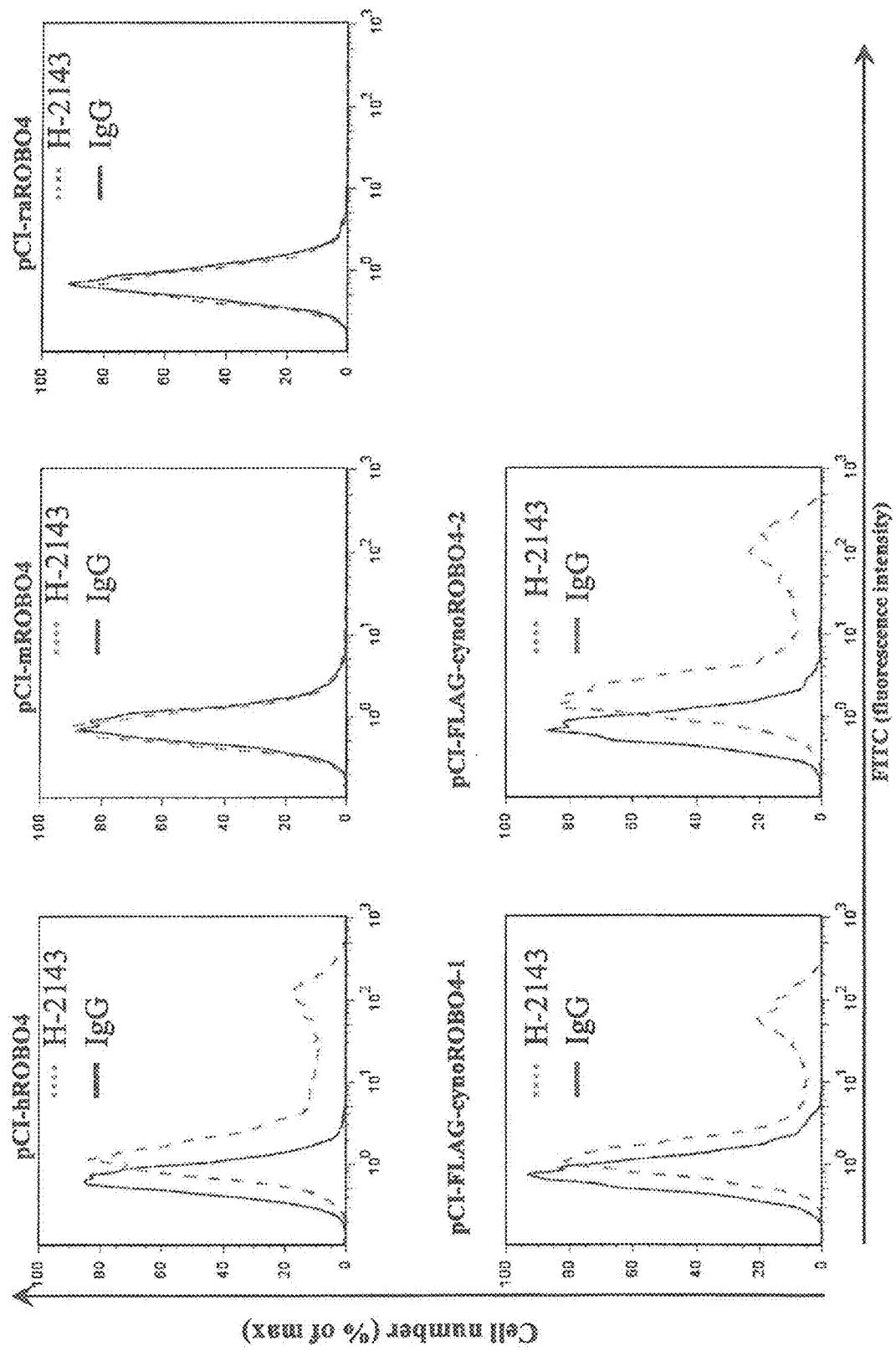
Figure 53 The cross-species reactivity of H-2143

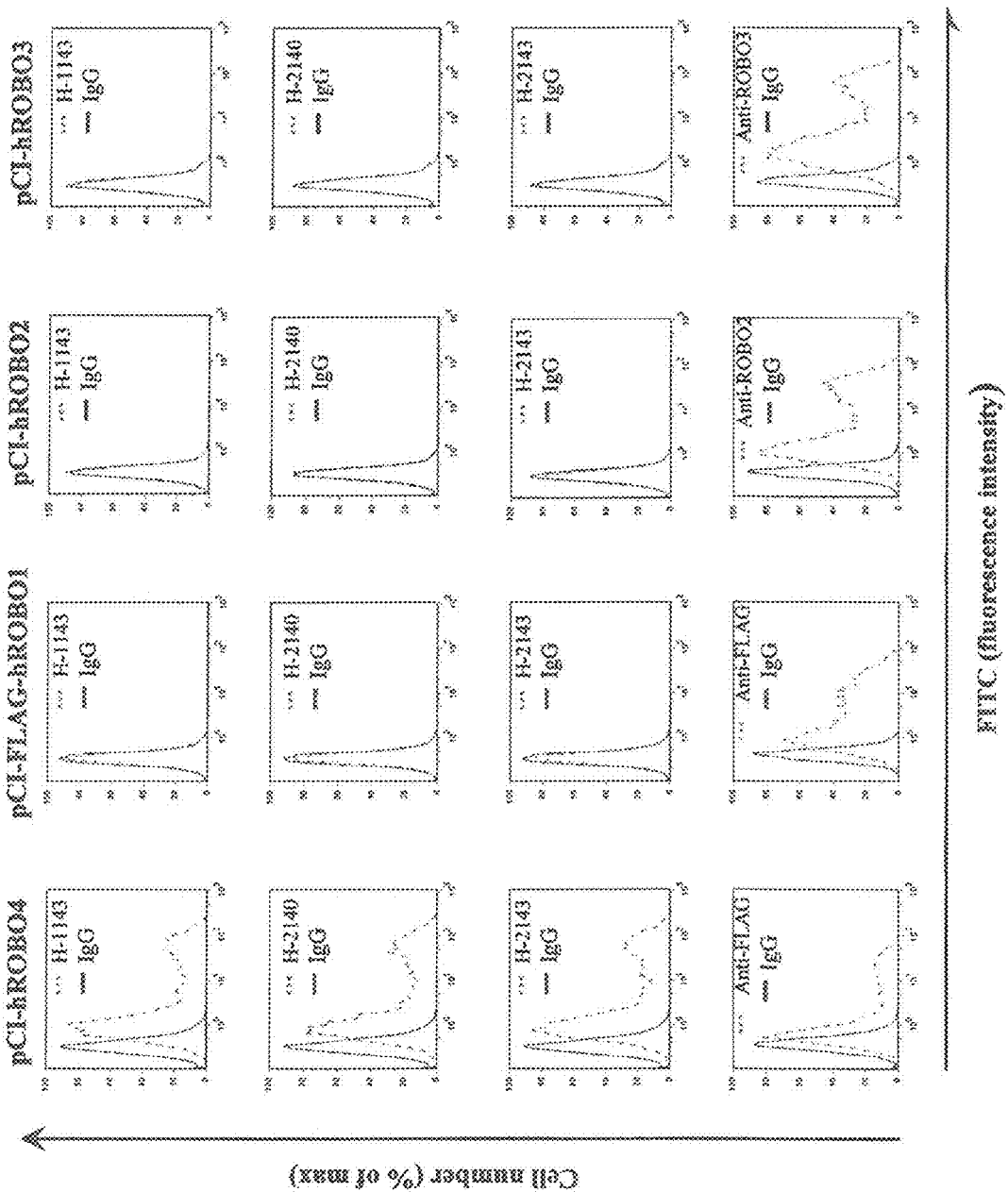
Figure 54 The binding specificity of H-1143, H-2140, or H-2143

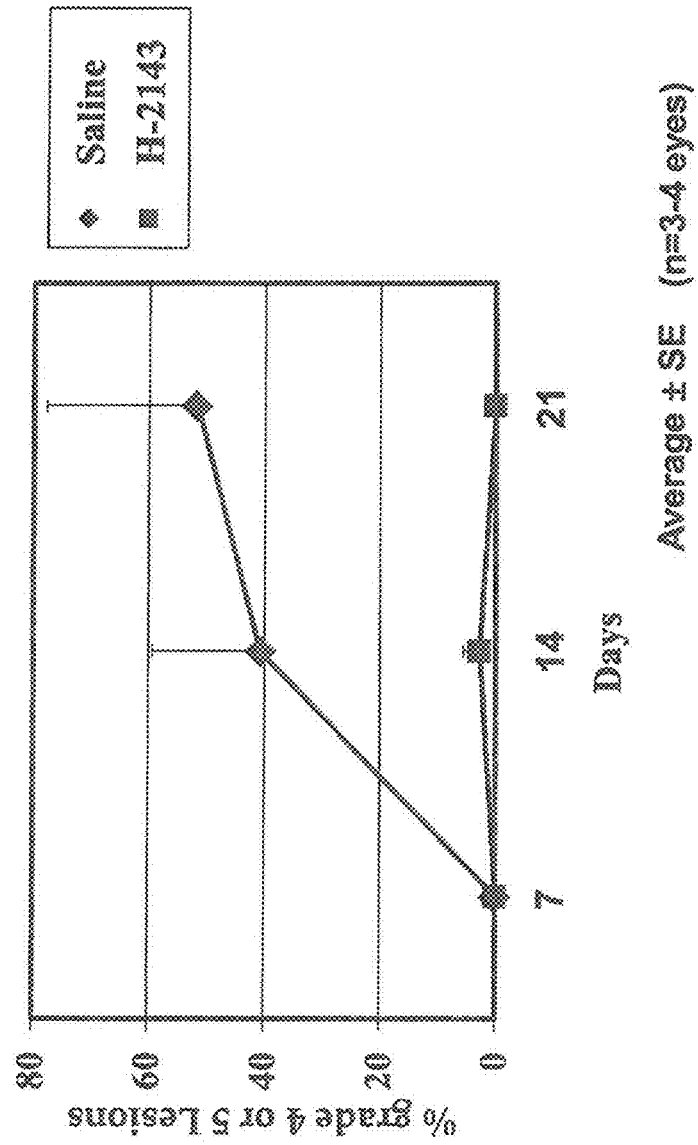
Figure 55 In vivo efficacy of H-2143

ANTI-ROBO4 ANTIBODY

CROSS-REFERENCE TO RELATED APPLICATIONS

This application is a continuation of U.S. Ser. No. 14/397,210, filed Oct. 27, 2014, which is the U.S. national stage application of International Patent Application No. PCT/IB2013/053312, filed Apr. 26, 2013.

The Sequence Listing for this application is labeled "Seq-List-replace.txt" which was created on Mar. 8, 2016 and is 249 KB. The entire content of the sequence listing is incorporated herein by reference in its entirety.

TECHNICAL FIELD

The present invention relates to an antibody having an anti-angiogenesis activity. More specifically, the present invention relates to an antibody against ROBO4 and a pharmaceutical composition containing the antibody.

BACKGROUND ART

Roundabout homolog 4 (ROBO4), a protein of 110 kDa in molecular weight, has a single-pass transmembrane structure (Non Patent Literature 1) and is known to suppress angiogenesis through the binding to a known angiogenesis suppressor Slit homolog 2 (Slit2) (Patent Literature 1 and Non Patent Literature 2). Slit2 has been reported to suppress the migration of HUVEC promoted by a vascular endothelial growth factor (VEGF) and has also been reported to suppress the promotion of cell migration by VEGF or bFGF for ROBO4 gene-transfected vascular endothelial cells (hereinafter, the vascular endothelial cell is also referred to as "EC") compared with empty vector-transfected EC (Patent Literature 1 and Non Patent Literatures 2 to 4).

Moreover, it has been reported that the suppressive effect of Slit2 on the promotion of cell migration, promotion of lumen formation, or increase in permeability by VEGF is observed in EC derived from a wild-type mouse or EC transfected with control siRNA, but not observed in EC derived from a ROBO4 gene-knockout mouse or EC transfected with siRNA to knock-down the ROBO4 gene (Patent Literature 2 and Non Patent Literatures 4 to 6). Furthermore, it has been reported that Slit2 suppresses, via ROBO4, angiogenesis or increase in vascular permeability in mouse models with laser-induced choroidal neovascularization or oxygen-induced retinopathy, which are animal disease models with exudative age-related macular degeneration or diabetic retinopathy (Patent Literature 2 and Non Patent Literature 4).

In spite of these findings, there are also reports showing that ROBO4 does not bind to Slit2 (Non Patent Literature 9 and Patent Literature 5). It has also been reported as to its functions that ROBO4 participates in the promotion of angiogenesis rather than the suppression of angiogenesis, because the migration or lumen formation of ROBO4 gene-knockout EC is inhibited (Non Patent Literatures 10 and 11).

In clinical practice, ROBO4 has been reported to be highly expressed in intratumoral vessels in liver metastasis from colon cancer, ganglioglioma, bladder cancer, breast cancer, metastatic melanoma, kidney cancer, lung cancer, liver cancer, or colon cancer (Patent Literature 3 and Non Patent Literatures 1, 3, and 7). Moreover, ROBO4 has been reported to be also expressed in blood vessels in the fibrovascular membranes of proliferative diabetic retinopathy patients (Non Patent Literature 8). As such, ROBO4 is expressed in vascular endothelial cells, particularly, endothelial cells in blood vessels newly formed in a pathological condition. This may suggest a pathological angiogenesis resulting from the high expression of ROBO4, but may also suggest the compensatory expression of ROBO4 for suppressing pathological angiogenesis.

As described above, ROBO4 is involved in an anti-angiogenesis effect. Thus, an antibody against ROBO4 and a functional fragment thereof are presumably useful in the treatment of a disease involving angiogenesis. However, it is uncertain whether either an agonistic or antagonistic antibody against ROBO4 suppresses or promotes angiogenesis.

Antibodies described in EP Patent No. 1,565,491 (Patent Literature 4) and WO2008/100805 (Patent Literature 5) are known as the antibody against ROBO4 (hereinafter, referred to as an "anti-ROBO4 antibody"). But none of these antibodies does not show a suppressive or inhibitory effect on angiogenesis in vivo.

CITATION LIST

Patent Literature

[Patent Literature 1] WO2004/003163
[Patent Literature 2] WO2008/073441
[Patent Literature 3] WO2002/036771
[Patent Literature 4] European Patent No. 1,565,491
[Patent Literature 5] WO2008/100805

Non Patent Literature

[Non Patent Literature 1] Genomics, 2002, vol. 79, p. 547-552
[Non Patent Literature 2] Developmental Biology, 2003, vol. 261, p. 251-267
[Non Patent Literature 3] Biochemical and Biophysical Research Communications, 2005, vol. 332, p. 533-541
[Non Patent Literature 4] Nature Medicine, 2008, No. 14, p. 448-453
[Non Patent Literature 5] Science Translational Medicine, 2010, vol. 2, p. 23ra19
[Non Patent Literature 6] Proceedings of the National Academy of Sciences, 2010, vol. 107, p. 10520-10525
[Non Patent Literature 7] Oncology Reports, 2006, vol. 15, p. 1437-1443
[Non Patent Literature 8] Molecular Vision, 2009, vol. 15, p. 1057-1069
[Non Patent Literature 9] The FASEB Journal, 2005, vol. 19, p. 121-123
[Non Patent Literature 10] BMC Cell Biology, 2008, vol. 9, p. 61-72
[Non Patent Literature 11] The FASEB Journal, 2009, vol. 23, p. 513-522

SUMMARY OF INVENTION

Problems to be Solved by the Invention

An object of the present invention is to provide an antibody against ROBO4.

A further object of the present invention is to provide a pharmaceutical composition containing an anti-ROBO4 antibody having an anti-angiogenesis effect, etc.

A further object of the present invention is to provide a method for producing the antibody.

A further object of the present invention is to provide a method for suppressing angiogenesis using the antibody, etc.

Means for Solving the Problems

The present inventors have conducted diligent studies to attain the objects and consequently successfully constructed a screening system that detects the activation of the downstream signal of ROBO4. Moreover, the present inventors have used the screening system to successfully obtain a novel anti-ROBO4 monoclonal antibody that activates the downstream signal of ROBO4, has a suppressive activity against cell migration induced by various angiogenic factors such as VEGF, bFGF, HGF, PDGF-BB and SDF-1 in ROBO4-expressing EC, and exhibits an anti-angiogenesis effect even in in-vivo models. In this way, the present invention has been completed.

Specifically, the present invention relates to:
(1) an antibody having properties described in the following (I) to (III) or a functional fragment thereof:
(I) binding to the ROBO4 protein, preferably with a $K_D$ value of $1 \times 10^{-8}$ or lower, specifically preferred $5 \times 10^{-9}$ or lower;
(II) suppressing or inhibiting vascular endothelial cell migration in the absence of a cross-linking antibody in vitro; and
(III) suppressing or inhibiting angiogenesis in vivo;
(2) the antibody or the functional fragment thereof according to (1), wherein the ROBO4 protein is the human ROBO4 protein;
(3) the antibody or the functional fragment thereof according to (1), wherein the ROBO4 protein is a protein consisting of an amino acid sequence of amino acid Nos. 1 to 1007 of SEQ ID NO: 2;
(4) the antibody or the functional fragment thereof according to (1), wherein the ROBO4 protein is a protein consisting of an amino acid sequence of amino acid Nos. 46 to 1007 of SEQ ID NO: 2;
(5) the antibody or the functional fragment thereof according to (3) or (4), wherein the antibody or the functional fragment thereof binds to a site consisting of an amino acid sequence of amino acid Nos. 132 to 209 of SEQ ID NO: 2;
(6) the antibody or the functional fragment thereof according to (1), wherein the antibody or the functional fragment thereof is a monoclonal antibody or a functional fragment thereof;
(7) the antibody or the functional fragment thereof according to any one of (1) to (6), wherein the antibody consists of a heavy chain comprising CDRH1 consisting of the amino acid sequence represented by SEQ ID NO: 44 (FIG. 25), CDRH2 consisting of the amino acid sequence represented by SEQ ID NO: 46 (FIG. 26) or an amino acid sequence derived from the amino acid sequence of SEQ ID NO: 46 by the substitution of one amino acid, and CDRH3 consisting of the amino acid sequence represented by SEQ ID NO: 48 (FIG. 27), and a light chain comprising CDRL1 consisting of the amino acid sequence represented by SEQ ID NO: 50 (FIG. 28) or an amino acid sequence derived from the amino acid sequence of SEQ ID NO: 50 by the substitution of one to three amino acid(s), CDRL2 consisting of the amino acid sequence represented by SEQ ID NO: 52 (FIG. 29), and CDRL3 consisting of the amino acid sequence represented by SEQ ID NO: 54 (FIG. 30);
(8) the antibody or the functional fragment thereof according to any one of (1) to (7), wherein the antibody consists of a heavy chain comprising CDRH1 consisting of the amino acid sequence represented by SEQ ID NO: 44 (FIG. 25), CDRH2 consisting of the amino acid sequence represented by SEQ ID NO: 46 (FIG. 26) or the amino acid sequence represented by SEQ ID NO: 68 (FIG. 44), and CDRH3 consisting of the amino acid sequence represented by SEQ ID NO: 48 (FIG. 27), and a light chain comprising CDRL1 consisting of the amino acid sequence represented by SEQ ID NO: 50 (FIG. 28) or the amino acid sequence represented by SEQ ID NO: 70 (FIG. 46), CDRL2 consisting of the amino acid sequence represented by SEQ ID NO: 52 (FIG. 29), and CDRL3 consisting of the amino acid sequence represented by SEQ ID NO: 54 (FIG. 30);
(9) the antibody or the functional fragment thereof according to any one of (1) to (7), wherein the antibody comprises a heavy chain variable region consisting of the amino acid sequence represented by SEQ ID NO: 31 (FIG. 16), and a light chain variable region consisting of the amino acid sequence represented by SEQ ID NO: 33 (FIG. 18);
(10) the antibody or the functional fragment thereof according to any one of (1) to (8), wherein the antibody comprises any one heavy chain variable region selected from the following a) to d) and a light chain variable region selected from e) and f):
a) a heavy chain (hMAb1-H1-type) variable region consisting of an amino acid sequence represented by amino acid Nos. 20 to 137 of SEQ ID NO: 56 (FIG. 32),
b) a heavy chain (hMAb1-H2-type) variable region consisting of an amino acid sequence represented by amino acid Nos. 20 to 137 of SEQ ID NO: 58 (FIG. 34),
c) a heavy chain (hMAb1-H3-type) variable region consisting of an amino acid sequence represented by amino acid Nos. 20 to 137 of SEQ ID NO: 60 (FIG. 36), and
d) a heavy chain (hMAb1-H4-type) variable region consisting of an amino acid sequence represented by amino acid Nos. 20 to 137 of SEQ ID NO: 62 (FIG. 38); and
e) a light chain (hMAb1-L1-type) variable region consisting of an amino acid sequence represented by amino acid Nos. 21 to 134 of SEQ ID NO: 64 (FIG. 40), and
f) a light chain (hMAb1-L2-type) variable region consisting of an amino acid sequence represented by amino acid Nos. 21 to 134 of SEQ ID NO: 66 (FIG. 42);
(11) the antibody or the functional fragment thereof according to any one of (1) to (8), wherein the antibody comprises any one of the following combinations 1) to 6) of a heavy chain variable region and a light chain variable region:
1) a heavy chain variable region consisting of an amino acid sequence represented by amino acid Nos. 20 to 137 of SEQ ID NO: 58 (FIG. 34) and a light chain variable region consisting of an amino acid sequence represented by amino acid Nos. 21 to 134 of SEQ ID NO: 64 (FIG. 40),
2) a heavy chain variable region consisting of an amino acid sequence represented by amino acid Nos. 20 to 137 of SEQ ID NO: 58 (FIG. 34) and a light chain variable region consisting of an amino acid sequence represented by amino acid Nos. 21 to 134 of SEQ ID NO: 66 (FIG. 42),
3) a heavy chain variable region consisting of an amino acid sequence represented by amino acid Nos. 20 to 137 of SEQ ID NO: 62 (FIG. 38) and a light chain variable region consisting of an amino acid sequence represented by amino acid Nos. 21 to 134 of SEQ ID NO: 66 (FIG. 42),
4) a heavy chain variable region consisting of an amino acid sequence represented by amino acid Nos. 20 to 137 of SEQ ID NO: 62 (FIG. 38) and a light chain variable region consisting of an amino acid sequence represented by amino acid Nos. 21 to 134 of SEQ ID NO: 64 (FIG. 40),
5) a heavy chain variable region consisting of an amino acid sequence represented by amino acid Nos. 20 to 137 of SEQ ID NO: 56 (FIG. 32) and a light chain variable region consisting of an amino acid sequence represented by amino acid Nos. 21 to 134 of SEQ ID NO: 64 (FIG. 40), and 6) a heavy chain variable region consisting of an amino acid sequence represented by amino acid Nos. 20 to 137 of SEQ ID NO: 60 (FIG. 36) and a light chain variable region consisting of an amino acid sequence represented by amino acid Nos. 21 to 134 of SEQ ID NO: 64 (FIG. 40),

(12) the antibody or the functional fragment thereof according to any one of (1) to (11), wherein the antibody or the functional fragment thereof is a chimeric antibody or a functional fragment thereof;

(13) the antibody or the functional fragment thereof according to any one of (1) to (11), wherein the antibody or the functional fragment thereof is a humanized antibody or a functional fragment thereof;

(14) the antibody or the functional fragment thereof according to any one of (1) to (13), wherein the antibody comprises a human IgG1 or human IgG2 heavy chain constant region;

(15) the antibody or the functional fragment thereof according to any one of (1) to (6), wherein the antibody or the functional fragment thereof binds to a site on an antigen recognized by any one antibody according to (7) to (14);

(16) the antibody or the functional fragment thereof according to any one of (1) to (6), wherein the antibody or the functional fragment thereof competes with any one antibody according to (7) to (14) for the binding to ROBO4 protein;

(17) the antibody according to any one of (1) to (8), wherein the antibody comprises any one of the following combinations 1) to 6) of a heavy chain and a light chain:

1) a heavy chain consisting of an amino acid sequence represented by amino acid Nos. 20 to 463 of SEQ ID NO: 58 (FIG. 34) and a light chain consisting of an amino acid sequence represented by amino acid Nos. 21 to 239 of SEQ ID NO: 64 (FIG. 40) (H-1140), 2) a heavy chain consisting of an amino acid sequence represented by amino acid Nos. 20 to 463 of SEQ ID NO: 58 (FIG. 34) and a light chain consisting of an amino acid sequence represented by amino acid Nos. 21 to 239 of SEQ ID NO: 66 (FIG. 42) (H-1143), 3) a heavy chain consisting of an amino acid sequence represented by amino acid Nos. 20 to 463 of SEQ ID NO: 62 (FIG. 38) and a light chain consisting of an amino acid sequence represented by amino acid Nos. 21 to 239 of SEQ ID NO: 66 (FIG. 42) (H-2143), 4) a heavy chain consisting of an amino acid sequence represented by amino acid Nos. 20 to 463 of SEQ ID NO: 62 (FIG. 38) and a light chain consisting of an amino acid sequence represented by amino acid Nos. 21 to 239 of SEQ ID NO: 64 (FIG. 40) (H-2140), 5) a heavy chain consisting of an amino acid sequence represented by amino acid Nos. 20 to 463 of SEQ ID NO: 56 (FIG. 32) and a light chain consisting of an amino acid sequence represented by amino acid Nos. 21 to 239 of SEQ ID NO: 64 (FIG. 40) (H-1040), and 6) a heavy chain consisting of an amino acid sequence represented by amino acid Nos. 20 to 463 of SEQ ID NO: 60 (FIG. 36) and a light chain consisting of an amino acid sequence represented by amino acid Nos. 21 to 239 of SEQ ID NO: 64 (FIG. 40) (H-2040),

(18) an antibody comprising a modified form of the heavy chain of any one antibody according to (17), wherein said modified form lacks one to several carboxyl-terminal amino acid(s) of said heavy chain, preferably one to eight carboxyl-terminal amino acid(s) of said heavy chain, more preferably one to two carboxyl-terminal amino acid(s) of said heavy chain;

(19) the antibody according to any one of (1) to (6), wherein the antibody is 95% or more identical in the amino acid sequence to any one antibody according to (17); has a $K_D$ value of $1 \times 10^{-8}$ or lower for a human ROBO4; suppresses or inhibits vascular endothelial cell migration in the absence of a cross-linking antibody in vitro; and suppresses or inhibits angiogenesis in vivo;

(20) the antibody or the functional fragment thereof according to (15), wherein the antibody or the functional fragment thereof is a human antibody or a functional fragment thereof;

(21) a nucleotide sequence selected from the group consisting of the following (I) to (III):

(I) a nucleotide sequence comprising a nucleotide sequence encoding the partial or whole amino acid sequence of the heavy chain or light chain of an antibody according to any one of (1) to (20);

(II) a nucleotide sequence consisting of a nucleotide sequence comprising a nucleotide sequence encoding the partial or whole amino acid sequence of the heavy chain or light chain of an antibody according to any one of (1) to (20); and (III) a nucleotide sequence consisting of a nucleotide sequence encoding the partial or whole amino acid sequence of the heavy chain or light chain of an antibody according to any one of (1) to (20);

(22) a recombinant vector containing an insert of a nucleotide sequence according to (21);

(23) a recombinant cell containing a nucleotide according to (21) or a recombinant vector according to (22) introduced therein;

(24) a cell producing an antibody according to any one of (1) to (20), wherein the cell is preferably a mammalian cell, more preferably a CHO cell and even more preferably a CHOK1SV;

(25) a method for producing an antibody or a functional fragment thereof according to any one of (1) to (20), comprising the following steps (I) and (II):

(I) culturing a cell according to (23) or (24); and (II) collecting the antibody or the functional fragment thereof according to any one of (1) to (20) from the culture obtained in the step (I);

(26) an antibody or a functional fragment thereof produced by a production method according to (25);

(27) a modified form of an antibody or a functional fragment thereof according to any one of (1) to (20) and (26);

(28) a pharmaceutical composition comprising an antibody or a functional fragment thereof according to any one of (1) to (20) and (26) or a modified form according to (27) as an active ingredient;

(29) the pharmaceutical composition according to (28), wherein the pharmaceutical composition is an agent for treating or preventing an angiogenic disease;

(30) the pharmaceutical composition according to (28), wherein the angiogenic disease is exudative age-related macular degeneration, diabetic retinopathy, macular edema, benign or malignant tumor, atherosclerosis, retrolental fibroplasia, angioma, chronic inflammation, ocular neovascular disease, proliferative retinopathy, neovascular glaucoma, immune rejection of a corneal tissue transplant or other tissue transplants, rheumatoid arthritis, psoriasis, acute inflammation, sepsis, or obesity;

(31) the pharmaceutical composition according to (28), wherein the angiogenic disease is exudative age-related macular degeneration, diabetic retinopathy, macular edema, retrolental fibroplasia, ocular neovascular disease, proliferative retinopathy, neovascular glaucoma, or immune rejection of a corneal tissue transplant;

(32) an angiogenesis inhibitor comprising an antibody or a functional fragment thereof according to any one of (1) to (20) and (26) or a modified form according to (27) as an active ingredient;

(33) a method for treating or preventing an angiogenic disease comprising administering to a subject in need thereof an effective amount of an antibody or a functional fragment thereof according to any one of (1) to (20) and (26) or a modified form according to (27), or the composition according to any one of (28) to (31), preferably wherein the angiogenic disease is the angiogenic disease in an individual having the expressed ROBO4 protein; and

(34) the pharmaceutical composition according to any one of claims 28 to 31, wherein said composition is used in combination with a further therapeutic or prophylactic agent, preferably wherein said agent is an anti-angiogenesis drug, anti-inflammatory drug, and/or an anticancer drug.

Advantageous Effects of Invention

According to the present invention, a therapeutic agent or the like for an angiogenic disease containing an antibody that binds to ROBO4 and has an anti-angiogenesis effect can be obtained.

BRIEF DESCRIPTION OF DRAWINGS

FIG. 1 is a diagram showing the presence or absence of change in reporter activity against NF-κB, GAS, ISRE, IL-8 promoter, or TCF as response elements in the transient expression of human ROBO4 in HEK293 cells. The error bar in the diagram represents standard deviation (n=3).

FIG. 2 is a diagram showing the presence or absence of change in IL-8 promoter activity in the transient expression of full-length human ROBO4 or an intracellular region deletion variant of human ROBO4 in HEK293 cells. The error bar in the diagram represents standard deviation (n=5 or 10).

FIG. 3 is a diagram showing change in IL-8 promoter activity in human ROBO4-transfected HEK293 cells caused by an anti-ROBO4 antibody MAb1. The error bar in the diagram represents standard deviation (n=3).

FIG. 4 is a diagram showing change in IL-8 promoter activity in human ROBO4-transfected HEK293 cells caused by an anti-ROBO4 antibody MAb2, MAb3, or MAb4. The error bar in the diagram represents standard deviation (n=3).

FIG. 5 is a diagram showing change in the migratory capacity of HUVEC in the presence of VEGF or bFGF caused by the anti-ROBO4 antibody MAb1. The error bar in the diagram represents standard deviation (n=3 or 4).

FIG. 6 is a diagram showing change in the migratory capacity of HUVEC in the presence of bFGF caused by the anti-ROBO4 antibody MAb2, MAb3, or MAb4. The error bar in the diagram represents standard deviation (n=4).

FIG. 7 is a diagram showing the presence or absence of the binding activity of the anti-ROBO4 antibody MAb1 against human ROBO4, mouse ROBO4, rat ROBO4, or cynomolgus monkey ROBO4.

FIG. 8 is a diagram showing the presence or absence of the binding activity of the anti-ROBO4 antibody MAb1 against human ROBO1, human ROBO2, or human ROBO3. The upper boxes show the results about MAb1, and the lower boxes show the results about a positive control antibody with which the expression of these proteins on cell surface was confirmed.

FIG. 9 is a diagram showing the presence or absence of the binding activity of the anti-ROBO4 antibody MAb1 against an extracellular region/domain deletion variant of human ROBO4. The upper boxes show the results about MAb1, and the lower boxes show the results about an anti-FLAG antibody with which the expression of these proteins on cell surface was confirmed.

FIG. 10 is a diagram showing change in angiogenesis in laser-induced choroidal neovascularization models caused by the anti-ROBO4 antibody MAb1. The error bar in the diagram represents standard deviation (n=4 eyes), and ■ or □ shows the results of each eye.

FIG. 11 is a diagram showing change in IL-8 promoter activity in human ROBO4-transfected HEK293 cells caused by an anti-ROBO4 chimeric antibody cMAb1-1 or cMAb1-2. The error bar in the diagram represents standard deviation (n=3).

FIG. 12 is a diagram showing change in the migratory capacity of HUVEC in the presence of bFGF caused by the anti-ROBO4 chimeric antibody cMAb1-1 or cMAb1-2. The error bar in the diagram represents standard deviation (n=4).

FIG. 13 shows cDNA encoding full-length human ROBO4 (SEQ ID NO: 1).

FIG. 14 shows the full-length amino acid sequence of human ROBO4 (SEQ ID NO: 2).

FIG. 15 shows the nucleotide sequence of cDNA encoding the heavy chain variable region of MAb1 (SEQ ID NO: 30).

FIG. 16 shows the amino acid sequence of the MAb1 heavy chain variable region (SEQ ID NO: 31).

FIG. 17 shows the nucleotide sequence of cDNA encoding the light chain variable region of MAb1 (SEQ ID NO: 32).

FIG. 18 shows the amino acid sequence of the MAb1 light chain variable region (SEQ ID NO: 33).

FIG. 19 shows the nucleotide sequence of cDNA encoding the light chain of cMAb1 (SEQ ID NO: 37).

FIG. 20 shows the amino acid sequence of the cMAb1 light chain (SEQ ID NO: 38).

FIG. 21 shows the nucleotide sequence of cDNA encoding the heavy chain of cMAb1-1 (SEQ ID NO: 39).

FIG. 22 shows the amino acid sequence of the cMAb1-1 heavy chain (SEQ ID NO: 40).

FIG. 23 shows the nucleotide sequence of cDNA encoding the heavy chain of cMAb1-2 (SEQ ID NO: 41).

FIG. 24 shows the amino acid sequence of the cMAb1-2 heavy chain (SEQ ID NO: 42).

FIG. 25 shows the amino acid sequence of the heavy chain CDRH1 of MAb1 (SEQ ID NO: 44).

FIG. 26 shows the amino acid sequence of the heavy chain CDRH2 of MAb1 (SEQ ID NO: 46).

FIG. 27 shows the amino acid sequence of the heavy chain CDRH3 of MAb1 (SEQ ID NO: 48).

FIG. 28 shows the amino acid sequence of the light chain CDRL1 of MAb1 (SEQ ID NO: 50).

FIG. 29 shows the amino acid sequence of the light chain CDRL2 of MAb1 (SEQ ID NO: 52).

FIG. 30 shows the amino acid sequence of the light chain CDRL3 of MAb1 (SEQ ID NO: 54).

FIG. 31 shows the nucleotide sequence of cDNA encoding a hMAb1-H1-type heavy chain (SEQ ID NO: 55).

FIG. 32 shows the amino acid sequence of the hMAb1-H1-type heavy chain (SEQ ID NO: 56).

FIG. 33 shows the nucleotide sequence of cDNA encoding a hMAb1-H2-type heavy chain (SEQ ID NO: 57).

FIG. 34 shows the amino acid sequence of the hMAb1-H2-type heavy chain (SEQ ID NO: 58).

FIG. 35 shows the nucleotide sequence of cDNA encoding a hMAb1-H3-type heavy chain (SEQ ID NO: 59).

FIG. 36 shows the amino acid sequence of the hMAb1-H3-type heavy chain (SEQ ID NO: 60).

FIG. 37 shows the nucleotide sequence of cDNA encoding a hMAb1-H4-type heavy chain (SEQ ID NO: 61).

FIG. 38 shows the amino acid sequence of the hMAb1-H4-type heavy chain (SEQ ID NO: 62).

FIG. 39 shows the nucleotide sequence of cDNA encoding a hMAb1-L1-type light chain (SEQ ID NO: 63).

FIG. 40 shows the amino acid sequence of the hMAb1-L1-type light chain (SEQ ID NO: 64).

FIG. 41 shows the nucleotide sequence of cDNA encoding a hMAb1-L2-type light chain (SEQ ID NO: 65).

FIG. 42 shows the amino acid sequence of the hMAb1-L2-type light chain (SEQ ID NO: 66).

FIG. 43 shows the amino acid sequence of CDRH1 of the hMAb1-H2- or hMAb1-H4-type heavy chain (SEQ ID NO: 67).

FIG. 44 shows the amino acid sequence of CDRH2 of the hMAb1-H2- or hMAb1-H4-type heavy chain (SEQ ID NO: 68).

FIG. 45 shows the amino acid sequence of CDRH3 of the hMAb1-H2- or hMAb1-H4-type heavy chain (SEQ ID NO: 69).

FIG. 46 shows the amino acid sequence of CDRL1 of the hMAb1-L2-type light chain (SEQ ID NO: 70).

FIG. 47 shows the amino acid sequence of CDRL2 of the hMAb1-L2-type light chain (SEQ ID NO: 71).

FIG. 48 shows the amino acid sequence of CDRL3 of the hMAb1-L2-type light chain (SEQ ID NO: 72).

FIG. 49 is a diagram showing change in IL-8 promoter activity in human ROBO4-transfected HEK293 cells caused by H-1040, H-1143, H-1140, H-2040, H-2143, or H-2140.

FIG. 50 is a diagram showing change in the migratory capacity of HUVEC in the presence of bFGF caused by H-1143, H-2140, or H-2143. The error bar in the diagram represents standard deviation (n=4).

FIG. 51 is a diagram showing the cross-species reactivity of H-1143.

FIG. 52 is a diagram showing the cross-species reactivity of H-2140.

FIG. 53 is a diagram showing the cross-species reactivity of H-2143.

FIG. 54 is a diagram showing the binding specificity of H-1143, H-2140, or H-2143.

FIG. 55 is a diagram showing change in angiogenesis in laser-induced choroidal neovascularization models caused by H-2143. The error bar in the diagram represents standard deviation (n=3-4 eyes).

MODE FOR CARRYING OUT THE INVENTION

1. Definition

In the present invention, "gene" means nucleotide(s) or nucleotide sequence comprising a nucleotide sequence encoding the amino acids of a protein, or its complementary strand. The "gene" is meant to include, for example, a polynucleotide, an oligonucleotide, DNA, mRNA, cDNA, and cRNA as the nucleotide sequence comprising a nucleotide sequence encoding the amino acids of a protein, or its complementary strand. Such a gene is a single-stranded, double-stranded, or triple or more stranded nucleotide sequence, and the "gene" is also meant to include an associate of DNA and RNA strands, a mixture of ribonucleotides (RNAs) and deoxyribonucleotides (DNAs) on one nucleotide strand, and a double-stranded or triple or more stranded nucleotide sequence comprising such a nucleotide strand. Examples of the "ROBO4 gene" of the present invention can include DNA, mRNA, cDNA, and cRNA comprising a nucleotide sequence encoding the amino acid sequence of the ROBO4 protein.

In the present invention, the term "nucleotide(s)" or "nucleotide sequence" has the same meaning as in a "nucleic acid" and is also meant to include, for example, DNA, RNA, a probe, an oligonucleotide, a polynucleotide, and a primer. Such a nucleotide sequence is a single-stranded, double-stranded or triple or more stranded nucleotide, and the "nucleotide" sequence is also meant to include an associate of DNA and RNA strands, a mixture of ribonucleotides (RNAs) and deoxyribonucleotides (DNAs) on one nucleotide strand, and an associate of two strands or three or more strands comprising such a nucleotide strand.

In the present invention, the terms "polypeptide", "peptide", and "protein" have the same meaning.

In the present invention, the "antigen" is also used as the meaning of an "immunogen".

In the present invention, the "cell" also includes various cells derived from animal individuals, subcultured cells, primary cultured cells, cell lines, recombinant cells, and the like.

In the present invention, an antibody recognizing the ROBO4 protein is also referred to as an "anti-ROBO4 antibody". The "anti-ROBO4 antibody" includes an anti-ROBO4 chimeric antibody, an anti-ROBO4 humanized antibody, an anti-ROBO4 human antibody, and the like.

In the present invention, the "functional fragment of the antibody" means an antibody fragment that exerts at least one of the functions, e.g., the binding affinity ($K_D$ value) of the original antibody. Examples of the "functional fragment of the antibody" can include, but not limited to, Fab, F(ab')2, scFv, Fab', single-chain immunoglobulin, and the like. Such a functional fragment of the antibody may be obtained by the treatment of a full-length molecule of the antibody protein with an enzyme such as papain or pepsin or may be a recombinant protein produced in an appropriate host cell using a recombinant gene. Preferred "functional fragments" also have at least one of the biological activities of the original antibody.

Further, in the context of the present invention, a nucleotide sequence encoding "the partial amino acid sequence" of the heavy or light chain is or includes a nucleotide sequence encoding a "functional fragment of the antibody" as defined herein above.

In the present invention, the "site" to which an antibody binds, i.e., the "site" recognized by an antibody, means a partial peptide or partial conformation on an antigen bound or recognized by the antibody. In the present invention, such a site is also called an epitope or an antibody-binding site. Examples of the site on the ROBO4 protein bound or recognized by the anti-ROBO4 antibody of the present invention can include a partial peptide or partial conformation on the ROBO4 protein.

The heavy and light chains of an antibody molecule are known to each have three complementarity determining regions (CDRs). The complementarity determining regions are also called hypervariable domains. They are located in the variable regions of the antibody heavy and light chains. These sites have a particularly highly variable primary structure and are usually separated at three positions on the respective primary structures of heavy and light chain polypeptide strands. In the present invention, the complementarity determining regions of the antibody are referred to as CDRH1, CDRH2, and CDRH3 from the amino terminus of the heavy chain amino acid sequence as to the complementarity determining regions of the heavy chain and as CDRL1, CDRL2, and CDRL3 from the amino terminus of the light chain amino acid sequence as to the complementarity determining regions of the light chain. These sites are proximal to each other on the three-dimensional structure and determine specificity for the antigen to be bound.

In the present invention, the "antibody mutant" means a polypeptide that has an amino acid sequence derived from the amino acid sequence of the original antibody by the substitution, deletion, addition, and/or insertion (hereinafter, collectively referred to as "mutation") of amino acid(s) and binds to the ROBO4 protein of the present invention. The number of the mutated amino acids in such an antibody mutant is 1 to 2, 1 to 3, 1 to 4, 1 to 5, 1 to 6, 1 to 7, 1 to 8, 1 to 9, 1 to 10, 1 to 12, 1 to 15, 1 to 20, 1 to 25, 1 to 30, 1 to 40, or 1 to 50. Such an antibody mutant is also encompassed by the "antibody" of the present invention.

In the present invention, the term "several" in "1 to several" refers to 2 to 10, preferably 2 to 8, more preferably 2.

Examples of activities or properties exerted by the antibody of the present invention can include biological activities or physicochemical properties and can specifically include various biological activities, a binding activity against an antigen or an epitope, stability during production or storage, and thermal stability.

In the present invention, the phrase "hybridizing under stringent conditions" means hybridization under conditions involving hybridization at 65° C. in a solution containing 5×SSC, followed by washing at 65° C. for 20 minutes in an aqueous solution containing 2×SSC-0.1% SDS, at 65° C. for 20 minutes in an aqueous solution containing 0.5×SSC-0.1% SDS, and at 65° C. for 20 minutes in an aqueous solution containing 0.2×SSC-0.1% SDS, or hybridization under conditions equivalent thereto. SSC means an aqueous solution of 150 mM NaCl-15 mM sodium citrate, and n×SSC means SSC with an n-fold concentration.

2. ROBO4 Protein

In the present specification, the terms "ROBO4" and "ROBO4 protein" are used as the same meaning.
(2-1) Property
The ROBO4 protein of the present invention has the following properties:
(i) ROBO4 has a molecular weight of approximately 110 kDa and a single-pass transmembrane structure and is a receptor protein of the SLIT2 protein involved in angiogenesis. Any ROBO4 protein of the present invention can be found in a form liberated from a membrane such as a cell membrane and may be in a form bound to a membrane such as a cell membrane. In this context, the molecular weight means an apparent molecular weight under the non-reducing conditions of SD S-PAGE. The N-terminal extracellular region of ROBO4 contains two immunoglobulin-like domains (hereinafter, referred to as "Ig-like domains") and two fibronectin type III domains, while its C-terminal intracellular region contains a protein-rich region. In the present specification, these two immunoglobulin-like domains are referred to as Ig-like domain 1 and Ig-like domain 2, respectively, from the amino terminus. The human ROBO4 protein consists of an amino acid sequence of amino acid Nos. 28 to 1007 of SEQ ID NO: 2. Amino acid Nos. 1 to 27 of SEQ ID NO: 2 represent a secretory signal; amino acid Nos. 28 to 467 thereof represent an extracellular region; amino acid Nos. 46 to 131 thereof represent Ig-like domain 1; amino acid Nos. 137 to 224 thereof represent Ig-like domain 2; amino acid Nos. 252 to 340 thereof represent fibronectin type III domain 1; amino acid Nos. 347 to 438 thereof represent fibronectin type III domain 2; amino acid Nos. 468 to 490 thereof represent a region in the cell membrane; and amino acid Nos. 491 to 1007 thereof represent an intracellular region.
(ii) ROBO4 has an anti-angiogenesis effect. In the present invention, the term "anti-angiogenesis" means that the molecule directly or indirectly suppresses and/or inhibits angiogenesis by itself, in collaboration with another factor, or as an associate with another factor. The anti-angiogenesis effect can be evaluated, for example, with a suppressive effect on increase in vascular permeability, cell migration promoting activity, or lumen formation activity by VEGF as an index.
(iii) ROBO4 comprises an amino acid sequence described in any one of the following (a) to (e) (hereinafter, referred to as a "ROBO4 amino acid sequence"), consists of an amino acid sequence comprising the ROBO4 amino acid sequence, or consists of the ROBO4 amino acid sequence:
(a) the amino acid sequence represented by SEQ ID NO: 2 (FIG. 14);
(b) the amino acid sequence of a polypeptide that exhibits 80% or more, 82% or more, 84% or more, 86% or more, 88% or more, 90% or more, 92% or more, 94% or more, 96% or more, 98% or more, or 99% or more sequence identity to the amino acid sequence represented by SEQ ID NO: 2 (FIG. 14) and exhibits an anti-angiogenesis effect;
(c) the amino acid sequence of a polypeptide that comprises an amino acid sequence represented by SEQ ID NO: 2 (FIG. 14) having a substitution, deletion, addition, or insertion of 1 to 50, 1 to 45, 1 to 40, 1 to 35, 1 to 30, 1 to 25, 1 to 20, 1 to 15, 1 to 10, 1 to 8, 1 to 6, 1 to 5, 1 to 4, 1 to 3, 1 or 2, or 1 amino acid(s) and suppresses angiogenesis;
(d) the amino acid sequence of a polypeptide that comprises an amino acid sequence of SEQ ID NO: 2 having the deletion of amino acid Nos. 1 to 45 or 1 to 131 and suppresses angiogenesis; and
(e) the amino acid sequence of a polypeptide that is encoded by the nucleotide sequence of a nucleotide hybridizing under stringent conditions to a nucleotide having a nucleotide sequence complementary to a nucleotide sequence encoding the amino acid sequence represented by SEQ ID NO: 2 (FIG. 14) and suppresses angiogenesis.

The ROBO4 protein may be present as the whole or a portion of a homo or hetero oligo associate constituted of two or more subunits.

The amino acid sequence and/or other properties of the ROBO4 protein may be neither the same nor homogeneous in an individual, a tissue, a body fluid, a cell, a ROBO4 protein-containing fraction, a purified or partially purified ROBO4 protein preparation, or the like, or among a plurality of individuals, tissues, cells, ROBO4 protein-containing fractions, or ROBO4 protein preparations. One individual, tissue, body fluid, cell, ROBO4 protein-containing fraction, purified or partially purified ROBO4 protein preparation, or the like may contain plural types of ROBO4 proteins differing in amino acid sequence and/or property. Alternatively, a plurality of individuals, tissues, cells, ROBO4 protein-containing fractions, or ROBO4 protein preparations may differ in the amino acid sequence and/or other properties of the ROBO4 protein. Even such proteins differing in amino acid sequence and/or properties from each other are all encompassed by the "ROBO4 protein" of the present invention as long as they possess the properties described above in (i) to (iii).

(iv) The ROBO4 protein of the present invention can be obtained from the tissue of a vertebrate, preferably a mammal, more preferably a rodent such as a mouse or a rat or a human, even more preferably tissues of a human or a mouse, cells derived from such a tissue, cultures of such cells, and the like. Such a tissue and cells are not particularly limited as long as they contain the ROBO4 protein. Examples thereof can include joint tissues, blood, lymph, thymus glands, spleens, and cells derived from any of them. Preferable tissues and cells are tissues and cells derived from animals or patients having angiogenesis. However, the origin of the ROBO4 protein of the present invention is not limited to those described above, and the ROBO4 protein of the present invention is also meant to include even ROBO4 proteins derived from other animal species, other tissues, other cells, or the like as long as they possess the properties described above in (i) to (iii).

The ROBO4 protein of the present invention may be any of native and recombinant proteins. The ROBO4 protein is also meant to include fusion products with another peptide or protein such as a carrier or a tag. The ROBO4 protein is further meant to include forms provided with chemical modification including the addition of a polymer such as PEG and/or with biological modification including sugar chain modification. Moreover, the ROBO4 protein of the present invention is meant to include a ROBO4 protein fragment. A ROBO4 protein fragment possessing the property described above in (ii) is called a functional fragment of the ROBO4 protein.

(2-2) ROBO4 Gene

The ROBO4 gene of the present invention comprises a nucleotide sequence described in any one of the following (a) to (c) (hereinafter, referred to as a "ROBO4 gene sequence"), consists of a nucleotide sequence comprising the ROBO4 gene sequence, or consists of the ROBO4 gene sequence:
(a) the nucleotide sequence represented by SEQ ID NO: 1 (FIG. 13);
(b) a nucleotide sequence that hybridizes under stringent conditions to a nucleotide consisting of a nucleotide sequence complementary to the nucleotide sequence represented by SEQ ID NO: 1 (FIG. 13) and encodes the amino acid sequence of a polypeptide suppressing angiogenesis; and
(c) a nucleotide sequence that comprises a nucleotide sequence represented by SEQ ID NO: 1 (FIG. 13) having a substitution, deletion, addition, or insertion of 1 to 150, 1 to 140, 1 to 130, 1 to 120, 1 to 110, 1 to 100, 1 to 90, 1 to 80, 1 to 70, 1 to 60, 1 to 50, 1 to 45, 1 to 40, 1 to 30, 1 to 25, 1 to 20, 1 to 15, 1 to 10, 1 to 8, 1 to 6, 1 to 5, 1 to 4, 1 to 3, 1 or 2, or 1 base(s) and encodes the amino acid sequence of a polypeptide suppressing angiogenesis.

The ROBO4 gene is overexpressed in blood vessels in fibrovascular membranes or intratumoral vessels of patients with a disease accompanied by angiogenesis, for example, proliferative diabetic retinopathy. In addition, the ROBO4 gene seems to be overexpressed in tissue or blood fractions derived from patients affected with a disease considered to involve angiogenesis, such as exudative age-related macular degeneration, macular edema, atherosclerosis, retrolental fibroplasia, angioma, chronic inflammation, ocular neovascular disease, proliferative retinopathy, neovascular glaucoma, immune rejection of a corneal tissue transplant or other tissue transplants, rheumatoid arthritis, psoriasis, acute inflammation, sepsis, or obesity, or from model animals of these diseases.

The expression and expression level of the ROBO4 gene may be assayed with any of a ROBO4 gene transcription product and the ROBO4 protein as an index and can be determined by RT-PCR, Northern blot hybridization, or the like for the upper index and by immunoassay (e.g., enzyme-linked immuno-sorbent assay; hereinafter, referred to as "ELISA") or the like for the latter index.

(2-3) Preparation of Protein

The ROBO4 protein of the present invention can be purified or isolated from animal tissues (including body fluids), cells derived from the tissues, or cultures of the cells and prepared by gene recombination, in-vitro translation, chemical synthesis, etc.

(2-3-1) Purification or Isolation of Native ROBO4

The native ROBO4 protein can be purified or isolated from, for example, tissues (including body fluids, cells, etc.) derived from patients or non-human animals affected with an angiogenic disease such as exudative age-related macular degeneration, diabetic retinopathy, macular edema, benign or malignant tumor, atherosclerosis, retrolental fibroplasia, angioma, chronic inflammation, ocular neovascular disease, proliferative retinopathy, neovascular glaucoma, immune rejection of a corneal tissue transplant or other tissue transplants, rheumatoid arthritis, psoriasis, acute inflammation, sepsis, or obesity, cells derived from the tissues, or cultures of the cells. Such non-human animals also include model animals of these diseases. Animals subjected to model preparation are not particularly limited as long as they are vertebrates. The animals are preferably mammals, more preferably rodents such as mice or rats, even more preferably mice or rats. The tissues and cells of such patients or model animals are not particularly limited as long as they contain the ROBO4 protein. Examples thereof can include joint tissues, blood, lymph, thymus glands, spleens, and cells derived from any of them. Preferable tissues and cells are derived from patients or model animals having angiogenesis or exhibiting similar symptoms. However, the origin of the ROBO4 protein of the present invention is not limited to those described above, and the ROBO4 protein of the present invention may be derived from other animal species, other tissues, other cells, or the like.

Purification or isolation from such tissues, cells, cell cultures, or the like can be performed by the combination of approaches well known by those skilled in the art, such as fractionation and chromatography. Such approaches include, but not limited to, salting out, gel filtration, ion-exchange chromatography, affinity chromatography, hydrophobic chromatography, normal-phase or reverse-phase chromatography, and the like. An affinity gel cross-linked with an anti-ROBO4 monoclonal antibody can be prepared and loaded to a column to thereby prepare a column for affinity chromatography. A crude or partially purified fraction containing the ROBO4 protein is added to such a column. Subsequently, non-specific adsorbed matter is removed with sterilized phosphate-buffered saline (PBS), and a buffer solution for elution can then be added thereto to thereby selectively collect the ROBO4 protein. The solution containing the ROBO4 protein can be subjected to gel filtration or to buffer replacement and/or concentration using a concentrator such as Centriprep.

(2-3-2) Preparation of Recombinant ROBO4 Protein

The ROBO4 protein of the present invention can also be prepared in a recombinant form. Specifically, host cells are transfected with a gene encoding the amino acid sequence of the ROBO4 protein or a ROBO4 protein fragment, and the ROBO4 protein can be collected from cultures of the cells. For example, the ROBO4 gene or its fragment is inserted into an expression vector. Subsequently, prokaryotic or eukaryotic host cells are transfected with the resulting recombinant vector, and the obtained recombinant cells can be incubated to thereby express the ROBO4 protein. An expression pattern known in the art, such as secretion expression, intracellular expression of soluble forms, or an inclusion body method can be used. Also, the ROBO4 protein can be expressed not only as a molecule having the same amino terminus (N-terminus) and/or carboxy terminus (C-terminus) as native ones, but also as a fusion protein with a secretory signal, an intracellular localization signal, a tag for affinity purification, or a partner peptide. The ROBO4 protein can be purified or isolated from such recombinant cell cultures by the appropriate combination of operations such as fractionation and chromatography described in (2-3-1) Purification or isolation of native ROBO4 protein.

The ROBO4 gene or its fragment can be prepared by a method well known by those skilled in the art.

Examples thereof can include: polymerase chain reaction (hereinafter, referred to as "PCR"; Saiki, R. K., et al., Science (1988) 239, p. 487-489) with a ROBO4 cDNA expression library as a template using one set of primers capable of specifically amplifying the sequence; reverse transcription PCR (hereinafter, referred to as "RT-PCR") with an mRNA fraction for ROBO4 expression as a template using a primer capable of reverse-transcribing the sequence and one set of primers capable of specifically amplifying the sequence; expression cloning using immunoassay; and cDNA cloning using the partial amino acid sequence of a purified ROBO4 protein.

(2-3-3) In-Vitro Translation

The ROBO4 protein of the present invention can also be prepared by in-vitro translation. Such a translation method is not particularly limited as long as it is a method using a cell-free translation system involving enzymes necessary for transcription and translation, substrates, and energy substances. Examples thereof can include a method using Rapid Translation System (RTS) manufactured by Roche Diagnostics.

(2-3-4) Chemical Synthesis

The ROBO4 protein of the present invention can also be prepared by chemical synthesis. Examples of the chemical synthesis method can include solid-phase peptide synthesis methods such as Fmoc synthesis and Boc synthesis methods.

3. Anti-ROBO4 Antibody (3-1) Type of Anti-ROBO4 Antibody

The antibody of the present invention may be any of monoclonal and polyclonal antibodies. Examples of the monoclonal antibody of the present invention can include a non-human animal-derived antibody (non-human animal antibody), a human-derived antibody (human antibody), a chimeric antibody, and a humanized antibody, preferably a chimeric antibody, a humanized antibody, and a human-derived antibody (human antibody), more preferably a humanized antibody, and a human-derived antibody (human antibody).

Examples of the non-human animal antibody can include antibodies derived from vertebrates such as mammals and birds. Examples of the mammal-derived antibody can include rodent-derived antibodies such as mouse antibodies and rat antibodies. Examples of the bird-derived antibody can include chicken antibodies.

Examples of the chimeric antibody can include, but not limited to, an antibody comprising non-human animal antibody-derived variable regions bound with human antibody (human immunoglobulin) constant regions. Examples of the non-human animal antibody-derived variable regions can include heavy and light chain variable regions derived from MAb1 described later.

Examples of the humanized antibody can include, but are not limited to, a human antibody (human immunoglobulin variable regions) grafted with CDRs in the variable regions of a non-human animal antibody, a human antibody grafted with the CDRs as well as with partial sequences of framework regions of a non-human animal antibody, and an antibody having human antibody amino acid(s) replaced for one or two or more non-human animal antibody-derived amino acid(s) in any of these humanized antibodies. Examples of the CDRs in the variable regions of a non-human animal antibody can include CDRH1 to 3 in the heavy chain variable region and CDRL1 to 3 in the light chain variable region derived from MAb1 described later.

The human antibody is not particularly limited as long as it is an antibody recognizing the antigen of the present invention. Examples thereof can include a human antibody binding to the same site as that bound by an antibody having the antibody CDRs of the present invention, and a human antibody binding to the same site on ROBO4 as that bound by MAb1 described above.

The antibody according to the present invention may be an antibody constituted of sites derived from a plurality of different antibodies. Examples thereof can include an antibody comprising heavy and/or light chains exchanged among a plurality of different antibodies, an antibody comprising full-length heavy and/or light chains exchanged thereamong, an antibody comprising variable or constant regions exchanged thereamong, and an antibody comprising all or some CDRs exchanged thereamong. The heavy and light chain variable regions of the chimeric antibody may be derived from different antibodies of the present invention. CDRH1 to 3 and CDRL1 to 3 in the heavy and light chain variable regions of the humanized antibody may be derived from two or more different antibodies of the present invention. CDRH1 to 3 and CDRL1 to 3 in the heavy and light chain variable regions of the human antibody may be the combination of CDRs carried by two or more different antibodies of the present invention.

The isotype of the monoclonal antibody of the present invention is not particularly limited, and examples thereof can include IgG such as IgG1, IgG2, IgG3, and IgG4, IgM, IgA such as IgA1 and IgA2, IgD, and IgE and can preferably include IgG and IgM, more preferably IgG2. The isotype and subclass of the monoclonal antibody can be determined by, for example, an Ouchterlony test, ELISA, radio immunoassay (hereinafter, referred to as "RIA"). A commercially available kit for identification (Mouse Typer Kit manufactured by Bio-Rad Laboratories, Inc., RAT MONOCLONAL ANTIBODY ISOTYPING TEST KIT manufactured by AbD Serotec, etc.) may be used.

(3-2) Binding Specificity of Anti-ROBO4 Antibody

The antibody of the present invention recognizes the ROBO4 protein. In other words, the antibody of the present invention binds to the ROBO4 protein. Such an antibody is referred to as an "anti-ROBO4 antibody". Moreover, the preferable antibody of the present invention specifically recognizes the ROBO4 protein. In other words, the preferable antibody of the present invention specifically binds to the ROBO4 protein. Furthermore, the more preferable antibody of the present invention specifically binds to an Ig-like domain carried by the ROBO4 protein. Examples of such an Ig-like domain can include Ig-like domain 1 and Ig-like domain 2. The more preferable antibody of the present invention recognizes a region consisting of an amino acid sequence of amino acid Nos. 132 to 209 of SEQ ID NO: 2. The antibody of the present invention binds to a human ROBO4 protein, a monkey, preferably cynomolgus monkey ROBO4 protein, and a rabbit ROBO4 protein, but does not bind to mouse and rat ROBO4 proteins (Cross-species reactivity in Example 4)-3 and Example 11)-4).

In the present invention, the "specific recognition", i.e., "specific binding", means binding which is not non-specific adsorption. Examples of criteria for determination on whether binding is specific or not can include a dissociation constant (hereinafter, referred to as "$K_D$"). The preferable antibody of the present invention has a $K_D$ value of $1 \times 10^{-5}$ or lower, $5 \times 10^{-6}$ or lower, $2 \times 10^{-6}$ or lower, or $1 \times 10^{-6}$ or lower, more preferably $5 \times 10^{-7}$ or lower, $2 \times 10^{-7}$ or lower, or $1 \times 10^{-7}$ or lower, even more preferably $5 \times 10^{-8}$ or lower, $2 \times 10^{-8}$ or lower, or $1 \times 10^{-8}$ or lower, further more preferably $5 \times 10^{-9}$ or lower, $2 \times 10^{-9}$ or lower, or $1 \times 10^{-9}$ or lower, most preferably $5 \times 10^{-10}$ or lower, $2 \times 10^{-10}$ or lower, or $1 \times 10^{-10}$ or lower for the ROBO4 protein. More specifically, the preferable antibody of the present invention has a $K_D$ value of $2 \times 10^{-8}$ or lower, more preferably $1 \times 10^{-8}$ or lower, even more preferably $5 \times 10^{-9}$ or lower for the ROBO4 protein.

In the present invention, the binding of the antibody to the antigen can be assayed or determined by ELISA, RIA, surface plasmon resonance (hereinafter, referred to as "SPR") analysis, or the like. Examples of equipment used in the SPR analysis can include BIAcore™ (manufactured by GE Healthcare Bio-Sciences Crop.), ProteOn™ (manufactured by Bio-Rad Laboratories, Inc.), SPR-Navi™ (manufactured by BioNavis Oy Ltd.), Spreeta™ (manufactured by Texas Instruments Inc.), SPRi-PlexII™ (manufactured by Horiba, Ltd.), and Autolab SPR™ (manufactured by Metrohm). The binding of the antibody to the antigen expressed on cell surface can be assayed by flow cytometry or the like.

(3-3) In-Vitro Anti-Angiogenesis Activity of Anti-ROBO4 Antibody

The antibody of the present invention has an anti-angiogenesis activity in the absence of a cross-linking antibody in vitro. It is known that certain antibodies do not exhibit a pharmacological activity in the absence of the cross-linking antibody in vitro, but exhibit a pharmacological activity in the absence of the cross-linking antibody in vivo (Cancer Cell (2011), 19, p. 101-113). This is probably because leukocytes are found in vivo to express Fcγ receptor having the same functions as those of the cross-linking antibody (Nature (2008), 8, p. 34-47); thus, the antibodies exhibit a pharmacological activity through crosslink in the presence of leukocytes even without the cross-linking antibody. In actual organisms, however, the number of leukocytes in lesions differs among individuals (Cancer Res (2011), 71, 5670-5677), presumably resulting in, among individuals, the different effects of the antibodies exhibiting a pharmacological activity dependent on crosslink induced by leucocytes. The antibody of the present invention exhibits an excellent anti-angiogenesis activity even in the absence of a cross-linking antibody in vitro. Thus, the antibody of the present invention can also have an anti-angiogenesis effect independent of the number of leukocytes in vivo and is thus pharmaceutically suitable.

The anti-angiogenesis activity means the activity of suppressing vascular endothelial cell growth, migration, lumen formation, etc. The in-vitro anti-angiogenesis activity can be evaluated by a vascular permeability, vascular endothelial cell migration, or lumen formation test.

For example, the vascular permeability test for such evaluation can involve inoculating a normal human umbilical vein endothelial cell (HUVEC) to the upper layer of Boyden Chamber having a pore size of 1 μm to form a single layer and then measuring the amount of FITC-labeled dextran or the like permeating through the cell layer. The amount of FITC-labeled dextran permeating through the cell layer may be measured using, for example, In Vitro Vascular Permeability Assay (Cat. ECM640, manufactured by Millipore Corp.). When the antibody added at a concentration of 5 μg/mL or lower exhibits the effect of suppressing the amount of FITC-labeled dextran permeating through the cell layer, this antibody can be evaluated as having a suppressive effect on vascular permeability and having an anti-angiogenesis activity. The antibody of the present invention exhibits a suppressive activity against vascular permeability at a concentration of preferably 5 μg/mL or lower, more preferably 1 μg/mL or lower, particularly preferably 0.5 μg/mL or lower, under the measurement conditions described above.

The cell migration test for such evaluation can involve inoculating HUVEC to the upper layer of Boyden Chamber having a pore size of 3 to 8 adding a medium containing an endothelial cell migration enhancer such as VEGF to the lower layer, and measuring the number of cells migrating to the lower layer. When the antibody exhibits the effect of decreasing the number of migrating HUVEC cells, this antibody can be evaluated as having a suppressive effect on vascular endothelial cell migration and having an anti-angiogenesis activity. The number of migrating cells may be measured using, for example, vascular endothelial cell migration assay system (Cat. 354143, manufactured by BD Biosciences). The antibody of the present invention exhibits a suppressive activity against cell migration at a concentration of preferably 5 μg/mL or lower, more preferably 1 μg/mL or lower, particularly preferably 0.5 μg/mL or lower, under the measurement conditions described above.

The lumen formation test for such evaluation can involve inoculating HUVEC to a cell culture container coated with Matrigel and measuring the number of branch points, tube length, or the like, of a lumen structure formed by HUVEC on the Matrigel. When the antibody exhibits the effect of decreasing the number of branch points or tube length of the lumen structure, this antibody can evaluated as having a suppressive effect on lumen formation and having an anti-angiogenesis activity. The number of branch points or tube length of the lumen structure may be measured using, for example, vascular endothelial cell tube formation assay system (Cat. 354149, manufactured by BD Biosciences). The antibody of the present invention exhibits a suppressive activity against lumen formation at a concentration of preferably 5 μg/mL or lower, more preferably 1 μg/mL or lower, particularly preferably 0.5 μg/mL or lower, under the measurement conditions described above.

Such an assay system, however, is not limited to these tests as long as it is capable of assaying angiogenesis and its suppression induced by the ROBO4 protein.

The cross-linking antibody means an antibody that binds to the Fc region of the antibody of the present invention and acts to cross-link two or more antibody molecules of the present invention. For example, when the Fc region of the antibody of the present invention is derived from a mouse, the cross-linking antibody refers to an antibody that binds to the mouse Fc region and associates two or more antibody molecules of the present invention through the binding of these two antibody molecules of the present invention at two binding sites, respectively, of the cross-linking antibody.

The phrase "having an anti-angiogenesis activity in the absence of a cross-linking antibody" means that the antibody exhibits an anti-angiogenesis effect in an evaluation system relating to angiogenesis suppression, for example, the evaluation system described above, even without coexisting with a cross-linking antibody.

The phrase "having an anti-angiogenesis activity in the presence of a cross-linking antibody" means that the antibody does not exhibit an anti-angiogenesis activity in the absence of a cross-linking antibody in an evaluation system relating to angiogenesis, for example, the anti-angiogenesis activity evaluation system described above, but exhibits the anti-angiogenesis activity when coexisting with one or more cross-linking antibody molecule(s), preferably two or more cross-linking antibody molecules, with respect to one antibody molecule of the present invention.

(3-4) In-Vivo Suppressive or Inhibitory Activity of Anti-ROBO4 Antibody Against Angiogenesis The antibody of the present invention suppresses or inhibits angiogenesis in vivo. The in-vivo suppressive or inhibitory activity against angiogenesis can be evaluated with animal disease models according to a standard method. For example, laser-induced choroidal neovascularization models described later in Example 4)-6 are widely used as disease models of angiogenesis and can be used in evaluation with the amount of blood vessels newly formed as a score. Also in the case of patients, for example, tumor samples are collected by biopsy from tumor patients before and after administration of the antibody of the present invention, and the vascular densities of their intratumoral vessels can be measured by immunohistochemical analysis (IHC) to score the amount of blood vessels newly formed.

(3-5) Activation of Downstream Signal by Anti-ROBO4 Antibody

The anti-ROBO4 antibody of the present invention may be subjected to an evaluation system using a cell line or primary cultured cells that exhibit some induced response to the ROBO4 protein. Examples of such a cell line can include a mouse vascular endothelial cell line (ATCC NO. CRL-2779). Examples of such primary cultured cells can include mouse vascular endothelial cells and human vascular endothelial cells.

The antibody of the present invention is an agonistic antibody against ROBO4. Specifically, the antibody of the present invention binds to ROBO4 and activates the downstream signal of ROBO4. Thus, the anti-angiogenesis effect of the antibody of the present invention may be evaluated with the activation of the ROBO4 downstream signal as an index. Examples of the ROBO4 downstream signal can include an IL-8 promoter activity. The IL-8 promoter activity was drastically increased in cells expressing full-length human ROBO4 compared with cells expressing no human ROBO4 and was hardly observed in cells expressing intracellular domain-deleted human ROBO4. Thus, the increase in IL-8 promoter activity demonstrated that the activation of the ROBO4 signal was detected (Example 3). The IL-8 promoter activity can be evaluated, for example, by the addition of the anti-ROBO4 antibody or the co-addition of the anti-ROBO4 antibody and a cross-linking antibody to cells transfected with a reporter vector having an IL-8 promoter sequence insert and a human ROBO4 expression plasmid, followed by the determination of the reporter activity.

(3-6) Anti-ROBO4 Mouse Monoclonal Antibody and the Chimeric Antibody

MAb1 is an anti-ROBO4 mouse monoclonal antibody obtained by a method described in Example 2.

The nucleotide sequence of cDNA encoding the heavy chain variable region of MAb1 is shown in SEQ ID NO: 30 (FIG. 15), and its amino acid sequence is shown in SEQ ID NO: 31 (FIG. 16). The amino acid sequence of CDRH1 is shown in SEQ ID NO: 44 (FIG. 25); the amino acid sequence of CDRH2 is shown in SEQ ID NO: 46 (FIG. 26); and the amino acid sequence of CDRH3 is shown in SEQ ID NO: 48 (FIG. 27). The nucleotide sequence of cDNA encoding the light chain variable region of MAb1 is shown in SEQ ID NO: 32 (FIG. 17), and its amino acid sequence is shown in SEQ ID NO: 33 (FIG. 18). The amino acid sequence of CDRL1 is shown in SEQ ID NO: 50 (FIG. 28); the amino acid sequence of CDRL2 is shown in SEQ ID NO: 52 (FIG. 29); and the amino acid sequence of CDRL3 is shown in SEQ ID NO: 54 (FIG. 30).

The antibody mutant of the present invention, preferably, exhibits reduced sensitivity to protein degradation or oxidation, an improved biological activity, an improved ability to bind to the antigen, or physicochemical or functional properties imparted thereto, or the like. Examples of such an antibody mutant can include an antibody having an amino acid sequence derived from the amino acid sequence of the original antibody by conservative amino acid substitution. The conservative amino acid substitution is substitution that occurs in an amino acid group related to amino acid side chains.

Preferable amino acid groups are as follows: an acidic group involving aspartic acid and glutamic acid; a basic group involving lysine, arginine, and histidine; a nonpolar group involving alanine, valine, leucine, isoleucine, proline, phenylalanine, methionine, and tryptophan; and an uncharged polar family involving glycine, asparagine, glutamine, cysteine, serine, threonine, and tyrosine. Other preferable amino acid groups are as follows: an aliphatic hydroxy group involving serine and threonine; an amide-containing group involving asparagine and glutamine; an aliphatic group involving alanine, valine, leucine, and isoleucine; and an aromatic group involving phenylalanine, tryptophan, and tyrosine. Such amino acid substitution in the antibody mutant is preferably performed without reducing the antigen binding activity of the original antibody.

An antibody mutant having an amino acid sequence derived from the amino acid sequence of MAb1 of the present invention by conservative amino acid substitution as well as a mouse antibody, rat antibody, chimeric antibody, humanized antibody, human antibody, or the like comprising a CDR amino acid sequence derived from the amino acid sequence of any of MAb1-derived CDRH1 to 3 and CDRL1 to 3 by conservative amino acid mutation is also encompassed by the present invention.

The constant regions of the antibody of the present invention are not particularly limited. Preferably, those derived from a human antibody are used in the antibody of the present invention for the treatment or prevention of a disease in a human. Examples of the heavy chain constant region of the human antibody can include Cγ1, Cγ2, Cγ3, Cγ4, Cμ, Cδ, Cα1, Cα2, and Cε. Examples of the light chain constant region of the human antibody can include Cκ and Cλ.

A nucleotide sequence encoding the secretory signal-containing light chain of cMAb1-1 exemplified as the mouse-human IgG1-type chimeric antibody of the present invention and its amino acid sequence as well as a nucleotide sequence encoding the heavy chain thereof and its amino acid sequence are shown in SEQ ID NOs: 37, 38, 39, and 40 (FIGS. 19, 20, 21, and 22), respectively. Likewise, a nucleotide sequence encoding the secretory signal-containing light chain of cMAb1-2 exemplified as the mouse-human IgG2-type chimeric antibody of the present invention and its amino acid sequence as well as a nucleotide sequence encoding the heavy chain thereof and its amino acid sequence are shown in SEQ ID NOs: 37, 38, 41, and 42 (FIGS. 19, 20, 23, and 24), respectively.

(3-7) Functional Fragment of Anti-ROBO4 Antibody

According to one aspect, the present invention provides a functional fragment of the anti-ROBO4 antibody of the present invention. The functional fragment of the antibody means a fragment maintaining at least a portion of the functions of the antibody, or a modified form thereof described later in (3-10). Examples of such functions of the antibody can generally include an antigen binding activity, an antigen activity-regulating activity, an antibody-dependent cytotoxic activity, and a complement-dependent cytotoxic activity. Examples of the functions of the anti-ROBO4 antibody of the present invention can include a ROBO4 protein binding activity, an anti-angiogenesis activity, and a ROBO4 downstream signal-activating effect. More specifically, any functional fragment having all or some of the above-described activities (3-3) to (3-5) exhibited by the antibody against ROBO4 of the present invention is included in the functional fragment of the antibody of the present invention.

The functional fragment of the antibody is not particularly limited as long as it is a fragment of the antibody maintaining at least a portion of the activities of the antibody, or a modified form thereof. Examples thereof can include, but not limited to, Fab, F(ab')2, Fv, single-chain Fv (scFv) comprising heavy and light chain Fvs linked via an appropriate linker, diabodies, linear antibodies, polyspecific antibodies formed from antibody fragments, and Fab', which is a monovalent fragment of antibody variable regions obtained by the treatment of F(ab')2 under reducing conditions. A molecule containing a moiety other than the fragment of the antibody of the present invention, as in scFv carrying the linker moiety, is also encompassed in the meaning of the functional fragment of the antibody of the present invention.

A molecule that is derived from the antibody protein by the deletion of 1 to several or more amino acid(s) at its amino terminus and/or carboxy terminus and maintains at least a portion of the functions of the antibody is also encompassed in the meaning of the functional fragment of the antibody of the present invention.

The antibody of the present invention or the functional fragment thereof may be a polyspecific antibody having specificity for at least 2 types of different antigens. The polyspecific antibody is not limited to a bispecific antibody, which binds to 2 types of different antigens, and an antibody having specificity for 3 or more types of different antigens is also encompassed in the meaning of the "polyspecific antibody" of the present invention.

The polyspecific antibody of the present invention may be a full-length antibody or a functional fragment thereof (e.g., bispecific F(ab')2 antibody). The bispecific antibody can also be prepared by binding the heavy and light chains (HL pairs) of two types of antibodies. The bispecific antibody can also be obtained by fusing two or more types of monoclonal antibody-producing hybridomas to prepare bispecific antibody-producing fusion cells (Millstein et al., Nature (1983) 305, p. 537-539). The polyspecific antibody can also be prepared in the same way as above.

According to one aspect, the antibody of the present invention is a single-chain antibody (single-chain Fv; hereinafter, referred to as "scFv"). The scFv is obtained by linking the heavy and light chain variable regions of the antibody via a polypeptide linker (Pluckthun, The Pharmacology of Monoclonal Antibodies, 113, ed Rosenburg and Moore, Springer Verlag, New York, p. 269-315 (1994), Nature Biotechnology (2005), 23, p. 1126-1136). Moreover, bi-scFv comprising two scFvs linked via a polypeptide linker can be used as a bispecific antibody. Furthermore, multi-scFv comprising three or more scFvs can also be used as a polyspecific antibody.

The present invention includes a single-chain immunoglobulin comprising full-length heavy and light chain sequences of the antibody linked via an appropriate linker (Lee, H-S, et. al., Molecular Immunology (1999) 36, p. 61-'71; Shirrmann, T. et. al., mAbs (2010), 2, (1) p. 1-4). Such a single-chain immunoglobulin can be dimerized to thereby maintain a structure and activities similar to those of the antibody, which is originally a tetramer. Also, the antibody of the present invention may be an antibody that has a single heavy chain variable region and has no light chain sequence. Such an antibody is called a single domain antibody (sdAb) or a nanobody and has been reported to maintain the ability to bind to the antigen (Muyldemans S. et. al., Protein Eng. (1994) 7 (9), 1129-35, Hamers-Casterman C. et. al., Nature (1993) 363 (6428) 446-8). These antibodies are also encompassed in the meaning of the functional fragment of the antibody according to the present invention.

(3-8) Anti-Human ROBO4 Humanized Antibody (Hereinafter "Anti-ROBO4 Humanized Antibody")

According to one aspect, the present invention provides a humanized antibody or a functional fragment thereof. The anti-ROBO4 humanized antibody of the present invention or the functional fragment thereof has an anti-angiogenesis activity and, preferably, has an anti-angiogenesis activity in vivo. Preferably, the humanized antibody or the functional fragment thereof specifically binds to the ROBO4 protein. Moreover, the humanized antibody or the functional fragment thereof is an agonistic antibody against ROBO4 and activates its downstream signal. Furthermore, the humanized antibody or the functional fragment thereof suppresses or inhibits vascular endothelial cell migration in the absence of a cross-linking antibody in vitro.

Examples of the humanized antibody of the present invention can include a human-derived antibody having MAb1 complementarity determining regions (CDRs) replaced with the CDRs of a non-human animal antibody (see Nature (1986) 321, p. 522-525), and a human antibody grafted with the CDR sequences and with some amino acid residues of framework regions by a CDR grafting method (International Publication No. WO90/07861). Furthermore, a variant derived from the humanized antibody by the substitution of 1 to 3 amino acid residues in each CDR with other amino acid residues is also included in the antibody of the present invention as long as the variant has all or some of the activities (3-3) to (3-5).

Preferred examples of the anti-ROBO4 humanized antibody of the present invention or the functional fragment thereof can include an antibody that consists of a heavy chain having a variable region comprising CDRH1 consisting of the amino acid sequence represented by SEQ ID NO: 44 (FIG. 25), CDRH2 consisting of the amino acid sequence represented by SEQ ID NO: 46 (FIG. 26) or an amino acid sequence derived from the amino acid sequence of SEQ ID NO: 46 by the substitution of one amino acid, and CDRH3 consisting of the amino acid sequence represented by SEQ ID NO: 48 (FIG. 27), and a light chain having a variable region comprising CDRL1 consisting of the amino acid sequence represented by SEQ ID NO: 50 (FIG. 28) or an amino acid sequence derived from the amino acid sequence of SEQ ID NO: 50 by the substitution of 1 to 3 amino acid(s), CDRL2 consisting of the amino acid sequence represented by SEQ ID NO: 52 (FIG. 29), and CDRL3 consisting of the amino acid sequence represented by SEQ ID NO: 54 (FIG. 30), and recognizes the ROBO4 protein of the present invention, and a fraction of the antibody maintaining the ROBO4 protein binding activity of the antibody.

Examples of the amino acid substitution in CDRH2 can include the substitution of the amino acid represented by amino acid No. 4 of SEQ ID NO: 46 in CDRH2. Specifically, an asparagine, amino acid No. 4 of SEQ ID NO: 46, can be replaced with a glutamine. The amino acid to be substituted therefor is not limited as long as the resulting antibody has all or some of the activities (3-3) to (3-5) exhibited by the antibody against ROBO4 of the present invention.

Examples of the amino acid substitution in CDRL1 can include the substitution of any 1 to 3, preferably 3, of the amino acids represented by amino acid Nos. 9, 11, and 13 of SEQ ID NO: 50 in CDRL1. Specifically, a serine (amino acid No. 9), a glycine (amino acid No. 11) and a threonine (amino acid No. 13) of SEQ ID NO: 50 can be replaced with an amino acid selected from a glutamic acid, a lysine and a leucine, preferably with a glutamic acid, a lysine and a leucine respectively. The amino acid(s) to be substituted therefor is not limited as long as the resulting antibody has all or some of the activities (3-3) to (3-5) exhibited by the antibody against ROBO4 of the present invention.

An asparagine residue in peptides or a protein is reported to easily undergo deamidation in some conditions (Gerger et al: The Journal of Biological Chemistry Vol. 262 No. 2, 785-794, 1987), therefore the amino acid replacement in CDRs described above can increase the stability of the humanized antibodies of the present invention.

Examples of the heavy chain variable region of the more preferred humanized antibody having these CDRHs can include an amino acid sequence represented by amino acid Nos. 20 to 137 of SEQ ID NO: 56 (FIG. 32), wherein CDRH1, CDRH2 and CDRH3 are represented by amino acid Nos. 50 to 54, 69 to 85 and 118 to 126 of SEQ ID NO: 56 (FIG. 32), respectively, an amino acid sequence represented by amino acid Nos. 20 to 137 of SEQ ID NO: 58 (FIG. 34), wherein CDRH1, CDRH2 and CDRH3 are represented by amino acid Nos. 50 to 54, 69 to 85 and 118 to 126 of SEQ ID NO: 58 (FIG. 34), respectively, an amino acid sequence represented by amino acid Nos. 20 to 137 of SEQ ID NO: 60 (FIG. 36), wherein CDRH1, CDRH2 and CDRH3 are represented by amino acid Nos. 50 to 54, 69 to 85 and 118 to 126 of SEQ ID NO: 60 (FIG. 36), respectively, and an amino acid sequence represented by amino acid Nos. 20 to 137 of SEQ ID NO: 62 (FIG. 38), wherein CDRH1, CDRH2 and CDRH3 are represented by amino acid Nos. 50 to 54, 69 to 85 and 118 to 126 of SEQ ID NO: 60 (FIG. 38). Examples of the light chain variable region of the more preferred humanized antibody having these CDRLs can include an amino acid sequence represented by amino acid Nos. 21 to 134 of SEQ ID NO: 64 (FIG. 40), wherein CDRL1, CDRL2 and CDRL3 are represented by amino acid Nos. 44 to 59, 75 to 81 and 114 to 122 of SEQ ID NO: 64 (FIG. 40), respectively, and an amino acid sequence represented by amino acid Nos. 21 to 134 of SEQ ID NO: 66 (FIG. 42), wherein CDRL1, CDRL2 and CDRL3 are represented by amino acid Nos. 44 to 59, 75 to 81 and 114 to 122 of SEQ ID NO: 66 (FIG. 42), respectively.

Examples of more preferable combinations of the heavy chain variable region and the light chain variable region of the more preferred humanized antibodies can include: a humanized antibody comprising a heavy chain variable region consisting of an amino acid sequence represented by amino acid Nos. 20 to 137 of SEQ ID NO: 58 (FIG. 34) and a light chain variable region consisting of an amino acid sequence represented by amino acid Nos. 21 to 134 of SEQ ID NO: 64 (FIG. 40); a humanized antibody comprising a heavy chain variable region consisting of an amino acid sequence represented by amino acid Nos. 20 to 137 of SEQ ID NO: 58 (FIG. 34) and a light chain variable region consisting of an amino acid sequence represented by amino acid Nos. 21 to 134 of SEQ ID NO: 66 (FIG. 42); a humanized antibody comprising a heavy chain variable region consisting of an amino acid sequence represented by amino acid Nos. 20 to 137 of SEQ ID NO: 62 (FIG. 38) and a light chain variable region consisting of an amino acid sequence represented by amino acid Nos. 21 to 134 of SEQ ID NO: 66 (FIG. 42); a humanized antibody comprising a heavy chain variable region consisting of an amino acid sequence represented by amino acid Nos. 20 to 137 of SEQ ID NO: 62 (FIG. 38) and a light chain variable region consisting of an amino acid sequence represented by amino acid Nos. 21 to 134 of SEQ ID NO: 64 (FIG. 40); a humanized antibody comprising a heavy chain variable region consisting of an amino acid sequence represented by amino acid Nos. 20 to 137 of SEQ ID NO: 56 (FIG. 32) and a light chain variable region consisting of an amino acid sequence represented by amino acid Nos. 21 to 134 of SEQ ID NO: 64 (FIG. 40); and a humanized antibody comprising a heavy chain variable region consisting of an amino acid sequence represented by amino acid Nos. 20 to 137 of SEQ ID NO: 60 (FIG. 36) and a light chain variable region consisting of an amino acid sequence represented by amino acid Nos. 21 to 134 of SEQ ID NO: 64 (FIG. 40).

Even more preferred examples of the full-length humanized antibody comprising the more preferred combination of the heavy chain variable region and the light chain variable region can include: a humanized antibody (H-1140) comprising a heavy chain consisting of an amino acid sequence represented by amino acid Nos. 20 to 463 of SEQ ID NO: 58 (FIG. 34) and a light chain consisting of an amino acid sequence represented by amino acid Nos. 21 to 239 of SEQ ID NO: 64 (FIG. 40); a humanized antibody (H-1143) comprising a heavy chain consisting of an amino acid sequence represented by amino acid Nos. 20 to 463 of SEQ ID NO: 58 (FIG. 34) and a light chain consisting of an amino acid sequence represented by amino acid Nos. 21 to 239 of SEQ ID NO: 66 (FIG. 42); a humanized antibody (H-2143) comprising a heavy chain consisting of an amino acid sequence represented by amino acid Nos. 20 to 463 of SEQ ID NO: 62 (FIG. 38) and a light chain consisting of an amino acid sequence represented by amino acid Nos. 21 to 239 of SEQ ID NO: 66 (FIG. 42); a humanized antibody (H-2140) comprising a heavy chain consisting of an amino acid sequence represented by amino acid Nos. 20 to 463 of SEQ ID NO: 62 (FIG. 38) and a light chain consisting of an amino acid sequence represented by amino acid Nos. 21 to 239 of SEQ ID NO: 64 (FIG. 40); a humanized antibody (H-1040) comprising a heavy chain consisting of an amino acid sequence represented by amino acid Nos. 20 to 463 of SEQ ID NO: 56 (FIG. 32) and a light chain consisting of an amino acid sequence represented by amino acid Nos. 21 to 239 of SEQ ID NO: 64 (FIG. 40); and a humanized antibody (H-2040) comprising a heavy chain consisting of an amino acid sequence represented by amino acid Nos. 20 to 463 of SEQ ID NO: 60 (FIG. 36) and a light chain consisting of an amino acid sequence represented by amino acid Nos. 21 to 239 of SEQ ID NO: 64 (FIG. 40).

The most preferable antibodies of the present invention are H-1140, H-1143, H-2140 and H-2143.

H-1140 has properties of 1) binding specifically to human ROBO4 and not to ROBO1, ROBO2, and ROBO3, 2) having a $K_D$ value of 3.9 nM for human ROBO4, 3) maintaining affinity to human ROBO4 under 40° C. for 4 weeks, 4) inhibiting HUVEC migration induced by one or more angiogenic factors selected from VEGF, bFGF, HGF, PDGF-BB and SDF-1, specifically VEGF or bFGF, 5) inhibiting angiogenesis in vivo, and 6) low immunogenicity in ISPRI Web-based Immunogenicity Screening (EpiVax, Inc).

H-1143 has properties of 1) binding specifically to human ROBO4 and not to ROBO1, ROBO2, and ROBO3, 2) having a $K_D$ value of 3.5 nM for human ROBO4, 3) maintaining affinity to human ROBO4 under 40° C. for 4 weeks, 4) inhibiting HUVEC migration induced by one or more angiogenic factors selected from VEGF, bFGF, HGF, PDGF-BB and SDF-1, specifically VEGF and bFGF, 5) inhibiting angiogenesis in vivo, and 6) low immunogenicity in EpiScreen™ immunogenicity testing (Antitope Ltd.)

H-2140 has properties of 1) binding specifically to human ROBO4 and not to ROBO1, ROBO2, and ROBO3, 2) having a $K_D$ value of 1.8 nM for human ROBO4, 3) maintaining affinity to human ROBO4 under 40° C. for 4 weeks, 4) inhibiting HUVEC migration induced by various angiogenic factors such as VEGF, bFGF, HGF, PDGF-BB and SDF-1, specifically VEGF and bFGF, 5) inhibiting angiogenesis in vivo, 6) low immunogenicity in EpiScreen™ immunogenicity testing (Antitope Ltd.)

H-2143 has properties of 1) binding specifically to human ROBO4 and not to ROBO1, ROBO2, and ROBO3, 2) having a $K_D$ value of 1.7 nM for human ROBO4, 3) maintaining affinity to human ROBO4 under 40° C. for 4 weeks, 4) inhibiting HUVEC migration induced by various angiogenic factors such as VEGF, bFGF, HGF, PDGF-BB and SDF-1, specifically VEGF and bFGF, 5) inhibiting angiogenesis in vivo, 6) low immunogenicity in EpiScreen™ immunogenicity testing (Antitope Ltd.), and 7) showing no serious change in clinical sign, body weight, food consumption, hematology, blood chemistry, pathology, electroretinography after single intravitreal injection (2.75 mg/eye) to a Cynomolgus monkey.

An antibody comprising an amino acid sequence having 95% or more, preferably 97% or more, more preferably 99% or more identity to the amino acid sequence of the antibody such as H-1140, H-1143, H-2143, H-2140, H-1040 and H-2040 is also included in the antibody of the present invention as long as the antibody has all or some of the activities (3-3) to (3-5). Moreover, an antibody that has CDRs identical in amino acid sequence to the CDRs of the antibody comprising the combination of the heavy chain variable region and the light chain variable region or the antibody comprising the combination of the heavy chain and the light chain, and has an amino acid sequence other than the CDR amino acid sequence having 95% or more, preferably 97% or more, more preferably 99% or more identity thereto is also included in the antibody of the present invention as long as the antibody has all or some of the activities (3-3) to (3-5).

(3-9) Antibody Binding to the Same Site

An "antibody binding to the same site" as that bound by the antibody provided by the present invention is also included in the antibody of the present invention. The "antibody binding to the same site" as that bound by a certain antibody means another antibody that binds to a site on an antigen molecule recognized by the antibody. If a second antibody binds to a partial peptide or a partial three-dimensional structure on an antigen molecule bound by a first antibody, the first and second antibodies can be determined to bind to the same site. Moreover, the first and second antibodies can be determined to bind to the same site by confirming that the second antibody competes with the first antibody for binding to the antigen, i.e., the second antibody interferes with the binding of the first antibody to the antigen, even if the peptide sequence or three-dimensional structure of the specific binding site is not determined. Furthermore, when the first and second antibodies bind to the same site and the first antibody has an effect characteristic of one aspect of the antibody of the present invention, such as an anti-angiogenesis activity, the second antibody also has an exceedingly high probability of having the same activity thereas. Thus, if a second anti-ROBO4 antibody binds to the site bound by a first anti-ROBO4 antibody, the first and second antibodies can be determined to bind to the same site on the ROBO4 protein. Moreover, the first and second antibodies can be determined to be antibodies binding to the same site on the ROBO4 protein by confirming that the second anti-ROBO4 antibody competes with the first anti-ROBO4 antibody for binding to the ROBO4 protein.

An antibody binding to a site on the ROBO4 protein recognized by MAb1 of the present invention is also included in the present invention.

The antibody-binding site can be determined by a method well known by those skilled in the art, such as immunoassay. For example, a series of peptides are prepared by the appropriate C-terminal or N-terminal truncation of the amino acid sequence of the antigen, and the reactivity of the antibody thereto is studied to roughly determine a recognition site. Then, shorter peptides are synthesized, and the reactivity of the antibody to these peptides can be studied to thereby determine the binding site. The antigen fragment peptides can be prepared using a technique such as gene recombination or peptide synthesis.

When the antibody binds to or recognizes the partial conformation of the antigen, the binding site for the antibody can be determined by identifying amino acid residues on the antigen adjacent to the antibody using an X-ray structural analysis.

(3-10) Modified Form of Anti-ROBO4 Antibody or Functional Fragment Thereof

The present invention provides a modified form of the antibody or the functional fragment thereof. The modified form of the antibody of the present invention or the functional fragment thereof means an antibody of the present invention or a functional fragment thereof provided with chemical or biological modification. The chemically modified form includes a form having an amino acid skeleton conjugated with a chemical moiety, a form having a chemically modified N-linked or O-linked carbohydrate chain, and the like. Said chemical moiety or form can be toxic or cytotoxic.

The biologically modified form includes a form that has undergone post-translational modification (e.g., N-linked or O-linked glycosylation, N-terminal or C-terminal processing, deamidation, isomerization of aspartic acid, or oxidation of methionine), a form containing a methionine residue added to the N-terminus by expression using prokaryotic host cells, and the like. Such a modified form is also meant to include a form labeled to permit detection or isolation of the antibody or the antigen of the present invention, for example, an enzyme-labeled form, a fluorescently labeled form, or an affinity-labeled form. Such a modified form of the antibody of the present invention or the functional fragment thereof is useful in improvement in the stability or blood retention of the original antibody of the present invention or functional fragment thereof, reduction in antigenicity, detection or isolation of the antibody or the antigen, etc.

Examples of the chemical moiety contained in the chemically modified form can include water-soluble polymers such as polyethylene glycol, ethylene glycol/propylene glycol copolymers, carboxymethylcellulose, dextran, and polyvinyl alcohol.

Examples of the biologically modified form can include a form modified by enzymatic treatment, cell treatment, or the like, a form fused with another peptide, such as a tag, added by gene recombination, and a form prepared from host cells expressing an endogenous or exogenous sugar chain-modifying enzyme.

Such a modification may be made at an arbitrary position or the desired position in the antibody or the functional fragment thereof. Alternatively, the same or two or more different modifications may be made at one or two or more positions therein.

In the present invention, the "modified form of the antibody fragment" is also meant to include even a "fragment of the modified form of the antibody".

For example, occasionally, an antibody produced by cultured mammalian cells is known to lack a carboxyl-terminal lysine residue in its heavy chain (Journal of Chromatography A, 705: 129-134 (1995)). It is also known that occasionally 2 carboxyl-terminal amino acid residues (i.e., glycine and lysine) of a heavy chain are missing and that a proline residue newly located at the carboxyl terminus is amidated (Analytical Biochemistry, 360: 75-83 (2007)). Such lack or modification in these heavy chain sequences, however, affects neither the ability of the antibody to bind to its antigen nor the effector functions (complement activation, antibody-dependent cytotoxicity, etc.) of the antibody. Thus, an antibody having the modification and a functional fragment of the antibody are also included in the antibody of the present invention. Examples of such an antibody can include a deletion mutant derived from the antibody of the present invention by the deletion or lack of 1 or 2 amino acid(s) in the carboxyl terminus of the heavy chain, and the deletion mutant having an amidated residue (e.g., an amidated proline residue at the carboxyl-terminal site of the heavy chain). However, the deletion mutant of the antibody according to the present invention is not limited to the types described above as long as the deletion mutant maintains the ability to bind to the antigen and all or some of the activities (3-3) to (3-5). Two heavy chains constituting the antibody according to the present invention may be composed of any one type of heavy chain selected from the group consisting of the full-length heavy chains and the heavy chains of the deletion mutant or may be composed of the combination of any two types selected therefrom. The quantitative ratio of the deletion variant heavy chain(s) is susceptible to, for example, the type of cultured mammalian cells producing the antibody according to the present invention, and the culture conditions of the cells. Examples of such deletion variant heavy chains as the main components of the antibody according to the present invention can include two heavy chains, both of which lack one carboxyl-terminal amino acid residue. All of these deletion variants are encompassed in the antibody variant, the functional fragment of the antibody, or the modified form thereof according to the present invention.

4. Method for Producing Antibody (4-1) Method Using Hybridoma

In order to prepare the anti-ROBO4 antibody of the present invention, anti-ROBO4 antibody-producing cells are isolated from the spleens of animals immunized with the ROBO4 protein according to the method of Kohler and Milstein (Kohler and Milstein, Nature (1975) 256, p. 495-49'7, Kennet, R. ed., Monoclonal Antibody, p. 365-36'7, Prenum Press, N. Y. (1980)). The cells are fused with myeloma cells to thereby establish hybridomas, and monoclonal antibodies can be obtained from cultures of these hybridomas.

(4-1-1) Preparation of Antigen

The antigen for the preparation of the anti-ROBO4 antibody can be obtained according to, for example, a native or recombinant ROBO4 protein preparation method described in other paragraphs of the present specification. Examples of the antigen that may be thus prepared can include the ROBO4 protein or a ROBO4 protein fragment comprising a partial sequence with at least 6 consecutive amino acids thereof, and their derivatives further comprising an arbitrary amino acid sequence or carrier added thereto (hereinafter, collectively referred to as a "ROBO4 antigen").

The recombinant ROBO4 antigen can be prepared by transfecting host cells with a gene comprising a nucleotide sequence encoding the amino acid sequence of the ROBO4 antigen, and collecting the antigen from cultures of the cells. The native ROBO4 antigen can be purified or isolated from, for example, human or rodent tissues with angiogenesis, cells derived from the tissues, or cultures of the cells. A ROBO4 antigen obtained in a cell-free in-vitro translation system from a gene comprising a nucleotide sequence encoding the amino acid sequence of the ROBO4 antigen is also included in the "ROBO4 antigen" of the present invention.

(4-1-2) Production of Anti-ROBO4 Monoclonal Antibody

The monoclonal antibody is typically produced by the following steps:

(a) preparing an antigen,
(b) preparing antibody-producing cells,
(c) preparing myeloma cells (hereinafter, referred to as "myelomas"),
(d) fusing the antibody-producing cells with the myelomas,
(e) screening for a hybridoma group producing the antibody of interest, and
(f) obtaining single cell clones (cloning).

This production method further involves (g) a step of culturing the hybridomas, a step of raising hybridoma-transplanted animals, etc., (h) a step of assaying or determining the biological activity of the monoclonal antibody, etc., if necessary.

Hereinafter, the method for preparing the monoclonal antibody will be described in detail with reference to these steps. However, the method for preparing the antibody is not limited to them, and, for example, antibody-producing cells other than spleen cells and myelomas may be used.

(a) Step of Preparing Antigen

An antigen can be prepared according to the ROBO4 protein preparation method described above in (2-3).

(b) Step of Preparing Antibody-Producing Cells

The antigen obtained in step (a) is mixed with an adjuvant such as a Freund's complete or incomplete adjuvant or potassium aluminum sulfate, and laboratory animals are immunized with the resulting immunogen. Any laboratory animal used in a hybridoma preparation method known in the art can be used without limitations. Specifically, for example, mice, rats, goats, sheep, cattle, or horses can be used. From the viewpoint of readily available myeloma cells to be fused with isolated antibody-producing cells, etc., the animals to be immunized are preferably mice or rats.

Mouse and rat strains actually used are not particularly limited. In the case of mice, for example, A, AKR, BALB/c, BALB/cAnNCrj, BDP, BA, CE, C3H, 57BL, C57BL, C57L, DBA, FL, HTH, HT1, LP, NZB, NZW, RF, R III, SJL, SWR, WB, 129 can be used. In the case of rats, for example, Wistar, Low, Lewis, Sprague-Dawley, ACI, BN, or Fischer can be used.

These mice and rats can be available from laboratory animal breeders/distributors, for example, CLEA Japan, Inc. or Charles River Laboratories Japan Inc.

Of them, a BALB/c mouse strain or Wistar and Low rat strains are particularly preferable as animals to be immunized in consideration of fusion compatibility with the myeloma cells described later.

Also in consideration of the homology between human and mouse antigens, mice whose biological mechanism to remove autoantibodies has been reduced, i.e., autoimmune disease mice, is also preferably used.

In this context, these mice or rats are preferably 5 to 12 weeks old, more preferably 6 to 8 weeks old at the time of immunization.

The animals can be immunized with the ROBO4 protein using, for example, the method of Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Spigfield, Ill. (1964).

Examples of antibody titer determination methods can include, but not limited to, immunoassay such as RIA and ELISA.

Antibody-producing cells derived from spleen cells or lymphocytes separated from the immunized animals can be prepared according to a method known in the art, for example, the method of Kohler et al., Nature (1975) 256, p. 495; Kohler et al., Eur. J. Immnol. (1977) 6, p. 511, Milstein et al., Nature (1977), 266, p. 550; Walsh, Nature, (1977) 266, p. 495,).

In the case of spleen cells, a general method can be adopted, which involves chopping the spleens, filtering cells through a stainless mesh, and then floating the resulting cells in an Eagle's minimum essential medium (MEM) or the like to separate antibody-producing cells.

(c) Step of Preparing Myelomas

The myeloma cells used in cell fusion are not particularly limited and can be selected appropriately for use from cell lines known in the art. An HGPRT (hypoxanthine-guanine phosphoribosyl transferase)-deficient line, i.e., mouse-derived X63-Ag8 (X63), NS1-ANS/1 (NS1), P3X63-Ag8.U1 (P3U1), X63-Ag8.653 (X63.653), SP2/0-Ag14 (SP2/0), MPC11-45.6TG1.7 (45.6TG), FO, S149/5XXO, BU.1 or the like, rat-derived 210.RSY3.Ag.1.2.3 (Y3) or the like, or human-derived U266AR (SKO-007), GM1500-GTG-A12 (GM1500), UC729-6, LICR-LOW-HMy2 (HMy2), 8226AR/NIP4-1 (NP41), or the like, whose screening procedures have already been established, is preferably used in consideration of convenience in the selection of hybridomas from fusion cells. These HGPRT-deficient lines can be available from, for example, American Type Culture Collection (ATCC).

These cell lines are subcultured in an appropriate medium, for example, an 8-azaguanine medium [RPMI-1640 medium supplemented with glutamine, 2-mercaptoethanol, gentamicin, and fetal calf serum (hereinafter, referred to as "FCS") and further supplemented with 8-azaguanine], an Iscove's modified Dulbecco's medium (hereinafter, referred to as "IMDM"), or a Dulbecco's modified Eagle medium (hereinafter, referred to as "DMEM") and subcultured 3 to 4 days before cell fusion in a normal medium [e.g., ASF 104 medium (manufactured by Ajinomoto Co., Inc.) containing 10% FCS] to secure the number of cells equal to or larger than $2 \times 10^7$ cells on the day of cell fusion.

(d) Step of Fusing the Antibody-Producing Cells with the Myeloma Cells

The antibody-producing cells can be fused with the myeloma cells under conditions that prevent cell viability from being exceedingly reduced, according to a method known in the art (Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Spigfield, Ill. (1964) etc.). For example, a chemical method which involves mixing antibody-producing cells with myeloma cells in a high-concentration solution of a polymer such as polyethylene glycol, or a physical method using electric stimulation can be used.

(e) Step of Screening for a Hybridoma Group Producing the Antibody of Interest

A selection method for the hybridomas obtained by cell fusion is not particularly limited, and HAT (hypoxanthine-aminopterin-thymidine) selection method (Kohler et al., Nature (1975) 256, p. 495; Milstein et al., Nature (1977) 266, p. 550) is typically used. This method is effective for obtaining hybridomas using an HGPRT-deficient myeloma cell line, which cannot survive in the presence of aminopterin. Specifically, unfused cells and hybridomas can be cultured in a HAT medium to thereby allow only hybridomas resistant to aminopterin to selectively remain and grow.

(f) Step of Obtaining Single Cell Clones (Cloning)

The hybridomas can be cloned using a method known in the art, for example, a methylcellulose, soft agarose, or limiting dilution method (see e.g., Barbara, B. M. and Stanley, M. S.: Selected Methods in Cellular Immunology, W. H. Freeman and Company, San Francisco (1980)). The limiting dilution method is preferable.

(g) Step of Culturing the Hybridomas and Step of Raising Hybridoma-Transplanted Animals The selected hybridomas can be cultured to thereby produce monoclonal antibodies. Preferably, the desired hybridomas are cloned and then subjected to antibody production.

The monoclonal antibody produced by this hybridoma can be collected from cultures of the hybridoma. Moreover, a recombinant antibody can also be collected from cultures of cells transfected with the monoclonal antibody gene. Furthermore, the hybridomas can be injected intraperitoneally to mice of the same strain (e.g., BALB/cAnNCrj described above) or Nu/Nu mice and allowed to grow. Then, the monoclonal antibody can also be collected from their ascites.

(h) Step of Assaying or Determining the Biological Activity of the Monoclonal Antibody Various biological tests can be selected and applied thereto according to the purpose.

(4-2) Cell Immunization Method

Cells expressing the native ROBO4 protein, cells expressing the recombinant ROBO4 protein or its fragment, or the like can be used as immunogens to thereby prepare an anti-ROBO4 antibody by the hybridoma method described above.

Examples of the cells expressing the native ROBO4 protein can include cells derived from patients affected with an angiogenic disease such as proliferative diabetic retinopathy or tumor, and cells derived from the tissues of these patients. Such cells are preferably vascular endothelial cells, but not limited to them. These ROBO4 protein-expressing cells are used in an amount of $1 \times 10^5$ to $1 \times 10^9$ cells, preferably $1 \times 10^6$ to $1 \times 10^8$ cells, more preferably 0.5 to $2 \times 10^7$ cells, even more preferably $1 \times 10^7$ cells, in one immunization. The number of cells subjected to immunization can be changed according to the expression level of the ROBO4 protein. The immunogens are generally administered intraperitoneally and may be administered through an intradermal route or the like. The method described in (4-1-2) can be applied to the hybridoma preparation approach.

(4-3) Gene Recombination and Host Cells

In order to prepare the antibody of the present invention, host cells are transfected with a nucleotide comprising a nucleotide sequence encoding the amino acid sequence of its heavy chain (heavy chain nucleotide) and a nucleotide comprising a nucleotide sequence encoding the amino acid sequence of its light chain (light chain nucleotide), or with a vector containing an insert of the heavy chain nucleotide and a vector containing an insert of the light chain nucleotide, and then cultured, and the antibody can be collected from the cultures. The heavy and light chain nucleotides may be inserted in one vector.

Prokaryotic or eukaryotic cells can be used as host cells. When eukaryotic cells are used as hosts, animal cells, plant cells, or eukaryotic microbes can be used.

Examples of the animal cells can include mammal-derived cells, i.e., monkey-derived COS cells (Gluzman, Y. Cell (1981) 23, p. 175-182, ATCC CRL-1650), mouse fibroblast NIH3T3 (ATCC No. CRL-1658), mouse NS0 cell lines (ECACC), Chinese hamster ovary cells (CHO cells, ATCC CCL-61), dihydrofolate reductase-deficient lines thereof (CHOdhfr-: Urlaub, G. and Chasin, L. A. Proc. Natl. Acad. Sci. U.S.A (1980) 77, p. 4126-4220), CHOK1SV developed by Lonza Biologics, cells derived from birds such as chickens, and cells derived from insects.

Also, host cells of the present invention include cells that may produce an antibody protein, wherein the structure of a sugar chain attached to the antibody protein is modified, wherein a biological activity of the antibody with the modification is preferably enhanced compared to the antibody without the modification. Example of such host cells of the present invention includes CHO cells that may produce an antibody protein having complex N-glycoside-linked sugar chains bound to the Fc region of the antibody, wherein among the total complex N-glycoside-linked sugar chains bound to the Fc region of the antibody, the ratio of a sugar chain in which fucose is not bound to N-acetylglucosamine in the reducing end in the sugar chain is 20% or more (WO2000/61739, WO2002/31140).

Examples of the eukaryotic microbes can include yeasts. Examples of the prokaryotic cells can include *E. coli* and *Bacillus subtilis*.

Mammal-derived cells are preferably used, CHO cells are more preferably used, and CHOK1SV are even more preferably used as host cells for producing the anti-ROBO4 antibodies of the present invention.

A signal peptide for the secretion of the antibody of the present invention (monoclonal antibodies derived from various animal species, rat antibody, mouse antibody, chimeric antibody, humanized antibody, human antibody, etc.) is not limited to the secretory signal of an antibody of the same species, the same type, and the same subtype as the antibody or to the secretory signal of the antibody itself. Any secretory signal of an antibody of different type or subtype therefrom or any secretory signal of a protein derived from a different eukaryotic species therefrom or a prokaryotic species can be selected and used.

(4-4) Methods for Designing and Preparing a Humanized Antibody

Examples of the humanized antibody can include, but not limited to, a human-derived antibody having CDRs replaced with the CDRs of a non-human animal antibody (see Nature (1986) 321, p. 522-525), a human antibody grafted with the CDR sequences and with some amino acid residues of framework regions by a CDR grafting method (see WO90/07861 and U.S. Pat. No. 6,972,323), and an antibody having human antibody amino acid(s) replaced for one or two or more non-human animal antibody-derived amino acid(s) in any of these humanized antibodies.

(4-5) Method for Preparing a Human Antibody

Further examples of the antibody of the present invention can include a human antibody. The anti-ROBO4 human antibody means an anti-ROBO4 antibody consisting of the amino acid sequence of a human-derived antibody. The anti-ROBO4 human antibody can be obtained by a method using human antibody-producing mice carrying a human genomic DNA fragment comprising human antibody heavy chain- and light chain-encoding genes (see Tomizuka, K. et al., Nature Genetics (1997) 16, p. 133-143; Kuroiwa, Y. et. al., Nuc. Acids Res. (1998) 26, p. 344'7-3448; Yoshida, H. et. al., Animal Cell Technology: Basic and Applied Aspects vol. 10, p. 69-73 (Kitagawa, Y., Matuda, T. and Iijima, S. eds.), Kluwer Academic Publishers, 1999; Tomizuka, K. et. al., Proc. Natl. Acad. Sci. USA (2000) 97, p. 722-727 etc.).

Specifically, such human antibody-producing animals can be prepared by disrupting the endogenous immunoglobulin heavy and light chain gene loci of non-human mammals and instead introducing thereto human immunoglobulin heavy and light chain gene loci via yeast artificial chromosome (YAC) vectors or the like. Alternatively, eukaryotic cells are transformed with heavy chain- and light chain-encoding cDNAs of such a human antibody, preferably with vectors comprising each of the cDNAs, by a gene recombination technique, and the transformed cells producing a recombinant human monoclonal antibody are cultured. This antibody can be obtained from the culture supernatant.

In this context, for example, eukaryotic cells, preferably mammalian cells such as CHO cells, lymphocytes, or myelomas can be used as hosts.

Also, a method for obtaining a phage display-derived human antibody selected from a human antibody library (see Wormstone, I. M. et. al, Investigative Ophthalmology & Visual Science. (2002) 43 (7), p. 2301-2308; Carmen, S. et. al., Briefings in Functional Genomics and Proteomics (2002), 1 (2), p. 189-203; Siriwardena, D. et. al., Opthalmology (2002) 109 (3), p. 427-431 etc.) is known.

For example, a phage display method (Nature Biotechnology (2005), 23, (9), p. 1105-1116) can be used, which involves allowing the variable regions of a human antibody to be expressed as a single-chain antibody (scFv) on phage surface and selecting a phage binding to the antigen.

The phage selected based on its binding to the antigen can be subjected to gene analysis to thereby determine DNA sequences encoding the variable regions of the human antibody binding to the antigen.

If the DNA sequence of scFv binding to the antigen is determined, an expression vector having this sequence is prepared and appropriate hosts can be transfected with the expression vector and allowed to express the human antibody (WO92/01047, WO92/20791, WO93/06213, WO93/11236, WO93/19172, WO95/01438, WO95/15388, Annu. Rev. Immunol (1994) 12, p. 433-455, Nature Biotechnology (2005) 23 (9), p. 1105-1116.

(4-6) Method for Preparing Functional Fragments of an Antibody

The method for preparing a single-chain antibody is well known in the art (see e.g., U.S. Pat. Nos. 4,946,778, 5,260,203, 5,091,513, and 5,455,030). In this scFv, a heavy chain variable region and a light chain variable region are linked via a linker that prevents them from forming a conjugate, preferably a polypeptide linker (Huston, J. S. et al., Proc. Natl. Acad. Sci. U.S.A. (1988), 85, p. 5879-5883). The heavy chain variable region and the light chain variable region in scFv may be derived from the same antibody or may be derived from different antibodies.

For example, an arbitrary single-chain peptide consisting of 12 to 19 residues is used as the polypeptide linker that links these variable regions.

In order to obtain scFv-encoding DNA, of the sequences of DNA encoding the heavy chain or heavy chain variable region of the antibody and DNA encoding the light chain or light chain variable region thereof, each DNA portion encoding the whole or desired amino acid sequence is used as a template and amplified by PCR using a primer pair flanking both ends of the template. Subsequently, DNA encoding the polypeptide linker moiety is further amplified in combination with a primer pair flanking both ends thereof to link them to the heavy and light chains, respectively.

The scFv-encoding DNA can be used to thereby prepare, according to a routine method, an expression vector containing the DNA and host cells transformed with the expression vector. In addition, the host cells are cultured, and the scFv can be collected from the cultures according to a routine method.

Also in order to obtain other functional fragments of the antibody, a gene encoding each functional fragment is obtained according to the method described above, and cells are transfected with the gene. The functional fragment of interest can be collected from cultures of the cells.

The antibody of the present invention may be multimerized to thereby enhance its affinity for the antigen. The antibodies to be multimerized may be antibodies of one type or may be a plurality of antibodies recognizing a plurality of epitopes, respectively, or the same antigen. Examples of antibody multimerization methods can include the binding of two scFvs to an IgG CH3 domain, the binding thereof to streptavidin, and the introduction of a helix-turn-helix motif.

The antibody of the present invention may be a mixture of plural types of anti-ROBO4 antibodies differing in amino acid sequence, i.e., a polyclonal antibody. Examples of the polyclonal antibody can include a mixture of plural types of antibodies differing in a portion or the whole of the CDR set. Such a polyclonal antibody can be collected from cultures of mixed-cultured different antibody-producing cells (WO2004/061104). Moreover, separately prepared antibodies may be mixed. Furthermore, antiserum, which is one aspect of the polyclonal antibody, can be prepared by immunizing animals with the desired antigen and collecting serum from the animals according to a standard method.

Antibodies conjugated with various molecules such as polyethylene glycol (PEG) can also be used as modified forms of the antibody.

The antibody of the present invention may further be any of conjugates formed by these antibodies with other drugs (immunoconjugates). Examples of such an antibody can include the antibody conjugated with a radioactive material or a compound having a pharmacological effect (Nature Biotechnology (2005) 23, p. 1137-1146).

(4-7) Purification of Antibody

The obtained antibody can be purified into a homogeneous level. Usual protein separation and purification methods can be used for the separation and purification of the antibody.

The antibody can be separated and purified by appropriately selected or combined approaches, for example, chromatography columns, filters, ultrafiltration, salting out, dialysis, preparative polyacrylamide gel electrophoresis, and/or isoelectric focusing (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)) but not limited to them.

Examples of chromatography include affinity chromatography, ion-exchange chromatography, hydrophobic chromatography, gel filtration, reverse-phase chromatography, and adsorption chromatography.

These chromatography approaches can be performed using liquid-phase chromatography such as HPLC or FPLC.

Examples of columns used in affinity chromatography can include protein A, protein G, and antigen columns.

Examples of the protein A column include Hyper D (manufactured by Pall Corp.), POROS (manufactured by Applied Biosystems, Inc.), and Sepharose F.F. (manufactured by GE Healthcare Bio-Sciences Crop.).

Also, the antibody may be purified based on its binding activity against the antigen using an antigen-immobilized carrier.

The present invention provides even a gene encoding the antibody of the present invention or the functional fragment thereof, or the modified form thereof, a recombinant vector containing an insert of the gene, a cell transfected with the gene or the vector, and a cell producing the antibody of the present invention.

An antibody or functional fragment thereof which is produced by any of the methods (4-1) to (4-6) can be included in the present invention.

5. Pharmaceutical Composition

The present invention provides a pharmaceutical composition comprising the anti-ROBO4 antibody or the functional fragment thereof, or the modified form thereof.

The pharmaceutical composition of the present invention is useful in the treatment or prevention of a disease that shows angiogenesis as one of pathological findings during the course of onset, progression, and/or exacerbation and can be improved by the suppression of this angiogenesis or vascular permeability (hereinafter, this disease is referred to as an "angiogenic disease" for the sake of convenience). Examples of the angiogenic disease can include exudative age-related macular degeneration, diabetic retinopathy, macular edema, benign or malignant tumor, atherosclerosis, retrolental fibroplasia, angioma, chronic inflammation, ocular neovascular disease, proliferative retinopathy, neovascular glaucoma, immune rejection of a corneal tissue transplant or other tissue transplants, rheumatoid arthritis, psoriasis, acute inflammation, sepsis, and obesity. The pharmaceutical composition of the present invention is useful as an agent in the treatment or prevention of an angiogenic disease, preferably useful in the treatment or prevention of exudative age-related macular degeneration, diabetic retinopathy, macular edema, benign or malignant tumor, retrolental fibroplasia, ocular neovascular disease, proliferative retinopathy, neovascular glaucoma, and immune rejection of a corneal tissue transplant, more preferably useful in the treatment or prevention of exudative age-related macular degeneration, diabetic retinopathy, macular edema, benign or malignant tumor, retrolental fibroplasia, ocular neovascular disease, proliferative retinopathy and neovascular glaucoma.

In the present invention, the treatment and/or treatment of a disease includes, but not limited to, the prevention of onset of the disease, preferably the disease in an individual having the expressed ROBO4 protein, the suppression or inhibition of exacerbation or progression thereof, the alleviation of one or two or more symptoms exhibited by an individual affected with the disease, the suppression or remission of exacerbation or progression thereof, the treatment or prevention of a secondary disease, and the like.

The pharmaceutical composition of the present invention can contain a therapeutically or preventively effective amount of the anti-ROBO4 antibody or the functional fragment of the antibody and a pharmaceutically acceptable diluent, vehicle, solubilizer, emulsifier, preservative, and/or additive.

The "therapeutically or preventively effective amount" means an amount that exerts therapeutic or preventive effects on a particular disease by means of a particular dosage form and administration route.

The pharmaceutical composition of the present invention may contain materials for changing, maintaining, or retaining pH, osmotic pressure, viscosity, transparency, color, tonicity, sterility, or the stability, solubility, sustained release, absorbability, permeability, dosage form, strength, properties, shape, etc., of the composition or the antibody contained therein (hereinafter, referred to as "pharmaceutical materials"). The pharmaceutical materials are not particularly limited as long as they are pharmacologically acceptable materials. For example, no or low toxicity is a property preferably possessed by these pharmaceutical materials.

Examples of the pharmaceutical materials can include, but not limited to, the followings: amino acids such as glycine, alanine, glutamine, asparagine, histidine, arginine, and lysine; antimicrobial agents; antioxidants such as ascorbic acid, sodium sulfate, and sodium bisulfite; buffers such as phosphate, citrate, or borate buffers, sodium bicarbonate, and Tris-HCl solutions; fillers such as mannitol and glycine; chelating agents such as ethylenediaminetetraacetic acid (EDTA); complexing agents such as caffeine, polyvinylpyrrolidine, β-cyclodextrin, and hydroxypropyl-β-cyclodextrin; bulking agents such as glucose, mannose, and dextrin; other hydrocarbons such as monosaccharides, disaccharides, glucose, mannose, and dextrin; coloring agents; corrigents; diluents; emulsifiers; hydrophilic polymers such as polyvinylpyrrolidine; low-molecular-weight polypeptides; salt-forming counterions; antiseptics such as benzalkonium chloride, benzoic acid, salicylic acid, thimerosal, phenethyl alcohol, methylparaben, propylparaben, chlorhexidine, sorbic acid, and hydrogen peroxide; solvents such as glycerin, propylene glycol, and polyethylene glycol; sugar alcohols such as mannitol and sorbitol; suspending agents; surfactants such as PEG, sorbitan ester, polysorbates such as polysorbate 20 and polysorbate 80, triton, tromethamine, lecithin, and cholesterol; stability enhancers such as sucrose and sorbitol; elasticity enhancers such as sodium chloride, potassium chloride, mannitol, and sorbitol; transport agents; diluents; excipients; and/or pharmaceutical additives.

The amount of these pharmaceutical materials added is 0.001 to 1000 times, preferably 0.01 to 100 times, more preferably 0.1 to 10 times the weight of the anti-ROBO4 antibody or the functional fragment thereof, or the modified form thereof.

A pharmaceutical composition containing an immunoliposome comprising the anti-ROBO4 antibody or the functional fragment thereof, or the modified form thereof encapsulated in a liposome or a modified antibody form comprising the antibody conjugated with a liposome (U.S. Pat. No. 6,214,388, etc.) is also included in the pharmaceutical composition of the present invention.

The excipients or vehicles are not particularly limited as long as they are liquid or solid materials usually used in injectable water, saline, artificial cerebrospinal fluids, and other preparations for oral or parenteral administration. Examples of the saline can include neutral saline and serum albumin-containing saline.

Examples of the buffers can include Tris buffers adjusted to bring about the final pH of the pharmaceutical composition to 7.0 to 8.5, acetate buffers adjusted to bring about the final pH thereof to 4.0 to 5.5, citrate buffers adjusted to bring about the final pH thereof to 5.0 to 8.0, and histidine buffers adjusted to bring about the final pH thereof to 5.0 to 8.0.

The pharmaceutical composition of the present invention is a solid, a liquid, a suspension, or the like. Another example of the pharmaceutical composition of the present invention can include freeze-dried preparations. The freeze-dried preparations can be formed using an excipient such as sucrose.

The administration route of the pharmaceutical composition of the present invention may be any of enteral administration, local administration, and parenteral administration and may be selected preferably according to the targeted disease. Specific examples thereof can include intravenous administration, intraarterial administration, intramuscular administration, intradermal administration, hypodermic administration, intraperitoneal administration, transdermal administration, intraosseous administration, and intraarticular administration. Also, intraocular administration can be used preferably for an ophthalmic angiogenic disease such as exudative age-related macular degeneration, diabetic retinopathy, macular edema, retrolental fibroplasia, ocular neovascular disease, proliferative retinopathy, neovascular glaucoma, or immune rejection of a corneal tissue transplant.

The recipe of the pharmaceutical composition can be determined according to the administration method, the binding affinity of the antibody for the ROBO4 protein, etc. The anti-ROBO4 antibody of the present invention or the functional fragment thereof, or the modified form thereof having higher affinity (lower $K_D$ value) for the ROBO4 protein can exert its drug efficacy at a lower dose.

The dose of the anti-ROBO4 antibody of the present invention can be determined appropriately according to the species of an individual, the type of a disease, symptoms, sex, age, pre-existing conditions, the binding affinity of the antibody for the ROBO4 protein or its biological activity, and other factors. A dose of usually 0.01 to 1000 mg/kg, preferably 0.1 to 100 mg/kg, can be administered once every day to 180 days or twice or three or more times a day.

Examples of the form of the pharmaceutical composition can include injections (including freeze-dried preparations and drops), suppositories, transnasal absorption preparations, transdermal absorption preparations, sublingual formulations, capsules, tablets, ointments, granules, aerosols, pills, powders, suspensions, emulsions, eye drops, and biological implant formulations.

The pharmaceutical composition comprising the anti-ROBO4 antibody of the present invention or the functional fragment thereof, or the modified form thereof as an active ingredient may be used in combination with a further therapeutic or prophylactic agent. Examples of said agent include an anti-angiogenesis drug, anti-inflammatory drug, and/or an anticancer drug. For example, the anti-angiogenesis drug, anti-inflammatory drug, and/or anticancer drug is administered to a subject, and then, the pharmaceutical composition comprising the anti-ROBO4 antibody or the functional fragment of the antibody as an active ingredient is administered thereto. Alternatively, the pharmaceutical composition is administered to a subject, and then, the anti-angiogenesis drug, anti-inflammatory drug, and/or anticancer drug is administered thereto. Alternatively, the pharmaceutical composition may be administered to a subject simultaneously with the anti-angiogenesis drug, anti-inflammatory drug, and/or anticancer drug. Examples of the anti-angiogenesis drug can include ranibizumab.

The present invention provides even a method for treating or preventing an angiogenic disease such as exudative age-related macular degeneration, diabetic retinopathy, macular edema, benign or malignant tumor, atherosclerosis, retrolental fibroplasia, angioma, chronic inflammation, ocular neovascular disease, proliferative retinopathy, neovascular glaucoma, immune rejection of a corneal tissue transplant or other tissue transplants, rheumatoid arthritis, psoriasis, acute inflammation, sepsis, or obesity, use of the antibody of the present invention for the preparation of a pharmaceutical composition for the treatment or prevention of the angiogenic disease, and use of the antibody of the present invention for the treatment or prevention of the angiogenic disease. A kit for treatment or prevention comprising the antibody of the present invention is also included in the present invention.

6. Composition for Diagnosis

The present invention provides a composition for examination or diagnosis comprising the anti-ROBO4 antibody of the present invention or the functional fragment thereof, or the modified form thereof (hereinafter, collectively referred to as a "composition for diagnosis").

The composition for diagnosis of the present invention is useful in the examination or diagnosis of an angiogenic disease such as exudative age-related macular degeneration, diabetic retinopathy, macular edema, benign or malignant tumor, atherosclerosis, retrolental fibroplasia, angioma, chronic inflammation, ocular neovascular disease, proliferative retinopathy, neovascular glaucoma, immune rejection of a corneal tissue transplant or other tissue transplants, rheumatoid arthritis, psoriasis, acute inflammation, sepsis, or obesity. The composition for diagnosis of the present invention is also useful in the examination or diagnosis of early angiogenesis or pre-angiogenesis symptoms, which do not satisfy the conventional diagnosis criteria, undiagnosed symptoms that evolve to angiogenesis, etc. In the present invention, the examination or the diagnosis includes, for example, the determination or testing of a risk of acquiring a disease, the determination of the presence or absence of a disease, the testing of the degree of progression or exacerbation, the testing or determination of the effect of drug therapy using the pharmaceutical composition comprising the anti-ROBO4 antibody or the like, the testing or determination of the effect of therapy other than drug therapy, the testing of a risk of recurrence, and the determination of the presence or absence of recurrence. However, the examination or the diagnosis according to the present invention is not limited to them as long as it is usual examination or diagnosis.

When the ROBO4 protein is detected in a 2, 3, 4, 5, 6, 7, 8, 9, 10, 11, 12, 13, 14, 15, 16, 17, 18, 19, or 20-fold or more amount, preferably 10-fold or more amount, in a sample derived from a test subject compared with a sample derived from a healthy individual, the test subject can be diagnosed as having an angiogenic disease or as being at a high risk of acquiring it. Moreover, when the serum concentration of the ROBO4 protein exceeds a particular reference value, the test subject is diagnosed as having an angiogenic disease or can be diagnosed as being at a high risk of acquiring it. The reference value is usually 0.01 to 10 ng/ml, preferably 0.1 to 1 ng/ml, more preferably 0.1 to 0.3 ng/ml.

Such a composition for diagnosis can contain a pH buffer, an osmoregulator, salts, a stabilizer, an antiseptic, a color developer, a sensitizer, an aggregation inhibitor, and the like.

The present invention provides even a method for examining or diagnosing an angiogenic disease such as exudative age-related macular degeneration, diabetic retinopathy, macular edema, benign or malignant tumor, atherosclerosis, retrolental fibroplasia, angioma, chronic inflammation, ocular neovascular disease, proliferative retinopathy, neovascular glaucoma, immune rejection of a corneal tissue transplant or other tissue transplants, rheumatoid arthritis, psoriasis, acute inflammation, sepsis, or obesity, use of the antibody of the present invention for the preparation of a composition for the diagnosis of the angiogenic disease, and use of the antibody of the present invention for the examination or diagnosis of the angiogenic disease. A kit for examination or diagnosis comprising the antibody of the present invention is also included in the present invention.

The examination or diagnosis method involving the antibody of the present invention is preferably sandwich ELISA. A usual detection method using antibodies, such as ELISA, RIA, ELISPOT (enzyme-linked immunospot) assay, dot blotting, an Ouchterlony test, or CIE (counterimmunoelectrophoresis), may be used. Antibodies applied to the sandwich ELISA assay system may be any combination of two antibodies that recognize ROBO4, but do not compete with each other. In addition to biotin, a labeling method that can be carried out in biochemical analysis, such as HRP, alkaline phosphatase, or FITC, can be used as a labeling method for the antibodies. A chromogenic substrate such as TMB (3,3', 5,5'-tetramethylbenzidine), BCIP (5-bromo-4-chloro-3-indolyl phosphate), ρ-NPP (ρ-nitrophenyl phosphate), OPD (o-Phenylenediamine), ABTS (3-Ethylbenzothiazoline-6-sulfonic acid), SuperSignal ELISA Pico Chemiluminescent Substrate (Thermo Fisher Scientific Inc.), a fluorescent substrate such as QuantaBlu™ Fluorogenic Peroxidase Substrate (Thermo Fisher Scientific Inc.), and a chemiluminescent substrate can be used in detection using enzymatic labeling. Samples derived from human or non-human animals as well as artificially treated samples such as recombinant proteins can be subjected to this assay. Examples of test samples derived from organism individuals can include, but not limited to, blood, synovial fluids, ascites, lymph, cerebrospinal fluids, and tissue homogenate supernatants.

The sandwich ELISA kit for examination or diagnosis comprising the antibody of the present invention may contain a solution of ROBO4 protein standards, a coloring reagent, a buffer solution for dilution, an antibody for solid phase, antibody for detection, and a washing solution, and the like. The amount of the antibody bound to the antigen can be measured preferably using a method such as an absorbance, fluorescence, luminescence, or RI (radioisotope) method. An absorbance plate reader, a fluorescence plate reader, a luminescence plate reader, an RI liquid scintillation counter, or the like is preferably used in the measurement.

EXAMPLES

Hereinafter, the present invention will be described in more detail with reference to Examples. However, the present invention is not intended to be limited to them.

In the Examples below, each operation for genetic engineering was performed by methods described in "Molecular Cloning" (Sambrook, J., Fritsch, E. F., and Maniatis, T., Cold Spring Harbor Laboratory Press, 1989) or methods described in other experimental manuals used by those skilled in the art, or performed according to the instructions of commercially available reagents or kits used, unless otherwise specified.

Example 1

Preparation of Expression Vector

1)-1 Preparation of Human ROBO4 Expression Vector
1)-1-1 Preparation of Full-Length Human ROBO4 Expression Vector Human ROBO4 cDNA was cleaved off with EcoRV and NotI from a plasmid (manufactured by Open Biosystems) comprising human ROBO4 cDNA (Accession No. BC039602) and incorporated between EcoRV and NotI of a pCI vector (manufactured by Promega Corp.) to prepare a full-length human ROBO4 expression vector (hereinafter, referred to as "pCI-hROBO4"). The sequence of the human ROBO4 gene cloned in this vector is shown in SEQ ID NO: 1. Also, the amino acid sequence of human ROBO4 is shown in SEQ ID NO: 2.

1)-1-2 Preparation of Human ROBO4 Extracellular Region Expression Vector cDNA encoding a human ROBO4 extracellular region polypeptide (consisting of an amino acid sequence represented by amino acid Nos. 1 to 461 of SEQ ID NO: 2; hereinafter, abbreviated to "human ROBO4-ECD") was amplified through PCR reaction using a primer set:

```
primer 1F:
                                    (SEQ ID NO: 73)
5'-aaaggtaccaccatgggctctggaggagacagcctcctg-3'
and primer 1R:
                                    (SEQ ID NO: 74)
5'-aaagatatcctgctccagggtccagggaccatgctcact-3'.
```

The obtained PCR product was cloned into a pEF6/V5-His-TOPO vector (manufactured by Life Technologies Corp.) (hereinafter, the resulting vector is abbreviated to "pEF6-ROBO4-ECD"; hereinafter, a recombinant protein expressed by "pEF6-ROBO4-ECD" is referred to as "rROBO4-ECD").

1)-1-3 Preparation of N-Terminal FLAG-Tagged Full-Length Human ROBO4 and Human ROBO4 Extracellular Region/Domain Deletion Variant Expression Vectors In order to construct vectors for expression of a protein comprising a region consisting of an amino acid sequence represented by amino acid Nos. 28 to 1007 of SEQ ID NO: 2 of human ROBO4 (in the diagram, this region is referred to as "hROBO4-28"), a region consisting of an amino acid sequence represented by amino acid Nos. 46 to 1007 thereof (in the diagram, this region is referred to as "hROBO4-46"), a region consisting of an amino acid sequence represented by amino acid Nos. 132 to 1007 thereof (in the diagram, this region is referred to as "hROBO4-132"), a region consisting of an amino acid sequence represented by amino acid Nos. 210 to 1007 thereof (in the diagram, this region is referred to as "hROBO4-210"), a region consisting of an amino acid sequence represented by amino acid Nos. 225 to 1007 thereof (in the diagram, this region is referred to as "hROBO4-225"), or a region consisting of an amino acid sequence represented by amino acid Nos. 341 to 1007 thereof (in the diagram, this region is referred to as "hROBO4-341") with the N-terminus tagged with FLAG, PCR reaction was performed with pCI-hROBO4 as a template using each primer set: primer set for hROBO4-28 amplification:
primer 2F: 5'-ggtaccgccatgggctctggaggagacagcctcctcggcg gcagaggttccctgcctctgctgctcctgctcatcatgggaggcatg gctgatta-caaggatgacgacgataagcaggactccccgccccagatcctagtccac-3' (SEQ ID NO: 75) and
primer 2R: 5'-gctagcggagtaatctacaggagaagcaccagccttg-3' (SEQ ID NO: 76),
primer set for hROBO4-46 amplification:
primer 3F: 5'-ggtaccgccatgggctctggaggagacagcctcctcggc ggcagaggttccctgcctctgctgctcctgctcatcatgggaggcatg gctgatta-caaggatgacgacgataagcctggccctgccaggatgagctgccaag-3' (SEQ ID NO: 77) and the primer 2R
primer set for hROBO4-132 amplification:
primer 4F: 5'-ggtaccgccatgggctctggaggagacagcctcctcggc ggcagaggttccctgcctctgctgctcctgctcatcatgggaggcatg gctgatta-caaggatgacgacgataaggtggctgtcctccgggaggatttccagatc-3' (SEQ ID NO: 78) and the primer 2R,
primer set for hROBO4-210 amplification:
primer 5F: 5'-ggtaccgccatgggctctggaggagacagcctcctcggcg-gcaga ggttccctgcctctgctgctcctgctcatcatgggaggcatg gctgatta-caaggatgacgacgataagaccaacagcgcaggacataggggagagcc-3' (SEQ ID NO: 79) and the primer 2R,
primer set for hROBO4-225 amplification:
primer 6F: 5'-ggtaccgccatgggctctggaggagacagcctcctcggcgg cagaggttccctgcctctgctgctcctgctcatcatgggaggcatg gctgatta-caaggatgacgacgataagatccaggagccccaggactacacggagcc-3' (SEQ ID NO: 80) and the primer 2R,
primer set for hROBO4-341 amplification:
primer 7F: 5'-ggtaccgccatgggctctggaggagacagcctcctcggcg-gca gaggttccctgcctctgctgctcctgctcatcatgggaggcatg gctgatta-caaggatgacgacgataagaggctgccggaaaaagtgcccagtgcccca-3' (SEQ ID NO: 81) and the primer 2R. The obtained PCR product was incorporated into a pCR4Blunt-TOPO vector (manufactured by Life Technologies Corp.) to prepare a cloning vector. From each cloning vector, the corresponding cDNA was cleaved off with KpnI and NheI and incorporated between KpnI and NheI of a pCI vector to prepare an N-terminal FLAG-tagged full-length human ROBO4 expression vector and four human ROBO4 extracellular region/domain deletion variant expression vectors. The N-terminal FLAG-tagged full-length human ROBO4 vector consists of a nucleotide encoding the signal sequence of ROBO4 (amino acids of amino acid Nos. 1 to 27 of SEQ ID NO: 2)+FLAG sequence (DYKDDDDK)+ROBO4 (amino acids of amino acid Nos. 28 to 1007 of SEQ ID NO: 2) from the N-terminus. Hereinafter, the vector for expression of N-terminal FLAG-tagged full-length human ROBO4 is referred to as "pCI-FLAG-hROBO4-28". Of the human ROBO4 extracellular region/domain deletion variant expression vectors, for example, the vector for expression of ROBO4 consisting of amino acid Nos. 46 to 1007 of SEQ ID NO: 2 consists of a nucleotide encoding the signal sequence of ROBO4 (amino acids of amino acid Nos. 1 to 27 of SEQ ID NO: 2)+FLAG sequence (DYKDDDDK)+ extracellular region-deleted ROBO4 (amino acids of amino acid Nos. 46 to 1007 of SEQ ID NO: 2). This vector is referred to as "pCI-hROBO4-46". Likewise, the vectors encoding ROBO4 having a partial deletion in the extracellular region of ROBO4 are referred to as "pCI-hROBO4-132", "pCI-hROBO4-210", "pCI-hROBO4-225", and "pCI-hROBO4-341", respectively.

The nucleotide sequence encoding the amino acid sequence of FLAG-tagged full-length human ROBO4 or each extracellular region/domain deletion variant of human ROBO4 cloned in the vector is shown in SEQ ID NO: 3, 5, 7, 9, 11, or 13. Also, the amino acid sequence of the corresponding FLAG-tagged full-length human ROBO4 or extracellular region/domain deletion variant of human ROBO4 is shown in SEQ ID NO: 4, 6, 8, 10, 12, or 14.

1)-1-4 Preparation of Human ROBO4 Intracellular Region Deletion Variant Expression Vector In order to construct a vector for expression of a protein comprising a region consisting of an amino acid sequence represented by amino acid Nos. 1 to 511 of SEQ ID NO: 2 of human ROBO4 (hereinafter, this region is referred to as "hROBO4-ΔC"), a stop codon was inserted immediately after a codon encoding the 511th amino acid of human ROBO4 with pCI-hROBO4 as a template using primer set for hROBO4-ΔC: primer 8F: 5'-cagatataccagtgaggatgcct-gaatcctaaaacacaggatggatc-3' (SEQ ID NO: 82) and primer 8R: 5'-gatccatcctgtgttttaggattcaggcatcctcactggtatatctg-3' (SEQ ID NO: 83), and QuikChange XL Site-Directed Mutagenesis Kit (manufactured by Agilent Technologies, Inc.) to prepare a hROBO4-ΔC expression vector (hereinafter, referred to as "pCI-hROBO4-ΔC").

1)-2 Preparation of Mouse ROBO4 Expression Vector

PCR reaction was performed with Mouse Heart QUICK-Clone cDNA (manufactured by Takara Bio Inc.) as a template using a primer set:

```
primer 9F:
                                        (SEQ ID NO: 84)
5'-ggtaccgccatgggacaaggagaggagccgagagcagccatg-3'
and primer 9R:
                                        (SEQ ID NO: 85)
5'-gcggccgcggaggaatcaccagccttgggcacagcaccag-3'.
```

The obtained PCR product was incorporated into a pCR-Blunt II-TOPO vector (manufactured by Life Technologies Corp.) to prepare a cloning vector comprising mouse ROBO4 cDNA. From the cloning vector, mouse ROBO4 cDNA was cleaved off with KpnI and NotI and incorporated between KpnI and NotI of a pCI vector to prepare a mouse ROBO4 expression vector (hereinafter, referred to as "pCI-mROBO4"). The sequence of an ORF site in the mouse ROBO4 gene cloned in this vector is shown in nucleotide Nos. 7 to 3051 of SEQ ID NO: 15. Also, the amino acid sequence of mouse ROBO4 is shown in SEQ ID NO: 16.

1)-3 Preparation of Rat ROBO4 Expression Vector

PCR reaction was performed with Rat Spleen QUICK-Clone cDNA (manufactured by Takara Bio Inc.) as a template using a primer set:

```
primer 10F:
                                        (SEQ ID NO: 86)
5'-ggtaccgccatgggacaaggagaggagctgagagcagcc-3'
and primer 10R:
                                        (SEQ ID NO: 87)
5'-gcggccgcggaggaatcaccagccttgggcacaacacc-3'.
```

The obtained PCR product was incorporated into a pCR4Blunt-TOPO vector to prepare a cloning vector comprising rat ROBO4 cDNA. From the cloning vector, rat ROBO4 cDNA was cleaved off with KpnI and NotI and incorporated between KpnI and NotI of a pCI vector to prepare a rat ROBO4 expression vector (hereinafter, referred to as "pCI-raROBO4"). The nucleotide sequence of rat ROBO4 cDNA is shown in SEQ ID NO: 17. The amino acid sequence encoded by this nucleotide sequence is shown in SEQ ID NO: 18.

1)-4 Preparation of N-Terminal FLAG-Tagged Cynomolgus Monkey ROBO4 Expression Vector PCR reaction was performed with cDNA synthesized from cynomolgus monkey kidney total RNA as a template using a primer set:

```
primer 11F:
                                        (SEQ ID NO: 88)
5'-ggtaccgccatgggctctggaggagaaagcctccggg-3'
and primer 11R:
                                        (SEQ ID NO: 89)
5'-ggagtaatctacaggagaagcaccagccttg-3'.
```

The obtained PCR product was incorporated into a pCR4Blunt-TOPO vector to prepare two types of cloning vectors comprising each cynomolgus monkey ROBO4 cDNA (hereinafter, referred to as cynoROBO4-1 or cynoROBO4-2) (hereinafter, these vectors are referred to as pCR-cynoROBO4-1 and pCR-cynoROBO4-2, respectively).

Next, PCR reaction was performed with pCR-cynoROBO4-1 or pCR-cynoROBO4-2 as a template using a primer set:

```
primer 12F:
                                        (SEQ ID NO: 90)
5'-ggatccgccatgggctctggaggagaaagcctccg-3'
and primer 12R:
                                        (SEQ ID NO: 91)
5'-gcggccgctcaggagtaatctacaggagaagcaccagccttg-3'.
```

The obtained PCR product was incorporated into a pCR4Blunt-TOPO vector to prepare a cloning vector comprising each cynomolgus monkey ROBO4 cDNA. From the cloning vector, the corresponding cynomolgus monkey ROBO4 cDNA was cleaved off with BamHI and NotI and incorporated between BamHI and NotI of a pCI vector to prepare two types of cynomolgus monkey ROBO4 expression vectors (hereinafter, referred to as pCI-cynoROBO4-1 and pCI-cynoROBO4-2, respectively).

Next, PCR reaction was performed with pCI-cynoROBO4-1 or pCI-cynoROBO4-2 as a template using a primer set:

primer 13F: 5'-ggtaccgccatgggctctggaggagaaagcctccgaggc tcccgggcttcccggcctctgctgctcctgctcatcatgggaggcatg gctgatta-caaggatgacgacgataagcaggactccccgccccagatccagtccac-3' (SEQ ID NO: 92) and the primer 12R.

The obtained PCR product was incorporated into a pCR-TOPO vector (manufactured by Life Technologies Corp.) to prepare each cloning vector comprising N-terminal FLAG-tagged cynomolgus monkey ROBO4 cDNA. From the cloning vector, the corresponding cynomolgus monkey ROBO4 cDNA was cleaved off with KpnI and NotI and incorporated between KpnI and NotI of a pCI vector to prepare N-terminal FLAG-tagged cynomolgus monkey ROBO4 expression vectors (hereinafter, referred to as "pCI-FLAG-cynoROBO4-1" and "pCI-FLAG-cynoROBO4-2", respectively). The nucleotide sequence of cynomolgus monkey ROBO4 cDNA cloned in each of pCI-FLAG-cynoROBO4-1 and pCI-FLAG-cynoROBO4-2 is shown in SEQ ID NOs: 19 and 21, respectively. The amino acid sequence encoded by each nucleotide sequence is shown in SEQ ID NOs: 20 and 22, respectively.

1)-5 Preparation of N-Terminal FLAG-Tagged Human ROBO1 Expression Vector

PCR reaction was performed with Human Heart QUICK-Clone cDNA (manufactured by Takara Bio Inc.) as a template using a primer set:

primer 13F:
(SEQ ID NO: 93)
5'-ggggacaagtttgtacaaaaaagcaggcttcaccatgattgcggagc ccgctcacttttacctg-3'
and primer 13R:
(SEQ ID NO: 94)
5'-ggggaccactttgtacaagaaagctgggtcgctttcagtttcctcta attcttc-3'.

The obtained PCR product and a pDONR221 vector (manufactured by Life Technologies Corp.) were subjected to BP reaction to prepare a donor vector comprising human ROBO1 cDNA.

Next, the PCR reaction was performed with the donor vector as a template using a primer set:

primer 14F:
(SEQ ID NO: 95)
5'-gcggccgcatgattgcggagcccgctcacttttacctgtttggatt aatatgtctctgttcaggctcccgtcttgattacaaggatgacgacgat aagcgtcaggaagattttccacctcgcattgttg-3'
and primer 14R:
(SEQ ID NO: 96)
5'-gctagctcagctttcagtttcctctaattcttc-3'.

The obtained PCR product was incorporated into a pCR4Blunt-TOPO vector to prepare a cloning vector comprising N-terminal FLAG-tagged human ROBO1 cDNA. From the cloning vector, N-terminal FLAG-tagged human ROBO1 cDNA was cleaved off with NheI and NotI and incorporated between NheI and NotI of a pCI vector to prepare an expression vector (hereinafter, referred to as "pCI-FLAG-hROBO1"). The nucleotide sequence of N-terminal FLAG-tagged human ROBO1 cDNA is shown in SEQ ID NO: 23. The amino acid sequence encoded by this nucleotide sequence is shown in SEQ ID NO: 24.

1)-6 Preparation of Human ROBO2 Expression Vector

PCR reaction was performed with Human Lung QUICK-Clone cDNA (manufactured by Takara Bio Inc.) as a template using a primer set:

primer 15F:
(SEQ ID NO: 97)
5'-gcggccgcatgagtctgctgatgtttacacaactactg-3'
and primer 15R:
(SEQ ID NO: 98)
5'-gctagcctataattcacctgtaaactgtccttgactgttg-3'.

The obtained PCR product was incorporated to a pCR4Blunt-TOPO vector to prepare a cloning vector comprising human ROBO2 cDNA. From the cloning vector, human ROBO2 cDNA was cleaved off with NotI and NheI and incorporated between NotI and NheI of a pCI vector to prepare an expression vector (hereinafter, referred to as "pCI-hROBO2"). The nucleotide sequence of human ROBO2 cDNA is shown in SEQ ID NO: 25. The amino acid sequence encoded by this nucleotide sequence is shown in SEQ ID NO: 26.

1)-7 Preparation of Human ROBO3 Expression Vector

PCR reaction was performed with human ROBO3/pENTR223.1 (manufactured by Open Biosystems) as a template using a primer set:

primer 16F:
(SEQ ID NO: 99)
5'-gcggccgcatgctgcgctacctgctgaaaacgctgctg-3'
and primer 16R:
(SEQ ID NO: 100)
5'-gctagctcatcttggttcctctcggcgtttctgtcc-3'.

The obtained PCR product was incorporated to a pCR4Blunt-TOPO vector to prepare a cloning vector comprising human ROBO3 cDNA. From the cloning vector, human ROBO3 cDNA was cleaved off with NotI and NheI and incorporated between NotI and NheI of a pCI vector to prepare an expression vector (hereinafter, referred to as "pCI-hROBO3"). The sequence of an ORF site in the human ROBO3 gene cloned in this vector is shown in nucleotide Nos. 35 to 4192 of SEQ ID NO: 27. Also, the amino acid sequence of human ROBO3 is shown in SEQ ID NO: 28.

Example 2

Preparation of Monoclonal Antibody

2)-1 Preparation of Antigenic Protein

In order to express rROBO4-ECD, FreeStyle 293-F cells (manufactured by Life Technologies Corp.) were transfected with pEF6-ROBO4-ECD using 293fectin (manufactured by Life Technologies Corp.) and cultured at 37° C. for 6 days under 8% $CO_2$ conditions. After completion of the culture, the culture solution was collected by centrifugation and used as a rROBO4-ECD purification stock. The obtained culture supernatant was dialyzed against 20 mM Tris-HCl, pH 7.5 using a dialysis tube having a molecular weight cutoff of 15000, filtered through a filter (0.45 μm), and then added to HiTrap 16/10 Q XL (manufactured by GE Healthcare Bio-Sciences Crop.) equilibrated with 20 mM Tris-HCl, pH 7.5. Elution was performed with a NaCl gradient (20 mM Tris-HCl, pH 7.5/0.2 M NaCl, 20 mM Tris-HCl, pH 7.5/1 M NaCl). A portion of the elution fraction was separated by SDS-polyacrylamide gel electrophoresis (hereinafter, abbreviated to "SDS-PAGE"). Then, the gel was subjected to Coomassie Brilliant Blue staining (hereinafter, abbreviated to "CBB staining") and detection by Western blotting to confirm a fraction containing rROBO4-ECD. Next, the fraction containing rROBO4-ECD was collected and added to HiLoad 16/60 Superdex 75 pg (manufactured by GE Healthcare Bio-Sciences Crop.) equilibrated with PBS. After elution with PBS, a portion of the elution fraction was separated by SDS-PAGE. Then, the gel was subjected to CBB staining and detection by Western blotting to confirm a fraction containing rROBO4-ECD. The fraction containing rROBO4-ECD was collected and used as an antigen for immunization and as an antigen for binding affinity assay. The protein concentration was measured using BCA Protein Assay Reagent (manufactured by Pierce Biotechnology, Inc.).

2)-2 Immunization

Six-week-old female BALB/c mice were used. At day 0, 50 µg of a mixture of rROBO4-ECD and a Freund's complete adjuvant was hypodermically or intradermally administered to each mouse. At days 7, 14, and 21, 50 µg of a mixture of rROBO4-ECD and a Freund's incomplete adjuvant was hypodermically or intradermally administered to the mouse. At day 38, 50 µg of rROBO4-ECD was intraperitoneally administered to the mouse. At day 42, the mouse lymph node or spleen was collected and used in hybridoma preparation.

2)-3 Hybridoma Preparation

The lymph node cells or spleen cells and mouse myeloma SP2/0-ag14 cells were electrically fused using Hybrimune Hybridoma Production System (manufactured by Cyto Pulse Sciences, Inc.), diluted with ClonaCell-HY Selection Medium D (manufactured by StemCell Technologies Inc.), and cultured. Hybridoma colonies that appeared were collected to prepare monoclonal hybridomas. Each hybridoma colony collected was cultured, and the obtained hybridoma culture supernatant was screened for anti-ROBO4 antibody-producing hybridomas.

2)-4 Antibody Screening

2)-4-1 Preparation of Antigen Gene-Expressing Cell for Cell-ELISA

HEK293 cells were adjusted to $7.5 \times 10^5$ cells/mL in a DMEM medium containing 10% FBS. The cells were transfected with pCI-hROBO4 or a negative control pCI-mock using Lipofectamine 2000 (manufactured by Life Technologies Corp.), dispensed at a concentration of 50 µL/well to a 96-well half area plate (manufactured by Corning Inc.), and cultured overnight in a DMEM medium containing 10% FBS at 37° C. under 5% $CO_2$ conditions. The obtained transfected cells were used in Cell-ELISA with them adhering to each other.

2)-4-2 Preparation of Antigen Gene-Expressing Cell for Flow Cytometry Analysis

HEK293T cells were inoculated at a concentration of $1.125 \times 10^7$ cells/flask to a 225-cm$^2$ flask (manufactured by Sumitomo Bakelite Co., Ltd.) and cultured overnight in a DMEM medium containing 10% FBS at 37° C. under 5% $CO_2$ conditions. On the next day, the HEK293T cells were transfected with pCI-ROBO4 or a negative control pCI-mock using Lipofectamine 2000 and further cultured overnight at 37° C. under 5% $CO_2$ conditions. On the next day, the expression vector-transfected HEK293T cells were treated with TrypLE Express (manufactured by Life Technologies Corp.), washed with DMEM containing 10% FBS, and then suspended in PBS containing 5% FBS. The obtained cell suspension was used in flow cytometry analysis.

2)-5 Cell-ELISA

After removal of a supernatant from the expression vector-transfected HEK293 cells prepared in 2)-4-1, the hybridoma culture supernatant was added to each of the pCI-hROBO4- and pCI-mock-transfected HEK293 cells, and the cells were left standing at 4° C. for 1 hour. The cells in each well were washed once with PBS containing 5% FBS. Then, Anti-Mouse IgG-Peroxidase antibody produced in goat (manufactured by Sigma-Aldrich Corp.) diluted 500-fold with PBS containing 5% FBS was added thereto, and the cells were left standing at 4° C. for 1 hour. The cells in each well were washed 5 times with PBS containing 5% FBS. Then, an OPD coloring solution (o-phenylenediamine dihydrochloride (manufactured by Wako Pure Chemical Industries, Ltd.) and $H_2O_2$ dissolved at concentrations of 0.4 mg/mL and 0.6% (v/v), respectively, in an OPD dissolving solution (0.05 M trisodium citrate, 0.1 M disodium hydrogen phosphate dodecahydrate, pH 4.5)) was added thereto at a concentration of 25 µL/well. Color reaction was performed with intermittent stirring and stopped by addition of 1 M HCl at a concentration of 25 µL/well. Then, absorbance at 490 nm was measured using a plate reader (ENVISION; manufactured by Perkin Elmer, Inc.). In order to select hybridomas producing an antibody specifically binding to ROBO4 expressed on cell membrane surface, hybridomas in the culture supernatants exhibiting higher absorbance in the pCI-hROBO4-transfected HEK293 cells compared with the negative control pCI-mock-transfected HEK293 cells were selected as anti-ROBO4 antibody production-positive hybridomas.

2)-6 Flow Cytometry Analysis

The antibody produced by each hybridoma determined to be positive in 2)-5 Cell-ELISA was further confirmed to bind to ROBO4 by flow cytometry. The HEK293T cell suspension prepared in 2)-4-2 was centrifuged. After removal of the supernatant, the hybridoma culture supernatant was added to each of the pCI-hROBO4-transfected cells and the pCI-mock-transfected cells, and the resulting suspension was left standing at 4° C. for 1 hour. The cells were washed twice with PBS containing 5% FBS. Then, Anti-Mouse IgG FITC conjugate (manufactured by Sigma-Aldrich Corp.) diluted 1000-fold with PBS containing 5% FBS or Anti-Rat IgG FITC conjugate (manufactured by Sigma-Aldrich Corp.) diluted 320-fold with PBS containing 5% FBS was added thereto, and the resulting suspension was left standing at 4° C. for 1 hour. The cells were washed three times with PBS containing 5% FBS, then resuspended in PBS containing 5% FBS and 2 µg/mL 7-aminoactinomycin D (manufactured by Molecular Probes), and subjected to detection using a flow cytometer (FC500; manufactured by Beckman Coulter, Inc.). Data was analyzed using Flowjo (manufactured by TreeStar Inc.). 7-aminoactinomycin D-positive dead cells were excluded by gating, and the histogram of FITC fluorescence intensity was then prepared for live cells. Hybridomas producing a sample in which the histogram of the pCI-ROBO4-transfected HEK293T cells was shifted to a stronger fluorescence intensity region compared with the histogram of the negative control pCI-mock-transfected 293T cells were obtained as anti-ROBO4 antibody-producing hybridomas. Anti-ROBO4 antibodies produced by the obtained hybridomas were designated as MAb1, MAb2, MAb3, and MAb4, respectively.

2)-7 Isotyping of Monoclonal Antibody

The isotype of each monoclonal antibody was determined using Mouse monoclonal isotyping kit or Rat monoclonal isotyping kit (manufactured by AbD Serotec). The results were IgG1 (MAb1 and MAb2) and IgG2b (MAb3 and MAb4).

2)-8 Preparation of Monoclonal Antibody

Each monoclonal antibody was purified from a hybridoma culture supernatant (hereinafter, referred to as an "antibody purification stock").

The antibody purification stock was prepared as follows: 8 to 9×10⁷ hybridomas were inoculated to a 1272-cm² flask (manufactured by Corning Inc.) and cultured in a hybridoma SFM medium (manufactured by Life Technologies Corp.) containing 20% Ultra-LoW IgG fetal bovine serum at 37° C. for 4 days under 5% $CO_2$ conditions, and the supernatant was then collected.

The antibody was purified using Hitrap Protein G HP or Hitrap MabSelect SuRe (manufactured by GE Healthcare Bio-Sciences Crop.). For Hitrap Protein G HP, the antibody purification stock was added to a column and washed with a binding buffer (0.02 M sodium phosphate, pH 7.0), followed by elution with 0.1 M glycine, pH 2.7. By contrast, for Hitrap MabSelect SuRe, the antibody purification stock was added to a column and washed with PBS, followed by elution with 2 M arginine-HCl, pH 4.0. The eluted antibody solution was neutralized, and the buffer was then replaced by PBS. The concentration of the antibody purified with Hitrap Protein G HP was measured using BCA Protein Assay Reagent. Mouse IgG2a (manufactured by R&D systems, Inc.) was used as a standard for a calibration curve. Alternatively, the concentration of the antibody purified with Hitrap MabSelect SuRe was determined by the measurement of absorbance (O.D. 280 nm) in an eluate of the antibody bound to POROS G 20 µm Column PEEK, 4.6 mm×50 mm, 0.83 mL (manufactured by Applied Biosystems, Inc.). Specifically, the antibody sample diluted with PBS was added to POROS G 20 µm equilibrated with an equilibration buffer (30.6 mM sodium dihydrogen phosphate dodecahydrate, 19.5 mM monopotassium phosphate, 0.15 M NaCl, pH 7.0). The column was washed with an equilibration buffer, and an antibody bound to the column was then eluted with an eluent (0.1% (v/v) HCl, 0.15 M NaCl). The peak area of absorbance (O.D.280 nm) in the eluate was measured, and the concentration was calculated according to the following equation: Antibody sample concentration (mg/mL)=(Peak area of antibody sample)/(Peak area of standard (human IgG1))×Concentration of standard (mg/mL)×Dilution ratio of sample.

Example 3

Detection of Activation of ROBO4 Downstream Signal

3)-1 Preparation of Reporter Vector Comprising Interleukin-8 (IL-8) Promoter Region as Response Element PCR reaction was performed with IL-8 promoter region DNA as a template using a primer set:

```
primer 17F:
                              (SEQ ID NO: 101)
5'-ggtaccgataaggaacaaataggaag-3'
and primer 17R:
                              (SEQ ID NO: 102)
5'-gagctcagcttgtgtgctctgctgtc-3'.
```

The obtained PCR product was incorporated to a pCR4Blunt-TOPO vector to prepare a cloning vector comprising IL-8 promoter region (−253 to −59) DNA. From the cloning vector, IL-8 promoter region (−253 to −59) DNA was cleaved off with KpnI and SacI and incorporated between KpnI and SacI of a pGL4.15 vector (manufactured by Promega Corp.) to prepare a reporter vector comprising the IL-8 promoter region as a response element. The nucleotide sequence of IL-8 promoter region (−253 to −59) DNA is shown in SEQ ID NO: 29.

3)-2 Reporter Vector Comprising Nuclear Factor-κB (NF-κB), Interferon Gamma Activation Sequence (GAS), Interferon Stimulated Response Element (ISRE), Transfection Grade T Cell Factor (TCF) as Response Element pGL4.32[luc2P/NF-κB-RE/Hygro] Vector (manufactured by Promega Corp.), pGAS-TA-Luc Vector (manufactured by Takara Bio Inc.), pISRE-TA-Luc Vector (manufactured by Takara Bio Inc.), and TOPflash (manufactured by Millipore Corp.) were respectively used as reporter vectors comprising NF-κB, GAS, ISRE, or TCF as a response element. Alternatively, response sequence-free pTA-Luc Vector (manufactured by Takara Bio Inc.) was used as a negative control. pRL-TK Vector (manufactured by Takara Bio Inc.) was used as an internal control.

3)-3 Analysis of Signal Varying in Cell Transiently Expressing Human ROBO4

HEK293 cells were inoculated at a concentration of 2×10⁴ cells/well to a 96-well plate (coated with collagen I; manufactured by Asahi Glass Co., Ltd.) and cultured overnight in a DMEM medium containing 10% FBS at 37° C. under 5% $CO_2$ conditions. On the next day, the HEK293 cells were transfected with pCI-ROBO4, pCI-ROBO4-ΔC, or a negative control pCI-mock and each of the reporter vectors shown in 3)-1 and 3)-2 using FuGene6 Transfection Reagent, and further cultured overnight at 37° C. under 5% $CO_2$ conditions. On the next day, the firefly luciferase and Renilla luciferase activities of each well were determined as luminescence intensity in a plate reader (Mithras; manufactured by Berthold Technologies GmbH & Co, KG) using Dual-Glo Luciferase Assay System (manufactured by Promega Corp.), and the reporter activity of each well was calculated according to the following equation: Reporter activity=Firefly luciferase activity-derived luminescence intensity/Renilla luciferase activity-derived luminescence intensity. As a result, only the IL-8 promoter activity was increased in the pCI-hROBO4-transfected cells compared with the negative control pCI-mock-transfected cells (FIG. 1). Moreover, this increase in the IL-8 promoter activity detected in the pCI-hROBO4-transfected cells was drastically attenuated in the cells transfected with pCI-hROBO4-ΔC (intracellular region deletion mutant of hROBO4), demonstrating that the increase in the IL-8 promoter activity detected in the pCI-hROBO4-transfected cells requires the intracellular region of ROBO4 (FIG. 2). Accordingly, the increase in the IL-8 promoter activity in the pCI-hROBO4-transfected cells demonstrated that the activation of the ROBO4 downstream signal was detected.

Example 4

Properties of MAb1

4)-1 Activation of ROBO4 Downstream Signal by MAb1

The pCI-hROBO4-transfected cells or the pCI-mock-transfected cells prepared in 3)-3 were cultured overnight. On the next day, each anti-ROBO4 antibody (MAb1, MAb2, MAb3, or MAb4) or a negative control Mouse IgG1 (manufactured by R&D systems, Inc.) was added thereto at concentrations of 0, 0.3125, 1.25, 5, and 20 µg/mL or 0, 0.25, 1, 4, and 16 µg/mL, and the cells were cultured at 37° C. for 5 hours under 5% $CO_2$ conditions. Then, the firefly luciferase and Renilla luciferase activities of each well were determined as luminescence intensity in a plate reader (Mithras) using Dual-Glo Luciferase Assay System (manufactured by Promega Corp.), and the reporter activity of each well was calculated according to the following equation: Reporter activity=Firefly luciferase activity-derived luminescence intensity/Renilla luciferase activity-derived luminescence intensity. As a result, the negative control mouse IgG did not influence the IL-8 promoter activity in the cells transiently expressing human ROBO4, whereas MAb1 increased the IL-8 promoter activity (FIG. 3). As in MAb1, MAb2 also increased the IL-8 promoter activity, whereas MAb3 or MAb4 did not increase the IL-8 promoter activity (FIG. 4). In the pCI-mock cells, MAb1 or MAb2 did not increase the IL-8 promoter activity. These results demonstrated that MAb1 activated the downstream signal of ROBO4 and not all antibodies against ROBO4 activated the downstream signal of ROBO4.

MAb3 and MAb4 that were confirmed not to increase the activity of the ROBO4 downstream signal were evaluated for promoter activity in the presence of cross-linking antibodies (AffiPure Goat Anti-Mouse IgG Fc Fragment Specific, Cat NO. 115-005-071, Jackson ImmunoResearch) (two cross-linking antibody molecules with respect to one molecule of MAb3 or MAb4). As a result, increase in the promoter activity was observed for both the antibodies.

4)-2 HUVEC Migration Test

HUVEC (manufactured by KURABO INDUSTRIES LTD.) was cultured overnight in HuMedia-EB2 (manufactured by KURABO INDUSTRIES LTD.) containing 0.1% BSA at 37° C. under 5% $CO_2$ conditions and then adjusted to $4\times10^5$ cells/mL with HuMedia-EB2 containing 0.1% BSA. 0.25 mL of the cell suspension having a concentration of $4\times10^5$ cells/mL was added to the upper layer of a chamber in BD Falcon FluoroBlok 24 multi-well insert system (Pore size: 8 μm) having a gelatin-coated membrane. Then, HuMedia-EB2 containing 0.1% BSA and 10 ng/mL human VEGF165 (manufactured by PeproTech Inc.) or human bFGF (BD Biosciences) and 2 μg/mL Mouse IgG2a or each anti-ROBO4 antibody (MAb1, MAb2, MAb3, or MAb4) was added to the lower layer of the chamber. After incubation at 37° C. for 2 to 3 hours under 5% $CO_2$ conditions, HUVEC that migrated to the lower layer was stained with HuMedia-EB2 containing 4 μg/mL Calcein-AM (manufactured by Life Technologies Corp.) for 15 minutes. Then, the fluorescence intensity (excitation wavelength/fluorescence wavelength: 485 nm/538 nm) of each well was measured using a plate reader (FlexStation; Molecular Devices, LLC.), and the amount of migrating cells in each well was calculated according to the following equation: Amount of migrating cells=Fluorescence intensity of HUVEC-supplemented well−Fluorescence intensity of HUVEC-unsupplemented well. As a result, MAb1 suppressed the migration of HUVEC induced by VEGF or bFGF (FIG. 5). As in MAb1, MAb2 also suppressed the migration of HUVEC induced by bFGF, whereas MAb3 or MAb4 did not suppress the cell migration (FIG. 6). These results demonstrated that the increase in the IL-8 promoter activity by the anti-ROBO4 antibody correlated with the suppressive activity against HUVEC migration.

4)-3 Cross-Species Reactivity

4)-3-1 Preparation of Antigen Gene-Expressing Cell

HEK293 cells were inoculated at a concentration of $1.5\times10^6$ cells/dish to a 60-mm dish (manufactured by Corning Inc.) and cultured overnight in a DMEM medium containing 10% FBS at 37° C. under 5% $CO_2$ conditions. On the next day, the HEK293 cells were transfected with pCI-hROBO4, pCI-mROBO4, pCI-raROBO4, pCI-FLAG-cynoROBO4-1, pCI-FLAG-cynoROBO4-2, pCI-hROBO1, pCI-hROBO2, or pCI-hROBO3 using FuGENE6 Transfection Reagent and further cultured overnight at 37° C. under 5% $CO_2$ conditions. On the next day, the expression vector-transfected cells were treated with TrypLE Express (manufactured by Life Technologies Corp.), washed with PBS containing 5% FBS, and then suspended in PBS containing 5% FBS. The obtained cell suspension was used in flow cytometry analysis.

4)-3-2 Flow Cytometry Analysis

Each cell suspension prepared in 4)-3-1 was centrifuged, and the supernatant was removed. Then, MAb1 or a negative control Mouse IgG2a was added at a concentration of 10 μg/mL to $2\times10^5$ expression vector-transfected cells, and the resulting suspension was left standing at 4° C. for 1 hour. The cells were washed once with PBS containing 5% FBS. Then, Anti-Mouse IgG FITC conjugate diluted 1000-fold with PBS containing 5% FBS was added thereto, and the resulting suspension was left standing at 4° C. for 1 hour. The cells were washed with three times with PBS containing 5% FBS, then resuspended in PBS containing 5% FBS, and subjected to detection using a flow cytometer (BD FACSCalibur). Data was analyzed using Flowjo. The histogram of FITC fluorescence intensity was prepared. The antibody was determined to bind in a cross-species manner when the histogram of MAb1 was shifted to a stronger fluorescence intensity region compared with the histogram of the negative control Mouse IgG2a. The results of cross-species reactivity study demonstrated that MAb1 did not bind to mouse ROBO4 or rat ROBO4, but bound to human ROBO4 and cynomolgus monkey ROBO4 (FIG. 7).

4)-4 Binding Specificity

4)-4-1 Preparation of Antigen Gene-Expressing Cell

HEK293 cells were inoculated at a concentration of $1.2\times10^6$ cells/dish or $1.5\times10^6$ cells/dish to a 60-mm dish (manufactured by Corning Inc.) and cultured overnight in a DMEM medium containing 10% FBS at 37° C. under 5% $CO_2$ conditions. On the next day, the HEK293 cells were transfected with pCI-hROBO4, pCI-FLAG-hROBO1, pCI-hROBO2, or pCI-hROBO3 using FuGENE6 Transfection Reagent and further cultured overnight at 37° C. under 5% $CO_2$ conditions. On the next day, the expression vector-transfected cells were treated with TrypLE Express (manufactured by Life Technologies Corp.), washed with PBS containing 5% FBS, and then suspended in PBS containing 5% FBS. The obtained cell suspension was used in flow cytometry analysis.

4)-4-2 Flow Cytometry Analysis

Each cell suspension prepared in 4)-4-1 was centrifuged, and the supernatant was removed. Then, MAb1, a positive control Human ROBO4 Antibody (manufactured by R&D systems, Inc.), Monoclonal ANTI-FLAG M2 antibody produced in mouse (manufactured by Sigma-Aldrich Corp.), Human ROBO2 Antibody (manufactured by R&D systems, Inc.), or Monoclonal Anti-human ROBO3 Antibody (manufactured by R&D systems, Inc.), or a negative control Mouse IgG1 or Mouse IgG2a was added at a concentration of 10 μg/mL to $2\times10^5$ expression vector-transfected cells, and the resulting suspension was left standing at 4° C. for 1 hour. The cells were washed once with PBS containing 5% FBS. Then, Anti-Mouse IgG FITC conjugate diluted 1000-fold with PBS containing 5% FBS was added thereto, and the resulting suspension was left standing at 4° C. for 1 hour. The cells were washed with three times with PBS containing 5% FBS, then resuspended in PBS containing 5% FBS, and subjected to detection using a flow cytometer (BD FAC- SCalibur). Data was analyzed using Flowjo. The histogram of FITC fluorescence intensity was prepared. The antibody was determined to bind in a specific manner when the histogram of MAb1 was shifted to a stronger fluorescence intensity region compared with the histogram of the negative control Mouse IgG1 or Mouse IgG2a. The results demonstrated that MAb1 did not bind to hROBO1, hROBO2, or hROBO3 and specifically bound to hROBO4 (FIG. 8). In this context, hROBO4, hROBO1, hROBO2, and hROBO3 were each confirmed to be expressed on the cell membrane using the positive control antibody (FIG. 8).

4)-5 Epitope Determination

4)-5-1 Preparation of Antigen Gene-Expressing Cell

HEK293 cells were inoculated at a concentration of $1.5 \times 10^6$ cells/dish to a 60-mm dish (manufactured by Corning Inc.) and cultured overnight in a DMEM medium containing 10% FBS at 37° C. under 5% $CO_2$ conditions. On the next day, the HEK293 cells were transfected with pCI-FLAG-hROBO4-28, pCI-FLAG-hROBO4-46, pCI-FLAG-hROBO4-132, pCI-FLAG-hROBO4-210, pCI-FLAG-hROBO4-225, pCI-FLAG-hROBO4-341 using FuGENE6 Transfection Reagent and further cultured overnight at 37° C. under 5% $CO_2$ conditions. On the next day, the expression vector-transfected cells were treated with TrypLE Express (manufactured by Life Technologies Corp.), washed with PBS containing 5% FBS, and then suspended in PBS containing 5% FBS. The obtained cell suspension was used in flow cytometry analysis.

4)-5-2 Flow Cytometry Analysis

Each cell suspension prepared in 4)-5-1 was centrifuged, and the supernatant was removed. Then, MAb1, a positive control Monoclonal ANTI-FLAG M2 antibody produced in mouse, or a negative control Mouse IgG2a was added at a concentration of 10 µg/mL to $2 \times 10^5$ expression vector-transfected cells, and the resulting suspension was left standing at 4° C. for 1 hour. The cells were washed once with PBS containing 5% FBS. Then, Anti-Mouse IgG FITC conjugate diluted 1000-fold with PBS containing 5% FBS was added thereto, and the resulting suspension was left standing at 4° C. for 1 hour. The cells were washed with three times with PBS containing 5% FBS, then resuspended in PBS containing 5% FBS, and subjected to detection using a flow cytometer (BD FACSCalibur; BD Biosciences). Data was analyzed using Flowjo. The histogram of FITC fluorescence intensity was prepared. The antibody was determined to bind to a cell when the histogram of MAb1 was shifted to a stronger fluorescence intensity region compared with the histogram of the negative control Mouse IgG2a. The results demonstrated that MAb1 bound to the pCI-FLAG-hROBO4-28-, pCI-FLAG-hROBO4-46-, or pCI-FLAG-hROBO4-132-transfected cell and did not bind to the pCI-FLAG-hROBO4-210-, pCI-FLAG-hROBO4-225-, or pCI-FLAG-hROBO4-341-transfected cell. Thus, MAb1 was shown to recognize the amino acid sequence of Nos. 132 to 209 in human ROBO4 shown in SEQ ID NO: 2 (FIG. 9). In this context, each intracellular region/domain deletion variant was confirmed to be expressed on the cell membrane using the positive control anti-FLAG antibody (FIG. 9).

4)-6 Drug Efficacy Evaluation in Monkey Models with Laser-Induced Choroidal Neovascularization 4)-6-1 Anesthesia Medetomidine hydrochloride (manufactured by Nippon Zenyaku Kogyo Co., Ltd.) was intramuscularly injected at a dose of 0.04 mg/kg to each cynomolgus monkey. 15 minutes thereafter, ketamine hydrochloride (manufactured by Daiichi Sankyo Co., Ltd.) was intramuscularly injected thereto at a dose of 15 mg/kg.

4)-6-2 Model Preparation

Each cynomolgus monkey anesthetized in 4)-6-1 was retained in a monkey chair. 4% Xylocaine eye drops (manufactured by AstraZeneca plc) were applied to both eyes for anesthetic/analgesic treatment of eye surface. 5 mg/mL tropicamide-5 mg/mL phenylephrine hydrochloride mixture eye drops (manufactured by Santen Pharmaceutical Co., Ltd.) were applied to the eyes for mydriasis. The macular region of the retina was thermally damaged by laser irradiation (quantity of heat irradiated: 350-500 mW, irradiation time: 0.1 seconds, spot size: 50 µm, the number of spots: 6 or 9 spots) using a green laser photocoagulator OcuLight GLx (manufactured by Iridex Corp.).

4)-6-3 Administration of Test Substance

At day 7 after the model preparation, a 33 G Nanopass needle was inserted into the vitreous body from the conjunctiva, and 50 µL of vehicle or 13.2 mg/mL MAb1 was injected thereto over 2 minutes using a 100-µL Hamilton syringe via a PE20 polyethylene tube. The test was conducted on each group involving 4 eyes. After completion of the administration, 0.5% levofloxacin hydrate eye drops (manufactured by Santen Pharmaceutical Co., Ltd.) were applied to the eyes.

4)-6-4 Drug Efficacy Evaluation

At days 7, 14, and 21 after the model preparation, the ocular fundus was photographed by a routine method using a hybrid fundus camera CX-1 (manufactured by Canon Inc.) under anesthesia. Then, 10% fluorescein was intravenously injected thereto at a dose of 0.1 mL/Kg. After completion of the intravenous injection of fluorescein, fluorescent angiography was performed every 1 minute up to 6 minutes later. The image data was stored, and the area of a site at which fluorescein accumulated was calculated using an image analyzer (WinRoof, manufactured by Mitani Corp.). The amount of blood vessels newly formed was calculated according to the following equation: Amount of blood vessels newly formed=Area of site at which fluorescein accumulated at day 21 after model preparation−Area of site at which fluorescein accumulated at day 7 after model preparation. As a result of comparing the amount of blood vessels newly formed between the vehicle-administered group and the MAb1-administered group, three out of the four eyes in the MAb1-administered group were confirmed to decrease the amount of blood vessels newly formed, though no difference was confirmed in the amount of blood vessels newly formed between the remaining one eye and the vehicle group. This means that the administration of MAb1 suppressed laser-induced choroidal neovascularization (FIG. 10).

Example 5

Cloning and Sequencing of MAb1 cDNA

5)-1 Determination of N-Terminal Amino Acid Sequences of MAb1 Heavy and Light Chains In order to determine the N-terminal amino acid sequences of the heavy and light chains of MAb1, MAb1 purified in Example 2)-8 was separated by SDS-PAGE. The proteins thus separated in the gel were transferred from the gel to a Sequi-Blot PVDF membrane (Bio-Rad Laboratories, Inc.), which was in turn washed with a washing buffer (25 mM NaCl, 10 mM sodium borate buffer, pH 8.0), then stained by dipping for 5 minutes in a staining solution (50% methanol, 20% acetic acid, 0.05% Coomassie Brilliant Blue), and then decolorized with 90% methanol. Band portions corresponding to the heavy chain (band with smaller mobility) and the light chain (band with larger mobility) visualized on the PVDF membrane were cleaved off. Their respective N-terminal amino acid sequences were identified according to the automatic Edman method (see Edman et al., (1967) Eur. J. Biochem. 1, 80) using Precise cLC protein sequencer Model 492cLC (Applied Biosystems, Inc.). As a result, the N-terminal amino acid sequence of the band corresponding to the heavy chain of MAb1 was EVQLVESGGGLVKPGGSLKL (SEQ ID NO: 103), and the N-terminal amino acid sequence of the band corresponding to the light chain was DAVMTQTPLSLPVSL (SEQ ID NO: 104).

5)-2 Preparation of mRNA from MAb1-Producing Hybridoma

In order to clone heavy chain- and light chain-encoding cDNAs of MAb1, mRNA was prepared from the MAb1-producing hybridoma using mRNA Isolation kit (Roche Applied Science).

5)-3 Cloning and Sequencing of MAb1 cDNA

Several oligonucleotide primers hybridizing to the 5'-terminal sequence of the coding region of the antibody gene and the stop codon-containing 3'-terminal sequence thereof, respectively, were synthesized with reference to the N-terminal amino acid sequences of the heavy and light chains determined based on the γ1 and κ isotypes of the MAb1 heavy and light chains, respectively (Examples 2)-7) and 5-1), and the antibody amino acid sequence database prepared by Kabat et al. (see Strausberg, R. L., et al. (2002) Proc. Natl. Acad. Sci. U.S.A. 99. 16899-16903, and Kabat, E. A., et al. (1991) in Sequences of Proteins of Immunological Interest Vol. I and II, U. S. Department of Health and Human Services). Heavy chain- and light chain-encoding cDNAs were amplified using the mRNA prepared in 5)-2 and TaKaRa One Step RNA PCR Kit (AMV) (Takara Bio Inc.). As a result, the heavy chain- and light chain-encoding cDNAs of the antibody were successfully amplified using the following primer set:

```
primer set for the heavy chain
LYHF6:
                                   (SEQ ID NO: 105)
5'-cctcaccatgaactttgg-3'

G1EVR1:
                                   (SEQ ID NO: 106)
5'-aagatatcttatttaccaggagagtgggagag-3' primer set for the light chain
MK19EIF1:
                                   (SEQ ID NO: 107)
5'-aagaattcatgaagttgcctgttagg-3'

KEVR1:
                                   (SEQ ID NO: 108)
5'-aagatatcttaacactcattcctgttgaagct-3'.
```

The heavy and light chain cDNAs amplified by PCR were separately cloned using pEF6/V5-His TOPO TA Expression Kit (Invitrogen Corp.). The nucleotide sequences of the cloned cDNAs encoding the respective variable regions of the heavy and light chains were determined using a gene sequencer ("ABI PRISM 3700 DNA Analyzer; Applied Biosystems" or "Applied Biosystems 3730xl Analyzer; Applied Biosystems"). The sequencing reaction was performed using GeneAmp 9700 (Applied Biosystems, Inc.).

The determined nucleotide sequence of cDNA encoding the heavy chain variable region of MAb1 is shown in SEQ ID NO: 30, and its amino acid sequence is shown in SEQ ID NO: 31. The nucleotide sequence of cDNA encoding the light chain variable region of the mouse antibody MAb1 is shown in SEQ ID NO: 32, and its amino acid sequence is shown in SEQ ID NO: 33.

Example 6

Preparation of Chimeric MAb1 (cMAb1)

6)-1 Preparation of Expression Vectors pCMA-LK, pCMA-G1, and pCMA-G2

6)-1-1 Construction of Chimeric and Humanized Light Chain Expression Vector pCMA-LK A plasmid pcDNA3.3-TOPO/LacZ (Invitrogen Corp.) was digested with restriction enzymes XbaI and PmeI, and the obtained fragment of approximately 5.4 kb was ligated to a DNA fragment comprising a DNA sequence (SEQ ID NO: 34) encoding a human κ chain secretory signal and a human κ chain constant region using In-Fusion Advantage PCR cloning kit (Clontech Laboratories, Inc.) to prepare pcDNA3.3/LK.

PCR was performed with pcDNA3.3/LK as a template using a primer set shown below. The obtained fragment of approximately 3.8 kb was phosphorylated and then self-ligated to construct, from pcDNA3.3/LK, a chimeric and humanized light chain expression vector pCMA-LK having a signal sequence-encoding sequence, a cloning site, and a human κ chain constant region-encoding sequence downstream of a CMV promoter.

```
Primer set
3.3-F1:
                                   (SEQ ID NO: 109)
5'-tataccgtcgacctctagctagagcttggc-3'

3.3-R1:
                                   (SEQ ID NO: 110)
5'-gctatggcagggcctgccgccccgacgttg-3'.
```

6)-1-2 Construction of Chimeric and Humanized IgG1-Type Heavy Chain Expression Vector pCMA-G1 pCMA-LK was digested with XbaI and PmeI to remove a sequence encoding a κ chain secretory signal and a human κ chain constant region. The resulting DNA fragment was ligated to a DNA fragment comprising a DNA sequence (SEQ ID NO: 35) encoding the amino acids of a human heavy chain signal sequence and a human IgG1 constant region using In-Fusion Advantage PCR cloning kit (Clontech Laboratories, Inc.) to construct a chimeric and humanized IgG1-type heavy chain expression vector pCMA-G1 having a signal sequence-encoding sequence, a cloning site, and a human IgG1 heavy chain constant region-encoding sequence downstream of a CMV promoter.

6)-1-3 Construction of Chimeric and Humanized IgG2-Type Heavy Chain Expression Vector pCMA-G2 pCMA-LK was digested with XbaI and PmeI to remove a sequence encoding a κ chain secretory signal and a human κ chain constant region. The resulting DNA fragment was ligated to a DNA fragment comprising a DNA sequence (SEQ ID NO: 36) encoding the amino acids of a human heavy chain signal sequence and a human IgG2 constant region using In-Fusion Advantage PCR cloning kit (Clontech Laboratories, Inc.) to construct a chimeric and humanized IgG2-type heavy chain expression vector pCMA-G2 having a signal sequence-encoding sequence, a cloning site, and a human IgG2 heavy chain constant region-encoding sequence downstream of a CMV promoter.

6)-2 Construction of Chimeric MAb1 Light Chain Expression Vector

A site comprising cDNA encoding the light chain variable region was amplified with cDNA encoding the light chain variable region of MAb1 as a template using KOD-Plus- (TOYOBO CO., LTD.) and a primer set shown below, and inserted into a restriction enzyme BsiWI-cleaved site of the general-purpose vector pCMA-LK for chimeric and humanized antibody light chain expression using In-Fusion Advantage PCR cloning kit (Clontech Laboratories, Inc.) to construct a chimeric MAb1 light chain expression vector. The obtained expression vector was designated as "pCMA-LK/ MAb1 L". The nucleotide sequence encoding the chimeric MAb1 light chain is shown in SEQ ID NO: 37, and its amino acid sequence is shown in SEQ ID NO: 38. Nucleotide Nos. 1 to 60 of SEQ ID NO: 37 represent the nucleotide sequence encoding the signal sequence. Nucleotide Nos. 61 to 402 thereof represent the nucleotide sequence encoding the variable region. Nucleotide Nos. 403 to 717 thereof represent the nucleotide sequence encoding the constant region. Amino acid Nos. 1 to 20 of SEQ ID NO: 38 represent the amino acids of the signal sequence. Amino acid Nos. 21 to 134 thereof represent the amino acids of the variable region. Amino acid Nos. 135 to 239 represent the amino acids of the constant region.

```
Primer set for the light chain
MAb1 LF:
                                       (SEQ ID NO: 111)
5'-tctccggcgcgtacggcgatgctgtgatgacccaaactccactc
tcc-3'

MAb1 LR:
                                       (SEQ ID NO: 112)
5'-ggaggggcggccacagcccgtttgatttccagcttggtgcctcc-3'
```

6)-3 Construction of Chimeric MAb1 IgG1-Type Heavy Chain Expression Vector

A site comprising cDNA encoding the heavy chain variable region was amplified with cDNA encoding the heavy chain variable region of MAb1 as a template using KOD-Plus-(TOYOBO CO., LTD.) and a primer set shown below, and inserted into a restriction enzyme BsiWI-cleaved site of the chimeric and humanized IgG1-type heavy chain expression vector pCMA-G1 using In-Fusion Advantage PCR cloning kit (Clontech Laboratories, Inc.) to construct a chimeric MAb1 IgG1-type heavy chain expression vector. The obtained expression vector was designated as "pCMA-G1/MAb1 H". The nucleotide sequence encoding the chimeric MAb1 IgG1-type heavy chain is shown in SEQ ID NO: 39, and its amino acid sequence is shown in SEQ ID NO: 40. Nucleotide Nos. 1 to 57 of SEQ ID NO: 39 represent the nucleotide sequence encoding the signal sequence. Nucleotide Nos. 58 to 411 thereof represent the nucleotide sequence encoding the variable region. Nucleotide Nos. 412 to 1401 thereof represent the nucleotide sequence encoding the constant region. Amino acid Nos. 1 to 19 of SEQ ID NO: 40 represent the amino acid sequence of the signal sequence. Amino acid Nos. 20 to 137 thereof represent the amino acid sequence of the variable region. Amino acid Nos. 138 to 467 represent the amino acid sequence of the constant region.

```
Primer set for the IgG1-type heavy chain
MAb1 HF:
                                       (SEQ ID NO: 113)
5'-cagatgggtgctgagcgaagtgcagctggtggagtctgggggag-3'

MAb1 H1R:
                                       (SEQ ID NO: 114)
5'-ttggtggaggctgagctgactgtgagagtggtgccgtggcccc
ag-3'.
```

6)-4 Construction of Chimeric MAb1 IgG2-Type Heavy Chain Expression Vector

A site comprising cDNA encoding the heavy chain variable region was amplified with cDNA encoding the heavy chain variable region of MAb1 as a template using KOD-Plus-(TOYOBO CO., LTD.) and a primer set shown below, and inserted into a restriction enzyme BsiWI-cleaved site of the chimeric and humanized IgG2-type heavy chain expression vector pCMA-G2 using In-Fusion Advantage PCR cloning kit (Clontech Laboratories, Inc.) to construct a chimeric MAb1 IgG2-type heavy chain expression vector. The obtained expression vector was designated as "pCMA-G2/MAb1". The nucleotide sequence encoding the chimeric MAb1 IgG2-type heavy chain is shown in SEQ ID NO: 41, and its amino acid sequence is shown in SEQ ID NO: 42.

```
Primer set for the IgG2-type heavy chain
MAb1 HF:
                                       (SEQ ID NO: 113)
5'-cagatgggtgctgagcgaagtgcagctggtggagtctgggggag-3'

MAb1 2R:
                                       (SEQ ID NO: 115)
5'-ttggtgctggctgagctgactgtgagagtggtgccgtggcccag-3'
```

Example 7

Preparation of IgG1-Type Chimeric MAb1 Antibody and IgG2-Type Chimeric MAb1 Antibody 7)-1 Production of IgG1-Type Chimeric MAb1 Antibody and IgG2-Type Chimeric MAb1 Antibody FreeStyle 293-F cells (Invitrogen Corp.) were subcultured and cultured according to the manual. $1.2 \times 10^9$ cells of FreeStyle 293-F cells (Invitrogen Corp.) at the logarithmic growth phase were inoculated to a 3 L Fernbach Erlenmeyer Flask (Corning Inc.), diluted with FreeStyle 293 expression medium (Invitrogen Corp.) into $1.0 \times 10^6$ cells/mL, and then shake-cultured in an 8% $CO_2$ incubator at 90 rpm at 37° C. for 1 hour. 3.6 mg of polyethyleneimine (Polysciences, Inc., #24765) was dissolved in 20 mL of Opti-Pro SFM medium (Invitrogen Corp.). Next, an H chain expression vector (0.4 mg) and an L chain expression vector (0.8 mg) prepared using PureLink HiPure Plasmid kit (Invitrogen Corp.) were suspended in 20 mL of Opti-Pro SFM medium (Invitrogen Corp.). 20 mL of the expression vector/Opti-Pro SFM mixture solution was added to 20 mL of the polyethyleneimine/ Opti-Pro SFM mixture solution, and the mixture was gradually stirred, further left for 5 minutes, and then added to the FreeStyle 293-F cells. The cells were shake-cultured in an 8% $CO_2$ incubator at 90 rpm at 37° C. for 7 days, and the obtained culture supernatant was filtered through Disposable Capsule Filter (Advantec, #CCS-045-E1H).

IgG1-type and IgG2-type chimeric MAb1 antibodies obtained by the combinations between pCMA-G1/MAb1 H and pCMA-LK/MAb1 L and between pCMA-G2/MAb1 H and pCMA-LK/MAb1 L are abbreviated to "cMAb1-1" and "cMAb1-2", respectively. The term "cMAb1" means both IgG1-type and IgG2-type chimeric MAb1 antibodies.

7)-2 Purification of cMAb1-1 and cMAb1-2

The culture supernatant obtained above in 7-1) was purified by rProtein A affinity chromatography (at 4-6° C.). A buffer replacement step after the rProtein A affinity chromatography purification was carried out at room temperature. First, 1100 to 1200 ml of the culture supernatant was applied to MabSelect SuRe (manufactured by GE Healthcare Bio-Sciences Crop., HiTrap column; volume 1 mL×2 connected) equilibrated with PBS. The whole culture solution was placed in the column, and the column was then washed with PBS. Next, elution was performed with a 2 M arginine hydrochloride solution (pH 4.0) to collect an antibody-containing fraction. The buffer in this fraction was replaced by PBS using a desalting column (manufactured by GE Healthcare Bio-Sciences Corp., HiTrap Desalting column; volume 5 mL×2 connected). Finally, the fraction was concentrated with Centrifugal UF Filter Device VIVASPIN20 (molecular weight cutoff: 30 K, Sartorius, at 4° C.) into an IgG concentration of 20.0 mg/mL or higher and used as a purification sample.

7)-3 Properties of cMAb1-1 and cMAb1-2

7)-3-1 Activation of ROBO4 Downstream Signal

This test was conducted according to the method of 4)-1 except that: Human IgG (manufactured by Sigma-Aldrich Corp.) was used as a negative control; and Human IgG, cMAb1-1, or cMAb1-2 was added at a final concentration of 0.313 μg/mL to a medium. As a result, the negative control Human IgG did not influence the IL-8 promoter activity in the cells transiently expressing human ROBO4, whereas cMAb1-1 and cMAb1-2 increased the IL-8 promoter activity (FIG. 11). These results demonstrated that cMAb1-1 or cMAb1-2 activated the downstream signal of ROBO4, as in MAb1.

7)-3-2 HUVEC Migration Test

This test was conducted according to the method of 4)-2 except that: Human IgG was used as a negative control; and Human IgG, cMAb1-1, or cMAb1-2 was added at a final concentration of 0.5 μg/mL to a medium. As a result, cMAb1-1 or cMAb1-2 suppressed the migration of HUVEC induced by bFGF (FIG. 12). These results demonstrated that cMAb1-1 or cMAb1-2 suppressed the migration of HUVEC, as in MAb1.

Example 8

Design of Humanized Antibody of Mouse Anti-Human ROBO4 Monoclonal Antibody MAb1

8)-1 Design of Humanized Version of MAb1
8)-1-1 Molecular Modeling of MAb1 Variable Region The molecular modeling of the MAb1 variable regions was carried out by a generally known homology modeling method (Methods in Enzymology, 203, 121-153, (1991)). The primary sequences (available as three-dimensional structures induced from x-ray crystal structures) of human immunoglobulin variable regions registered in Protein Data Bank (Nuc. Acid Res. 35, D301-D303 (2007)) were compared with those of the MAb1 variable regions thus determined. As a result, 3FFD was selected because of its highest sequence homology to the MAb1 heavy chain variable region among antibodies deficient in framework. Also, 1T66 was selected because of its highest sequence homology to the MAb1 light chain variable region. The three-dimensional structures of the framework regions were prepared by obtaining a "framework model" from the combination of the coordinates of 3FFD and 1T66 corresponding to the MAb1 heavy and light chains. As for the CDRs of MAb1, CDRL1, CDRL2, CDRL3, CDRH1, and CDRH2 were assigned to clusters 16A, 7A, 9A, 10A, and 10B, respectively, according to the classification of Thornton et al. (J. Mol. Biol., 263, 800-815, (1996)). CDRH3 was classified into k(7)B using the H3 rule (FEBS letter 399, 1-8 (1996)). Subsequently, the typical conformation of each CDR was incorporated into the framework model.

Finally, energy calculation for excluding disadvantageous interatomic contact was conducted to obtain a molecular model likely to be the MAb1 variable regions in terms of energy. These procedures were performed using a commercially available protein three-dimensional structure prediction program Prime and coordinate searching program MacroModel (Schrodinger, LLC).

8)-1-2 Design of Humanized MAb1 Amino Acid Sequence

Each humanized MAb1 antibody (hMAb1) was constructed by a generally known CDR grafting method (Proc. Natl. Acad. Sci. USA 86, 10029-10033 (1989)). Two different acceptor antibodies were selected on the basis of the homology of amino acids in framework regions. The sequences of the MAb1 framework regions were compared with all human frameworks in the Kabat antibody amino acid sequence database (Nuc. Acid Res. 29, 205-206 (2001)). As a result, a B3 antibody was selected as an acceptor because of its 83% sequence homology to the framework regions. The amino acid residues of the B3 framework regions were aligned with those of MAb1 to identify the positions of different amino acids used. These positions of the residues were analyzed using the three-dimensional model of MAb1 constructed above. Then, donor residues to be grafted onto the acceptor were selected according to the criteria given by Queen et al. (Proc. Natl. Acad. Sci. USA 86, 10029-10033 (1989)). Some selected donor residues were integrated into the acceptor antibody to construct the sequence of humanized MAb1 as described in Examples below. Also, hMAb1 variants were constructed by the substitution of 1 to 3 amino acid residue(s) in each CDR of hMAb1 with other amino acid residues, as described in Examples below.

8)-2 Humanization of cMAb1 Heavy Chain
8)-2-1 hMAb1-H1-Type Heavy Chain:

A humanized MAb1 heavy chain designed by replacing amino acid No. 32 (lysine) with glutamine, amino acid No. 38 (lysine) with arginine, amino acid No. 59 (threonine) with alanine, amino acid No. 61 (glutamic acid) with glycine, amino acid No. 63 (arginine) with glycine, amino acid No. 95 (glutamic acid) with lysine, amino acid No. 103 (serine) with asparagine, amino acid No. 107 (serine) with alanine, amino acid No. 112 (methionine) with valine, amino acid No. 114 (phenylalanine) with tyrosine, amino acid No. 129 (histidine) with glutamine, amino acid No. 132 (threonine) with leucine, and amino acid No. 133 (leucine) with valine, in the cMAb1-2 heavy chain represented by SEQ ID NO: 42 was designated as a "hMAb1-H1-type heavy chain".

The amino acid sequence of the hMAb1-H1-type heavy chain is shown in SEQ ID NO: 56. A sequence consisting of amino acid residues 1 to 19, a sequence consisting of amino acid residues 20 to 137, and a sequence consisting of amino acid residues 138 to 463 in the amino acid sequence of SEQ ID NO: 56 correspond to a signal sequence, a heavy chain variable region, and a heavy chain constant region, respectively. A sequence consisting of amino acid residues 50 to 54, a sequence consisting of amino acid residues 69 to 85, and a sequence consisting of amino acid residues 118 to 126 in the amino acid sequence of SEQ ID NO: 56 correspond to a CDRH1 sequence, a CDRH2 sequence, and a CDRH3 sequence, respectively. A nucleotide sequence encoding the amino acid sequence of SEQ ID NO: 56 is shown in SEQ ID NO: 55. A sequence consisting of nucleotides 1 to 57, a sequence consisting of nucleotides 58 to 411, and a sequence consisting of nucleotides 412 to 1389 in the nucleotide sequence of SEQ ID NO: 55 encode the signal sequence, the heavy chain variable region sequence, and the heavy chain constant region sequence, respectively. The nucleotide sequence of SEQ ID NO: 55 and the amino acid sequence of SEQ ID NO: 56 are also shown in FIGS. 31 and 32, respectively.

8)-2-2 hMAb1-H2-Type Heavy Chain:

A humanized MAb1 heavy chain designed by replacing amino acid No. 32 (lysine) with glutamine, amino acid No. 38 (lysine) with arginine, amino acid No. 59 (threonine) with alanine, amino acid No. 61 (glutamic acid) with glycine, amino acid No. 63 (arginine) with glycine, amino acid No. 72 (asparagine) with glutamine, amino acid No. 95 (glutamic acid) with lysine, amino acid No. 103 (serine) with asparagine, amino acid No. 107 (serine) with alanine, amino acid No. 112 (methionine) with valine, amino acid No. 114 (phenylalanine) with tyrosine, amino acid No. 129 (histidine) with glutamine, amino acid No. 132 (threonine) with leucine, and amino acid No. 133 (leucine) with valine, in the cMAb1-2 heavy chain represented by SEQ ID NO: 42 was designated as a "hMAb1-H2-type heavy chain".

The amino acid sequence of the hMAb1-H2-type heavy chain is shown in SEQ ID NO: 58. A sequence consisting of amino acid residues 1 to 19, a sequence consisting of amino acid residues 20 to 137, and a sequence consisting of amino acid residues 138 to 463 in the amino acid sequence of SEQ ID NO: 58 correspond to a signal sequence, a heavy chain variable region, and a heavy chain constant region, respectively. A sequence consisting of amino acid residues 50 to 54, a sequence consisting of amino acid residues 69 to 85, and a sequence consisting of amino acid residues 118 to 126 in the amino acid sequence of SEQ ID NO: 58 correspond to a CDRH1 sequence, a CDRH2 sequence, and a CDRH3 sequence, respectively. A nucleotide sequence encoding the amino acid sequence of SEQ ID NO: 58 is shown in SEQ ID NO: 57. A sequence consisting of nucleotides 1 to 57, a sequence consisting of nucleotides 58 to 411, and a sequence consisting of nucleotides 412 to 1389 in the nucleotide sequence of SEQ ID NO: 57 encode the signal sequence, the heavy chain variable region sequence, and the heavy chain constant region sequence, respectively. The nucleotide sequence of SEQ ID NO: 57 and the amino acid sequence of SEQ ID NO: 58 are also shown in FIGS. 33 and 34, respectively.

8)-2-3 hMAb1-H3-Type Heavy Chain:

A humanized MAb1 heavy chain designed by replacing amino acid No. 32 (lysine) with glutamine, amino acid No. 38 (lysine) with arginine, amino acid No. 59 (threonine) with alanine, amino acid No. 61 (glutamic acid) with glycine, amino acid No. 95 (glutamic acid) with lysine, amino acid No. 103 (serine) with asparagine, amino acid No. 107 (serine) with alanine, amino acid No. 112 (methionine) with valine, amino acid No. 114 (phenylalanine) with tyrosine, amino acid No. 129 (histidine) with glutamine, amino acid No. 132 (threonine) with leucine, and amino acid No. 133 (leucine) with valine, in the cMAb1-2 heavy chain represented by SEQ ID NO: 42 was designated as a "hMAb1-H3-type heavy chain".

The amino acid sequence of the hMAb1-H3-type heavy chain is shown in SEQ ID NO: 60. A sequence consisting of amino acid residues 1 to 19, a sequence consisting of amino acid residues 20 to 137, and a sequence consisting of amino acid residues 138 to 463 in the amino acid sequence of SEQ ID NO: 60 correspond to a signal sequence, a heavy chain variable region, and a heavy chain constant region, respectively. A sequence consisting of amino acid residues 50 to 54, a sequence consisting of amino acid residues 69 to 85, and a sequence consisting of amino acid residues 118 to 126 in the amino acid sequence of SEQ ID NO: 60 correspond to a CDRH1 sequence, a CDRH2 sequence, and a CDRH3 sequence, respectively. A nucleotide sequence encoding the amino acid sequence of SEQ ID NO: 60 is shown in SEQ ID NO: 59. A sequence consisting of nucleotides 1 to 57, a sequence consisting of nucleotides 58 to 411, and a sequence consisting of nucleotides 412 to 1389 in the nucleotide sequence of SEQ ID NO: 59 encode the signal sequence, the heavy chain variable region sequence, and the heavy chain constant region sequence, respectively. The nucleotide sequence of SEQ ID NO: 59 and the amino acid sequence of SEQ ID NO: 60 are also shown in FIGS. 35 and 36, respectively.

8)-2-4 hMAb1-H4-Type Heavy Chain:

A humanized MAb1 heavy chain designed by replacing amino acid No. 32 (lysine) with glutamine, amino acid No. 38 (lysine) with arginine, amino acid No. 59 (threonine) with alanine, amino acid No. 61 (glutamic acid) with glycine, amino acid No. 72 (asparagine) with glutamine, amino acid No. 95 (glutamic acid) with lysine, amino acid No. 103 (serine) with asparagine, amino acid No. 107 (serine) with alanine, amino acid No. 112 (methionine) with valine, amino acid No. 114 (phenylalanine) with tyrosine, amino acid No. 129 (histidine) with glutamine, amino acid No. 132 (threonine) with leucine, and amino acid No. 133 (leucine) with valine, in the cMAb1-2 heavy chain represented by SEQ ID NO: 42 was designated as a "hMAb1-H4-type heavy chain".

The amino acid sequence of the hMAb1-H4-type heavy chain is shown in SEQ ID NO: 62. A sequence consisting of amino acid residues 1 to 19, a sequence consisting of amino acid residues 20 to 137, and a sequence consisting of amino acid residues 138 to 463 in the amino acid sequence of SEQ ID NO: 62 correspond to a signal sequence, a heavy chain variable region, and a heavy chain constant region, respectively. A sequence consisting of amino acid residues 50 to 54, a sequence consisting of amino acid residues 69 to 85, and a sequence consisting of amino acid residues 118 to 126 in the amino acid sequence of SEQ ID NO: 62 correspond to a CDRH1 sequence, a CDRH2 sequence, and a CDRH3 sequence, respectively. A nucleotide sequence encoding the amino acid sequence of SEQ ID NO: 62 is shown in SEQ ID NO: 61. A sequence consisting of nucleotides 1 to 57, a sequence consisting of nucleotides 58 to 411, and a sequence consisting of nucleotides 412 to 1389 in the nucleotide sequence of SEQ ID NO: 61 encode the signal sequence, the heavy chain variable region sequence, and the heavy chain constant region sequence, respectively. The nucleotide sequence of SEQ ID NO: 61 and the amino acid sequence of SEQ ID NO: 62 are also shown in FIGS. 37 and 38, respectively.

8)-3 Humanization of MAb1 Light Chain

8)-3-1 hMAb1-L1-Type Light Chain:

A humanized MAb1 light chain designed by replacing amino acid No. 22 (alanine) with isoleucine, amino acid No. 27 (threonine) with serine, amino acid No. 34 (serine) with threonine, amino acid No. 37 (aspartic acid) with glutamic acid, amino acid No. 38 (glutamine) with proline, amino acid No. 62 (phenylalanine) with leucine, amino acid No. 84 (leucine) with proline, amino acid No. 108 (phenylalanine) with valine, amino acid No. 112 (phenylalanine) with tyrosine, amino acid No. 125 (glycine) with proline, amino acid No. 129 (leucine) with valine, amino acid No. 130 (glutamic acid) with aspartic acid, and amino acid No. 134 (alanine)

with threonine, in the cMAb1 light chain represented by SEQ ID NO: 38 was designated as a "hMAb1-L1-type light chain".

The amino acid sequence of the hMAb1-L1-type light chain is shown in SEQ ID NO: 64. A sequence consisting of amino acid residues 1 to 20, a sequence consisting of amino acid residues 21 to 134, and a sequence consisting of amino acid residues 135 to 239 in the amino acid sequence of SEQ ID NO: 64 correspond to a signal sequence, a light chain variable region, and a light chain constant region, respectively. A sequence consisting of amino acid residues 44 to 59, a sequence consisting of amino acid residues 75 to 81, and a sequence consisting of amino acid residues 114 to 122 in the amino acid sequence of SEQ ID NO: 64 correspond to a CDRL1 sequence, a CDRL2 sequence, and a CDRL3 sequence, respectively. A nucleotide sequence encoding the amino acid sequence of SEQ ID NO: 64 is shown in SEQ ID NO: 63. A sequence consisting of nucleotides 1 to 60, a sequence consisting of nucleotides 61 to 402, and a sequence consisting of nucleotides 403 to 717 in the nucleotide sequence of SEQ ID NO: 63 encode the signal sequence, the light chain variable region sequence, and the light chain constant region sequence, respectively. The nucleotide sequence of SEQ ID NO: 63 and the amino acid sequence of SEQ ID NO: 64 are also shown in FIGS. 39 and 40, respectively.

8)-3-2 hMAb1-L2-Type Light Chain:

A humanized MAb1 light chain designed by replacing amino acid No. 22 (alanine) with isoleucine, amino acid No. 27 (threonine) with serine, amino acid No. 34 (serine) with threonine, amino acid No. 37 (aspartic acid) with glutamic acid, amino acid No. 38 (glutamine) with proline, amino acid No. 52 (serine) with glutamic acid, amino acid No. 54 (glycine) with lysine, amino acid No. 56 (threonine) with leucine, amino acid No. 62 (phenylalanine) with leucine, amino acid No. 84 (leucine) with proline, amino acid No. 108 (phenylalanine) with valine, amino acid No. 112 (phenylalanine) with tyrosine, amino acid No. 125 (glycine) with proline, amino acid No. 129 (leucine) with valine, amino acid No. 130 (glutamic acid) with aspartic acid, and amino acid No. 134 (alanine) with threonine, in the cMAb1 light chain represented by SEQ ID NO: 38 was designated as a "hMAb1-L2-type light chain".

The amino acid sequence of the hMAb1-L2-type light chain is shown in SEQ ID NO: 66. A sequence consisting of amino acid residues 1 to 20, a sequence consisting of amino acid residues 21 to 134, and a sequence consisting of amino acid residues 135 to 239 in the amino acid sequence of SEQ ID NO: 66 correspond to a signal sequence, a light chain variable region, and a light chain constant region, respectively. A sequence consisting of amino acid residues 44 to 59, a sequence consisting of amino acid residues 75 to 81, and a sequence consisting of amino acid residues 114 to 122 in the amino acid sequence of SEQ ID NO: 66 correspond to a CDRL1 sequence, a CDRL2 sequence, and a CDRL3 sequence, respectively. A nucleotide sequence encoding the amino acid sequence of SEQ ID NO: 66 is shown in SEQ ID NO: 65. A sequence consisting of nucleotides 1 to 60, a sequence consisting of nucleotides 61 to 402, and a sequence consisting of nucleotides 403 to 717 in the nucleotide sequence of SEQ ID NO: 65 encode the signal sequence, the light chain variable region sequence, and the light chain constant region sequence, respectively. The nucleotide sequence of SEQ ID NO: 65 and the amino acid sequence of SEQ ID NO: 66 are also shown in FIGS. 41 and 42, respectively.

Example 9

Preparation of Humanized MAb1

9)-1 Construction of Humanized MAb1 Heavy Chain Expression Vector

9)-1-1 Construction of hMAb1-H1-Type Heavy Chain Expression Vector

DNA comprising the gene encoding the hMAb1-H1-type heavy chain variable region represented by amino acid Nos. 20 to 137 of SEQ ID NO: 56 was synthesized (GeneArt artificial gene synthesis service) and cleaved with a restriction enzyme BlpI. The obtained DNA fragment was inserted to a restriction enzyme BlpI-cleaved site of the chimeric and humanized IgG2-type heavy chain expression vector (pCMA-G2) to construct a hMAb1-H1-type heavy chain expression vector. The obtained expression vector was designated as "pCMA-G2/hMAb1-H1". The nucleotide sequence of the hMAb1-H1-type heavy chain is shown in SEQ ID NO: 55.

9)-1-2 Construction of hMAb1-H2-Type Heavy Chain Expression Vector

A hMAb1-H2-type heavy chain expression vector was constructed with the pCMA-G2/hMAb1-H1 constructed in 9)-1-1 as a template using a primer set shown below and QuikChange XL Site-Directed Mutagenesis Kit (Agilent Technologies, Inc.). The obtained expression vector was designated as "pCMA-G1/hMAb1-H2". The nucleotide sequence of the hMAb1-H2-type heavy chain is shown in SEQ ID NO: 57, and its amino acid sequence is shown in SEQ ID NO: 58.

```
Primer set:
H-N53Q-F:
                                         (SEQ ID NO: 116)
5'-gggtggcaaccatcagccaaggcggcacctacacctac-3'

H-N53Q-R:
                                         (SEQ ID NO: 117)
5'-gtaggtgtaggtgccgccttggctgatggttgccaccc-3'
```

9)-1-3 Construction of hMAb1-H3-Type Heavy Chain Expression Vector

DNA comprising the gene encoding the hMAb1-H3-type heavy chain variable region represented by amino acid Nos. 20 to 137 of SEQ ID NO: 60 was synthesized (GeneArt artificial gene synthesis service) and cleaved with a restriction enzyme BlpI. The obtained DNA fragment was inserted to a restriction enzyme BlpI-cleaved site of the chimeric and humanized IgG2-type heavy chain expression vector (pCMA-G2) to construct a hMAb1-H3-type heavy chain expression vector. The obtained expression vector was designated as "pCMA-G2/hMAb1-H3". The nucleotide sequence of the hMAb1-H3-type heavy chain is shown in SEQ ID NO: 59.

9)-1-4 Construction of hMAb1-H4-Type Heavy Chain Expression Vector

A hMAb1-H4-type heavy chain expression vector was constructed with the pCMA-G2/hMAb1-H3 constructed in 9)-1-3 as a template using a primer set shown below and QuikChange XL Site-Directed Mutagenesis Kit (Agilent Technologies, Inc.). The obtained expression vector was designated as "pCMA-G1/hMAb1-H4". The nucleotide sequence of the hMAb1-H4-type heavy chain is shown in SEQ ID NO: 61, and its amino acid sequence is shown in SEQ ID NO: 62.

Primer set:
H-N53Q-F:
(SEQ ID NO: 116)
5'-gggtggcaaccatcagccaaggcggcacctacacctac-3'

H-N53Q-R:
(SEQ ID NO: 117)
5'-gtaggtgtaggtgccgccttggctgatggttgccaccc-3'

9)-2 Construction of Humanized MAb1 Light Chain Expression Vector

9)-2-1 Construction of hMAb1-L1-Type Light Chain Expression Vector

DNA comprising the gene encoding the hMAb1-L1-type light chain variable region represented by amino acid Nos. 21 to 134 of SEQ ID NO: 64 was synthesized (GeneArt artificial gene synthesis service) and cleaved with a restriction enzyme BsiWI. The obtained DNA fragment was inserted to a restriction enzyme BsiWI-cleaved site of the general-purpose vector (pCMA-LK) for chimeric and humanized antibody light chain expression to construct a hMAb1-L1-type light chain expression vector. The obtained expression vector was designated as "pCMA-LK/hMAb1-L1". The nucleotide sequence of the hMAb1-L1-type light chain is shown in SEQ ID NO: 63.

9)-2-2 Construction of hMAb1-L2-Type Light Chain Expression Vector

DNA fragments were obtained by PCR with the pCMA-LK/hMAb1-L1 constructed in 9)-2-1 as a template using KOD-Plus-(TOYOBO CO., LTD.) and each of primer sets A and B, and linked by overlap extension PCR using primer set C to prepare DNA comprising a gene encoding the hMAb1-L2-type light chain. This DNA was cleaved with restriction enzymes XbaI and PmeI to obtain a DNA fragment, which was then inserted to a restriction enzyme XbaI/PmeI-cleaved site of the general-purpose vector (pCMA-LK) for chimeric and humanized antibody light chain expression to construct a hMAb1-L2-type light chain expression vector. The obtained expression vector was designated as "pCMA-LK/hMAb1-L2". The nucleotide sequence of the hMAb1-L2-type light chain is shown in SEQ ID NO: 65, and its amino acid sequence is shown in SEQ ID NO: 66.

```
Primer set A
L inf-F:
                                    (SEQ ID NO: 118)
5'-gcctccggactctagagccaccatggtgctgcagacccaggtgt
tc-3'

L-EKL-R:
                                    (SEQ ID NO: 119)
5'-caggtacaggttcttgttctcgttttccaggctctggctgcttc
tgcagc-3'

Primer set B
L-EKL-F:
                                    (SEQ ID NO: 120)
5'-gaaaacgagaacaagaacctgtacctgaactggtatctgcaga
agcccg-3'

L inf-R:
                                    (SEQ ID NO: 121)
5'-tagcctccccgtttaaacgggcccctaacactccccctg-3'

Primer set C
L inf-F:
                                    (SEQ ID NO: 118)
5'-gcctccggactctagagccaccatggtgctgcagacccaggtg
ttc-3'
```

```
L inf-R:
                                    (SEQ ID NO: 212)
5'-tagcctccccgtttaaacgggcccctaacactccccctg-3'
```

Example 10

Preparation of Humanized MAb1

10-7-1) Production of Humanized MAb1

FreeStyle 293-F cells (Invitrogen Corp.) were subcultured and cultured according to the manual.

$1.2 \times 10^9$ cells of FreeStyle 293-F cells (Invitrogen Corp.) at the logarithmic growth phase were inoculated to 3 L Fernbach Erlenmeyer Flask (Corning Inc.), diluted with FreeStyle 293 expression medium (Invitrogen Corp.) into $1.0 \times 10^6$ cells/mL, and then shake-cultured in an 8% $CO_2$ incubator at 90 rpm at 37° C. for 1 hour. 3.6 mg of polyethyleneimine (Polysciences, Inc., #24765) was dissolved in 20 mL of Opti-Pro SFM medium (Invitrogen Corp.). Next, an H chain expression vector (0.4 mg) and an L chain expression vector (0.8 mg) prepared using PureLink HiPure Plasmid kit (Invitrogen Corp.) were suspended in 20 mL of Opti-Pro SFM medium (Invitrogen Corp.). 20 mL of the expression vector/Opti-Pro SFM mixture solution was added to 20 mL of the polyethyleneimine/Opti-Pro SFM mixture solution, and the mixture was gradually stirred, further left for 5 minutes, and then added to the FreeStyle 293-F cells. The cells were shake-cultured in an 8% $CO_2$ incubator at 90 rpm at 37° C. for 7 days, and the obtained culture supernatant was filtered through Disposable Capsule Filter (Advantec, #CCS-045-E1H), and purified in the same way as in 7)-2.

The humanized MAb1 antibody obtained by the combination between pCMA-G2/hMAb1-H1 and pCMA-LK/hMAb1-L1 was designated as "H-1040". The humanized MAb1 antibody obtained by the combination between pCMA-G2/hMAb1-H2 and pCMA-LK/hMAb1-L1 was designated as "H-1140". The humanized MAb1 antibody obtained by the combination between pCMA-G2/hMAb1-H2 and pCMA-LK/hMAb1-L2 was designated as "H-1143". The humanized MAb1 antibody obtained by the combination between pCMA-G2/hMAb1-H3 and pCMA-LK/hMAb1-L1 was designated as "H-2040". The humanized MAb1 antibody obtained by the combination between pCMA-G2/hMAb1-H4 and pCMA-LK/hMAb1-L1 was designated as "H-2140". The humanized MAb1 antibody obtained by the combination between pCMA-G2/hMAb1-H4 and pCMA-LK/hMAb1-L2 was designated as "H-2143".

Example 11

Property of Anti-ROBO4 Humanized Antibody

11)-1 Binding Affinity

The dissociation constant between each antibody and rROBO4-ECD was determined with the antibody immobilized as a ligand and the antigen as an analyte using Biacore 3000 (manufactured by GE Healthcare Bio-Sciences Corp.). Approximately 80 RU of the antibody was bound via an anti-human IgG antibody (manufactured by GE Healthcare Bio-Sciences Corp.) immobilized on a sensor chip CM5 (manufactured by GE Healthcare Bio-Sciences Corp.) by an amine coupling method. The running buffer used was PBS containing 0.05% Surfactant P20. Dilution series solutions (0.1-200 nM) of the antigen were added at a flow rate of 30

μL/min. for 300 seconds onto the antibody-bound chip. Subsequently, a dissociation phase was monitored for 300 seconds. 3 M MgCl$_2$ was added thereto as a regeneration solution at a flow rate of 10 μL/min. for 30 seconds. Data was analyzed using the 1:1 binding model of analysis software (BIAevaluation Software, version 4.1) to calculate an association rate constant kon, a dissociation rate constant koff, and a dissociation constant ($K_D$; $K_D$=koff/kon). As a result, the $K_D$ value was 0.41 nM for H-1040, 3.5 nM for H-1143, 3.9 nM for H-1140, 0.40 nM for H-2040, 1.7 nM for H-2143, and 1.8 nM for H-2140.

11)-2 Activation of ROBO4 Downstream Signal

This test was conducted according to the method of 4)-1 except that: human IgG was used as a negative control; and Human IgG, H-1040, H-1140, H-1143, H-2040, H-2140, H-2143, or cMAb1-2 was added at a final concentration of 0.63 μg/mL to a medium. As a result, the negative control human IgG did not influence the IL-8 promoter activity in the cells transiently expressing human ROBO4, whereas all the anti-ROBO4 humanized antibodies increased the IL-8 promoter activity at a level equivalent to cMAb1-2 (FIG. 49). These results demonstrated that all the anti-ROBO4 humanized antibodies activated the downstream signal of ROBO4, as in MAb1.

11)-3 HUVEC Migration Test

This test was conducted according to the method of 4)-2 except that: human IgG was used as a negative control; human IgG, H-1143, H-2140, or H-2143 was added at a final concentration of 0.5 μg/mL to a medium; and the fluorescence intensity (excitation wavelength/fluorescent wavelength: 485 nm/538 nm) of each well was measured using a plate reader (EnVision: Perkin Elmer, Inc.). As a result, H-1143, H-2140, or H-2143 suppressed the migration of HUVEC induced by bFGF (FIG. 50). Additionally, H-1140 showed the suppressive activity against HUVEC migration. These results demonstrated that H-1140, H-1143, H-2140, or H-2143 suppressed the migration of HUVEC.

11)-4 Cross-Species Reactivity

11)-4-1 Preparation of Antigen Gene-Expressing Cell

The cells were prepared according to the method of 4)-3-1.

11)-4-2 Flow Cytometry Analysis

This test was conducted according to the method of 4)-3-2 except that: human IgG was used as a negative control; FITC-AffiniPure Goat Anti-Human IgG, Fcγ Fragment Specific (manufactured by Jackson ImmunoResearch Laboratories, Inc.) was used as a secondary antibody; and a flow cytometer (FC500; manufactured by Beckman Coulter, Inc.) was used as a detector. As a result, H-1143, H-2140, or H-2143 did not bind to mouse ROBO4 or rat ROBO4, but was shown to bind to human ROBO4 and cynomolgus monkey ROBO4, as in the parent antibody MAb1 (FIGS. 51, 52, and 53). Additionally, H-1140 showed the same result as H-1143, H-2140 and H-2143.

11)-5 Binding Specificity of H-1140, H-1143, H-2140, or H-2143

11)-5-1 Preparation of Antigen Gene-Expressing Cell

The cells were prepared according to the method of 4)-4-1 except that pCI-FLAG-hROBO4-28 was used as a human ROBO4 expression vector.

11)-5-2 Flow Cytometry Analysis

This test was conducted according to the method of 4)-4-2 except that: human IgG or mouse IgG2A was used as a negative control; Fluorescein-conjugated goat IgG fraction to mouse IgG (manufactured by Cappel Laboratories, Inc.) or FITC-AffiniPure Goat Anti-Human IgG, Fcγ Fragment Specific was used as a secondary antibody; and a flow cytometer (FC500) was used as a detector. As a result, H-1143, H-2140, or H-2143 did not bind to hROBO1, hROBO2, or hROBO3, but was shown to specifically bind to hROBO4, as in the parent antibody MAb1 (FIG. 54). Additionally, H-1140 showed the same result as H-1143, H-2140 and H-2143. In this context, hROBO4, hROBO1, hROBO2, and hROBO3 were each confirmed to be expressed on the cell membrane using the positive control antibody (FIG. 54).

11)-6 Drug Efficacy Evaluation in Monkey Models with Laser-Induced Choroidal Neovascularization 11)-6-1 Anesthesia Medetomidine hydrochloride was intramuscularly injected at a dose of 0.08 mg/kg to each cynomolgus monkey. 15 minutes thereafter, ketamine hydrochloride was intramuscularly injected thereto at a dose of 15 mg/kg.

11)-6-2 Model Preparation

Each cynomolgus monkey anesthetized in 11)-6-1 was retained on a stainless operating table in the supine position. 5 mg/mL tropicamide-5 mg/mL phenylephrine hydrochloride mixture eye drops were applied to the eyes for mydriasis. The macular region of the retina was thermally damaged by laser irradiation (quantity of heat irradiated: 500 mW, irradiation time: 0.1 seconds, spot size: 50 μm, the number of spots: 9 spots) using a green laser photocoagulator OcuLight GLx. After the operation, Cravit eye drops were added dropwise to the operated eyes.

11)-6-3 Administration of Test Substance

At day 7 after the model preparation, each cynomolgus monkey was anesthetized and then retained on a stainless operating table in the supine position. Then, PA IODO Ophthalmic and Eye washing Solution (Nitten Pharmaceutical Co., Ltd.) diluted 4-fold with sterile purified water was applied to the eyes to disinfect the external eyes. A 33 G needle was inserted into the vitreous body from the conjunctiva, and saline or 0.05 mL of H-2143 adjusted to 1.1 mg/0.05 mL was injected thereto using a 1-mL syringe. After completion of the administration, Rinderon-A Ointment for Eye and Ear was applied to the conjunctiva using a swab and spread throughout the surfaces of the eyes by the opening and closing of the eyes.

11)-6-4 Drug Efficacy Evaluation

At days 7, 14, and 21 after the model preparation, the ocular fundus was photographed by a routine method using a hybrid fundus camera CX-1 under anesthesia. Then, fluorescein was intravenously injected thereto at a dose of 0.05 mL/Kg. After completion of the intravenous injection of fluorescein, fluorescent angiography was performed every 1 minute up to 10 minutes later, and image data was stored. From the image data, severity was classified at a scale of grades 1 to 5 based on the fluorescence intensity of each laser-irradiated site at which fluorescein accumulated according to the method of Zahn G et al. (Zahn G et al., Arch. Ophthalmol. 2009 127: 1329-1335). Then, the ratio of a site corresponding to grades 4 and 5 in the severity classification among all the laser-irradiated sites was calculated on the percentage basis to evaluate choroidal neovascularization. As a result of comparing choroidal neovascularization between the saline-administered group and the H-2143-administered group, the ratio of grades 4 and 5 increased in the saline-administered group with a lapse of time from the model preparation, whereas such increase was not observed in the H-2143-administered group. This means that the administration of H-2143 suppressed laser-induced choroidal neovascularization (FIG. 55).

INDUSTRIAL APPLICABILITY

Use of an antibody provided by the present invention enables the treatment or prevention of an angiogenic disease such as exudative age-related macular degeneration, diabetic retinopathy, macular edema, benign or malignant tumor, atherosclerosis, retrolental fibroplasia, angioma, chronic inflammation, ocular neovascular disease, proliferative retinopathy, neovascular glaucoma, immune rejection of a corneal tissue transplant or other tissue transplants, rheumatoid arthritis, psoriasis, acute inflammation, sepsis, or obesity, and the examination or diagnosis of the angiogenic disease.

FREE TEXT OF SEQUENCE LISTING

SEQ ID NO: 1: Nucleotide sequence of full-length human ROBO4 cDNA (FIG. 13).

SEQ ID NO: 2: Amino acid sequence of human ROBO4 (FIG. 14).

SEQ ID NO: 3: Nucleotide sequence encoding the amino acid sequence of N-terminal FLAG-tagged full-length human ROBO4.

SEQ ID NO: 4: Amino acid sequence of N-terminal FLAG-tagged full-length human ROBO4.

SEQ ID NO: 5: Nucleotide sequence encoding the amino acid sequence of an N-terminal FLAG-tagged extracellular region/domain deletion variant of human ROBO4 consisting of an amino acid sequence of amino acid Nos. 46 to 1007 of SEQ ID NO: 2.

SEQ ID NO: 6: Amino acid sequence of an N-terminal FLAG-tagged extracellular region/domain deletion variant of human ROBO4 consisting of an amino acid sequence of amino acid Nos. 46 to 1007 of SEQ ID NO: 2.

SEQ ID NO: 7: Nucleotide sequence encoding the amino acid sequence of an N-terminal FLAG-tagged extracellular region/domain deletion variant of human ROBO4 consisting of an amino acid sequence of amino acid Nos. 132 to 1007 of SEQ ID NO: 2.

SEQ ID NO: 8: Amino acid sequence of an N-terminal FLAG-tagged extracellular region/domain deletion variant of human ROBO4 consisting of an amino acid sequence of amino acid Nos. 132 to 1007 of SEQ ID NO: 2

SEQ ID NO: 9: Nucleotide sequence encoding the amino acid sequence of an N-terminal FLAG-tagged extracellular region/domain deletion variant of human ROBO4 consisting of an amino acid sequence of amino acid Nos. 210 to 1007 of SEQ ID NO: 2.

SEQ ID NO: 10: Amino acid sequence of an N-terminal FLAG-tagged extracellular region/domain deletion variant of human ROBO4 consisting of an amino acid sequence of amino acid Nos. 210 to 1007 of SEQ ID NO: 2.

SEQ ID NO: 11: Nucleotide sequence encoding the amino acid sequence of an N-terminal FLAG-tagged extracellular region/domain deletion variant of human ROBO4 consisting of an amino acid sequence of amino acid Nos. 225 to 1007 of SEQ ID NO: 2.

SEQ ID NO: 12: Amino acid sequence of an N-terminal FLAG-tagged extracellular region/domain deletion variant of human ROBO4 consisting of an amino acid sequence of amino acid Nos. 225 to 1007 of SEQ ID NO: 2.

SEQ ID NO: 13: Nucleotide sequence encoding the amino acid sequence of an N-terminal FLAG-tagged extracellular region/domain deletion variant of human ROBO4 consisting of an amino acid sequence of amino acid Nos. 341 to 1007 of SEQ ID NO: 2.

SEQ ID NO: 14: Amino acid sequence of an N-terminal FLAG-tagged extracellular region/domain deletion variant of human ROBO4 consisting of an amino acid sequence of amino acid Nos. 341 to 1007 of SEQ ID NO: 2.

SEQ ID NO: 15: Nucleotide sequence of mouse ROBO4 cDNA.

SEQ ID NO: 16: Amino acid sequence of mouse ROBO4.

SEQ ID NO: 17: Nucleotide sequence of rat ROBO4 cDNA.

SEQ ID NO: 18: Amino acid sequence of rat ROBO4.

SEQ ID NO: 19: Nucleotide sequence of monkey ROBO4 cDNA1.

SEQ ID NO: 20: Monkey ROBO4 amino acid sequence 1.

SEQ ID NO: 21: Nucleotide sequence of monkey ROBO4 cDNA2.

SEQ ID NO: 22: Monkey ROBO4 amino acid sequence 2.

SEQ ID NO: 23: Nucleotide sequence of human ROBO1 cDNA.

SEQ ID NO: 24: Amino acid sequence of human ROBO1.

SEQ ID NO: 25: Nucleotide sequence of human ROBO2 cDNA.

SEQ ID NO: 26: Amino acid sequence of human ROBO2.

SEQ ID NO: 27: Nucleotide sequence of human ROBO3 cDNA.

SEQ ID NO: 28: Amino acid sequence of human ROBO4.

SEQ ID NO: 29: Nucleotide sequence of an IL-8 promoter region.

SEQ ID NO: 30: Nucleotide sequence of cDNA encoding MAb1 heavy chain variable region (FIG. 15).

SEQ ID NO: 31: Amino acid sequence of MAb1 heavy chain variable region (FIG. 16).

SEQ ID NO: 32: Nucleotide sequence of cDNA encoding MAb1 light chain variable region (FIG. 17).

SEQ ID NO: 33: Amino acid sequence of MAb1 light chain variable region (FIG. 18).

SEQ ID NO: 34: Nucleotide sequence comprising cDNA encoding the amino acids of human κ chain secretory signal and human κ chain constant region.

SEQ ID NO: 35: Nucleotide sequence comprising cDNA encoding the amino acids of human heavy chain signal sequence and human IgG1 constant region.

SEQ ID NO: 36: Nucleotide sequence comprising cDNA encoding the amino acids of human heavy chain signal sequence and human IgG2 constant region.

SEQ ID NO: 37: Nucleotide sequence of cDNA encoding cMAb1 light chain (FIG. 19).

SEQ ID NO: 38: Amino acid sequence of cMAb1 light chain (FIG. 20).

SEQ ID NO: 39: Nucleotide sequence of cDNA encoding cMAb1-1 heavy chain (FIG. 21).

SEQ ID NO: 40: Amino acid sequence of cMAb1-1 heavy chain (FIG. 22).

SEQ ID NO: 41: Nucleotide sequence of cDNA encoding cMAb1-2 heavy chain (FIG. 23).

SEQ ID NO: 42: Amino acid sequence of cMAb1-2 heavy chain (FIG. 24).

SEQ ID NO: 43: Nucleotide sequence encoding the amino acid sequence of MAb1 heavy chain CDRH1.

SEQ ID NO: 44: Amino acid sequence of MAb1 heavy chain CDRH1 (FIG. 25).

SEQ ID NO: 45: Nucleotide sequence encoding the amino acid sequence of MAb1 heavy chain CDRH2.

SEQ ID NO: 46: Amino acid sequence of MAb1 heavy chain CDRH2 (FIG. 26).

SEQ ID NO: 47: Nucleotide sequence encoding the amino acid sequence of MAb1 heavy chain CDRH3.

SEQ ID NO: 48: Amino acid sequence of MAb1 heavy chain CDRH3 (FIG. 27).

SEQ ID NO: 49: Nucleotide sequence encoding the amino acid sequence of MAb1 light chain CDRL1.

SEQ ID NO: 50: Amino acid sequence of MAb1 light chain CDRL1 (FIG. 28).

SEQ ID NO: 51: Nucleotide sequence encoding the amino acid sequence of MAb1 light chain CDRL2.

SEQ ID NO: 52: Amino acid sequence of MAb1 light chain CDRL2 (FIG. 29).

SEQ ID NO: 53: Nucleotide sequence encoding the amino acid sequence of MAb1 light chain CDRL3.

SEQ ID NO: 54: Amino acid sequence of MAb1 light chain CDRL3 (FIG. 30).

SEQ ID NO: 55: Nucleotide sequence of cDNA encoding hMAb1-H1-type heavy chain (FIG. 31).

SEQ ID NO: 56: Amino acid sequence of hMAb1-H1-type heavy chain (FIG. 32).

SEQ ID NO: 57: Nucleotide sequence of cDNA encoding hMAb1-H2-type heavy chain (FIG. 33).

SEQ ID NO: 58: Amino acid sequence of hMAb1-H2-type heavy chain (FIG. 34).

SEQ ID NO: 59: Nucleotide sequence of cDNA encoding hMAb1-H3-type heavy chain (FIG. 35).

SEQ ID NO: 60: Amino acid sequence of hMAb1-H3-type heavy chain (FIG. 36).

SEQ ID NO: 61: Nucleotide sequence of cDNA encoding hMAb1-H4-type heavy chain (FIG. 37).

SEQ ID NO: 62: Amino acid sequence of hMAb1-H4-type heavy chain (FIG. 38).

SEQ ID NO: 63: Nucleotide sequence of cDNA encoding hMAb1-L1-type light chain (FIG. 39).

SEQ ID NO: 64: Amino acid sequence of hMAb1-L1-type heavy chain (FIG. 40).

SEQ ID NO: 65: Nucleotide sequence of cDNA encoding hMAb1-L2-type heavy chain (FIG. 41).

SEQ ID NO: 66: Amino acid sequence of hMAb1-L2-type heavy chain (FIG. 42).

SEQ ID NO: 67: CDRH1 of hMAb1-H2 or hMAb1-H4-type heavy chain (FIG. 43).

SEQ ID NO: 68: CDRH2 of hMAb1-H2 or hMAb1-H4-type heavy chain (FIG. 44).

SEQ ID NO: 69: CDRH3 of hMAb1-H2 or hMAb1-H4-type heavy chain (FIG. 45).

SEQ ID NO: 70: CDRL1 of hMAb1-L2-type light chain (FIG. 46).

SEQ ID NO: 71: CDRL2 of hMAb1-L2-type light chain (FIG. 47).

SEQ ID NO: 72: CDRL3 of hMAb1-L2-type light chain (FIG. 48).

We claim:
1. An antibody or antigen binding fragment thereof comprising any one of the following combinations of a heavy chain and a light chain:
   a) a heavy chain comprising amino acid Nos. 20 to 463 of SEQ ID NO: 58 and a light chain comprising amino acid Nos. 21 to 239 of SEQ ID NO: 64 (H-1140), said heavy chain optionally lacking one to five carboxyl-terminal amino acids,
   b) a heavy chain comprising amino acid Nos. 20 to 463 of SEQ ID NO: 58 and a light chain comprising amino acid Nos. 21 to 239 of SEQ ID NO: 66 (H-1143), said heavy chain optionally lacking one to five carboxyl-terminal amino acids,
   c) a heavy chain comprising amino acid Nos. 20 to 463 of SEQ ID NO: 62 and a light chain comprising amino acid Nos. 21 to 239 of SEQ ID NO: 66 (H-2143), said heavy chain optionally lacking one to five carboxyl-terminal amino acids,
   d) a heavy chain comprising amino acid Nos. 20 to 463 of SEQ ID NO: 62 and a light chain comprising amino acid Nos. 21 to 239 of SEQ ID NO: 64 (H-2140), said heavy chain optionally lacking one to five carboxyl-terminal amino acids,
   e) a heavy chain comprising amino acid Nos. 20 to 463 of SEQ ID NO: 56 and a light chain comprising amino acid Nos. 21 to 239 of SEQ ID NO: 64 (H-1040), said heavy chain optionally lacking one to five carboxyl-terminal amino acids, or
   f) a heavy chain comprising amino acid Nos. 20 to 463 of SEQ ID NO: 60 and a light chain comprising amino acid Nos. 21 to 239 of SEQ ID NO: 64 (H-2040), said heavy chain optionally lacking one to five carboxyl-terminal amino acids.

2. The antibody according to claim 1, wherein said antibody lacks one to five carboxyl-terminal amino acid(s) of said heavy chain.

3. A pharmaceutical composition comprising an antibody or an antigen binding fragment thereof comprising any one of the following combinations of a heavy chain and a light chain:
   a) a heavy chain comprising amino acid Nos. 20 to 463 of SEQ ID NO: 58 and a light chain comprising amino acid Nos. 21 to 239 of SEQ ID NO: 64 (H-1140), said heavy chain optionally lacking one to five carboxyl-terminal amino acids,
   b) a heavy chain comprising amino acid Nos. 20 to 463 of SEQ ID NO: 58 and a light chain comprising amino acid Nos. 21 to 239 of SEQ ID NO: 66 (H-1143), said heavy chain optionally lacking one to five carboxyl-terminal amino acids,
   c) a heavy chain comprising amino acid Nos. 20 to 463 of SEQ ID NO: 62 and a light chain comprising amino acid Nos. 21 to 239 of SEQ ID NO: 66 (H-2143), said heavy chain optionally lacking one to five carboxyl-terminal amino acids,
   d) a heavy chain comprising amino acid Nos. 20 to 463 of SEQ ID NO: 62 and a light chain comprising amino acid Nos. 21 to 239 of SEQ ID NO: 64 (H-2140), said heavy chain optionally lacking one to five carboxyl-terminal amino acids,
   e) a heavy chain comprising amino acid Nos. 20 to 463 of SEQ ID NO: 56 and a light chain comprising amino acid Nos. 21 to 239 of SEQ ID NO: 64 (H-1040), said heavy chain optionally lacking one to five carboxyl-terminal amino acids, or
   f) a heavy chain comprising amino acid Nos. 20 to 463 of SEQ ID NO: 60 and a light chain comprising amino acid Nos. 21 to 239 of SEQ ID NO: 64 (H-2040), said heavy chain optionally lacking one to five carboxyl-terminal amino acids.

4. A method for treating an angiogenic disease comprising administering to a subject in need thereof an effective amount of an antibody or an antigen binding fragment thereof according to claim 1 or administering an effective amount of a composition comprising said antibody to said subject.

5. The method according to claim 4, wherein said angiogenic disease is exudative age-related macular degeneration, diabetic retinopathy, macular edema, retrolental fibroplasia, ocular neovascular disease, proliferative retinopathy, neovascular glaucoma, or immune rejection of a corneal tissue transplant.

6. The antibody or antigen binding fragment thereof according to claim 1, said antibody or antigen binding fragment thereof comprising a heavy chain comprising amino acid Nos. 20 to 463 of SEQ ID NO: 58 and a light chain comprising amino acid Nos. 21 to 239 of SEQ ID NO: 64 (H-1140).

7. The antibody or antigen binding fragment thereof according to claim 1, said antibody or antigen binding fragment thereof comprising a heavy chain comprising amino acid Nos. 20 to 463 of SEQ ID NO: 58 and a light chain comprising amino acid Nos. 21 to 239 of SEQ ID NO: 66 (H-1143).

8. The antibody or antigen binding fragment thereof according to claim 1, said antibody or antigen binding fragment thereof comprising a heavy chain comprising amino acid Nos. 20 to 463 of SEQ ID NO: 62 and a light chain comprising amino acid Nos. 21 to 239 of SEQ ID NO: 64 (H-2140).

9. The antibody or antigen binding fragment thereof according to claim 1, said antibody or antigen binding fragment thereof comprising a heavy chain comprising amino acid Nos. 20 to 463 of SEQ ID NO: 56 and a light chain comprising amino acid Nos. 21 to 239 of SEQ ID NO: 64 (H-1040).

10. The antibody or antigen binding fragment thereof according to claim 1, said antibody or antigen binding fragment thereof comprising a heavy chain comprising amino acid Nos. 20 to 463 of SEQ ID NO: 60 and a light chain comprising amino acid Nos. 21 to 239 of SEQ ID NO: 64 (H-2040).

11. The pharmaceutical composition according to claim 3, said antibody or antigen binding fragment thereof comprising a heavy chain comprising amino acid Nos. 20 to 463 of SEQ ID NO: 58 and a light chain comprising amino acid Nos. 21 to 239 of SEQ ID NO: 64 (H-1140).

12. The pharmaceutical composition according to claim 3, said antibody or antigen binding fragment thereof comprising a heavy chain comprising amino acid Nos. 20 to 463 of SEQ ID NO: 58 and a light chain comprising amino acid Nos. 21 to 239 of SEQ ID NO: 66 (H-1143).

13. The pharmaceutical composition according to claim 3, said antibody or antigen binding fragment thereof comprising a heavy chain comprising amino acid Nos. 20 to 463 of SEQ ID NO: 62 and a light chain comprising amino acid Nos. 21 to 239 of SEQ ID NO: 66 (H-2143).

14. The pharmaceutical composition according to claim 3, said antibody or antigen binding fragment thereof comprising a heavy chain comprising amino acid Nos. 20 to 463 of SEQ ID NO: 62 and a light chain comprising amino acid Nos. 21 to 239 of SEQ ID NO: 64 (H-2140).

15. The pharmaceutical composition according to claim 3, said antibody or antigen binding fragment thereof comprising a heavy chain comprising amino acid Nos. 20 to 463 of SEQ ID NO: 56 and a light chain comprising amino acid Nos. 21 to 239 of SEQ ID NO: 64 (H-1040).

16. The antibody or antigen binding fragment thereof according to claim 1, said antibody or antigen binding fragment thereof comprising a heavy chain comprising amino acid Nos. 20 to 463 of SEQ ID NO: 58 and a light chain comprising amino acid Nos. 21 to 239 of SEQ ID NO: 64 (H-1140) and said heavy chain lacking one to five carboxyl-terminal amino acids.

17. The antibody or antigen binding fragment thereof according to claim 1, said antibody or antigen binding fragment thereof comprising a heavy chain comprising amino acid Nos. 20 to 463 of SEQ ID NO: 58 and a light chain comprising amino acid Nos. 21 to 239 of SEQ ID NO: 66 (H-1143) and said heavy chain lacking one to five carboxyl-terminal amino acids.

18. The antibody or antigen binding fragment thereof according to claim 1, said antibody or antigen binding fragment thereof comprising a heavy chain comprising amino acid Nos. 20 to 463 of SEQ ID NO: 62 and a light chain comprising amino acid Nos. 21 to 239 of SEQ ID NO: 66 (H-2143) and said heavy chain lacking one to five carboxyl-terminal amino acids.

19. The antibody or antigen binding fragment thereof according to claim 1, said antibody or antigen binding fragment thereof comprising a heavy chain comprising amino acid Nos. 20 to 463 of SEQ ID NO: 62 and a light chain comprising amino acid Nos. 21 to 239 of SEQ ID NO: 64 (H-2140) and said heavy chain lacking one to five carboxyl-terminal amino acids.

20. The antibody or antigen binding fragment thereof according to claim 1, said antibody or antigen binding fragment thereof comprising a heavy chain comprising amino acid Nos. 20 to 463 of SEQ ID NO: 56 and a light chain comprising amino acid Nos. 21 to 239 of SEQ ID NO: 64 (H-1040) and said heavy chain lacking one to five carboxyl-terminal amino acids.

21. The antibody or antigen binding fragment thereof according to claim 1, said antibody or antigen binding fragment thereof comprising a heavy chain comprising amino acid Nos. 20 to 463 of SEQ ID NO: 60 and a light chain comprising amino acid Nos. 21 to 239 of SEQ ID NO: 64 (H-2040) and said heavy chain lacking one to five carboxyl-terminal amino acids.

22. The pharmaceutical composition according to claim 3, said antibody or antigen binding fragment thereof comprising a heavy chain comprising amino acid Nos. 20 to 463 of SEQ ID NO: 58 and a light chain comprising amino acid Nos. 21 to 239 of SEQ ID NO: 64 (H-1140) and said heavy chain lacking one to five carboxyl-terminal amino acids.

23. The pharmaceutical composition according to claim 3, said antibody or antigen binding fragment thereof comprising a heavy chain comprising amino acid Nos. 20 to 463 of SEQ ID NO: 58 and a light chain comprising amino acid Nos. 21 to 239 of SEQ ID NO: 66 (H-1143) and said heavy chain lacking one to five carboxyl-terminal amino acids.

24. The pharmaceutical composition according to claim 3, said antibody or antigen binding fragment thereof comprising a heavy chain comprising amino acid Nos. 20 to 463 of SEQ ID NO: 62 and a light chain comprising amino acid Nos. 21 to 239 of SEQ ID NO: 66 (H-2143) and said heavy chain lacking one to five carboxyl-terminal amino acids.

25. The pharmaceutical composition according to claim 3, said antibody or antigen binding fragment thereof comprising a heavy chain comprising amino acid Nos. 20 to 463 of SEQ ID NO: 62 and a light chain comprising amino acid Nos. 21 to 239 of SEQ ID NO: 64 (H-2140) and said heavy chain lacking one to five carboxyl-terminal amino acids.

26. The pharmaceutical composition according to claim 3, said antibody or antigen binding fragment thereof comprising a heavy chain comprising amino acid Nos. 20 to 463 of SEQ ID NO: 56 and a light chain comprising amino acid Nos. 21 to 239 of SEQ ID NO: 64 (H-1040) and said heavy chain lacking one to five carboxyl-terminal amino acids.

27. An antibody or antigen binding fragment thereof comprising any one of the following combinations of a heavy chain variable region and a light chain variable region:
  1) a heavy chain variable region comprising amino acid Nos. 20 to 137 of SEQ ID NO: 58 and a light chain variable region comprising amino acid Nos. 21 to 134 of SEQ ID NO: 64,
  2) a heavy chain variable region comprising amino acid Nos. 20 to 137 of SEQ ID NO: 58 and a light chain variable region comprising amino acid Nos. 21 to 134 of SEQ ID NO: 66,
  3) a heavy chain variable region comprising amino acid Nos. 20 to 137 of SEQ ID NO: 62 and a light chain variable region comprising amino acid Nos. 21 to 134 of SEQ ID NO: 66,
  4) a heavy chain variable region comprising amino acid Nos. 20 to 137 of SEQ ID NO: 62 and a light chain variable region comprising amino acid Nos. 21 to 134 of SEQ ID NO: 64,
  5) a heavy chain variable region comprising amino acid Nos. 20 to 137 of SEQ ID NO: 56 and a light chain variable region comprising amino acid Nos. 21 to 134 of SEQ ID NO: 64, or
  6) a heavy chain variable region comprising amino acid Nos. 20 to 137 of SEQ ID NO: 60 and a light chain variable region comprising amino acid Nos. 21 to 134 of SEQ ID NO: 64.

28. The antibody or antigen binding fragment of claim 27, said antibody or antigen binding fragment comprising a heavy chain variable region comprising amino acid Nos. 20 to 137 of SEQ ID NO: 58 and a light chain variable region comprising amino acid Nos. 21 to 134 of SEQ ID NO: 64.

29. A pharmaceutical composition comprising an antibody or an antigen binding fragment thereof according to claim 27.

30. A pharmaceutical composition comprising an antibody or an antigen binding fragment thereof according to claim 28.

31. The antibody or antigen binding fragment thereof according to claim 1, said antibody or antigen binding fragment thereof comprising a heavy chain comprising amino acid Nos. 20 to 463 of SEQ ID NO: 62 and a light chain comprising amino acid Nos. 21 to 239 of SEQ ID NO: 66 (H-2143).

32. The pharmaceutical composition according to claim 3, said antibody or antigen binding fragment thereof comprising a heavy chain comprising amino acid Nos. 20 to 463 of SEQ ID NO: 60 and a light chain comprising amino acid Nos. 21 to 239 of SEQ ID NO: 64 (H-2040).

33. The pharmaceutical composition according to claim 3, said antibody or antigen binding fragment thereof comprising a heavy chain comprising amino acid Nos. 20 to 463 of SEQ ID NO: 60 and a light chain comprising amino acid Nos. 21 to 239 of SEQ ID NO: 64 (H-2040) and said heavy chain lacking one to five carboxyl-terminal amino acids.

34. The antibody or antigen binding fragment of claim 27, said antibody or antigen binding fragment comprising a heavy chain variable region comprising amino acid Nos. 20 to 137 of SEQ ID NO: 58 and a light chain variable region comprising amino acid Nos. 21 to 134 of SEQ ID NO: 66.

35. The antibody or antigen binding fragment of claim 27, said antibody or antigen binding fragment comprising a heavy chain variable region comprising amino acid Nos. 20 to 137 of SEQ ID NO: 62 and a light chain variable region comprising amino acid Nos. 21 to 134 of SEQ ID NO: 66.

36. The antibody or antigen binding fragment of claim 27, said antibody or antigen binding fragment comprising a heavy chain variable region comprising amino acid Nos. 20 to 137 of SEQ ID NO: 62 and a light chain variable region comprising amino acid Nos. 21 to 134 of SEQ ID NO: 64.

37. The antibody or antigen binding fragment of claim 27, said antibody or antigen binding fragment comprising a heavy chain variable region comprising amino acid Nos. 20 to 137 of SEQ ID NO: 56 and a light chain variable region comprising amino acid Nos. 21 to 134 of SEQ ID NO: 64.

38. The antibody or antigen binding fragment of claim 27, said antibody or antigen binding fragment comprising a heavy chain variable region comprising amino acid Nos. 20 to 137 of SEQ ID NO: 60 and a light chain variable region comprising amino acid Nos. 21 to 134 of SEQ ID NO: 64.

* * * * *

UNITED STATES PATENT AND TRADEMARK OFFICE
CERTIFICATE OF CORRECTION

PATENT NO. : 9,562,096 B2  
APPLICATION NO. : 14/966292  
DATED : February 7, 2017  
INVENTOR(S) : Yoshitaka Isumi et al.

Page 1 of 1

It is certified that error appears in the above-identified patent and that said Letters Patent is hereby corrected as shown below:

Column 18,  
Line 23, "3 to 8 adding" should read --3 to 8 µm, adding--.

Column 22,  
Line 14, "61-'71;" should read --61-71;--.

Signed and Sealed this  
Nineteenth Day of September, 2017

Joseph Matal  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 121

<210> SEQ ID NO 1
<211> LENGTH: 3024
<212> TYPE: DNA
<213> ORGANISM: Homo sapiens

<400> SEQUENCE: 1
atgggctctg gaggagacag cctcctgggg ggcaggggtt ccctgcctct gctgctcctg      60
ctcatcatgg gaggcatggc tcaggactcc ccgccccaga tcctagtcca cccccaggac     120
cagctgttcc agggccctgg ccctgccagg atgagctgcc aagcctcagg ccagccacct     180
cccaccatcc gctggttgct gaatgggcag cccctgagca tggtgccccc agacccacac     240
cacctcctgc ctgatgggac ccttctgctg ctacagcccc ctgcccgggg acatgccac     300 gatggccagg ccctgtccac agacctgggt gtctacacat gtgaggccag caaccggctt     360
ggcacggcag tcagcagagg cgctcggctg tctgtggctg tcctccggga ggatttccag     420
atccagcctc gggacatggt ggctgtggtg ggtgagcagt ttactctgga atgtgggccg     480 ccctgggcc acccagagcc cacagtctca tggtggaaag atgggaaacc cctggccctc     540
cagcccggaa ggcacacagt gtccgggggg tccctgctga tggcaagagc agagaagagt     600
gacgaaggga cctacatgtg tgtggccacc aacagcgcag acatagggga gagccgcgca     660
gcccgggttt ccatccagga gccccaggac tacacggagc ctgtggagct tctggctgtg     720
cgaattcagc tggaaaatgt gacactgctg aacccggatc ctgcagaggg ccccaagcct     780
agaccggcgg tgtggctcag ctggaaggtc agtgccctg ctgcgcctgc ccaatcttac     840
acggccttgt tcaggaccca gactgccccg ggaggccagg agctccgtg ggcagaggag     900 ctgctggccg gctggcagag cgcagagctt ggaggcctcc actggggcca agactacgag     960
ttcaaagtga gaccatcctc tggccgggct cgaggccctg acagcaacgt gctgctcctg    1020
aggctgccgg aaaaagtgcc cagtgcccca cctcaggaag tgactctaaa gcctggcaat    1080
ggcactgtct ttgtgagctg ggtcccacca cctgctgaaa accacaatgg catcatccgt    1140
```

```
ggctaccagg tctggagcct gggcaacaca tcactgccac cagccaactg gactgtagtt    1200
ggtgagcaga cccagctgga aatcgccacc catatgccag gctcctactg cgtgcaagtg    1260
gctgcagtca ctggtgctgg agctggggag cccagtagac ctgtctgcct cctttttagag   1320 caggccatgg agcgagccac ccaagaaccc agtgagcatg gtccctggac cctggagcag    1380
ctgagggcta ccttgaagcg gcctgaggtc attgccacct gcggtgttgc actctggctg    1440
ctgcttctgg gcaccgccgt gtgtatccac cgccggcgcc gagctagggt gcacctgggc    1500
ccaggtctgt acagatatac cagtgaggat gccatcctaa aacacaggat ggatcacagt    1560
gactcccagt ggttggcaga cacttggcgt tccacctctg gctctcggga cctgagcagc    1620
agcagcagcc tcagcagtcg gctgggggcg gatgcccggg acccactaga ctgtcgtcgc    1680
tccttgctct cctgggactc ccgaagcccc ggcgtgcccc tgcttccaga caccagcact    1740 tttatggct ccctcatcgc tgagctgccc tccagtaccc cagccaggcc aagtccccag     1800
gtcccagctg tcaggcgcct cccacccag ctggcccagc tctccagccc ctgttccagc     1860
tcagacagcc tctgcagccg caggggactc tcttctcccc gcttgtctct ggcccctgca    1920
gaggcttgga aggccaaaaa gaagcaggag ctgcagcatg ccaacagttc cccactgctc    1980
cggggcagcc actccttgga gctccgggcc tgtgagttag gaaatagagg ttccaagaac    2040
ctttcccaaa gcccaggagc tgtgcccaa gctctggttg cctggcgggc cctgggaccg     2100
aaactcctca gctcctcaaa tgagctggtt actcgtcatc tccctccagc accctctttt    2160
cctcatgaaa ctcccccaac tcagagtcaa cagacccagc ctccggtggc accacaggct    2220
ccctcctcca tcctgctgcc agcagccccc atccccatcc ttagccctg cagtcccct      2280 agcccccagg cctcttccct ctctggcccc agcccagctt ccagtcgcct gtccagctcc    2340
tcactgtcat ccctggggga ggatcaagac agcgtgctga cccctgagga ggtagccctg    2400
tgcttggaac tcagtgaggg tgaggagact cccaggaaca gcgtctctcc catgccaagg    2460
gctccttcac cccccaccac ctatgggtac atcagcgtcc caacagcctc agagttcacg    2520
gacatgggca ggactggagg aggggtgggg cccaaggggg gagtcttgct gtgcccacct    2580
cggccctgcc tcaccccac ccccagcgag ggctccttag ccaatggttg gggctcagcc     2640
tctgaggaca atgccgccag cgccagagcc agccttgtca gctcctccga tggctccttc    2700
ctcgctgatg ctcactttgc ccgggccctg gcagtggctg tggatagctt tggttctcgt    2760
ctagagccca gggaggcaga ctgcgtcttc atagatgcct catcacctcc ctccccacgg    2820
gatgagatct tcctgacccc caacctctcc ctgcccctgt gggagtggag gccagactgg    2880
ttggaagaca tggaggtcag ccacacccag cggctgggaa gggggatgcc tccctggccc    2940
cctgactctc agatctcttc ccagagaagt cagctccact gtcgtatgcc caaggctggt    3000
gcttctcctg tagattactc ctga                                           3024
```

<210> SEQ ID NO 2
<211> LENGTH: 1007
<212> TYPE: PRT
<213> ORGANISM: Homo sapiens

<400> SEQUENCE: 2

Met Gly Ser Gly Gly Asp Ser Leu Leu Gly Gly Arg Gly Ser Leu Pro
1               5                   10                  15

Leu Leu Leu Leu Leu Ile Met Gly Gly Met Ala Gln Asp Ser Pro
            20                  25                  30

Gln Ile Leu Val His Pro Gln Asp Gln Leu Phe Gln Gly Pro Gly Pro

```
                35                  40                  45
Ala Arg Met Ser Cys Gln Ala Ser Gly Gln Pro Pro Thr Ile Arg
 50                  55                  60

Trp Leu Leu Asn Gly Gln Pro Leu Ser Met Val Pro Pro Asp Pro His
 65                  70                  75                  80

His Leu Leu Pro Asp Gly Thr Leu Leu Leu Gln Pro Pro Ala Arg
                 85                  90                  95

Gly His Ala His Asp Gly Gln Ala Leu Ser Thr Asp Leu Gly Val Tyr
                100                 105                 110

Thr Cys Glu Ala Ser Asn Arg Leu Gly Thr Ala Val Ser Arg Gly Ala
                115                 120                 125

Arg Leu Ser Val Ala Val Leu Arg Glu Asp Phe Gln Ile Gln Pro Arg
130                 135                 140

Asp Met Val Ala Val Val Gly Glu Gln Phe Thr Leu Glu Cys Gly Pro
145                 150                 155                 160

Pro Trp Gly His Pro Glu Pro Thr Val Ser Trp Trp Lys Asp Gly Lys
                165                 170                 175

Pro Leu Ala Leu Gln Pro Gly Arg His Thr Val Ser Gly Gly Ser Leu
                180                 185                 190

Leu Met Ala Arg Ala Glu Lys Ser Asp Glu Gly Thr Tyr Met Cys Val
                195                 200                 205

Ala Thr Asn Ser Ala Gly His Arg Glu Ser Arg Ala Ala Arg Val Ser
210                 215                 220

Ile Gln Glu Pro Gln Asp Tyr Thr Glu Pro Val Glu Leu Leu Ala Val
225                 230                 235                 240

Arg Ile Gln Leu Glu Asn Val Thr Leu Leu Asn Pro Asp Pro Ala Glu
                245                 250                 255

Gly Pro Lys Pro Arg Pro Ala Val Trp Leu Ser Trp Lys Val Ser Gly
                260                 265                 270

Pro Ala Ala Pro Ala Gln Ser Tyr Thr Ala Leu Phe Arg Thr Gln Thr
                275                 280                 285

Ala Pro Gly Gly Gln Gly Ala Pro Trp Ala Glu Leu Leu Ala Gly
                290                 295                 300

Trp Gln Ser Ala Glu Leu Gly Gly Leu His Trp Gly Gln Asp Tyr Glu
305                 310                 315                 320

Phe Lys Val Arg Pro Ser Ser Gly Arg Ala Arg Gly Pro Asp Ser Asn
                325                 330                 335

Val Leu Leu Leu Arg Leu Pro Glu Lys Val Pro Ser Ala Pro Pro Gln
                340                 345                 350

Glu Val Thr Leu Lys Pro Gly Asn Gly Thr Val Phe Val Ser Trp Val
                355                 360                 365

Pro Pro Pro Ala Glu Asn His Asn Gly Ile Ile Arg Gly Tyr Gln Val
370                 375                 380

Trp Ser Leu Gly Asn Thr Ser Leu Pro Pro Ala Asn Trp Thr Val Val
385                 390                 395                 400

Gly Glu Gln Thr Gln Leu Glu Ile Ala Thr His Met Pro Gly Ser Tyr
                405                 410                 415

Cys Val Gln Val Ala Ala Val Thr Gly Ala Gly Ala Gly Glu Pro Ser
                420                 425                 430

Arg Pro Val Cys Leu Leu Leu Glu Gln Ala Met Glu Arg Ala Thr Gln
                435                 440                 445

Glu Pro Ser Glu His Gly Pro Trp Thr Leu Glu Gln Leu Arg Ala Thr
                450                 455                 460
```

```
Leu Lys Arg Pro Glu Val Ile Ala Thr Cys Gly Val Ala Leu Trp Leu
465                 470                 475                 480

Leu Leu Leu Gly Thr Ala Val Cys Ile His Arg Arg Arg Arg Ala Arg
                485                 490                 495

Val His Leu Gly Pro Gly Leu Tyr Arg Tyr Thr Ser Glu Asp Ala Ile
                500                 505                 510

Leu Lys His Arg Met Asp His Ser Asp Ser Gln Trp Leu Ala Asp Thr
                515                 520                 525

Trp Arg Ser Thr Ser Gly Ser Arg Asp Leu Ser Ser Ser Ser Ser Leu
                530                 535                 540

Ser Ser Arg Leu Gly Ala Asp Ala Arg Asp Pro Leu Asp Cys Arg Arg
545                 550                 555                 560

Ser Leu Leu Ser Trp Asp Ser Arg Ser Pro Gly Val Pro Leu Leu Pro
                565                 570                 575

Asp Thr Ser Thr Phe Tyr Gly Ser Leu Ile Ala Glu Leu Pro Ser Ser
                580                 585                 590

Thr Pro Ala Arg Pro Ser Pro Gln Val Pro Ala Val Arg Arg Leu Pro
                595                 600                 605

Pro Gln Leu Ala Gln Leu Ser Ser Pro Cys Ser Ser Ser Asp Ser Leu
                610                 615                 620

Cys Ser Arg Arg Gly Leu Ser Ser Pro Arg Leu Ser Leu Ala Pro Ala
625                 630                 635                 640

Glu Ala Trp Lys Ala Lys Lys Gln Glu Leu Gln His Ala Asn Ser
                645                 650                 655

Ser Pro Leu Leu Arg Gly Ser His Ser Leu Glu Leu Arg Ala Cys Glu
                660                 665                 670

Leu Gly Asn Arg Gly Ser Lys Asn Leu Ser Gln Ser Pro Gly Ala Val
                675                 680                 685

Pro Gln Ala Leu Val Ala Trp Arg Ala Leu Gly Pro Lys Leu Leu Ser
                690                 695                 700

Ser Ser Asn Glu Leu Val Thr Arg His Leu Pro Pro Ala Pro Leu Phe
705                 710                 715                 720

Pro His Glu Thr Pro Thr Gln Ser Gln Thr Gln Pro Pro Val
                725                 730                 735

Ala Pro Gln Ala Pro Ser Ser Ile Leu Leu Pro Ala Ala Pro Ile Pro
                740                 745                 750

Ile Leu Ser Pro Cys Ser Pro Pro Ser Pro Gln Ala Ser Ser Leu Ser
                755                 760                 765

Gly Pro Ser Pro Ala Ser Ser Arg Leu Ser Ser Ser Ser Leu Ser Ser
                770                 775                 780

Leu Gly Glu Asp Gln Asp Ser Val Leu Thr Pro Glu Glu Val Ala Leu
785                 790                 795                 800

Cys Leu Glu Leu Ser Glu Gly Glu Glu Thr Pro Arg Asn Ser Val Ser
                805                 810                 815

Pro Met Pro Arg Ala Pro Ser Pro Pro Thr Thr Tyr Gly Tyr Ile Ser
                820                 825                 830

Val Pro Thr Ala Ser Glu Phe Thr Asp Met Gly Arg Thr Gly Gly Gly
                835                 840                 845

Val Gly Pro Lys Gly Gly Val Leu Leu Cys Pro Pro Arg Pro Cys Leu
                850                 855                 860

Thr Pro Thr Pro Ser Glu Gly Ser Leu Ala Asn Gly Trp Gly Ser Ala
865                 870                 875                 880
```

```
Ser Glu Asp Asn Ala Ala Ser Ala Arg Ala Ser Leu Val Ser Ser
            885                 890                 895

Asp Gly Ser Phe Leu Ala Asp Ala His Phe Ala Arg Ala Leu Ala Val
        900                 905                 910

Ala Val Asp Ser Phe Gly Phe Gly Leu Glu Pro Arg Glu Ala Asp Cys
    915                 920                 925

Val Phe Ile Asp Ala Ser Ser Pro Ser Pro Arg Asp Glu Ile Phe
930                 935                 940

Leu Thr Pro Asn Leu Ser Leu Pro Leu Trp Glu Trp Arg Pro Asp Trp
945                 950                 955                 960

Leu Glu Asp Met Glu Val Ser His Thr Gln Arg Leu Gly Arg Gly Met
            965                 970                 975

Pro Pro Trp Pro Pro Asp Ser Gln Ile Ser Ser Gln Arg Ser Gln Leu
        980                 985                 990

His Cys Arg Met Pro Lys Ala Gly  Ala Ser Pro Val Asp Tyr Ser
    995                 1000                1005
```

<210> SEQ ID NO 3
<211> LENGTH: 3045
<212> TYPE: DNA
<213> ORGANISM: Artificial Sequence
<220> FEATURE:
<223> OTHER INFORMATION: FLAG-hROBO4-28

<400> SEQUENCE: 3

```
atgggctctg gaggagacag cctcctcggc ggcagaggtt ccctgcctct gctgctcctg      60
ctcatcatgg gaggcatggc tgattacaag gatgacgacg ataagcagga ctccccgccc     120
cagatcctag tccacccccca ggaccagctg ttccagggcc ctggccctgc aggatgagc     180
tgccaagcct caggccagcc acctcccacc atccgctggt tgctgaatgg cagcccctg      240
agcatggtgc ccccagaccc acaccacctc ctgcctgatg gaccccttct gctgctacag     300
ccccctgccc ggggacatgc ccacgatggc caggccctgt ccacagacct gggtgtctac     360
acatgtgagg ccagcaaccg gcttggcacg gcagtcagca gaggcgctcg gctgtctgtg     420
gctgtcctcc gggaggattt ccagatccag cctcgggaca tggtggctgt ggtgggtgag     480
cagtttactc tggaatgtgg gccgccctgg ggccacccag agcccacagt ctcatggtgg     540
aaagatggga acccctggcc cctccagccc ggaaggcaca cagtgtccgg ggggtccctg     600
ctgatggcaa gagcagagaa gagtgacgaa gggacctaca tgtgtgtggc caccaacagc     660
gcaggacata gggagagccg cgcagcccgg gtttccatcc aggagcccca ggactacacg     720
gagcctgtgg agcttctggc tgtgcgaatt cagctggaaa atgtgacact gctgaacccg     780
gatcctgcag agggccccaa gcctagaccg gcggtgtggc tcagctggaa ggtcagtggc     840
cctgctgcgc tgcccaatc ttacacggcc ttgttcagga cccagactgc cccgggaggc     900
caaggagctc cgtgggcaga ggagctgctg gccggctggc agagcgcaga gcttggaggc     960
ctccactggg gccaagacta cgagttcaaa gtgagaccat cctctggccg gctcgaggc    1020
cctgacagca acgtgctgct cctgaggctg ccggaaaaag tgcccagtgc cccacctcag    1080
gaagtgactc taaagcctgg caatggcact gtctttgtga gctgggtccc accacctgct    1140
gaaaaccaca atggcatcat ccgtggctac caggtctgga gcctgggcaa cacatcactg    1200
ccaccagcca actggactgt agttggtgag cagaccccagc tggaaatcgc caccatatg    1260
ccaggctcct actgcgtgca agtggctgca gtcactggtg ctggagctgg ggagcccagt    1320
agacctgtct gcctcctttt agagcaggcc atggagcgag ccacccaaga acccagtgag    1380
```

```
catggtccct ggaccctgga gcagctgagg gctaccttga agcggcctga ggtcattgcc    1440
acctgcggtg ttgcactctg gctgctgctt ctgggcaccg ccgtgtgtat ccaccgccgg    1500
cgccgagcta gggtgcacct gggcccaggt ctgtacagat ataccagtga ggatgccatc    1560
ctaaaacaca ggatggatca cagtgactcc cagtggttgg cagacacttg gcgttccacc    1620
tctggctctc gggacctgag cagcagcagc agcctcagca gtcggctggg ggcggatgcc    1680
cgggacccac tagactgtcg tcgctccttg ctctcctggg actcccgaag ccccggcgtg    1740
cccctgcttc cagacaccag cacttttat ggctccctca tcgctgagct gccctccagt    1800
accccagcca ggccaagtcc ccaggtccca gctgtcaggc gctcccaccc ccagctggcc    1860
cagctctcca gcccctgttc cagctcagac agcctctgca gccgcagggg actctcttct    1920
ccccgcttgt ctctggcccc tgcagaggct tggaaggcca aaaagaagca ggagctgcag    1980
catgccaaca gttccccact gctccggggc agccactcct ggagctccg ggcctgtgag     2040
ttaggaaata gaggttccaa gaacctttcc caaagcccag gagctgtgcc ccaagctctg    2100
gttgcctggc gggccctggg accgaaactc ctcagctcct caaatgagct ggttactcgt    2160
catctccctc cagcaccct ctttcctcat gaaactcccc caactcagag tcaacagacc      2220
cagcctccgg tggcaccaca ggctccctcc tccatcctgc tgccagcagc cccatcccc     2280
atccttagcc cctgcagtcc ccctagcccc caggcctctt ccctctctgg ccccagccca    2340
gcttccagtc gcctgtccag ctcctcactg tcatccctgg gggaggatca agacagcgtg    2400
ctgaccctg aggaggtagc cctgtgcttg gaactcagtg agggtgagga gactcccagg      2460
aacagcgtct ctcccatgcc aagggctcct tcaccccca ccacctatgg gtacatcagc      2520
gtcccaacag cctcagagtt cacggacatg ggcaggactg aggagggggt ggggcccaag    2580
gggggagtct tgctgtgccc acctcggccc tgcctcaccc ccaccccag cgagggctcc      2640
ttagccaatg gttggggctc agcctctgag gacaatgccg ccagcgccag agccagcctt    2700
gtcagctcct ccgatggctc cttcctcgct gatgctcact ttgcccgggc cctggcagtg    2760
gctgtggata gctttggttt cggtctagag cccaggagg cagactgcgt cttcatagat      2820
gcctcatcac ctccctcccc acgggatgag atcttcctga ccccaacct ctccctgccc      2880
ctgtgggagt ggaggccaga ctggttggaa gacatggagg tcagccacac ccagcggctg    2940
ggaaggggga tgcctccctg gcccctgac tctcagatct cttcccagag aagtcagctc      3000
cactgtcgta tgcccaaggc tggtgcttct cctgtagatt actcc                    3045
```

<210> SEQ ID NO 4
<211> LENGTH: 1015
<212> TYPE: PRT
<213> ORGANISM: Artificial Sequence
<220> FEATURE:
<223> OTHER INFORMATION: FLAG-hROBO4-28aa

<400> SEQUENCE: 4

Met Gly Ser Gly Gly Asp Ser Leu Leu Gly Gly Arg Gly Ser Leu Pro
1               5                   10                  15

Leu Leu Leu Leu Leu Ile Met Gly Gly Met Ala Asp Tyr Lys Asp Asp
            20                  25                  30

Asp Asp Lys Gln Asp Ser Pro Pro Gln Ile Leu Val His Pro Gln Asp
        35                  40                  45

Gln Leu Phe Gln Gly Pro Gly Pro Ala Arg Met Ser Cys Gln Ala Ser
    50                  55                  60

```
Gly Gln Pro Pro Pro Thr Ile Arg Trp Leu Leu Asn Gly Gln Pro Leu
 65                  70                  75                  80

Ser Met Val Pro Asp Pro His His Leu Leu Pro Asp Gly Thr Leu
                 85                  90                  95

Leu Leu Leu Gln Pro Ala Arg Gly His Ala His Asp Gly Gln Ala
            100                 105                 110

Leu Ser Thr Asp Leu Gly Val Tyr Thr Cys Glu Ala Ser Asn Arg Leu
        115                 120                 125

Gly Thr Ala Val Ser Arg Gly Ala Arg Leu Ser Val Ala Val Leu Arg
    130                 135                 140

Glu Asp Phe Gln Ile Gln Pro Arg Asp Met Val Ala Val Val Gly Glu
145                 150                 155                 160

Gln Phe Thr Leu Glu Cys Gly Pro Pro Trp Gly His Pro Glu Pro Thr
                165                 170                 175

Val Ser Trp Trp Lys Asp Gly Lys Pro Leu Ala Leu Gln Pro Gly Arg
            180                 185                 190

His Thr Val Ser Gly Gly Ser Leu Leu Met Ala Arg Ala Glu Lys Ser
        195                 200                 205

Asp Glu Gly Thr Tyr Met Cys Val Ala Thr Asn Ser Ala Gly His Arg
    210                 215                 220

Glu Ser Arg Ala Ala Arg Val Ser Ile Gln Glu Pro Gln Asp Tyr Thr
225                 230                 235                 240

Glu Pro Val Glu Leu Leu Ala Val Arg Ile Gln Leu Glu Asn Val Thr
                245                 250                 255

Leu Leu Asn Pro Asp Pro Ala Glu Gly Pro Lys Pro Arg Pro Ala Val
            260                 265                 270

Trp Leu Ser Trp Lys Val Ser Gly Pro Ala Pro Ala Gln Ser Tyr
    275                 280                 285

Thr Ala Leu Phe Arg Thr Gln Thr Ala Pro Gly Gly Gln Gly Ala Pro
    290                 295                 300

Trp Ala Glu Glu Leu Leu Ala Gly Trp Gln Ser Ala Glu Leu Gly Gly
305                 310                 315                 320

Leu His Trp Gly Gln Asp Tyr Glu Phe Lys Val Arg Pro Ser Ser Gly
                325                 330                 335

Arg Ala Arg Gly Pro Asp Ser Asn Val Leu Leu Arg Leu Pro Glu
            340                 345                 350

Lys Val Pro Ser Ala Pro Gln Glu Val Thr Leu Lys Pro Gly Asn
    355                 360                 365

Gly Thr Val Phe Val Ser Trp Val Pro Pro Ala Glu Asn His Asn
    370                 375                 380

Gly Ile Ile Arg Gly Tyr Gln Val Trp Ser Leu Gly Asn Thr Ser Leu
385                 390                 395                 400

Pro Pro Ala Asn Trp Thr Val Val Gly Glu Gln Thr Gln Leu Glu Ile
                405                 410                 415

Ala Thr His Met Pro Gly Ser Tyr Cys Val Gln Val Ala Ala Val Thr
            420                 425                 430

Gly Ala Gly Ala Gly Glu Pro Ser Arg Pro Val Cys Leu Leu Leu Glu
        435                 440                 445

Gln Ala Met Glu Arg Ala Thr Gln Glu Pro Ser Glu His Gly Pro Trp
    450                 455                 460

Thr Leu Glu Gln Leu Arg Ala Thr Leu Lys Arg Pro Glu Val Ile Ala
465                 470                 475                 480

Thr Cys Gly Val Ala Leu Trp Leu Leu Leu Leu Gly Thr Ala Val Cys
```

```
                    485                 490                 495
Ile His Arg Arg Arg Ala Arg Val His Leu Gly Pro Gly Leu Tyr
                500                 505                 510

Arg Tyr Thr Ser Glu Asp Ala Ile Leu Lys His Arg Met Asp His Ser
                515                 520                 525

Asp Ser Gln Trp Leu Ala Asp Thr Trp Arg Ser Thr Ser Gly Ser Arg
                530                 535                 540

Asp Leu Ser Ser Ser Ser Leu Ser Ser Arg Leu Gly Ala Asp Ala
545                 550                 555                 560

Arg Asp Pro Leu Asp Cys Arg Arg Ser Leu Leu Ser Trp Asp Ser Arg
                565                 570                 575

Ser Pro Gly Val Pro Leu Leu Pro Asp Thr Ser Thr Phe Tyr Gly Ser
                580                 585                 590

Leu Ile Ala Glu Leu Pro Ser Ser Thr Pro Ala Arg Pro Ser Pro Gln
                595                 600                 605

Val Pro Ala Val Arg Arg Leu Pro Pro Gln Leu Ala Gln Leu Ser Ser
                610                 615                 620

Pro Cys Ser Ser Ser Asp Ser Leu Cys Ser Arg Arg Gly Leu Ser Ser
625                 630                 635                 640

Pro Arg Leu Ser Leu Ala Pro Ala Glu Ala Trp Lys Ala Lys Lys Lys
                645                 650                 655

Gln Glu Leu Gln His Ala Asn Ser Ser Pro Leu Leu Arg Gly Ser His
                660                 665                 670

Ser Leu Glu Leu Arg Ala Cys Glu Leu Gly Asn Arg Gly Ser Lys Asn
                675                 680                 685

Leu Ser Gln Ser Pro Gly Ala Val Pro Gln Ala Leu Ala Trp Arg
                690                 695                 700

Ala Leu Gly Pro Lys Leu Leu Ser Ser Asn Glu Leu Val Thr Arg
705                 710                 715                 720

His Leu Pro Pro Ala Pro Leu Phe Pro His Glu Thr Pro Thr Gln
                725                 730                 735

Ser Gln Gln Thr Gln Pro Pro Val Ala Pro Gln Ala Pro Ser Ser Ile
                740                 745                 750

Leu Leu Pro Ala Ala Pro Ile Pro Ile Leu Ser Pro Cys Ser Pro Pro
                755                 760                 765

Ser Pro Gln Ala Ser Ser Leu Ser Gly Pro Ser Pro Ala Ser Ser Arg
                770                 775                 780

Leu Ser Ser Ser Ser Leu Ser Ser Leu Gly Glu Asp Gln Asp Ser Val
785                 790                 795                 800

Leu Thr Pro Glu Glu Val Ala Leu Cys Leu Glu Leu Ser Glu Gly Glu
                805                 810                 815

Glu Thr Pro Arg Asn Ser Val Ser Pro Met Pro Arg Ala Pro Ser Pro
                820                 825                 830

Pro Thr Thr Tyr Gly Tyr Ile Ser Val Pro Thr Ala Ser Glu Phe Thr
                835                 840                 845

Asp Met Gly Arg Thr Gly Gly Val Gly Pro Lys Gly Gly Val Leu
850                 855                 860

Leu Cys Pro Pro Arg Pro Cys Leu Thr Pro Thr Pro Ser Glu Gly Ser
865                 870                 875                 880

Leu Ala Asn Gly Trp Gly Ser Ala Ser Glu Asp Asn Ala Ala Ser Ala
                885                 890                 895

Arg Ala Ser Leu Val Ser Ser Ser Asp Gly Ser Phe Leu Ala Asp Ala
                900                 905                 910
```

His Phe Ala Arg Ala Leu Ala Val Ala Val Asp Ser Phe Gly Phe Gly
    915                 920                 925

Leu Glu Pro Arg Glu Ala Asp Cys Val Phe Ile Asp Ala Ser Ser Pro
    930                 935                 940

Pro Ser Pro Arg Asp Glu Ile Phe Leu Thr Pro Asn Leu Ser Leu Pro
945                 950                 955                 960

Leu Trp Glu Trp Arg Pro Asp Trp Leu Glu Asp Met Glu Val Ser His
                965                 970                 975

Thr Gln Arg Leu Gly Arg Gly Met Pro Pro Trp Pro Pro Asp Ser Gln
            980                 985                 990

Ile Ser Ser Gln Arg Ser Gln Leu His Cys Arg Met Pro Lys Ala Gly
        995                 1000                1005

Ala Ser Pro Val Asp Tyr Ser
    1010                1015

<210> SEQ ID NO 5
<211> LENGTH: 2997
<212> TYPE: DNA
<213> ORGANISM: Artificial Sequence
<220> FEATURE:
<223> OTHER INFORMATION: FLAG-hROBO4-46 na

<400> SEQUENCE: 5

```
atgggctctg gaggagacag cctcctcggc ggcagaggtt ccctgcctct gctgctcctg      60
ctcatcatgg gaggcatggc tgattacaag gatgacgacg ataagcctgg ccctgccagg     120
atgagctgcc aagcctcagg ccagccacct cccaccatcc gctggttgct gaatgggcag     180 ccctgagca tggtgccccc agacccacac cacctcctgc ctgatgggac ccttctgctg      240
ctacagcccc ctgcccgggg acatgccac gatggccagg ccctgtccac agacctgggt      300
gtctacacat gtgaggccag caaccggctt ggcacggcag tcagcagagg cgctcggctg      360
tctgtggctg tcctccggga ggatttccag atccagcctc gggacatggt ggctgtggtg      420
ggtgagcagt ttactctgga atgtgggccg ccctgggcc acccagagcc acagtctca       480 tggtggaaag atgggaaacc cctggccctc cagcccggaa ggcacacagt gtccgggggg     540
tccctgctga tggcaagagc agagaagagt gacgaaggga cctacatgtg tgtggccacc     600
aacagcgcag acataggga gagccgcgca gcccgggttt ccatccagga gccccaggac      660
tacacggagc ctgtggagct tctggctgtg cgaattcagc tggaaaatgt gacactgctg     720
aacccggatc ctgcagaggg ccccaagcct agaccggcgg tgtggctcag ctggaaggtc     780
agtggccctg ctgcgcctgc ccaatcttac acggccttgt tcaggaccca gactgccccg     840
ggaggccagg gagctccgtg gcagaggag ctgctggccg gctggcagag cgcagagctt      900
ggaggcctcc actggggcca agactacgag ttcaaagtga ccatcctc tggccgggct       960 cgaggccctg acagcaacgt gctgctcctg aggctgccgg aaaaagtgcc cagtgcccca    1020
cctcaggaag tgactctaaa gcctggcaat ggcactgtct tgtgagctg gtcccacca     1080 cctgctgaaa accacaatgg catcatccgt ggctaccagg tctggagcct gggcaacaca    1140
tcactgccac cagccaactg gactgtagtt ggtgagcaga cccagctgga aatcgccacc    1200
catatgccag ctcctactg cgtgcaagtg gctgcagtca ctggtgctgg agctggggag    1260
cccagtagac ctgtctgcct ccttttagag caggccatgg agcgagccac ccaagaaccc    1320
agtgagcatg gtccctggac cctggagcag ctgagggcta ccttgaagcg gcctgaggtc    1380
attgccacct gcggtgttgc actctggctg ctgcttctgg gcaccgccgt gtgtatccac    1440
```

```
cgccggcgcc gagctagggt gcacctgggc ccaggtctgt acagatatac cagtgaggat    1500
gccatcctaa aacacaggat ggatcacagt gactcccagt ggttggcaga cacttggcgt    1560
tccacctctg gctctcggga cctgagcagc agcagcagcc tcagcagtcg gctgggggcg    1620
gatgcccggg acccactaga ctgtcgtcgc tccttgctct cctgggactc ccgaagcccc    1680
ggcgtgcccc tgcttccaga caccagcact ttttatggct ccctcatcgc tgagctgccc    1740
tccagtaccc cagccaggcc aagtcccag gtcccagctg tcaggcgcct ccaccccag      1800 ctggcccagc tctccagccc ctgttccagc tcagacagcc tctgcagccg caggggactc    1860
tcttctcccc gcttgtctct ggcccctgca gaggcttgga aggccaaaaa gaagcaggag    1920
ctgcagcatg ccaacagttc cccactgctc cggggcagcc actccttgga gctccgggcc    1980
tgtgagttag gaaatagagg ttccaagaac ctttcccaaa gcccaggagc tgtgccccaa    2040
gctctggttg cctggcgggc cctgggaccg aaactcctca gctcctcaaa tgagctggtt    2100
actcgtcatc tccctccagc acccctcttt cctcatgaaa ctcccccaac tcagagtcaa    2160
cagacccagc ctccggtggc accacaggct ccctcctcca tcctgctgcc agcagccccc    2220
atccccatcc ttagcccctg cagtcccct agccccagg cctcttccct ctctggcccc     2280
agcccagctt ccagtcgcct gtccagctcc tcactgtcat ccctggggga ggatcaagac    2340
agcgtgctga cccctgagga ggtagccctg tgcttggaac tcagtgaggg tgaggagact    2400
cccaggaaca gcgtctctcc catgccaagg gctccttcac cccccaccac ctatgggtac    2460
atcagcgtcc caacagcctc agagttcacg gacatgggca ggactggagg aggggtgggg    2520
cccaaggggg gagtcttgct gtgcccacct cggccctgcc tcaccccac ccccagcgag     2580 ggctccttag ccaatggttg gggctcagcc tctgaggaca atgccgccag cgccagagcc    2640
agccttgtca gctcctccga tggctccttc ctcgctgatg ctcactttgc ccgggccctg    2700
gcagtggctg tggatagctt tggtttcggt ctagagccca gggaggcaga ctgcgtcttc    2760
atagatgcct catcacctcc ctccccacgg gatgagatct tcctgacccc caacctctcc    2820
ctgcccctgt gggagtggag gccagactgt tggaagaca tggaggtcag ccacacccag     2880
cggctgggaa gggggatgcc tccctggccc cctgactctc agatctcttc ccagagaagt    2940
cagctccact gtcgtatgcc caaggctggt gcttctcctg tagattactc cgctagc       2997
```

<210> SEQ ID NO 6
<211> LENGTH: 999
<212> TYPE: PRT
<213> ORGANISM: Artificial Sequence
<220> FEATURE:
<223> OTHER INFORMATION: FLAG-hROBO4-46aa

<400> SEQUENCE: 6

```
Met Gly Ser Gly Gly Asp Ser Leu Leu Gly Gly Arg Gly Ser Leu Pro
1               5                   10                  15

Leu Leu Leu Leu Ile Met Gly Gly Met Ala Asp Tyr Lys Asp Asp
            20                  25                  30

Asp Asp Lys Pro Gly Pro Ala Arg Met Ser Cys Gln Ala Ser Gly Gln
        35                  40                  45

Pro Pro Pro Thr Ile Arg Trp Leu Leu Asn Gly Gln Pro Leu Ser Met
    50                  55                  60

Val Pro Pro Asp Pro His His Leu Leu Pro Asp Gly Thr Leu Leu Leu
65                  70                  75                  80

Leu Gln Pro Pro Ala Arg Gly His Ala His Asp Gly Gln Ala Leu Ser
```

```
            85                  90                  95
Thr Asp Leu Gly Val Tyr Thr Cys Glu Ala Ser Asn Arg Leu Gly Thr
            100                 105                 110

Ala Val Ser Arg Gly Ala Arg Leu Ser Val Ala Val Leu Arg Glu Asp
            115                 120                 125

Phe Gln Ile Gln Pro Arg Asp Met Val Ala Val Gly Glu Gln Phe
            130                 135                 140

Thr Leu Glu Cys Gly Pro Pro Trp Gly His Pro Glu Pro Thr Val Ser
145                 150                 155                 160

Trp Trp Lys Asp Gly Lys Pro Leu Ala Leu Gln Pro Gly Arg His Thr
                165                 170                 175

Val Ser Gly Gly Ser Leu Leu Met Ala Arg Ala Glu Lys Ser Asp Glu
                180                 185                 190

Gly Thr Tyr Met Cys Val Ala Thr Asn Ser Ala Gly His Arg Glu Ser
                195                 200                 205

Arg Ala Ala Arg Val Ser Ile Gln Glu Pro Gln Asp Tyr Thr Glu Pro
            210                 215                 220

Val Glu Leu Leu Ala Val Arg Ile Gln Leu Glu Asn Val Thr Leu Leu
225                 230                 235                 240

Asn Pro Asp Pro Ala Glu Gly Pro Lys Pro Arg Pro Ala Val Trp Leu
                245                 250                 255

Ser Trp Lys Val Ser Gly Pro Ala Ala Pro Ala Gln Ser Tyr Thr Ala
                260                 265                 270

Leu Phe Arg Thr Gln Thr Ala Pro Gly Gly Gln Gly Ala Pro Trp Ala
                275                 280                 285

Glu Glu Leu Leu Ala Gly Trp Gln Ser Ala Glu Leu Gly Gly Leu His
            290                 295                 300

Trp Gly Gln Asp Tyr Glu Phe Lys Val Arg Pro Ser Ser Gly Arg Ala
305                 310                 315                 320

Arg Gly Pro Asp Ser Asn Val Leu Leu Leu Arg Leu Pro Glu Lys Val
                325                 330                 335

Pro Ser Ala Pro Pro Gln Glu Val Thr Leu Lys Pro Gly Asn Gly Thr
                340                 345                 350

Val Phe Val Ser Trp Val Pro Pro Ala Glu Asn His Asn Gly Ile
                355                 360                 365

Ile Arg Gly Tyr Gln Val Trp Ser Leu Gly Asn Thr Ser Leu Pro Pro
            370                 375                 380

Ala Asn Trp Thr Val Val Gly Glu Gln Thr Gln Leu Glu Ile Ala Thr
385                 390                 395                 400

His Met Pro Gly Ser Tyr Cys Val Gln Val Ala Ala Val Thr Gly Ala
                405                 410                 415

Gly Ala Gly Glu Pro Ser Arg Pro Val Cys Leu Leu Leu Glu Gln Ala
                420                 425                 430

Met Glu Arg Ala Thr Gln Glu Pro Ser Glu His Gly Pro Trp Thr Leu
            435                 440                 445

Glu Gln Leu Arg Ala Thr Leu Lys Arg Pro Glu Val Ile Ala Thr Cys
            450                 455                 460

Gly Val Ala Leu Trp Leu Leu Leu Gly Thr Ala Val Cys Ile His
465                 470                 475                 480

Arg Arg Arg Arg Ala Arg Val His Leu Gly Pro Gly Leu Tyr Arg Tyr
                485                 490                 495

Thr Ser Glu Asp Ala Ile Leu Lys His Arg Met Asp His Ser Asp Ser
                500                 505                 510
```

-continued

```
Gln Trp Leu Ala Asp Thr Trp Arg Ser Thr Ser Gly Ser Arg Asp Leu
            515                 520                 525

Ser Ser Ser Ser Ser Leu Ser Ser Arg Leu Gly Ala Asp Ala Arg Asp
        530                 535                 540

Pro Leu Asp Cys Arg Arg Ser Leu Leu Ser Trp Asp Ser Arg Ser Pro
545                 550                 555                 560

Gly Val Pro Leu Leu Pro Asp Thr Ser Thr Phe Tyr Gly Ser Leu Ile
                565                 570                 575

Ala Glu Leu Pro Ser Ser Thr Pro Ala Arg Pro Ser Pro Gln Val Pro
            580                 585                 590

Ala Val Arg Arg Leu Pro Pro Gln Leu Ala Gln Leu Ser Ser Pro Cys
        595                 600                 605

Ser Ser Ser Asp Ser Leu Cys Ser Arg Arg Gly Leu Ser Ser Pro Arg
    610                 615                 620

Leu Ser Leu Ala Pro Ala Glu Ala Trp Lys Ala Lys Lys Gln Glu
625                 630                 635                 640

Leu Gln His Ala Asn Ser Ser Pro Leu Leu Arg Gly Ser His Ser Leu
                645                 650                 655

Glu Leu Arg Ala Cys Glu Leu Gly Asn Arg Gly Ser Lys Asn Leu Ser
            660                 665                 670

Gln Ser Pro Gly Ala Val Pro Gln Ala Leu Val Ala Trp Arg Ala Leu
        675                 680                 685

Gly Pro Lys Leu Leu Ser Ser Asn Glu Leu Val Thr Arg His Leu
690                 695                 700

Pro Pro Ala Pro Leu Phe Pro His Glu Thr Pro Thr Gln Ser Gln
705                 710                 715                 720

Gln Thr Gln Pro Val Ala Pro Gln Ala Pro Ser Ser Ile Leu Leu
            725                 730                 735

Pro Ala Ala Pro Ile Pro Ile Leu Ser Pro Cys Ser Pro Pro Ser Pro
                740                 745                 750

Gln Ala Ser Ser Leu Ser Gly Pro Ser Pro Ala Ser Ser Arg Leu Ser
    755                 760                 765

Ser Ser Ser Leu Ser Ser Leu Gly Glu Asp Gln Asp Ser Val Leu Thr
    770                 775                 780

Pro Glu Glu Val Ala Leu Cys Leu Glu Leu Ser Glu Gly Glu Glu Thr
785                 790                 795                 800

Pro Arg Asn Ser Val Ser Pro Met Pro Arg Ala Pro Ser Pro Pro Thr
            805                 810                 815

Thr Tyr Gly Tyr Ile Ser Val Pro Thr Ala Ser Glu Phe Thr Asp Met
                820                 825                 830

Gly Arg Thr Gly Gly Gly Val Gly Pro Lys Gly Val Leu Leu Cys
            835                 840                 845

Pro Pro Arg Pro Cys Leu Thr Pro Thr Pro Ser Glu Gly Ser Leu Ala
850                 855                 860

Asn Gly Trp Gly Ser Ala Ser Glu Asp Asn Ala Ala Ser Ala Arg Ala
865                 870                 875                 880

Ser Leu Val Ser Ser Asp Gly Ser Phe Leu Ala Asp Ala His Phe
                885                 890                 895

Ala Arg Ala Leu Ala Val Ala Val Asp Ser Phe Gly Phe Gly Leu Glu
            900                 905                 910

Pro Arg Glu Ala Asp Cys Val Phe Ile Asp Ala Ser Ser Pro Pro Ser
            915                 920                 925
```

```
Pro Arg Asp Glu Ile Phe Leu Thr Pro Asn Leu Ser Leu Pro Leu Trp
    930                 935                 940
Glu Trp Arg Pro Asp Trp Leu Glu Asp Met Glu Val Ser His Thr Gln
945                 950                 955                 960
Arg Leu Gly Arg Gly Met Pro Pro Trp Pro Pro Asp Ser Gln Ile Ser
                965                 970                 975
Ser Gln Arg Ser Gln Leu His Cys Arg Met Pro Lys Ala Gly Ala Ser
            980                 985                 990
Pro Val Asp Tyr Ser Ala Ser
            995
```

<210> SEQ ID NO 7
<211> LENGTH: 2733
<212> TYPE: DNA
<213> ORGANISM: Artificial Sequence
<220> FEATURE:
<223> OTHER INFORMATION: FLAG-hROBO4-132na

<400> SEQUENCE: 7

| | | |
|---|---|---|
| atgggctctg gaggagacag cctcctcggc ggcagaggtt ccctgcctct gctgctcctg | 60 |
| ctcatcatgg gaggcatggc tgattacaag gatgacgacg ataaggtggc tgtcctccgg | 120 |
| gaggatttcc agatccagcc tcgggacatg gtggctgtgg tgggtgagca gtttactctg | 180 |
| gaatgtgggc cgccctgggg ccacccagag cccacagtct catggtggaa agatgggaaa | 240 |
| cccctggccc tccagcccgg aaggcacaca gtgtccgggg gtccctgct gatggcaaga | 300 |
| gcagagaaga gtgacgaagg gacctacatg tgtgtggcca ccaacagcgc aggacatagg | 360 |
| gagagccgcg cagcccgggt tccatccag gagccccagg actacacgga gcctgtggag | 420 |
| cttctggctg tgcgaattca gctggaaaat gtgacactgc tgaacccgga tcctgcagag | 480 |
| ggccccaagc ctagaccggc ggtgtggctc agctggaagg tcagtggccc tgctgcgcct | 540 |
| gcccaatctt acacggcctt gttcaggacc cagactgccc gggaggcca gggagctccg | 600 |
| tgggcagagg agctgctggc cggctggcag agcgcagagc ttggaggcct ccactgggggc | 660 |
| caagactacg agttcaaagt gagaccatcc tctggccggg ctcgaggccc tgacagcaac | 720 |
| gtgctgctcc tgaggctgcc ggaaaaagtg cccagtgccc cacctcagga agtgactcta | 780 |
| aagcctggca atggcactgt ctttgtgagc tgggtcccac cacctgctga aaaccacaat | 840 |
| ggcatcatcc gtggctacca ggtctggagc ctgggcaaca tcactgcc accagccaac | 900 |
| tggactgtag ttggtgagca gacccagctg gaaatcgcca cccatatgcc aggctcctac | 960 |
| tgcgtgcaag tggctgcagt cactggtgct ggagctgggg agcccagtag acctgtctgc | 1020 |
| ctccttttag gcaggccat ggagcgagcc acccaagaac ccagtgagca tggtccctgg | 1080 |
| accctggagc agctgagggc taccttgaag cggcctgagg tcattgccac ctgcggtgtt | 1140 |
| gcactctggc tgctgcttct gggcaccgcc gtgtgtatcc accgccggcg ccgagctagg | 1200 |
| gtgcacctgg gccaggtct gtacagatat accagtgagg atgccatcct aaaacacagg | 1260 |
| atggatcaca gtgactccca gtggttggca gacacttggc gttccacctc tggctctcgg | 1320 |
| gacctgagca gcagcagcag cctcagcagt cggctggggg cggatgcccg ggacccacta | 1380 |
| gactgtcgtc gctccttgct ctcctgggac tcccgaagcc ccggcgtgcc cctgcttcca | 1440 |
| gacaccagca cttttttatgg ctccctcatc gctgagctgc cctccagtac cccagccagg | 1500 |
| ccaagtcccc aggtcccagc tgtcaggcgc tccccacccc agctggccca gctctccagc | 1560 |
| ccctgttcca gctcagacag cctctgcagc cgcagggac tctcttctcc ccgcttgtct | 1620 |

```
ctggcccctg cagaggcttg gaaggccaaa aagaagcagg agctgcagca tgccaacagt    1680
tccccactgc tccggggcag ccactccttg gagctccggg cctgtgagtt aggaaataga    1740
ggttccaaga acctttccca agcccagga gctgtgcccc aagctctggt tgcctggcgg    1800
gccctgggac cgaaactcct cagctcctca aatgagctgg ttactcgtca tctccctcca    1860
gcacccctct ttcctcatga aactccccca actcagagtc aacagaccca gcctccggtg    1920
gcaccacagg ctccctcctc catcctgctg ccagcagccc ccatccccat ccttagcccc    1980
tgcagtcccc ctagccccca ggcctcttcc ctctctggcc cagcccagc ttccagtcgc     2040
ctgtccagct cctcactgtc atccctgggg gaggatcaag acagcgtgct gacccctgag    2100
gaggtagccc tgtgcttgga actcagtgag ggtgaggaga ctcccaggaa cagcgtctct    2160
cccatgccaa gggctccttc accccccacc acctatgggt acatcagcgt cccaacagcc    2220
tcagagttca cggacatggg caggactgga ggaggggtgg ggcccaaggg gggagtcttg    2280
ctgtgcccac ctcggccctg cctcaccccc accccagcg agggctcctt agccaatggt     2340
tggggctcag cctctgagga caatgccgcc agcgccagag ccagccttgt cagctcctcc    2400
gatggctcct cctcgctga tgctcacttt gcccgggccc tggcagtggc tgtggatagc     2460
tttggtttcg gtctagagcc cagggaggca gactgcgtct tcatagatgc ctcatcacct    2520
ccctccccac gggatgagat cttcctgacc ccaacctct ccctgccct gtgggagtgg      2580
aggccagact ggttggaaga catggaggtc agccacaccc agcggctggg aaggggatg     2640
cctccctggc ccctgactc tcagatctct tcccagagaa gtcagctcca ctgtcgtatg     2700
cccaaggctg gtgcttctcc tgtagattac tcc                                 2733
```

<210> SEQ ID NO 8
<211> LENGTH: 911
<212> TYPE: PRT
<213> ORGANISM: Artificial Sequence
<220> FEATURE:
<223> OTHER INFORMATION: FLAG-hROBO4-132aa

<400> SEQUENCE: 8

```
Met Gly Ser Gly Gly Asp Ser Leu Leu Gly Gly Arg Gly Ser Leu Pro
1               5                   10                  15

Leu Leu Leu Leu Leu Ile Met Gly Gly Met Ala Asp Tyr Lys Asp Asp
            20                  25                  30

Asp Asp Lys Val Ala Val Leu Arg Glu Asp Phe Gln Ile Gln Pro Arg
        35                  40                  45

Asp Met Val Ala Val Gly Glu Gln Phe Thr Leu Glu Cys Gly Pro
    50                  55                  60

Pro Trp Gly His Pro Glu Pro Thr Val Ser Trp Trp Lys Asp Gly Lys
65                  70                  75                  80

Pro Leu Ala Leu Gln Pro Gly Arg His Thr Val Ser Gly Gly Ser Leu
                85                  90                  95

Leu Met Ala Arg Ala Glu Lys Ser Asp Glu Gly Thr Tyr Met Cys Val
            100                 105                 110

Ala Thr Asn Ser Ala Gly His Arg Glu Ser Arg Ala Ala Arg Val Ser
        115                 120                 125

Ile Gln Glu Pro Gln Asp Tyr Thr Glu Pro Val Leu Leu Ala Val
    130                 135                 140

Arg Ile Gln Leu Glu Asn Val Thr Leu Leu Asn Pro Asp Pro Ala Glu
145                 150                 155                 160

Gly Pro Lys Pro Arg Pro Ala Val Trp Leu Ser Trp Lys Val Ser Gly
```

```
                    165                 170                 175
        Pro Ala Ala Pro Ala Gln Ser Tyr Thr Ala Leu Phe Arg Thr Gln Thr
                        180                 185                 190
        Ala Pro Gly Gly Gln Gly Ala Pro Trp Ala Glu Glu Leu Leu Ala Gly
                        195                 200                 205
        Trp Gln Ser Ala Glu Leu Gly Gly Leu His Trp Gly Gln Asp Tyr Glu
                210                 215                 220
        Phe Lys Val Arg Pro Ser Ser Gly Arg Ala Arg Gly Pro Asp Ser Asn
        225                 230                 235                 240
        Val Leu Leu Arg Leu Pro Glu Lys Val Pro Ser Ala Pro Pro Gln
                        245                 250                 255
        Glu Val Thr Leu Lys Pro Gly Asn Gly Thr Val Phe Val Ser Trp Val
                        260                 265                 270
        Pro Pro Pro Ala Glu Asn His Asn Gly Ile Ile Arg Gly Tyr Gln Val
                        275                 280                 285
        Trp Ser Leu Gly Asn Thr Ser Leu Pro Pro Ala Asn Trp Thr Val Val
                290                 295                 300
        Gly Glu Gln Thr Gln Leu Glu Ile Ala Thr His Met Pro Gly Ser Tyr
        305                 310                 315                 320
        Cys Val Gln Val Ala Ala Val Thr Gly Ala Gly Ala Gly Glu Pro Ser
                        325                 330                 335
        Arg Pro Val Cys Leu Leu Leu Gln Ala Met Glu Arg Ala Thr Gln
                        340                 345                 350
        Glu Pro Ser Glu His Gly Pro Trp Thr Leu Glu Gln Leu Arg Ala Thr
                        355                 360                 365
        Leu Lys Arg Pro Glu Val Ile Ala Thr Cys Gly Val Ala Leu Trp Leu
                370                 375                 380
        Leu Leu Leu Gly Thr Ala Val Cys Ile His Arg Arg Arg Ala Arg
        385                 390                 395                 400
        Val His Leu Gly Pro Gly Leu Tyr Arg Tyr Thr Ser Glu Asp Ala Ile
                        405                 410                 415
        Leu Lys His Arg Met Asp His Ser Asp Ser Gln Trp Leu Ala Asp Thr
                        420                 425                 430
        Trp Arg Ser Thr Ser Gly Ser Arg Asp Leu Ser Ser Ser Ser Ser Leu
                        435                 440                 445
        Ser Ser Arg Leu Gly Ala Asp Ala Arg Asp Pro Leu Asp Cys Arg Arg
        450                 455                 460
        Ser Leu Leu Ser Trp Asp Ser Arg Ser Pro Gly Val Pro Leu Leu Pro
                        465                 470                 475                 480
        Asp Thr Ser Thr Phe Tyr Gly Ser Leu Ile Ala Glu Leu Pro Ser Ser
                        485                 490                 495
        Thr Pro Ala Arg Pro Ser Pro Gln Val Pro Ala Val Arg Leu Pro
                        500                 505                 510
        Pro Gln Leu Ala Gln Leu Ser Ser Pro Cys Ser Ser Asp Ser Leu
                        515                 520                 525
        Cys Ser Arg Arg Gly Leu Ser Ser Pro Arg Leu Ser Leu Ala Pro Ala
        530                 535                 540
        Glu Ala Trp Lys Ala Lys Lys Gln Glu Leu Gln His Ala Asn Ser
        545                 550                 555                 560
        Ser Pro Leu Leu Arg Gly Ser His Ser Leu Glu Leu Arg Ala Cys Glu
                        565                 570                 575
        Leu Gly Asn Arg Gly Ser Lys Asn Leu Ser Gln Ser Pro Gly Ala Val
                        580                 585                 590
```

Pro Gln Ala Leu Val Ala Trp Arg Ala Leu Gly Pro Lys Leu Leu Ser
            595                 600                 605

Ser Ser Asn Glu Leu Val Thr Arg His Leu Pro Pro Ala Pro Leu Phe
        610                 615                 620

Pro His Glu Thr Pro Pro Thr Gln Ser Gln Gln Thr Gln Pro Pro Val
625                 630                 635                 640

Ala Pro Gln Ala Pro Ser Ser Ile Leu Leu Pro Ala Ala Pro Ile Pro
            645                 650                 655

Ile Leu Ser Pro Cys Ser Pro Ser Pro Gln Ala Ser Ser Leu Ser
            660                 665                 670

Gly Pro Ser Pro Ala Ser Ser Arg Leu Ser Ser Ser Leu Ser Ser
            675                 680                 685

Leu Gly Glu Asp Gln Asp Ser Val Leu Thr Pro Glu Glu Val Ala Leu
        690                 695                 700

Cys Leu Glu Leu Ser Glu Gly Glu Thr Pro Arg Asn Ser Val Ser
705                 710                 715                 720

Pro Met Pro Arg Ala Pro Ser Pro Pro Thr Thr Tyr Gly Tyr Ile Ser
            725                 730                 735

Val Pro Thr Ala Ser Glu Phe Thr Asp Met Gly Arg Thr Gly Gly Gly
        740                 745                 750

Val Gly Pro Lys Gly Gly Val Leu Leu Cys Pro Pro Arg Pro Cys Leu
        755                 760                 765

Thr Pro Thr Pro Ser Glu Gly Ser Leu Ala Asn Gly Trp Gly Ser Ala
        770                 775                 780

Ser Glu Asp Asn Ala Ala Ser Ala Arg Ala Ser Leu Val Ser Ser Ser
785                 790                 795                 800

Asp Gly Ser Phe Leu Ala Asp Ala His Phe Ala Arg Ala Leu Ala Val
            805                 810                 815

Ala Val Asp Ser Phe Gly Phe Gly Leu Glu Pro Arg Glu Ala Asp Cys
            820                 825                 830

Val Phe Ile Asp Ala Ser Ser Pro Ser Pro Arg Asp Glu Ile Phe
835                 840                 845

Leu Thr Pro Asn Leu Ser Leu Pro Leu Trp Glu Trp Arg Pro Asp Trp
        850                 855                 860

Leu Glu Asp Met Glu Val Ser His Thr Gln Arg Leu Gly Arg Gly Met
865                 870                 875                 880

Pro Pro Trp Pro Pro Asp Ser Gln Ile Ser Ser Gln Arg Ser Gln Leu
            885                 890                 895

His Cys Arg Met Pro Lys Ala Gly Ala Ser Pro Val Asp Tyr Ser
            900                 905                 910

<210> SEQ ID NO 9
<211> LENGTH: 2505
<212> TYPE: DNA
<213> ORGANISM: Artificial Sequence
<220> FEATURE:
<223> OTHER INFORMATION: FLAG-hROBO4-210na

<400> SEQUENCE: 9
atgggctctg gaggagacag cctcctcggc ggcagaggtt ccctgcctct gctgctcctg      60
ctcatcatgg gaggcatggc tgattacaag gatgacgacg ataagaccaa cagcgcagga     120
catagggaga gccgcgcagc ccgggttttcc atccaggagc cccaggacta cacgagcct     180 gtggagcttc tggctgtgcg aattcagctg gaaaatgtga cactgctgaa cccggatcct     240

-continued

| | |
|---|---|
| gcagagggcc ccaagcctag accggcggtg tggctcagct ggaaggtcag tggccctgct | 300 |
| gcgcctgccc aatcttacac ggccttgttc aggacccaga ctgccccggg aggccaggga | 360 |
| gctccgtggg cagaggagct gctggccggc tggcagagcg cagagcttgg aggcctccac | 420 |
| tggggccaag actacgagtt caaagtgaga ccatcctctg gccgggctcg aggccctgac | 480 |
| agcaacgtgc tgctcctgag gctgccggaa aaagtgccca gtgccccacc tcaggaagtg | 540 |
| actctaaagc ctggcaatgg cactgtcttt gtgagctggg tcccaccacc tgctgaaaac | 600 |
| cacaatggca tcatccgtgg ctaccaggtc tggagcctgg gcaacacatc actgccacca | 660 |
| gccaactgga ctgtagttgg tgagcagacc cagctggaaa tcgccaccca tatgccaggc | 720 |
| tcctactgcg tgcaagtggc tgcagtcact ggtgctggag ctggggagcc cagtagacct | 780 |
| gtctgcctcc ttttagagca ggccatggag cgagccaccc aagaacccag tgagcatggt | 840 |
| ccctggaccc tggagcagct gagggctacc ttgaagcggc ctgaggtcat tgccacctgc | 900 |
| ggtgttgcac tctggctgct gcttctgggc accgccgtgt gtatccaccg ccggcgccga | 960 |
| gctagggtgc acctgggccc aggtctgtac agatatacca gtgaggatgc catcctaaaa | 1020 |
| cacaggatgg atcacagtga ctcccagtgg ttggcagaca cttggcgttc cacctctggc | 1080 |
| tctcgggacc tgagcagcag cagcagcctc agcagtcggc tgggggcgga tgcccgggac | 1140 |
| ccactagact gtcgtcgctc cttgctctcc tgggactccc gaagcccggg cgtgcccctg | 1200 |
| cttccagaca ccagcacttt ttatggctcc ctcatcgctg agctgccctc cagtacccca | 1260 |
| gccaggccaa gtccccaggt cccagctgtc aggcgcctcc cacccagct ggcccagctc | 1320 |
| tccagcccct gttccagctc agacagcctc tgcagccgca ggggactctc ttctccccgc | 1380 |
| ttgtctctgg cccctgcaga ggcttggaag ccaaaaaga agcaggagct gcagcatgcc | 1440 |
| aacagttccc cactgctccg gggcagccac tccttggagc tccgggcctg tgagttagga | 1500 |
| aatagaggtt ccaagaacct ttcccaaagc ccaggagctg tgccccaagc tctggttgcc | 1560 |
| tggcgggccc tgggaccgaa actcctcagc tcctcaaatg agctggttac tcgtcatctc | 1620 |
| cctccagcac ccctctttcc tcatgaaact cccccaactc agagtcaaca gacccagcct | 1680 |
| ccggtggcac cacaggctcc ctcctccatc ctgctgccag cagcccccat ccccatcctt | 1740 |
| agccctgca gtccccctag cccccaggcc tcttccctct ctggccccag cccagcttcc | 1800 |
| agtcgcctgt ccagctcctc actgtcatcc ctggggagg atcaagacag cgtgctgacc | 1860 |
| cctgaggagg tagccctgtg cttggaactc agtgagggtg aggagactcc caggaacagc | 1920 |
| gtctctccca tgccaagggc tccttcaccc ccaccacct atgggtacat cagcgtccca | 1980 |
| acagcctcag agttcacgga catgggcagg actggaggag gggtggggcc caaggggga | 2040 |
| gtcttgctgt gccacctcg gccctgcctc accccaccc ccagcgaggg ctccttagcc | 2100 |
| aatggttggg gctcagcctc tgaggacaat gccgccagcg ccagagccag ccttgtcagc | 2160 |
| tcctccgatg gctccttcct cgctgatgct cactttgccc gggccctggc agtggctgtg | 2220 |
| gatagctttg gtttcggtct agagcccagg gaggcagact gcgtcttcat agatgcctca | 2280 |
| tcacctccct ccccacggga tgagatcttc ctgaccccca acctctccct gccctgtgg | 2340 |
| gagtggaggc cagactggtt ggaagacatg gaggtcagcc acacccagcg gctgggaagg | 2400 |
| gggatgcctc cctggccccc tgactctcag atctcttccc agagaagtca gctccactgt | 2460 |
| cgtatgccca aggctggtgc ttctcctgta gattactccg ctagc | 2505 |

<210> SEQ ID NO 10
<211> LENGTH: 835

```
<212> TYPE: PRT
<213> ORGANISM: Artificial Sequence
<220> FEATURE:
<223> OTHER INFORMATION: FLAG-hROBO4-210aa

<400> SEQUENCE: 10
```

| | | | | | | | | | | | | | | |
|---|---|---|---|---|---|---|---|---|---|---|---|---|---|---|
| Met | Gly | Ser | Gly | Gly | Asp | Ser | Leu | Leu | Gly | Gly | Arg | Gly | Ser | Leu | Pro |
| 1 | | | | 5 | | | | | 10 | | | | | 15 | |
| Leu | Leu | Leu | Leu | Leu | Ile | Met | Gly | Gly | Met | Ala | Asp | Tyr | Lys | Asp |
| | | | 20 | | | | | 25 | | | | | 30 | |
| Asp | Asp | Lys | Thr | Asn | Ser | Ala | Gly | His | Arg | Glu | Ser | Arg | Ala | Ala | Arg |
| | | | 35 | | | | | 40 | | | | | 45 | | |
| Val | Ser | Ile | Gln | Glu | Pro | Gln | Asp | Tyr | Thr | Glu | Pro | Val | Glu | Leu | Leu |
| | 50 | | | | | 55 | | | | | 60 | | | | |
| Ala | Val | Arg | Ile | Gln | Leu | Glu | Asn | Val | Thr | Leu | Leu | Asn | Pro | Asp | Pro |
| 65 | | | | | 70 | | | | | 75 | | | | | 80 |
| Ala | Glu | Gly | Pro | Lys | Pro | Arg | Pro | Ala | Val | Trp | Leu | Ser | Trp | Lys | Val |
| | | | | 85 | | | | | 90 | | | | | 95 | |
| Ser | Gly | Pro | Ala | Ala | Pro | Ala | Gln | Ser | Tyr | Thr | Ala | Leu | Phe | Arg | Thr |
| | | | | 100 | | | | | 105 | | | | | 110 | |
| Gln | Thr | Ala | Pro | Gly | Gln | Gly | Ala | Pro | Trp | Ala | Glu | Glu | Leu | Leu |
| | | 115 | | | | | 120 | | | | | 125 | | |
| Ala | Gly | Trp | Gln | Ser | Ala | Glu | Leu | Gly | Gly | Leu | His | Trp | Gly | Gln | Asp |
| | 130 | | | | | 135 | | | | | 140 | | | | |
| Tyr | Glu | Phe | Lys | Val | Arg | Pro | Ser | Ser | Gly | Arg | Ala | Arg | Gly | Pro | Asp |
| 145 | | | | | 150 | | | | | 155 | | | | | 160 |
| Ser | Asn | Val | Leu | Leu | Leu | Arg | Leu | Pro | Glu | Lys | Val | Pro | Ser | Ala | Pro |
| | | | | 165 | | | | | 170 | | | | | 175 | |
| Pro | Gln | Glu | Val | Thr | Leu | Lys | Pro | Gly | Asn | Gly | Thr | Val | Phe | Val | Ser |
| | | | 180 | | | | | 185 | | | | | 190 | | |
| Trp | Val | Pro | Pro | Pro | Ala | Glu | Asn | His | Asn | Gly | Ile | Ile | Arg | Gly | Tyr |
| | | 195 | | | | | 200 | | | | | 205 | | | |
| Gln | Val | Trp | Ser | Leu | Gly | Asn | Thr | Ser | Leu | Pro | Pro | Ala | Asn | Trp | Thr |
| | 210 | | | | | 215 | | | | | 220 | | | | |
| Val | Val | Gly | Glu | Gln | Thr | Gln | Leu | Glu | Ile | Ala | Thr | His | Met | Pro | Gly |
| 225 | | | | | 230 | | | | | 235 | | | | | 240 |
| Ser | Tyr | Cys | Val | Gln | Val | Ala | Ala | Val | Thr | Gly | Ala | Gly | Ala | Gly | Glu |
| | | | | 245 | | | | | 250 | | | | | 255 | |
| Pro | Ser | Arg | Pro | Val | Cys | Leu | Leu | Leu | Glu | Gln | Ala | Met | Glu | Arg | Ala |
| | | | 260 | | | | | 265 | | | | | 270 | | |
| Thr | Gln | Glu | Pro | Ser | Glu | His | Gly | Pro | Trp | Thr | Leu | Glu | Gln | Leu | Arg |
| | | 275 | | | | | 280 | | | | | 285 | | | |
| Ala | Thr | Leu | Lys | Arg | Pro | Glu | Val | Ile | Ala | Thr | Cys | Gly | Val | Ala | Leu |
| | 290 | | | | | 295 | | | | | 300 | | | | |
| Trp | Leu | Leu | Leu | Leu | Gly | Thr | Ala | Val | Cys | Ile | His | Arg | Arg | Arg | Arg |
| 305 | | | | | 310 | | | | | 315 | | | | | 320 |
| Ala | Arg | Val | His | Leu | Gly | Pro | Gly | Leu | Tyr | Arg | Tyr | Thr | Ser | Glu | Asp |
| | | | | 325 | | | | | 330 | | | | | 335 | |
| Ala | Ile | Leu | Lys | His | Arg | Met | Asp | His | Ser | Asp | Ser | Gln | Trp | Leu | Ala |
| | | | 340 | | | | | 345 | | | | | 350 | | |
| Asp | Thr | Trp | Arg | Ser | Thr | Ser | Gly | Ser | Arg | Asp | Leu | Ser | Ser | Ser | Ser |
| | | 355 | | | | | 360 | | | | | 365 | | | |
| Ser | Leu | Ser | Ser | Arg | Leu | Gly | Ala | Asp | Ala | Arg | Asp | Pro | Leu | Asp | Cys |
| | 370 | | | | | 375 | | | | | 380 | | | | |

-continued

```
Arg Arg Ser Leu Leu Ser Trp Asp Ser Arg Ser Pro Gly Val Pro Leu
385                 390                 395                 400

Leu Pro Asp Thr Ser Thr Phe Tyr Gly Ser Leu Ile Ala Glu Leu Pro
                405                 410                 415

Ser Ser Thr Pro Ala Arg Pro Ser Pro Gln Val Pro Ala Val Arg Arg
            420                 425                 430

Leu Pro Pro Gln Leu Ala Gln Leu Ser Ser Pro Cys Ser Ser Ser Asp
        435                 440                 445

Ser Leu Cys Ser Arg Arg Gly Leu Ser Ser Pro Arg Leu Ser Leu Ala
    450                 455                 460

Pro Ala Glu Ala Trp Lys Ala Lys Lys Gln Glu Leu Gln His Ala
465                 470                 475                 480

Asn Ser Ser Pro Leu Leu Arg Gly Ser His Ser Leu Glu Leu Arg Ala
                485                 490                 495

Cys Glu Leu Gly Asn Arg Gly Ser Lys Asn Leu Ser Gln Ser Pro Gly
            500                 505                 510

Ala Val Pro Gln Ala Leu Val Ala Trp Arg Ala Leu Gly Pro Lys Leu
        515                 520                 525

Leu Ser Ser Asn Glu Leu Val Thr Arg His Leu Pro Pro Ala Pro
530                 535                 540

Leu Phe Pro His Glu Thr Pro Pro Thr Gln Ser Gln Gln Thr Gln Pro
545                 550                 555                 560

Pro Val Ala Pro Gln Ala Pro Ser Ser Ile Leu Leu Pro Ala Ala Pro
                565                 570                 575

Ile Pro Ile Leu Ser Pro Cys Ser Pro Pro Ser Pro Gln Ala Ser Ser
            580                 585                 590

Leu Ser Gly Pro Ser Pro Ala Ser Ser Arg Leu Ser Ser Ser Ser Leu
        595                 600                 605

Ser Ser Leu Gly Glu Asp Gln Asp Ser Val Leu Thr Pro Glu Glu Val
    610                 615                 620

Ala Leu Cys Leu Glu Leu Ser Glu Gly Glu Thr Pro Arg Asn Ser
625                 630                 635                 640

Val Ser Pro Met Pro Arg Ala Pro Ser Pro Thr Thr Tyr Gly Tyr
                645                 650                 655

Ile Ser Val Pro Thr Ala Ser Glu Phe Thr Asp Met Gly Arg Thr Gly
            660                 665                 670

Gly Gly Val Gly Pro Lys Gly Val Leu Leu Cys Pro Arg Pro
        675                 680                 685

Cys Leu Thr Pro Thr Pro Ser Glu Gly Ser Leu Ala Asn Gly Trp Gly
    690                 695                 700

Ser Ala Ser Glu Asp Asn Ala Ala Ser Ala Arg Ala Ser Leu Val Ser
705                 710                 715                 720

Ser Ser Asp Gly Ser Phe Leu Ala Asp Ala His Phe Ala Arg Ala Leu
                725                 730                 735

Ala Val Ala Val Asp Ser Phe Gly Phe Gly Leu Glu Pro Arg Glu Ala
            740                 745                 750

Asp Cys Val Phe Ile Asp Ala Ser Ser Pro Ser Pro Arg Asp Glu
    755                 760                 765

Ile Phe Leu Thr Pro Asn Leu Ser Leu Pro Leu Trp Glu Trp Arg Pro
        770                 775                 780

Asp Trp Leu Glu Asp Met Glu Val Ser His Thr Gln Arg Leu Gly Arg
785                 790                 795                 800

Gly Met Pro Pro Trp Pro Pro Asp Ser Gln Ile Ser Ser Gln Arg Ser
```

805                 810                 815
Gln Leu His Cys Arg Met Pro Lys Ala Gly Ala Ser Pro Val Asp Tyr
            820                 825                 830

Ser Ala Ser
        835

<210> SEQ ID NO 11
<211> LENGTH: 2454
<212> TYPE: DNA
<213> ORGANISM: Artificial Sequence
<220> FEATURE:
<223> OTHER INFORMATION: FLAG-hROBO4-225na

<400> SEQUENCE: 11

| | | | | | |
|---|---|---|---|---|---|
| atgggctctg | gaggagacag | cctcctcggc | ggcagaggtt | ccctgcctct | gctgctcctg | 60 |
| ctcatcatgg | gaggcatggc | tgattacaag | gatgacgacg | ataagatcca | ggagccccag | 120 |
| gactacacgg | agcctgtgga | gcttctggct | gtgcgaattc | agctggaaaa | tgtgacactg | 180 |
| ctgaacccgg | atcctgcaga | gggccccaag | cctagaccgg | cggtgtggct | cagctggaag | 240 |
| gtcagtggcc | ctgctgcgcc | tgcccaatct | tacacggcct | tgttcaggac | ccagactgcc | 300 |
| ccgggaggcc | agggagctcc | gtgggcagag | gagctgctgg | ccggctggca | gagcgcagag | 360 |
| cttggaggcc | tccactgggg | ccaagactac | gagttcaaag | tgagaccatc | ctctggccgg | 420 |
| gctcgaggcc | ctgacagcaa | cgtgctgctc | ctgaggctgc | cggaaaaagt | gcccagtgcc | 480 |
| ccacctcagg | aagtgactct | aaagcctggc | aatggcactg | tctttgtgag | ctgggtccca | 540 |
| ccacctgctg | aaaaccacaa | tggcatcatc | cgtggctacc | aggtctggag | cctgggcaac | 600 |
| acatcactgc | caccagccaa | ctggactgta | gttggtgagc | agacccagct | ggaaatcgcc | 660 |
| acccatatgc | caggctccta | ctgcgtgcaa | gtggctgcag | tcactggtgc | tggagctggg | 720 |
| gagcccagta | gacctgtctg | cctcctttta | gagcaggcca | tggagcgagc | acccaagaa | 780 |
| cccagtgagc | atggtccctg | gaccctggag | cagctgaggg | ctaccttgaa | gcggcctgag | 840 |
| gtcattgcca | cctgcggtgt | tgcactctgg | ctgctgcttc | tgggcaccgc | cgtgtgtatc | 900 |
| caccgccggc | gccagctagg | ggtgcacctg | ggcccaggtc | tgtacagata | taccagtgag | 960 |
| gatgccatcc | taaaacacag | gatggatcac | agtgactccc | agtggttggc | agacacttgg | 1020 |
| cgttccacct | ctggctctcg | ggacctgagc | agcagcagca | gcctcagcag | tcggctgggg | 1080 |
| gcggatgccc | gggacccact | agactgtcgt | cgctccttgc | tctcctggga | ctcccgaagc | 1140 |
| cccgccgtgc | ccctgcttcc | agacaccagc | acttttttatg | ctccctcat | cgctgagctg | 1200 |
| ccctccagta | ccccagccag | gccaagtccc | caggtcccag | ctgtcaggcg | cctcccaccc | 1260 |
| cagctggccc | agctctccag | cccctgttcc | agctcagaca | gcctctgcag | ccgcagggga | 1320 |
| ctctcttctc | cccgcttgtc | tctggcccct | gcagaggctt | ggaaggccaa | aaagaagcag | 1380 |
| gagctgcagc | atgccaacag | ttccccactg | ctccggggca | gccactcctt | ggagctccgg | 1440 |
| gcctgtgagt | taggaaatag | aggttccaag | aacctttccc | aaagcccagg | agctgtgccc | 1500 |
| caagctctgg | ttgcctggcg | ggccctggga | ccgaaactcc | tcagctcctc | aaatgagctg | 1560 |
| gttactcgtc | atctccctcc | agcacccctc | tttcctcatg | aaactcccc | aactcagagt | 1620 |
| caacagaccc | agcctccggt | ggcaccacag | gctcccctcct | ccatcctgct | gccagcagcc | 1680 |
| cccatcccca | tccttagccc | ctgcagtccc | cctagcccca | aggcctcttc | cctctctggc | 1740 |
| cccagcccag | cttccagtcg | cctgtccagc | tcctcactgt | catccctggg | ggaggatcaa | 1800 |
| gacagcgtgc | tgacccctga | ggaggtagcc | ctgtgcttgg | aactcagtga | gggtgaggag | 1860 |

```
actcccagga acagcgtctc tcccatgcca agggctcctt caccccccac cacctatggg    1920
tacatcagcg tcccaacagc ctcagagttc acggacatgg gcaggactgg aggaggggtg    1980
gggcccaagg ggggagtctt gctgtgccca cctcggccct gcctcacccc caccccagc    2040 gagggctcct tagccaatgg ttggggctca gcctctgagg acaatgccgc cagcgccaga    2100
gccagccttg tcagctcctc cgatggctcc ttcctcgctg atgctcactt tgcccgggcc    2160
ctggcagtgg ctgtggatag ctttggtttc ggtctagagc ccagggaggc agactgcgtc    2220
ttcatagatg cctcatcacc tccctcccca cgggatgaga tcttcctgac ccccaacctc    2280
tccctgcccc tgtgggagtg gaggccagac tggttggaag acatggaggt cagccacacc    2340
cagcggctgg aaggggggat gcctccctgg cccctgact ctcagatctc ttcccagaga    2400
agtcagctcc actgtcgtat gcccaaggct ggtgcttctc ctgtagatta ctcc          2454
```

<210> SEQ ID NO 12
<211> LENGTH: 818
<212> TYPE: PRT
<213> ORGANISM: Artificial Sequence
<220> FEATURE:
<223> OTHER INFORMATION: FLAG-hROBO4-225aa

<400> SEQUENCE: 12

```
Met Gly Ser Gly Gly Asp Ser Leu Leu Gly Gly Arg Gly Ser Leu Pro
 1               5                  10                  15

Leu Leu Leu Leu Leu Ile Met Gly Gly Met Ala Asp Tyr Lys Asp Asp
             20                  25                  30

Asp Asp Lys Ile Gln Glu Pro Gln Asp Tyr Thr Glu Pro Val Glu Leu
         35                  40                  45

Leu Ala Val Arg Ile Gln Leu Glu Asn Val Thr Leu Leu Asn Pro Asp
     50                  55                  60

Pro Ala Glu Gly Pro Lys Pro Arg Pro Ala Val Trp Leu Ser Trp Lys
 65                  70                  75                  80

Val Ser Gly Pro Ala Ala Pro Ala Gln Ser Tyr Thr Ala Leu Phe Arg
                 85                  90                  95

Thr Gln Thr Ala Pro Gly Gly Gln Gly Ala Pro Trp Ala Glu Glu Leu
            100                 105                 110

Leu Ala Gly Trp Gln Ser Ala Glu Leu Gly Gly Leu His Trp Gly Gln
        115                 120                 125

Asp Tyr Glu Phe Lys Val Arg Pro Ser Ser Gly Arg Ala Arg Gly Pro
    130                 135                 140

Asp Ser Asn Val Leu Leu Leu Arg Leu Pro Glu Lys Val Pro Ser Ala
145                 150                 155                 160

Pro Pro Gln Glu Val Thr Leu Lys Pro Gly Asn Gly Thr Val Phe Val
                165                 170                 175

Ser Trp Val Pro Pro Ala Glu Asn His Asn Gly Ile Ile Arg Gly
            180                 185                 190

Tyr Gln Val Trp Ser Leu Gly Asn Thr Ser Leu Pro Pro Ala Asn Trp
        195                 200                 205

Thr Val Val Gly Glu Gln Thr Gln Leu Glu Ile Ala Thr His Met Pro
    210                 215                 220

Gly Ser Tyr Cys Val Gln Val Ala Val Thr Gly Ala Gly Ala Gly
225                 230                 235                 240

Glu Pro Ser Arg Pro Val Cys Leu Leu Leu Glu Gln Ala Met Glu Arg
                245                 250                 255
```

-continued

```
Ala Thr Gln Glu Pro Ser Glu His Gly Pro Trp Thr Leu Glu Gln Leu
            260                 265                 270

Arg Ala Thr Leu Lys Arg Pro Glu Val Ile Ala Thr Cys Gly Val Ala
        275                 280                 285

Leu Trp Leu Leu Leu Leu Gly Thr Ala Val Cys Ile His Arg Arg Arg
    290                 295                 300

Arg Ala Arg Val His Leu Gly Pro Gly Leu Tyr Arg Tyr Thr Ser Glu
305                 310                 315                 320

Asp Ala Ile Leu Lys His Arg Met Asp His Ser Asp Ser Gln Trp Leu
                325                 330                 335

Ala Asp Thr Trp Arg Ser Thr Ser Gly Ser Arg Asp Leu Ser Ser Ser
            340                 345                 350

Ser Ser Leu Ser Ser Arg Leu Gly Ala Asp Ala Arg Asp Pro Leu Asp
        355                 360                 365

Cys Arg Arg Ser Leu Leu Ser Trp Asp Ser Arg Ser Pro Gly Val Pro
    370                 375                 380

Leu Leu Pro Asp Thr Ser Thr Phe Tyr Gly Ser Leu Ile Ala Glu Leu
385                 390                 395                 400

Pro Ser Ser Thr Pro Ala Arg Pro Ser Pro Gln Val Pro Ala Val Arg
                405                 410                 415

Arg Leu Pro Pro Gln Leu Ala Gln Leu Ser Ser Pro Cys Ser Ser Ser
            420                 425                 430

Asp Ser Leu Cys Ser Arg Arg Gly Leu Ser Ser Pro Arg Leu Ser Leu
        435                 440                 445

Ala Pro Ala Glu Ala Trp Lys Ala Lys Lys Gln Glu Leu Gln His
    450                 455                 460

Ala Asn Ser Ser Pro Leu Leu Arg Gly Ser His Ser Leu Glu Leu Arg
465                 470                 475                 480

Ala Cys Glu Leu Gly Asn Arg Gly Ser Lys Asn Leu Ser Gln Ser Pro
                485                 490                 495

Gly Ala Val Pro Gln Ala Leu Val Ala Trp Arg Ala Leu Gly Pro Lys
            500                 505                 510

Leu Leu Ser Ser Ser Asn Glu Leu Val Thr Arg His Leu Pro Pro Ala
        515                 520                 525

Pro Leu Phe Pro His Glu Thr Pro Thr Gln Ser Gln Gln Thr Gln
    530                 535                 540

Pro Pro Val Ala Pro Gln Ala Pro Ser Ser Ile Leu Leu Pro Ala Ala
545                 550                 555                 560

Pro Ile Pro Ile Leu Ser Pro Cys Ser Pro Pro Ser Pro Gln Ala Ser
                565                 570                 575

Ser Leu Ser Gly Pro Ser Pro Ala Ser Ser Arg Leu Ser Ser Ser Ser
            580                 585                 590

Leu Ser Ser Leu Gly Glu Asp Gln Asp Ser Val Leu Thr Pro Glu Glu
        595                 600                 605

Val Ala Leu Cys Leu Glu Leu Ser Glu Gly Glu Thr Pro Arg Asn
    610                 615                 620

Ser Val Ser Pro Met Pro Arg Ala Pro Ser Pro Thr Thr Tyr Gly
625                 630                 635                 640

Tyr Ile Ser Val Pro Thr Ala Ser Glu Phe Thr Asp Met Gly Arg Thr
                645                 650                 655

Gly Gly Gly Val Gly Pro Lys Gly Gly Val Leu Leu Cys Pro Pro Arg
            660                 665                 670

Pro Cys Leu Thr Pro Thr Pro Ser Glu Gly Ser Leu Ala Asn Gly Trp
```

|     |     |     | 675 |     |     |     | 680 |     |     |     | 685 |     |     |
| --- | --- | --- | --- | --- | --- | --- | --- | --- | --- | --- | --- | --- | --- |

Gly Ser Ala Ser Glu Asp Asn Ala Ala Ser Ala Arg Ala Ser Leu Val
            690                 695                 700

Ser Ser Ser Asp Gly Ser Phe Leu Ala Asp Ala His Phe Ala Arg Ala
705                 710                 715                 720

Leu Ala Val Ala Val Asp Ser Phe Gly Phe Gly Leu Glu Pro Arg Glu
                        725                 730                 735

Ala Asp Cys Val Phe Ile Asp Ala Ser Ser Pro Ser Pro Arg Asp
                    740                 745                 750

Glu Ile Phe Leu Thr Pro Asn Leu Ser Leu Pro Leu Trp Glu Trp Arg
                755                 760                 765

Pro Asp Trp Leu Glu Asp Met Glu Val Ser His Thr Gln Arg Leu Gly
770                 775                 780

Arg Gly Met Pro Pro Trp Pro Pro Asp Ser Gln Ile Ser Ser Gln Arg
785                 790                 795                 800

Ser Gln Leu His Cys Arg Met Pro Lys Ala Gly Ala Ser Pro Val Asp
                805                 810                 815

Tyr Ser

<210> SEQ ID NO 13
<211> LENGTH: 2106
<212> TYPE: DNA
<213> ORGANISM: Artificial Sequence
<220> FEATURE:
<223> OTHER INFORMATION: FLAG-hROBO4-341na

<400> SEQUENCE: 13

| | | |
|---|---|---|
| atgggctctg gaggagacag cctcctcggc ggcagaggtt ccctgcctct gctgctcctg | 60 |
| ctcatcatgg gaggcatggc tgattacaag gatgacgacg ataaggaggct gccggaaaaa | 120 |
| gtgcccagtg ccccacctca ggaagtgact ctaaagcctg gcaatggcac tgtctttgtg | 180 |
| agctgggtcc caccacctgc tgaaaaccac aatggcatca tccgtggcta ccaggtctgg | 240 |
| agcctgggca acacatcact gccaccagcc aactggactg tagttggtga gcagacccag | 300 |
| ctggaaatcg ccacccatat gccaggctcc tactgcgtgc aagtggctgc agtcactggt | 360 |
| gctggagctg gggagcccag tagacctgtc tgcctccttt tagagcaggc catggagcga | 420 |
| gccacccaag aacccagtga gcatggtccc tggaccctgg agcagctgag gctaccttg | 480 |
| aagcggcctg aggtcattgc cacctgcggt gttgcactct ggctgctgct tctgggcacc | 540 |
| gccgtgtgta tccaccgccg gcgccgagct agggtgcacc tgggcccagg tctgtacaga | 600 |
| tataccagtg aggatgccat cctaaaacac aggatggatc acagtgactc ccagtggttg | 660 |
| gcagacactt ggcgttccac ctctggctct cgggacctga gcagcagcag cagcctcagc | 720 |
| agtcggctgg gggcggatgc ccgggaccca ctagactgtc gtcgctcctt gctctcctgg | 780 |
| gactcccgaa gccccggcgt gcccctgctt ccagacacca gcacttttta tggctccctc | 840 |
| atcgctgagc tgccctccag taccccagcc aggccaagtc cccaggtccc agctgtcagg | 900 |
| cgcctcccac cccagctggc ccagctctcc agcccctgtt ccagctcaga cagcctctgc | 960 |
| agccgcaggg gactctcttc tccccgcttg tctctggccc ctgcagaggc ttggaaggcc | 1020 |
| aaaaagaagc aggagctgca gcatgccaac agttccccac tgctccgggg cagccactcc | 1080 |
| ttggagctcc gggcctgtga gttaggaaat agaggttcca gaacctttc ccaaagccca | 1140 |
| ggagctgtgc cccaagctct ggttgcctgg cgggccctgg accgaaaact cctcagctcc | 1200 |
| tcaaatgagc tggttactcg tcatctccct ccagcacccc tctttcctca tgaaactccc | 1260 |

```
ccaactcaga gtcaacagac ccagcctccg gtggcaccac aggctccctc ctccatcctg    1320
ctgccagcag cccccatccc catccttagc ccctgcagtc ccctagcccc caggcctct      1380 tccctctctg gccccagccc agcttccagt cgcctgtcca gctcctcact gtcatccctg    1440
ggggaggatc aagacagcgt gctgaccect gaggaggtag ccctgtgctt ggaactcagt    1500
gagggtgagg agactcccag gaacagcgtc tctcccatgc caagggctcc ttcaccccccc  1560 accacctatg ggtacatcag cgtcccaaca gcctcagagt tcacggacat gggcaggact    1620
ggaggagggg tggggcccaa gggggagtc ttgctgtgcc cacctcggcc ctgcctcacc     1680
cccaccccca gcgagggctc cttagccaat ggttggggct cagcctctga ggacaatgcc   1740
gccagcgcca gagccagcct tgtcagctcc tccgatggct ccttcctcgc tgatgctcac   1800
tttgcccggg ccctggcagt ggctgtggat agctttggtt tcggtctaga gcccagggag   1860
gcagactgcg tcttcataga tgcctcatca cctccctccc cacgggatga gatcttcctg   1920
acccccaacc tctccctgcc cctgtgggag tggaggccag actggttgga agacatggag   1980
gtcagccaca cccagcggct gggaaggggg atgcctccct ggcccctga ctctcagatc     2040 tcttcccaga gaagtcagct ccactgtcgt atgcccaagg ctggtgcttc tcctgtagat   2100
tactcc                                                              2106
```

<210> SEQ ID NO 14
<211> LENGTH: 702
<212> TYPE: PRT
<213> ORGANISM: Artificial Sequence
<220> FEATURE:
<223> OTHER INFORMATION: FLAG-hROBO4-341aa

<400> SEQUENCE: 14

```
Met Gly Ser Gly Gly Asp Ser Leu Leu Gly Gly Arg Gly Ser Leu Pro
1               5                   10                  15

Leu Leu Leu Leu Leu Ile Met Gly Gly Met Ala Asp Tyr Lys Asp Asp
            20                  25                  30

Asp Asp Lys Arg Leu Pro Glu Lys Val Pro Ser Ala Pro Pro Gln Glu
        35                  40                  45

Val Thr Leu Lys Pro Gly Asn Gly Thr Val Phe Val Ser Trp Val Pro
    50                  55                  60

Pro Pro Ala Glu Asn His Asn Gly Ile Ile Arg Gly Tyr Gln Val Trp
65                  70                  75                  80

Ser Leu Gly Asn Thr Ser Leu Pro Pro Ala Asn Trp Thr Val Gly
                85                  90                  95

Glu Gln Thr Gln Leu Glu Ile Ala Thr His Met Pro Gly Ser Tyr Cys
            100                 105                 110

Val Gln Val Ala Ala Val Thr Gly Ala Gly Ala Gly Glu Pro Ser Arg
        115                 120                 125

Pro Val Cys Leu Leu Leu Glu Gln Ala Met Glu Arg Ala Thr Gln Glu
    130                 135                 140

Pro Ser Glu His Gly Pro Trp Thr Leu Glu Gln Leu Arg Ala Thr Leu
145                 150                 155                 160

Lys Arg Pro Glu Val Ile Ala Thr Cys Gly Val Ala Leu Trp Leu Leu
                165                 170                 175

Leu Leu Gly Thr Ala Val Cys Ile His Arg Arg Arg Ala Arg Val
            180                 185                 190

His Leu Gly Pro Gly Leu Tyr Arg Tyr Thr Ser Glu Asp Ala Ile Leu
        195                 200                 205
```

```
Lys His Arg Met Asp His Ser Asp Ser Gln Trp Leu Ala Asp Thr Trp
210                 215                 220
Arg Ser Thr Ser Gly Ser Arg Asp Leu Ser Ser Ser Ser Ser Leu Ser
225                 230                 235                 240
Ser Arg Leu Gly Ala Asp Ala Arg Asp Pro Leu Asp Cys Arg Arg Ser
                245                 250                 255
Leu Leu Ser Trp Asp Ser Arg Ser Pro Gly Val Pro Leu Leu Pro Asp
                260                 265                 270
Thr Ser Thr Phe Tyr Gly Ser Leu Ile Ala Glu Leu Pro Ser Ser Thr
            275                 280                 285
Pro Ala Arg Pro Ser Pro Gln Val Pro Ala Val Arg Arg Leu Pro Pro
290                 295                 300
Gln Leu Ala Gln Leu Ser Ser Pro Cys Ser Ser Ser Asp Ser Leu Cys
305                 310                 315                 320
Ser Arg Arg Gly Leu Ser Ser Pro Arg Leu Ser Leu Ala Pro Ala Glu
                325                 330                 335
Ala Trp Lys Ala Lys Lys Lys Gln Glu Leu Gln His Ala Asn Ser Ser
                340                 345                 350
Pro Leu Leu Arg Gly Ser His Ser Leu Glu Leu Arg Ala Cys Glu Leu
            355                 360                 365
Gly Asn Arg Gly Ser Lys Asn Leu Ser Gln Ser Pro Gly Ala Val Pro
370                 375                 380
Gln Ala Leu Val Ala Trp Arg Ala Leu Gly Pro Lys Leu Leu Ser Ser
385                 390                 395                 400
Ser Asn Glu Leu Val Thr Arg His Leu Pro Pro Ala Pro Leu Phe Pro
                405                 410                 415
His Glu Thr Pro Pro Thr Gln Ser Gln Gln Thr Gln Pro Pro Val Ala
            420                 425                 430
Pro Gln Ala Pro Ser Ser Ile Leu Leu Pro Ala Ala Pro Ile Pro Ile
            435                 440                 445
Leu Ser Pro Cys Ser Pro Pro Ser Pro Gln Ala Ser Ser Leu Ser Gly
450                 455                 460
Pro Ser Pro Ala Ser Ser Arg Leu Ser Ser Ser Ser Leu Ser Ser Leu
465                 470                 475                 480
Gly Glu Asp Gln Asp Ser Val Leu Thr Pro Glu Glu Val Ala Leu Cys
                485                 490                 495
Leu Glu Leu Ser Glu Gly Glu Thr Pro Arg Asn Ser Val Ser Pro
            500                 505                 510
Met Pro Arg Ala Pro Ser Pro Pro Thr Thr Tyr Gly Tyr Ile Ser Val
                515                 520                 525
Pro Thr Ala Ser Glu Phe Thr Asp Met Gly Arg Thr Gly Gly Val
530                 535                 540
Gly Pro Lys Gly Gly Val Leu Leu Cys Pro Arg Pro Cys Leu Thr
545                 550                 555                 560
Pro Thr Pro Ser Glu Gly Ser Leu Ala Asn Gly Trp Gly Ser Ala Ser
                565                 570                 575
Glu Asp Asn Ala Ala Ser Ala Arg Ala Ser Leu Val Ser Ser Ser Asp
                580                 585                 590
Gly Ser Phe Leu Ala Asp Ala His Phe Ala Arg Ala Leu Ala Val Ala
            595                 600                 605
Val Asp Ser Phe Gly Phe Gly Leu Glu Pro Arg Glu Ala Asp Cys Val
610                 615                 620
```

```
Phe Ile Asp Ala Ser Ser Pro Pro Ser Pro Arg Asp Glu Ile Phe Leu
625                 630                 635                 640

Thr Pro Asn Leu Ser Leu Pro Leu Trp Glu Trp Arg Pro Asp Trp Leu
            645                 650                 655

Glu Asp Met Glu Val Ser His Thr Gln Arg Leu Gly Arg Gly Met Pro
        660                 665                 670

Pro Trp Pro Pro Asp Ser Gln Ile Ser Ser Gln Arg Ser Gln Leu His
    675                 680                 685

Cys Arg Met Pro Lys Ala Gly Ala Ser Pro Val Asp Tyr Ser
690                 695                 700

<210> SEQ ID NO 15
<211> LENGTH: 3045
<212> TYPE: DNA
<213> ORGANISM: Mus musculus

<400> SEQUENCE: 15
```

| | | | | | |
|---|---|---|---|---|---|
| atgggacaag | gagaggagcc | gagagcagcc | atgggctctg | gaggaacggg | cctcctgggg | 60 |
| acggagtggc | ctctgcctct | gctgctgctt | ttcatcatgg | gaggtgaggc | tctggattct | 120 |
| ccacccagag | tcctagttca | cccccaggac | cagctacttc | agggctctgg | cccagccaag | 180 |
| atgaggtgca | gatcatccgg | ccaaccacct | cccactatcc | gctggctgct | gaatgggcag | 240 |
| cccctcagca | tggccacccc | agacctacat | taccttttgc | cggatgggac | cctcctgtta | 300 |
| catcggccct | ctgtccaggg | acggccacaa | gatgaccaga | acatcctctc | agcaatcctg | 360 |
| ggtgtctaca | catgtgaggc | cagcaaccgg | ctgggcacag | cagtgagccg | ggtgctagg | 420 |
| ctgtctgtgg | ctgtcctcca | ggaggacttc | cagatccaac | tcgggacac | agtggccgtg | 480 |
| gtgggagaga | gcttggttct | tgagtgtggt | cctccctggg | gctacccaaa | accctcggtc | 540 |
| tcatggtgga | agacgggaa | accctggtc | ctccagccag | ggaggcgcac | agtatctggg | 600 |
| gattccctga | tggtgtcaag | agcagagaag | aatgactcgg | ggacctatat | gtgtatggcc | 660 |
| accaacaatg | ctgggcaacg | ggagagccga | gcagccaggg | tgtctatcca | ggaatcccag | 720 |
| gaccacaagg | aacatctaga | gcttctggct | gttcgcattc | agctggaaaa | tgtgaccctg | 780 |
| ctaaaccccg | aacctgtaaa | aggtcccaag | cctgggccat | ccgtgtggct | cagctggaag | 840 |
| gtgagcggcc | ctgctgcacc | tgctgagtca | tacacagctc | tgttcaggac | tcagaggtcc | 900 |
| cccagggacc | aaggatctcc | atggacagag | gtgctgctgc | gtggcttgca | gagtgcaaag | 960 |
| cttgggggtc | tccactgggg | ccaagactat | gaattcaaag | tgagaccgtc | ctccggccgg | 1020 |
| gctcgaggcc | ctgacagcaa | tgtgttgctc | ctgaggctgc | ctgaacaggt | gcccagtgcc | 1080 |
| ccacctcaag | gagtgacctt | aagatctgg | aacggtagtg | tctttgtgag | ttgggctcca | 1140 |
| ccacctgctg | aaagccataa | tggtgtcatc | cgtggttacc | aggtctggag | cctgggcaat | 1200 |
| gcctcattgc | ctgctgccaa | ctggaccgta | gtgggtgaac | agacccagct | ggagatcgcc | 1260 |
| acacgactgc | caggctccta | ttgtgtgcaa | gtggctgcag | tcactggagc | tggtgctgga | 1320 |
| gaactcagta | cccctgtctg | cctccttta | gagcaggcca | tggagcaatc | agcacgagac | 1380 |
| cccaggaaac | atgttccctg | gaccctgaa | cagctgaggg | ccaccttgag | acgaccagaa | 1440 |
| gtcattgcca | gtagtgctgt | cctactctgg | ttgctgctac | taggcattac | tgtgtgtatc | 1500 |
| tacagacgac | gcaaagctgg | ggtgcacctg | gcccaggtc | tgtacagata | caccagcgag | 1560 |
| gacgccattc | taaaacacag | gatggaccac | agtgactccc | catggctggc | agacacctgg | 1620 |
| cgttccacct | ctggctctcg | agacctgagc | agcagcagca | gccttagtag | tcggctggga | 1680 |

```
ttggaccctc gggacccact agagggcagg cgctccttga tctcctggga ccctcggagc    1740
cccggtgtac ccctgcttcc agacacgagc acgttttacg gctccctcat tgcagagcag    1800
ccttccagcc ctccagtccg gccaagcccc aagacaccag ctgctaggcg ctttccatcc    1860
aagttggctg gaacctccag cccctgggct agctcagata gtctctgcag ccgcagggga    1920
ctctgttccc cacgcatgtc tctgaccct acagaggctt ggaaggccaa aaagaagcag    1980
gaattgcacc aagctaacag ctccccactg ctccggggca gccacccat ggaaatctgg    2040
gcctgggagt tgggaagcag agcctccaag aacctttctc aaagcccagg agaagcgccc    2100
cgagccgtgg tatcctggcg tgctgtggga ccacaacttc accgcaactc cagtgagctg    2160
gcatctcgtc cactccctcc aacaccctt tctcttcgtg gagcttccag tcatgaccca    2220
cagagccagt gtgtggagaa gctccaagct ccctcctctg acccactgcc agcagcccct    2280
ctctccgtcc tcaactcttc cagaccttcc agccccagg cctctttcct ctcctgtcct    2340
agcccatcct ccagcaacct gtccagctcc tcgctgtcat ccttagagga ggaggaggat    2400
caggacagcg tgctcacccc cgaggaggta gccctgtgtc tggagctcag tgatggggag    2460
gagacaccca cgaacagtgt atctcctatg ccaagagctc cttccccgcc aacaacctat    2520
ggctatatca gcataccaac ctgctcagga ctggcagaca tgggcagagc tggcggggc    2580
gtggggtctg aggttgggaa cttactgtat ccacctcggc cctgccccac ccctacaccc    2640
agcgagggct ccctggccaa tggttggggc tcagcttctg aggacaatgt ccccagcgcc    2700
agggccagcc tggttagctc ttctgatggc tccttcctcg ctgatactca ctttgctcgt    2760
gccctggcag tggctgtgga tagctttggc ctcagtctgg atcccaggga agctgactgt    2820
gtcttcactg atgcctcatc acctccctcc cctcggggtg atctctccct gacccgaagc    2880
ttctctctgc ctttgtggga gtggaggcca gactggttgg aagatgctga gatcagccac    2940
acccagaggc tggggagggg gctgcctccc tggcctcctg attctagggc ctcttcccag    3000
cgaagttggc taactggtgc tgtgcccaag gctggtgatt cctcc                   3045
```

<210> SEQ ID NO 16
<211> LENGTH: 1015
<212> TYPE: PRT
<213> ORGANISM: Mus musculus

<400> SEQUENCE: 16

Met Gly Gln Gly Glu Glu Pro Arg Ala Ala Met Gly Ser Gly Gly Thr
1               5                   10                  15

Gly Leu Leu Gly Thr Glu Trp Pro Leu Pro Leu Leu Leu Phe Ile
            20                  25                  30

Met Gly Gly Glu Ala Leu Asp Ser Pro Pro Gln Ile Leu Val His Pro
        35                  40                  45

Gln Asp Gln Leu Leu Gln Gly Ser Gly Pro Ala Lys Met Arg Cys Arg
    50                  55                  60

Ser Ser Gly Gln Pro Pro Thr Ile Arg Trp Leu Leu Asn Gly Gln
65                  70                  75                  80

Pro Leu Ser Met Ala Thr Pro Asp Leu His Tyr Leu Leu Pro Asp Gly
                85                  90                  95

Thr Leu Leu Leu His Arg Pro Ser Val Gln Gly Arg Pro Gln Asp Asp
            100                 105                 110

Gln Asn Ile Leu Ser Ala Ile Leu Gly Val Tyr Thr Cys Glu Ala Ser
        115                 120                 125

Asn Arg Leu Gly Thr Ala Val Ser Arg Gly Ala Arg Leu Ser Val Ala

-continued

```
                130                 135                 140
Val Leu Gln Glu Asp Phe Gln Ile Gln Pro Arg Asp Thr Val Ala Val
145                 150                 155                 160

Val Gly Glu Ser Leu Val Leu Glu Cys Gly Pro Pro Trp Gly Tyr Pro
                165                 170                 175

Lys Pro Ser Val Ser Trp Trp Lys Asp Gly Lys Pro Leu Val Leu Gln
                180                 185                 190

Pro Gly Arg Arg Thr Val Ser Gly Asp Ser Leu Met Val Ser Arg Ala
                195                 200                 205

Glu Lys Asn Asp Ser Gly Thr Tyr Met Cys Met Ala Thr Asn Asn Ala
                210                 215                 220

Gly Gln Arg Glu Ser Arg Ala Ala Arg Val Ser Ile Gln Glu Ser Gln
225                 230                 235                 240

Asp His Lys Glu His Leu Glu Leu Leu Ala Val Arg Ile Gln Leu Glu
                245                 250                 255

Asn Val Thr Leu Leu Asn Pro Glu Pro Val Lys Gly Pro Lys Pro Gly
                260                 265                 270

Pro Ser Val Trp Leu Ser Trp Lys Val Ser Gly Pro Ala Ala Pro Ala
                275                 280                 285

Glu Ser Tyr Thr Ala Leu Phe Arg Thr Gln Arg Ser Pro Arg Asp Gln
                290                 295                 300

Gly Ser Pro Trp Thr Glu Val Leu Leu Arg Gly Leu Gln Ser Ala Lys
305                 310                 315                 320

Leu Gly Gly Leu His Trp Gly Gln Asp Tyr Glu Phe Lys Val Arg Pro
                325                 330                 335

Ser Ser Gly Arg Ala Arg Gly Pro Asp Ser Asn Val Leu Leu Leu Arg
                340                 345                 350

Leu Pro Glu Gln Val Pro Ser Ala Pro Gln Gly Val Thr Leu Arg
                355                 360                 365

Ser Gly Asn Gly Ser Val Phe Val Ser Trp Ala Pro Pro Ala Glu
370                 375                 380

Ser His Asn Gly Val Ile Arg Gly Tyr Gln Val Trp Ser Leu Gly Asn
385                 390                 395                 400

Ala Ser Leu Pro Ala Ala Asn Trp Thr Val Val Gly Glu Gln Thr Gln
                405                 410                 415

Leu Glu Ile Ala Thr Arg Leu Pro Gly Ser Tyr Cys Val Gln Val Ala
                420                 425                 430

Ala Val Thr Gly Ala Gly Ala Gly Glu Leu Ser Thr Pro Val Cys Leu
                435                 440                 445

Leu Leu Glu Gln Ala Met Glu Gln Ser Ala Arg Asp Pro Arg Lys His
                450                 455                 460

Val Pro Trp Thr Leu Glu Gln Leu Arg Ala Thr Leu Arg Arg Pro Glu
465                 470                 475                 480

Val Ile Ala Ser Ser Ala Val Leu Leu Trp Leu Leu Leu Gly Ile
                485                 490                 495

Thr Val Cys Ile Tyr Arg Arg Lys Ala Gly Val His Leu Gly Pro
                500                 505                 510

Gly Leu Tyr Arg Tyr Thr Ser Glu Asp Ala Ile Leu Lys His Arg Met
                515                 520                 525

Asp His Ser Asp Ser Pro Trp Leu Ala Asp Thr Trp Arg Ser Thr Ser
                530                 535                 540

Gly Ser Arg Asp Leu Ser Ser Ser Ser Leu Ser Ser Arg Leu Gly
545                 550                 555                 560
```

```
Leu Asp Pro Arg Asp Pro Leu Glu Gly Arg Ser Leu Ile Ser Trp
            565                 570                 575

Asp Pro Arg Ser Pro Gly Val Pro Leu Leu Pro Asp Thr Ser Thr Phe
            580                 585                 590

Tyr Gly Ser Leu Ile Ala Glu Gln Pro Ser Ser Pro Val Arg Pro
            595                 600                 605

Ser Pro Lys Thr Pro Ala Ala Arg Arg Phe Pro Ser Lys Leu Ala Gly
            610                 615                 620

Thr Ser Ser Pro Trp Ala Ser Ser Asp Ser Leu Cys Ser Arg Arg Gly
625                 630                 635                 640

Leu Cys Ser Pro Arg Met Ser Leu Thr Pro Thr Glu Ala Trp Lys Ala
            645                 650                 655

Lys Lys Lys Gln Glu Leu His Gln Ala Asn Ser Ser Pro Leu Leu Arg
            660                 665                 670

Gly Ser His Pro Met Glu Ile Trp Ala Trp Glu Leu Gly Ser Arg Ala
            675                 680                 685

Ser Lys Asn Leu Ser Gln Ser Pro Gly Glu Ala Pro Arg Ala Val Val
            690                 695                 700

Ser Trp Arg Ala Val Gly Pro Gln Leu His Arg Asn Ser Ser Glu Leu
705                 710                 715                 720

Ala Ser Arg Pro Leu Pro Pro Thr Pro Leu Ser Leu Arg Gly Ala Ser
            725                 730                 735

Ser His Asp Pro Gln Ser Gln Cys Val Glu Lys Leu Gln Ala Pro Ser
            740                 745                 750

Ser Asp Pro Leu Pro Ala Ala Pro Leu Ser Val Leu Asn Ser Ser Arg
            755                 760                 765

Pro Ser Ser Pro Gln Ala Ser Phe Leu Ser Cys Pro Ser Pro Ser Ser
            770                 775                 780

Ser Asn Leu Ser Ser Ser Leu Ser Ser Leu Glu Glu Glu Asp
785                 790                 795                 800

Gln Asp Ser Val Leu Thr Pro Glu Glu Val Ala Leu Cys Leu Glu Leu
            805                 810                 815

Ser Asp Gly Glu Glu Thr Pro Thr Asn Ser Val Ser Pro Met Pro Arg
            820                 825                 830

Ala Pro Ser Pro Pro Thr Thr Tyr Gly Tyr Ile Ser Ile Pro Thr Cys
            835                 840                 845

Ser Gly Leu Ala Asp Met Gly Arg Ala Gly Gly Val Gly Ser Glu
850                 855                 860

Val Gly Asn Leu Leu Tyr Pro Pro Arg Pro Cys Pro Thr Pro Thr Pro
865                 870                 875                 880

Ser Glu Gly Ser Leu Ala Asn Gly Trp Gly Ser Ala Ser Glu Asp Asn
            885                 890                 895

Val Pro Ser Ala Arg Ala Ser Leu Val Ser Ser Ser Asp Gly Ser Phe
            900                 905                 910

Leu Ala Asp Thr His Phe Ala Arg Ala Leu Ala Val Ala Val Asp Ser
            915                 920                 925

Phe Gly Leu Ser Leu Asp Pro Arg Glu Ala Asp Cys Val Phe Thr Asp
            930                 935                 940

Ala Ser Ser Pro Pro Ser Pro Arg Gly Asp Leu Ser Leu Thr Arg Ser
945                 950                 955                 960

Phe Ser Leu Pro Leu Trp Glu Trp Arg Pro Asp Trp Leu Glu Asp Ala
            965                 970                 975
```

```
Glu Ile Ser His Thr Gln Arg Leu Gly Arg Gly Leu Pro Pro Trp Pro
            980                 985                 990

Pro Asp Ser Arg Ala Ser Ser Gln  Arg Ser Trp Leu Thr Gly Ala Val
        995                 1000                 1005

Pro Lys  Ala Gly Asp Ser Ser
    1010             1015

<210> SEQ ID NO 17
<211> LENGTH: 3063
<212> TYPE: DNA
<213> ORGANISM: Rattus norvegicus

<400> SEQUENCE: 17
```

| | | | | | |
|---|---|---|---|---|---|
| atgggacaag | gagaggagct | gagagcagcc | gttgactctg | gaggaatggg | cctcctgggg      60 |
| actaagtgtc | ctctgcctct | actgcttctt | ttcatcatgg | gaggcaaggc | tctggattct     120 |
| ccacccccaga | tcctagttca | tccccaggac | cagctacttc | agggctccgg | gccggccaag     180 |
| atgagttgca | gagcatcggg | ccaaccactt | cccactatcc | gctggctgct | gaatgggcag     240 |
| cccctcagca | tggcgacccc | agacctacat | tacctccaat | cagatgggac | cctcctgcta     300 |
| catcggcccc | ctacccatgg | acggccgcaa | gacgaccaga | acattctctc | agcaatcctg     360 |
| ggtgtctaca | catgtgaggc | cagcaaccgg | ctgggcacag | cagtgagccg | ggtgctagg     420 |
| ctgtctgtgg | ctgtcctcca | ggaggacttc | cgaatccaac | ctcgggacac | agtgccgtg     480 |
| gtgggcgaga | gcttggttct | cgagtgtggt | cctccctggg | gctacccaaa | gccttcagtc     540 |
| tcctggtgga | agatgggaa | accccctggtc | ctccagccag | ggaagcgcac | agtgtctggg     600 |
| gattctctga | tggtggcaag | agcagagaag | aatgacacgg | ggacctatat | gtgtatggcc     660 |
| accaacaatg | ccggacaacg | ggagagtcgg | gcagccaggg | tgtctatcca | ggagtcaccg     720 |
| gaccacaagg | agcatctaga | gcttctggct | gttcgaattc | agctggaaaa | tgtgaccctg     780 |
| ctgaacccag | aacctgtaaa | aggccccaag | cctgggccag | ctgtgtggct | cagctggaag     840 |
| gtgagcggcc | ctgctgcacc | tgcccagtca | tacacagccc | tgttcagggc | gcagagggac     900 |
| cccagggacc | agggatctcc | atggacagag | gtgctgctgg | atggcttgct | gaatgcaaag     960 |
| cttggggggtc | tccgctgggg | ccaagactac | gaattcaaag | tgagaccgtc | ctccggccgg    1020 |
| gctcgaggcc | ctgatagcaa | tgtgttgctc | ctgaggctgc | ctgaacaggt | gccagtgcc    1080 |
| ccacctcaag | aagtgaccct | aagacctggc | aacggtagtg | tctttgtgag | ttgggcccca    1140 |
| cctcctgctg | aaaaccataa | cggtttcatc | cgtggctacc | aggtctggag | cctgggcaat    1200 |
| gcctcattgc | ctgctgccaa | ctggaccgta | gtgggtgaac | agacacagct | ggagattgcc    1260 |
| gcacgaatgc | caggctccta | ttgtgtgcag | gtggctgcag | tcactggtgc | tggggctgga    1320 |
| gagcccagta | tccctgtctg | cctccttta | gagcaggcca | tggagcaatc | agcacgagac    1380 |
| cccagtaaac | atgtttcctg | gaccctggaa | cagctgaggg | ccaccttgaa | cgaccagaa    1440 |
| gtcattgcca | gtggtgccgt | cctgctctgg | ttgctgctcc | taggcattgc | tgtgtgtatc    1500 |
| tacaggcgac | ggaaagctgg | ggtgcacctg | gcccaggtc | tctacagata | caccagtgag    1560 |
| gatgccattt | taaaacacag | gatggaccac | agtgactccc | catggctggc | agacaccctgg    1620 |
| cgctccacct | ctggctctag | agatctgagc | agcagcagca | gctcagtag | tcgactagga    1680 |
| gtggaccctc | gggacccact | ggacggcagg | cgttccttga | tctcctggga | ccccggagc    1740 |
| cccggtgtac | ccctgcttcc | agacactagc | acgttttacg | gctccctcat | tgcagagcag    1800 |
| acttccagcc | ctccagtccg | gccaagcccg | cagacgccag | ctgctaggcg | ccttccaccc    1860 |

```
aagctgaccg gaacctccag ccctgggct agctcagata gtctctgcag ccgcaggga     1920 ctctgttccc cacgcatgtc tctggcccct gcagaggctt ggaaggccaa aaagaagcag     1980
gaactgcacc aagctaacag ctccccgctg ctccagggta gccaccccat ggaaatctgg     2040
gcctgggagt tgggaagcag agcctccaag aacctttctc aaagcccggg cccaaacact     2100
tgttccccac gagaagctcc cggagcagtg gtagcctggc gtgccctggg accacaactt     2160
caccgcaact ccagtgagct agcagctcgt ccactccctc cgacacccct ttctcttcgt     2220
ggagccccca gtcatgatcc gcagagccag tgtgtggaga agctccaagc tccctcctct     2280
gacccactgc cagcagcccc tctctccgtc tcaactctt ccaggccttc cagccccag     2340 gcctcttcc tctctgttcc tagcccagga tccagcaacc tgtccagctc ctcactgtca     2400
tccttagagg aggaggatca ggacagtgta ctcaccctg aggaggtagc cctgtgtctg     2460
gagctcagtg atggggagga cacccacg aacagtgtat ctcctatgcc aagagctcct     2520
tcacccccag caacctatgg ctatatcagc ataccaacct cctcaggact ggcagacatg     2580
ggcagagctg gtgggggcgt ggggtctgag gtcgggaact tactgtgccc acctcggctc     2640
tgccccacac ctacacccag cgaggggctcc ctggccaatg gttggggctc agcttcagag     2700
gacaatgtcc ccgcgccag ggccagcctg gttagctctt ctgatggctc cttccttgct     2760
gacgctcact tgctcgtgc cctggcagtg gctgtggaca gcttcggttt cagtctggag     2820
cccagggaag ctgactgtgt ctttactgat gcctcatcac cccatccc tcgggatgat     2880 ctttctctga cccgaagctt ctctctgcca ctgtgggagt ggaggccaga ctggttggaa     2940
gatgctgaga tcaaccacac ccagaggctg ggaggggc tgcctccctg gcctcctgat     3000
tctagagtct cttcccagcg aagttggctc actggtgttg tgcccaaggc tggtgattcc     3060
tcc                                                                   3063
```

<210> SEQ ID NO 18
<211> LENGTH: 1021
<212> TYPE: PRT
<213> ORGANISM: Rattus norvegicus

<400> SEQUENCE: 18

```
Met Gly Gln Gly Glu Glu Leu Arg Ala Ala Val Asp Ser Gly Gly Met
1               5                   10                  15

Gly Leu Leu Gly Thr Lys Cys Pro Leu Pro Leu Leu Leu Phe Ile
            20                  25                  30

Met Gly Gly Lys Ala Leu Asp Ser Pro Pro Gln Ile Leu Val His Pro
        35                  40                  45

Gln Asp Gln Leu Leu Gln Gly Ser Gly Pro Ala Lys Met Ser Cys Arg
    50                  55                  60

Ala Ser Gly Gln Pro Leu Pro Thr Ile Arg Trp Leu Leu Asn Gly Gln
65                  70                  75                  80

Pro Leu Ser Met Ala Thr Pro Asp Leu His Tyr Leu Gln Ser Asp Gly
                85                  90                  95

Thr Leu Leu Leu His Arg Pro Thr His Gly Arg Pro Gln Asp Asp
            100                 105                 110

Gln Asn Ile Leu Ser Ala Ile Leu Gly Val Tyr Thr Cys Glu Ala Ser
        115                 120                 125

Asn Arg Leu Gly Thr Ala Val Ser Arg Gly Ala Arg Leu Ser Val Ala
    130                 135                 140

Val Leu Gln Glu Asp Phe Arg Ile Gln Pro Arg Asp Thr Val Ala Val
145                 150                 155                 160
```

```
Val Gly Glu Ser Leu Val Leu Glu Cys Gly Pro Pro Trp Gly Tyr Pro
            165                 170                 175

Lys Pro Ser Val Ser Trp Trp Lys Asp Gly Lys Pro Leu Val Leu Gln
            180                 185                 190

Pro Gly Lys Arg Thr Val Ser Gly Asp Ser Leu Met Val Ala Arg Ala
            195                 200                 205

Glu Lys Asn Asp Thr Gly Thr Tyr Met Cys Met Ala Thr Asn Asn Ala
        210                 215                 220

Gly Gln Arg Glu Ser Arg Ala Ala Arg Val Ser Ile Gln Glu Ser Pro
225                 230                 235                 240

Asp His Lys Glu His Leu Glu Leu Leu Ala Val Arg Ile Gln Leu Glu
                245                 250                 255

Asn Val Thr Leu Leu Asn Pro Glu Pro Val Lys Gly Pro Lys Pro Gly
            260                 265                 270

Pro Ala Val Trp Leu Ser Trp Lys Val Ser Gly Pro Ala Ala Pro Ala
            275                 280                 285

Gln Ser Tyr Thr Ala Leu Phe Arg Ala Gln Arg Asp Pro Arg Asp Gln
        290                 295                 300

Gly Ser Pro Trp Thr Glu Val Leu Leu Asp Gly Leu Leu Asn Ala Lys
305                 310                 315                 320

Leu Gly Gly Leu Arg Trp Gly Gln Asp Tyr Glu Phe Lys Val Arg Pro
                325                 330                 335

Ser Ser Gly Arg Ala Arg Gly Pro Asp Ser Asn Val Leu Leu Leu Arg
            340                 345                 350

Leu Pro Glu Gln Val Pro Ser Ala Pro Gln Glu Val Thr Leu Arg
            355                 360                 365

Pro Gly Asn Gly Ser Val Phe Val Ser Trp Ala Pro Pro Ala Glu
        370                 375                 380

Asn His Asn Gly Phe Ile Arg Gly Tyr Gln Val Trp Ser Leu Gly Asn
385                 390                 395                 400

Ala Ser Leu Pro Ala Ala Asn Trp Thr Val Val Gly Glu Gln Thr Gln
                405                 410                 415

Leu Glu Ile Ala Ala Arg Met Pro Gly Ser Tyr Cys Val Gln Val Ala
            420                 425                 430

Ala Val Thr Gly Ala Gly Ala Gly Glu Pro Ser Ile Pro Val Cys Leu
        435                 440                 445

Leu Leu Glu Gln Ala Met Glu Gln Ser Ala Arg Asp Pro Ser Lys His
        450                 455                 460

Val Ser Trp Thr Leu Glu Gln Leu Arg Ala Thr Leu Lys Arg Pro Glu
465                 470                 475                 480

Val Ile Ala Ser Gly Ala Val Leu Leu Trp Leu Leu Leu Gly Ile
                485                 490                 495

Ala Val Cys Ile Tyr Arg Arg Lys Ala Gly Val His Leu Gly Pro
            500                 505                 510

Gly Leu Tyr Arg Tyr Thr Ser Glu Asp Ala Ile Leu Lys His Arg Met
        515                 520                 525

Asp His Ser Asp Ser Pro Trp Leu Ala Asp Thr Trp Arg Ser Thr Ser
        530                 535                 540

Gly Ser Arg Asp Leu Ser Ser Ser Ser Leu Ser Ser Arg Leu Gly
545                 550                 555                 560

Val Asp Pro Arg Asp Pro Leu Asp Gly Arg Arg Ser Leu Ile Ser Trp
                565                 570                 575
```

```
Asp Pro Arg Ser Pro Gly Val Pro Leu Leu Pro Asp Thr Ser Thr Phe
            580                 585                 590

Tyr Gly Ser Leu Ile Ala Glu Gln Thr Ser Ser Pro Val Arg Pro
        595                 600                 605

Ser Pro Gln Thr Pro Ala Ala Arg Arg Leu Pro Pro Lys Leu Thr Gly
    610                 615                 620

Thr Ser Ser Pro Trp Ala Ser Ser Asp Ser Leu Cys Ser Arg Arg Gly
625                 630                 635                 640

Leu Cys Ser Pro Arg Met Ser Leu Ala Pro Ala Glu Ala Trp Lys Ala
                645                 650                 655

Lys Lys Lys Gln Glu Leu His Gln Ala Asn Ser Ser Pro Leu Leu Gln
            660                 665                 670

Gly Ser His Pro Met Glu Ile Trp Ala Trp Glu Leu Gly Ser Arg Ala
        675                 680                 685

Ser Lys Asn Leu Ser Gln Ser Pro Gly Pro Asn Thr Cys Ser Pro Arg
    690                 695                 700

Glu Ala Pro Gly Ala Val Val Ala Trp Arg Ala Leu Gly Pro Gln Leu
705                 710                 715                 720

His Arg Asn Ser Ser Glu Leu Ala Ala Arg Pro Leu Pro Pro Thr Pro
                725                 730                 735

Leu Ser Leu Arg Gly Ala Pro Ser His Asp Pro Gln Ser Gln Cys Val
            740                 745                 750

Glu Lys Leu Gln Ala Pro Ser Ser Asp Pro Leu Pro Ala Ala Pro Leu
        755                 760                 765

Ser Val Leu Asn Ser Ser Arg Pro Ser Pro Gln Ala Ser Phe Leu
770                 775                 780

Ser Val Pro Ser Pro Gly Ser Ser Asn Leu Ser Ser Ser Ser Leu Ser
785                 790                 795                 800

Ser Leu Glu Glu Glu Asp Gln Asp Ser Val Leu Thr Pro Glu Glu Val
                805                 810                 815

Ala Leu Cys Leu Glu Leu Ser Asp Gly Glu Thr Pro Thr Asn Ser
            820                 825                 830

Val Ser Pro Met Pro Arg Ala Pro Ser Pro Ala Thr Tyr Gly Tyr
        835                 840                 845

Ile Ser Ile Pro Thr Ser Ser Gly Leu Ala Asp Met Gly Arg Ala Gly
850                 855                 860

Gly Gly Val Gly Ser Glu Val Gly Asn Leu Leu Cys Pro Pro Arg Leu
865                 870                 875                 880

Cys Pro Thr Pro Thr Pro Ser Glu Gly Ser Leu Ala Asn Gly Trp Gly
                885                 890                 895

Ser Ala Ser Glu Asp Asn Val Pro Ser Ala Arg Ala Ser Leu Val Ser
            900                 905                 910

Ser Ser Asp Gly Ser Phe Leu Ala Asp Ala His Phe Ala Arg Ala Leu
        915                 920                 925

Ala Val Ala Val Asp Ser Phe Gly Phe Ser Leu Glu Pro Arg Glu Ala
    930                 935                 940

Asp Cys Val Phe Thr Asp Ala Ser Ser Pro Ser Pro Arg Asp Asp
945                 950                 955                 960

Leu Ser Leu Thr Arg Ser Phe Ser Leu Pro Leu Trp Glu Trp Arg Pro
                965                 970                 975

Asp Trp Leu Glu Asp Ala Glu Ile Asn His Thr Gln Arg Leu Gly Arg
            980                 985                 990

Gly Leu Pro Pro Trp Pro Pro Asp  Ser Arg Val Ser Ser  Gln Arg Ser
```

|   |   |   |   |   | 995 |   |   |   | 1000 |   |   |   |   | 1005 |
|---|---|---|---|---|---|---|---|---|---|---|---|---|---|---|

Trp Leu Thr Gly Val Val Pro Lys Ala Gly Asp Ser Ser
  1010              1015              1020

<210> SEQ ID NO 19
<211> LENGTH: 3021
<212> TYPE: DNA
<213> ORGANISM: Macaca fascicularis

<400> SEQUENCE: 19

| atgggctctg | gaggagaaag | cctccggggg | tcccgggctt | ccggcctct | gctgctcctg | 60 |
|---|---|---|---|---|---|---|
| ctcatcatgg | gaggcatggc | tcaggactcc | ccgccccaga | tcctagtcca | cccgcaagac | 120 |
| cagctgttcc | agggccctgg | ccctgccagg | atgagctgcc | gagcctcggg | ccagccacct | 180 |
| cccaccatcc | gctggctgct | gaatgggcag | cccctgagca | tggtgccccc | agacccacac | 240 |
| cacctcctgc | ctgatgggac | ccttctgctg | ctgcagcccc | ctgcctgggg | acatgcccac | 300 |
| gatggccagg | ccctgtccac | agaccttggt | gtctacacat | gtgaggccag | caaccggctg | 360 |
| ggcacagcag | tcagcagagg | cgctcggctc | tctgtggctg | tcctccggga | ggatttccag | 420 |
| atccagcctc | gggacatggt | agctgtggtg | ggtgagcagt | taactctgga | atgtgggccg | 480 |
| ccctggggcc | acccagagcc | cacagtctca | tggtggaaag | atgggaaacc | cctggtcctc | 540 |
| cagcctggaa | ggtacacggt | gtccgggggg | tccctgctga | tggcaagagc | agagaagagt | 600 |
| gacgcagggg | cctacatgtg | tgtggccgcc | aacagcgcag | acacaggga | gagccacgca | 660 |
| gcccgggtgt | ccatccagga | gccccaggac | tacacagagc | ctgtggagct | tttggctgtg | 720 |
| cgaattcagc | tggaaaatgt | gacactgctg | aacccggacc | ccgcaaaggg | ccccaagcct | 780 |
| ggaccggctg | tgtggctcag | ctggaaggtg | agcggccctg | ctgcacctgc | ccaatcttac | 840 |
| acggccttgt | tcaggaccca | gactgccccg | ggagaccagg | gagctccatg | gacagaggag | 900 |
| ctgctggctg | gctggcagag | cgcagagctt | ggaggcctcc | actggggcca | agactatgag | 960 |
| ttcaaagtga | gaccatcctc | cggccgggct | cgaggccctg | cagcaacgt | gctgctcctg | 1020 |
| aggctgccgg | aaaaagtgcc | cagtgcccca | ccccaggagg | tgaccctaaa | acctggcaat | 1080 |
| ggcagtgtcc | ttgtgagctg | gtcccacca | cctgctgaaa | accacaatgg | catcatccgt | 1140 |
| ggctaccagg | tctggagcct | gggcaacacg | tcactgcccc | cagccaactg | gactgtggtt | 1200 |
| ggtgagcaga | cccagctgga | aatcgccacc | cgcatgccag | gctcctactg | tgtgcaagtg | 1260 |
| gctgcagtca | ctggtgctgg | agctggggaa | cccagtagcc | ctgtctgcct | ccttttagag | 1320 |
| caggccatga | gcgagccac | ccgagaaccc | agtgagcatg | gtccctggac | cctggagcag | 1380 |
| ctgagggcca | ccttgaagcg | gcctgaggtc | attgccacct | gtggtgttgt | gctctggctg | 1440 |
| ctgcttctgg | gcaccgctgt | gtgtatccac | cgccggcgcc | gagctggggt | gcacctaggc | 1500 |
| ccaggtctgt | acagatatac | cagtaaggac | gccatcctaa | aacacaggat | ggatcacagt | 1560 |
| gactcccagt | ggttggcaga | cacttggcgt | tccacctctg | gctctcggga | cttgagcagc | 1620 |
| agcagcagcc | tcagcagtag | gctggggggcg | gaccccgg | acccgctaga | ctgtcgtcgc | 1680 |
| tccttgctct | cctgggactc | ccgaagcccc | ggcgtgcccc | tgcttccaga | caccagcact | 1740 |
| tttttatggct | ccctcatcgc | tgagctgccc | tccagtcccc | cagccaggcc | aagtccccag | 1800 |
| gtcccagctg | tcaggcgcct | accaccccag | ctggcccgac | tttccagccc | ctgttccagc | 1860 |
| tcagacagcc | tctgcagcca | cagggggattc | tcttctccac | gcttgtctct | ggcacctaca | 1920 |
| gaggcttgga | aggccaaaaa | gaagcaggag | ctgcagcatg | tcaacagttc | cccactgctc | 1980 |

-continued

```
cggggcagcc aacccttgga gctccgggcc tgtgagttgg gaaatagagg ttccaagaac    2040
ctttcccaaa gcccaggagc tgtgcccaa  gctctggttg cttggcgggc cctgggaccg    2100
aaactcctca gctcctcaaa tgagctggtt actcgtcctc tccctccagc accctctttt   2160
cctcatgaaa ctccccaaac tcagagtcaa cagacccagc ctccggtggc accacaggct    2220
ccctcctcca tcctgctggc aacagccccc attcccatcc ttagcccctg cagtcccccct  2280 agccctcagg cctcttccct ctctggcccc agcccagctt ccagtcacct gtccagctct    2340
tcactgtcat ccctggggga ggatcaagac agcgtgctga cccctgagga ggtagccctg    2400
tgtttggaac tcagtgaggg tgaggagact cccaggaaca gcgtctctcc catgccaaga    2460
gctccttcac cccccaccac ctatgggtat atcagcaccc caacagcctc agagttcacg    2520
ggcatggaca ggaccggagg agggtgggg  tccgagggggg gagtcttgct gtgcccacct   2580
cggccctgcc tcaccccac  ccccagcgag ggctccttag ccaatggttg gggctcagcc    2640
tctgaggaca atgctgccag cgccagagcc agccttgtca gctcctccga tggctccttc    2700
ctcgctgatg cccactttgc ccgggccctg gcagtggcag tggatagctt tggttttggt    2760
ctagagccca gggaggcaga ctgcgtcttc acagatgcct catcacctcc ctccccaagg    2820
gatgacatct tcctgacccc caacctctcc ctgcccctgt gggagtggag gccagactgg    2880
ttggaagaca tggaggtcaa ccacacccag ctgctgggaa gggggatgcc tccctggtcc    2940
cctgactctc ggatctcttc ccagagaagt cagctccact gtcctgtgcc caaggctggt    3000
gcttctcctg tagattactc c                                              3021
```

<210> SEQ ID NO 20
<211> LENGTH: 1007
<212> TYPE: PRT
<213> ORGANISM: Macaca fascicularis

<400> SEQUENCE: 20

```
Met Gly Ser Gly Gly Glu Ser Leu Arg Gly Ser Arg Ala Ser Arg Pro
1               5                   10                  15

Leu Leu Leu Leu Leu Ile Met Gly Gly Met Ala Gln Asp Ser Pro Pro
            20                  25                  30

Gln Ile Leu Val His Pro Gln Asp Gln Leu Phe Gln Gly Pro Gly Pro
        35                  40                  45

Ala Arg Met Ser Cys Arg Ala Ser Gly Gln Pro Pro Thr Ile Arg
    50                  55                  60

Trp Leu Leu Asn Gly Gln Pro Leu Ser Met Val Pro Pro Asp Pro His
65                  70                  75                  80

His Leu Leu Pro Asp Gly Thr Leu Leu Leu Gln Pro Pro Ala Trp
                85                  90                  95

Gly His Ala His Asp Gly Gln Ala Leu Ser Thr Asp Leu Gly Val Tyr
            100                 105                 110

Thr Cys Glu Ala Ser Asn Arg Leu Gly Thr Ala Val Ser Arg Gly Ala
        115                 120                 125

Arg Leu Ser Val Ala Val Leu Arg Glu Asp Phe Gln Ile Gln Pro Arg
    130                 135                 140

Asp Met Val Ala Val Gly Glu Gln Leu Thr Leu Glu Cys Gly Pro
145                 150                 155                 160

Pro Trp Gly His Pro Glu Pro Thr Val Ser Trp Trp Lys Asp Gly Lys
                165                 170                 175

Pro Leu Val Leu Gln Pro Gly Arg Tyr Thr Val Ser Gly Gly Ser Leu
            180                 185                 190
```

```
Leu Met Ala Arg Ala Glu Lys Ser Asp Ala Gly Ala Tyr Met Cys Val
        195                 200                 205

Ala Ala Asn Ser Ala Gly His Arg Glu Ser His Ala Ala Arg Val Ser
    210                 215                 220

Ile Gln Glu Pro Gln Asp Tyr Thr Glu Pro Val Glu Leu Leu Ala Val
225                 230                 235                 240

Arg Ile Gln Leu Glu Asn Val Thr Leu Leu Asn Pro Asp Pro Ala Lys
                245                 250                 255

Gly Pro Lys Pro Gly Pro Ala Val Trp Leu Ser Trp Lys Val Ser Gly
            260                 265                 270

Pro Ala Pro Ala Gln Ser Tyr Thr Ala Leu Phe Arg Thr Gln Thr
        275                 280                 285

Ala Pro Gly Asp Gln Gly Ala Pro Trp Thr Glu Glu Leu Leu Ala Gly
    290                 295                 300

Trp Gln Ser Ala Glu Leu Gly Gly Leu His Trp Gly Gln Asp Tyr Glu
305                 310                 315                 320

Phe Lys Val Arg Pro Ser Ser Gly Arg Ala Arg Gly Pro Asp Ser Asn
                325                 330                 335

Val Leu Leu Leu Arg Leu Pro Glu Lys Val Pro Ser Ala Pro Pro Gln
            340                 345                 350

Glu Val Thr Leu Lys Pro Gly Asn Gly Ser Val Leu Val Ser Trp Val
        355                 360                 365

Pro Pro Pro Ala Glu Asn His Asn Gly Ile Ile Arg Gly Tyr Gln Val
    370                 375                 380

Trp Ser Leu Gly Asn Thr Ser Leu Pro Pro Ala Asn Trp Thr Val Val
385                 390                 395                 400

Gly Glu Gln Thr Gln Leu Glu Ile Ala Thr Arg Met Pro Gly Ser Tyr
                405                 410                 415

Cys Val Gln Val Ala Ala Val Thr Gly Ala Gly Ala Gly Glu Pro Ser
            420                 425                 430

Ser Pro Val Cys Leu Leu Glu Gln Ala Met Glu Arg Ala Thr Arg
        435                 440                 445

Glu Pro Ser Glu His Gly Pro Trp Thr Leu Glu Gln Leu Arg Ala Thr
    450                 455                 460

Leu Lys Arg Pro Glu Val Ile Ala Thr Cys Gly Val Val Leu Trp Leu
465                 470                 475                 480

Leu Leu Leu Gly Thr Ala Val Cys Ile His Arg Arg Arg Ala Gly
                485                 490                 495

Val His Leu Gly Pro Gly Leu Tyr Arg Tyr Thr Ser Lys Asp Ala Ile
            500                 505                 510

Leu Lys His Arg Met Asp His Ser Asp Ser Gln Trp Leu Ala Asp Thr
        515                 520                 525

Trp Arg Ser Thr Ser Gly Ser Arg Asp Leu Ser Ser Ser Ser Leu
    530                 535                 540

Ser Ser Arg Leu Gly Ala Asp Pro Arg Asp Pro Leu Asp Cys Arg Arg
545                 550                 555                 560

Ser Leu Leu Ser Trp Asp Ser Arg Ser Pro Gly Val Pro Leu Leu Pro
                565                 570                 575

Asp Thr Ser Thr Phe Tyr Gly Ser Leu Ile Ala Glu Leu Pro Ser Ser
            580                 585                 590

Pro Pro Ala Arg Pro Ser Pro Gln Val Pro Ala Val Arg Arg Leu Pro
        595                 600                 605
```

-continued

```
Pro Gln Leu Ala Arg Leu Ser Ser Pro Cys Ser Ser Asp Ser Leu
610                 615                 620
Cys Ser His Arg Gly Phe Ser Pro Arg Leu Ser Leu Ala Pro Thr
625                 630                 635                 640
Glu Ala Trp Lys Ala Lys Lys Gln Glu Leu Gln His Val Asn Ser
                645                 650                 655
Ser Pro Leu Leu Arg Gly Ser Gln Pro Leu Glu Leu Arg Ala Cys Glu
                660                 665                 670
Leu Gly Asn Arg Gly Ser Lys Asn Leu Ser Gln Ser Pro Gly Ala Val
                675                 680                 685
Pro Gln Ala Leu Val Ala Trp Arg Ala Leu Gly Pro Lys Leu Leu Ser
690                 695                 700
Ser Ser Asn Glu Leu Val Thr Arg Pro Leu Pro Pro Ala Pro Leu Phe
705                 710                 715                 720
Pro His Glu Thr Pro Gln Thr Gln Ser Gln Gln Thr Gln Pro Pro Val
                725                 730                 735
Ala Pro Gln Ala Pro Ser Ser Ile Leu Leu Ala Thr Ala Pro Ile Pro
                740                 745                 750
Ile Leu Ser Pro Cys Ser Pro Pro Ser Pro Gln Ala Ser Ser Leu Ser
                755                 760                 765
Gly Pro Ser Pro Ala Ser Ser His Leu Ser Ser Ser Leu Ser Ser
770                 775                 780
Leu Gly Glu Asp Gln Asp Ser Val Leu Thr Pro Glu Glu Val Ala Leu
785                 790                 795                 800
Cys Leu Glu Leu Ser Glu Gly Glu Thr Pro Arg Asn Ser Val Ser
                805                 810                 815
Pro Met Pro Arg Ala Pro Ser Pro Pro Thr Thr Tyr Gly Tyr Ile Ser
                820                 825                 830
Thr Pro Thr Ala Ser Glu Phe Thr Gly Met Asp Arg Thr Gly Gly Gly
                835                 840                 845
Val Gly Ser Glu Gly Gly Val Leu Leu Cys Pro Arg Pro Cys Leu
850                 855                 860
Thr Pro Thr Pro Ser Glu Gly Ser Leu Ala Asn Gly Trp Gly Ser Ala
865                 870                 875                 880
Ser Glu Asp Asn Ala Ala Ser Ala Arg Ala Ser Leu Val Ser Ser Ser
                885                 890                 895
Asp Gly Ser Phe Leu Ala Asp Ala His Phe Ala Arg Ala Leu Ala Val
                900                 905                 910
Ala Val Asp Ser Phe Gly Phe Gly Leu Glu Pro Arg Glu Ala Asp Cys
                915                 920                 925
Val Phe Thr Asp Ala Ser Ser Pro Ser Pro Arg Asp Asp Ile Phe
930                 935                 940
Leu Thr Pro Asn Leu Ser Leu Pro Leu Trp Glu Trp Arg Pro Asp Trp
945                 950                 955                 960
Leu Glu Asp Met Glu Val Asn His Thr Gln Leu Leu Gly Arg Gly Met
                965                 970                 975
Pro Pro Trp Ser Pro Asp Ser Arg Ile Ser Gln Arg Ser Gln Leu
                980                 985                 990
His Cys Pro Val Pro Lys Ala Gly Ala Ser Pro Val Asp Tyr Ser
                995                 1000                1005
```

<210> SEQ ID NO 21
<211> LENGTH: 3021
<212> TYPE: DNA

<213> ORGANISM: Macaca fascicularis

<400> SEQUENCE: 21

```
atgggctctg gaggagaaag cctccggggg tcccgggctt cccggcctct gctgctcctg      60
ctcatcatgg gaggtatggc tcaggactcc ccgccccaga tcctagtcca cccgcaagac     120
cagctgttcc agggccctgg ccctgccagg atgagctgcc gagcctcggg ccagccacct     180
cccaccatcc gctggctgct gaatgggcag ccctgagca tggtacccc agacccacac      240
cacctcctgc ctgatgggac ccttctgctg ctgcagcccc tgcccgggg acatgcccac     300
gatggccagg ccctgtccac agaccttggt gtctacacat gtgaggccag caaccggctg     360
ggcacagcag tcagcagagg cgctcggctc tctgtggctg tcctccggga ggatttccag     420
atccagcctc gggacatggt agctgtgtgt ggtgagcagt taactctgga atgtgggccg     480
ccctgggggcc acccagagcc cacagtctca tggtggaaag atgggaaacc cctggtcctc     540
cagcccggaa ggtacacggt gtccgggggg tccctgctga tggcaagagc agagaagagt     600
gacacagggg cctacatgtg tgtggccgcc aacagcgcag acacaggga gagccgcgca     660
gcccgggtgt ccatccagga gccccaggac tacacagagc ctgtggagct tttggctgtg     720
cgaattcagc tggaaaatgt gacactgctg aacccgacc ccgcaaaggg ccccaagcct     780
ggaccggctg tgtggctcag ctggaaggtg agcggccctg ctgcacctgc ccaatcttac     840
acggccttgt tcaggaccca gactgccccg ggagaccagg gagctccatg acagaggag     900
ctgctggctg gctggcagag cgcagagctt ggaggcctcc actggggcca agactatgag     960
ttcaaagtga gaccatcctc cggccgggct cgaggccctg acagcaacgt gctgctcctg    1020
aggctgccgg aaaaagtgcc cagtgcccca ccccaggagg tgaccctaaa acctggcaat    1080
ggcagtgtcc ttgtgagctg gtcccacca cctgctgaaa accacaatgg catcatccgt    1140
ggctaccagg tctggagcct gggcaacacg tcactgcccc cagccaactg gactgtggtt    1200
ggtgagcaga cccagctgga aatgccacc cgcatgccag gctcctactg tgtgcaagtg    1260
gctgcagtca ctggtgctgg agctggggaa cccagtagcc ctgtctgcct ccttttagag    1320
caggccatga gcgagccac ccgagaactc agtgagcatg gtccctggac cctggagcag    1380
ctgagggcca ccttgaagcg gcctgaggtc attgccacct gtggtgttgt gctctggctg    1440
ctgcttctgg gcaccgctgt gtgtatccac cgccggcgcc gagctggggt gcacctaggc    1500
ccaggtctgt acagatatac cagtaaggac gccatcctaa acacaggat ggatcacagt    1560
gactcccagt ggttggcaga cacttggcgt tccacctctg gctctcggga cttgagcagc    1620
agcagcagcc tcagcagtag gctggggggcg gaccccgggg acccgctaga ctgtcgtcgc    1680
tccttgctct cctgggactc ccgaagcccc ggcgtgcccc tgcttctaga caccagcact    1740
ttttatggct ccctcatcgc tgagctgccc tccagtcccc tagccaggcc aagtccccag    1800
gtcccagctg tcaggcgcct accacccag ctggcccgac tttccagccc ctgttccagc    1860
tcagacagcc tctgcagcca caggggactc tcttctccac gcttgtctct ggcacctaca    1920
gaggcttgga aggccaaaaa gaagcaggag ctgcagcatg tcaacagttc cccactgctc    1980
cggggcagcc aaacccttga gctccggggcc tgtgagttgg aaacagagg ttccaagaac    2040
cttccccaaa gcccaggagc tgtgccccaa gctctggttg cttggcgggc cctgggaccg    2100
aaactcctca gctcctcaaa tgagctggtt actcgtcctc tccctccagc accctctttt    2160
cctcatgaaa ctccccaaac tcagagtcaa cagacccagc ctccgggtggc accacaggct    2220
ccctcctcca tcctgctggc aacagccccc attcccatcc ttagcccctg cagtcccccct    2280
```

```
agccctcagg cctcttccct ctctggcccc agcccagctt ccagtcacct gtccagctct    2340
tcactgtcat ccctggggga ggatcaagac agcgtgctga cccctgagga ggtagccctg    2400
tgtttggaac tcagtgaggg tgaggagact cccaggaaca gcgtctctcc catgccaaga    2460
gctccttcac cccccaccac ctatgggtat atcagcaccc caacagcctc agagttcacg    2520
ggcatggaca ggaccggagg aggggtgggg tccgagggg gagtcttgct gtgcccacct     2580
cggccctgcc tcaccccac ccccagcgag ggctccttag ccaatggttg gggctcagcc     2640
tctgaggaca atgctgccag tgccagagcc agccttgtca gctcctccga tggctccttc    2700
ctcgctgatg cccactttgc ccgggccctg gcagtggcag tggatagctt tggttttggt    2760
ctagagccca gggaggcaga ctgcgtcttc acagatgcct catcacctcc ctccccaagg    2820
gatgacatct tcctgacccc caacctctcc ctgcccctgt gggagtggag gccagactgg    2880
ttggaagaca tggaggtcaa ccacacccag ctgctgggaa gggggatgcc tccctggtcc    2940
cctgactctc ggatctcttc ccagagaagt cagctccact gtcctgtgcc caaggctggt    3000
gcttctcctg tagattactc c                                              3021

<210> SEQ ID NO 22
<211> LENGTH: 1007
<212> TYPE: PRT
<213> ORGANISM: Macaca fascicularis

<400> SEQUENCE: 22

Met Gly Ser Gly Gly Glu Ser Leu Arg Gly Ser Arg Ala Ser Arg Pro
1               5                   10                  15

Leu Leu Leu Leu Leu Ile Met Gly Gly Met Ala Gln Asp Ser Pro Pro
            20                  25                  30

Gln Ile Leu Val His Pro Gln Asp Gln Leu Phe Gln Gly Pro Gly Pro
        35                  40                  45

Ala Arg Met Ser Cys Arg Ala Ser Gly Gln Pro Pro Pro Thr Ile Arg
    50                  55                  60

Trp Leu Leu Asn Gly Gln Pro Leu Ser Met Val Pro Pro Asp Pro His
65                  70                  75                  80

His Leu Leu Pro Asp Gly Thr Leu Leu Leu Gln Pro Pro Ala Arg
                85                  90                  95

Gly His Ala His Asp Gly Gln Ala Leu Ser Thr Asp Leu Gly Val Tyr
            100                 105                 110

Thr Cys Glu Ala Ser Asn Arg Leu Gly Thr Ala Val Ser Arg Gly Ala
        115                 120                 125

Arg Leu Ser Val Ala Val Leu Arg Glu Asp Phe Gln Ile Gln Pro Arg
    130                 135                 140

Asp Met Val Ala Val Gly Glu Gln Leu Thr Leu Glu Cys Gly Pro
145                 150                 155                 160

Pro Trp Gly His Pro Glu Pro Thr Val Ser Trp Trp Lys Asp Gly Lys
                165                 170                 175

Pro Leu Val Leu Gln Pro Gly Arg Tyr Thr Val Ser Gly Gly Ser Leu
            180                 185                 190

Leu Met Ala Arg Ala Glu Lys Ser Asp Thr Gly Ala Tyr Met Cys Val
        195                 200                 205

Ala Ala Asn Ser Ala Gly His Arg Glu Ser Arg Ala Ala Arg Val Ser
    210                 215                 220

Ile Gln Glu Pro Gln Asp Tyr Thr Glu Pro Val Glu Leu Leu Ala Val
225                 230                 235                 240
```

```
Arg Ile Gln Leu Glu Asn Val Thr Leu Leu Asn Pro Asp Pro Ala Lys
                245                 250                 255

Gly Pro Lys Pro Gly Pro Ala Val Trp Leu Ser Trp Lys Val Ser Gly
                260                 265                 270

Pro Ala Ala Pro Ala Gln Ser Tyr Thr Ala Leu Phe Arg Thr Gln Thr
                275                 280                 285

Ala Pro Gly Asp Gln Gly Ala Pro Trp Thr Glu Glu Leu Leu Ala Gly
                290                 295                 300

Trp Gln Ser Ala Glu Leu Gly Gly Leu His Trp Gly Gln Asp Tyr Glu
305                 310                 315                 320

Phe Lys Val Arg Pro Ser Ser Gly Arg Ala Arg Gly Pro Asp Ser Asn
                325                 330                 335

Val Leu Leu Leu Arg Leu Pro Glu Lys Val Pro Ser Ala Pro Pro Gln
                340                 345                 350

Glu Val Thr Leu Lys Pro Gly Asn Gly Ser Val Leu Val Ser Trp Val
                355                 360                 365

Pro Pro Pro Ala Glu Asn His Asn Gly Ile Ile Arg Gly Tyr Gln Val
                370                 375                 380

Trp Ser Leu Gly Asn Thr Ser Leu Pro Pro Ala Asn Trp Thr Val Val
385                 390                 395                 400

Gly Glu Gln Thr Gln Leu Glu Ile Ala Thr Arg Met Pro Gly Ser Tyr
                405                 410                 415

Cys Val Gln Val Ala Ala Val Thr Gly Ala Gly Ala Gly Glu Pro Ser
                420                 425                 430

Ser Pro Val Cys Leu Leu Leu Glu Gln Ala Met Glu Arg Ala Thr Arg
                435                 440                 445

Glu Leu Ser Glu His Gly Pro Trp Thr Leu Gln Leu Arg Ala Thr
                450                 455                 460

Leu Lys Arg Pro Glu Val Ile Ala Thr Cys Gly Val Val Leu Trp Leu
465                 470                 475                 480

Leu Leu Leu Gly Thr Ala Val Cys Ile His Arg Arg Arg Arg Ala Gly
                485                 490                 495

Val His Leu Gly Pro Gly Leu Tyr Arg Tyr Thr Ser Lys Asp Ala Ile
                500                 505                 510

Leu Lys His Arg Met Asp His Ser Asp Ser Gln Trp Leu Ala Asp Thr
                515                 520                 525

Trp Arg Ser Thr Ser Gly Ser Arg Asp Leu Ser Ser Ser Ser Ser Leu
530                 535                 540

Ser Ser Arg Leu Gly Ala Asp Pro Arg Asp Pro Leu Asp Cys Arg Arg
545                 550                 555                 560

Ser Leu Leu Ser Trp Asp Ser Arg Ser Pro Gly Val Pro Leu Leu Leu
                565                 570                 575

Asp Thr Ser Thr Phe Tyr Gly Ser Leu Ile Ala Glu Leu Pro Ser Ser
                580                 585                 590

Pro Leu Ala Arg Pro Ser Pro Gln Val Pro Ala Val Arg Leu Pro
                595                 600                 605

Pro Gln Leu Ala Arg Leu Ser Ser Pro Cys Ser Ser Ser Asp Ser Leu
                610                 615                 620

Cys Ser His Arg Gly Leu Ser Ser Pro Arg Leu Ser Leu Ala Pro Thr
625                 630                 635                 640

Glu Ala Trp Lys Ala Lys Lys Lys Gln Glu Leu Gln His Val Asn Ser
                645                 650                 655
```

| | | | | | | | | | | | |
|---|---|---|---|---|---|---|---|---|---|---|---|
|Ser|Pro|Leu|Leu|Arg|Gly|Ser|Gln|Pro|Leu|Glu|Leu|Arg|Ala|Cys|Glu|
| | | |660| | | |665| | | |670| | | | |

Ser Pro Leu Leu Arg Gly Ser Gln Pro Leu Glu Leu Arg Ala Cys Glu
            660                 665                 670

Leu Gly Asn Arg Gly Ser Lys Asn Leu Ser Gln Ser Pro Gly Ala Val
            675                 680                 685

Pro Gln Ala Leu Val Ala Trp Arg Ala Leu Gly Pro Lys Leu Leu Ser
            690                 695                 700

Ser Ser Asn Glu Leu Val Thr Arg Pro Leu Pro Ala Pro Leu Phe
705                 710                 715                 720

Pro His Glu Thr Pro Gln Thr Gln Ser Gln Thr Gln Pro Pro Val
                725                 730                 735

Ala Pro Gln Ala Pro Ser Ser Ile Leu Leu Ala Thr Ala Pro Ile Pro
            740                 745                 750

Ile Leu Ser Pro Cys Ser Pro Ser Pro Gln Ala Ser Ser Leu Ser
                755                 760                 765

Gly Pro Ser Pro Ala Ser Ser His Leu Ser Ser Ser Leu Ser Ser
            770                 775                 780

Leu Gly Glu Asp Gln Asp Ser Val Leu Thr Pro Glu Glu Val Ala Leu
785                 790                 795                 800

Cys Leu Glu Leu Ser Glu Gly Glu Thr Pro Arg Asn Ser Val Ser
                805                 810                 815

Pro Met Pro Arg Ala Pro Ser Pro Thr Thr Tyr Gly Tyr Ile Ser
                820                 825                 830

Thr Pro Thr Ala Ser Glu Phe Thr Gly Met Asp Arg Thr Gly Gly
            835                 840                 845

Val Gly Ser Glu Gly Gly Val Leu Leu Cys Pro Pro Arg Pro Cys Leu
            850                 855                 860

Thr Pro Thr Pro Ser Glu Gly Ser Leu Ala Asn Gly Trp Gly Ser Ala
865                 870                 875                 880

Ser Glu Asp Asn Ala Ala Ser Ala Arg Ala Ser Leu Val Ser Ser Ser
                885                 890                 895

Asp Gly Ser Phe Leu Ala Asp Ala His Phe Ala Arg Ala Leu Ala Val
            900                 905                 910

Ala Val Asp Ser Phe Gly Phe Gly Leu Glu Pro Arg Glu Ala Asp Cys
            915                 920                 925

Val Phe Thr Asp Ala Ser Ser Pro Ser Pro Arg Asp Asp Ile Phe
930                 935                 940

Leu Thr Pro Asn Leu Ser Leu Pro Leu Trp Glu Trp Arg Pro Asp Trp
945                 950                 955                 960

Leu Glu Asp Met Glu Val Asn His Thr Gln Leu Leu Gly Arg Gly Met
                965                 970                 975

Pro Pro Trp Ser Pro Asp Ser Arg Ile Ser Ser Gln Arg Ser Gln Leu
            980                 985                 990

His Cys Pro Val Pro Lys Ala Gly  Ala Ser Pro Val Asp Tyr Ser
            995                 1000                1005

<210> SEQ ID NO 23
<211> LENGTH: 4845
<212> TYPE: DNA
<213> ORGANISM: Homo sapiens

<400> SEQUENCE: 23
atgattgcgg agcccgctca cttttacctg tttggattaa tatgtctctg ttcaggctcc      60
cgtcttgatt acaaggatga cgacgataag cgtcaggaag attttccacc tcgcattgtt     120 gaacacccctt cagacctgat tgtctcaaaa ggagaacctg caactttgaa ctgcaaagct    180

```
gaaggccgcc ccacacccac tattgaatgg tacaaagggg gagagagagt ggagacagac    240
aaagatgacc ctcgctcaca ccgaatgttg ctgccgagtg gatctttatt tttcttacgt    300
atagtacatg gacggaaaag tagacctgat gaaggagtct atgtctgtgt agcaaggaat    360
taccttggag aggctgtgag ccacaatgca tcgctggaag tagccatact tcgggatgac    420
ttcagacaaa acccttcgga tgtcatggtt gcagtaggag agcctgcagt aatggaatgc    480
caacctccac gaggccatcc tgagcccacc atttcatgga agaaagatgg ctctccactg    540
gatgataaag atgaaagaat aactatacga ggaggaaagc tcatgatcac ttacacccgt    600
aaaagtgacg ctggcaaata tgtttgtgtt ggtaccaata tggttgggga acgtgagagt    660
gaagtagccg agctgactgt cttagagaga ccatcatttg tgaagagacc cagtaacttg    720
gcagtaactg tggatgacag tgcagaattt aaatgtgagg cccgaggtga ccctgtacct    780
acagtacgat ggaggaaaga tgatggagag ctgcccaaat ccagatatga aatccgagat    840
gatcatacct tgaaaattag gaaggtgaca gctggtgaca tgggttcata cacttgtgtt    900
gcagaaaata tggtgggcaa agctgaagca tctgctactc tgactgttca agttgggtct    960
gaacctccac attttgttgt gaaacccgt gaccaggttg ttgctttggg acggactgta   1020
acttttcagt gtgaagcaac cggaaatcct caaccagcta ttttctggag gagagaaggg   1080
agtcagaatc tactttttctc atatcaacca ccacagtcat ccagccgatt ttcagtctcc   1140
cagactggcg acctcacaat tactaatgtc cagcgatctg atgttggtta ttacatctgc   1200
cagactttaa atgttgctgg aagcatcatc acaaaggcat attttggaagt tacagatgtg   1260 attgcagatc ggcctccccc agttattcga caaggtcctg tgaatcagac tgtagccgtg   1320
gatggcactt tcgtcctcag ctgtgtggcc acaggcagtc cagtgcccac cattctgtgg   1380
agaaaggatg gagtcctcgt ttcaacccaa gactctcgaa tcaaacagtt ggagaatgga   1440
gtactgcaga tccgatatgc taagctgggt gatactggtc ggtacacctg cattgcatca   1500
acccccagtg gtgaagcaac atggagtgct tacattgaag ttcaagaatt tggagttcca   1560
gttcagcctc caagacctac tgacccaaat ttaatcccta gtgccccatc aaaacctgaa   1620
gtgacagatg tcagcagaaa tacagtcaca ttatcgtggc aaccaaattt gaattcagga   1680
gcaactccaa catcttatat tatagaagcc ttcagccatg catctggtag cagctggcag   1740
accgtagcag agaatgtgaa aacagaaaca tctgccatta aaggactcaa acctaatgca   1800
atttaccttt tccttgtgag ggcagctaat gcatatggaa ttagtgatcc aagccaaata   1860
tcagatccag tgaaaacaca agatgtccta ccaacaagtc aggggtgga ccacaagcag   1920 gtccagagag agctgggaaa tgctgttctg cacctccaca accccaccgt cctttcttcc   1980
tcttccatcg aagtgcactg gacagtagat caacagtctc agtatataca aggatataaa   2040
attctctatc ggccatctgg agccaaccac ggagaatcag actggttagt ttttgaagtg   2100
aggacgccag ccaaaaacag tgtggtaatc cctgatctca gaaagggagt caactatgaa   2160
attaaggctc gccctttttt taatgaattt caaggagcag atagtgaaat caagtttgcc   2220 aaaacccctgg aagaagcacc cagtgcccca ccccaaggtg taactgtatc caagaatgat   2280
ggaaacggaa ctgcaattct agttagttgg cagccacctc cagaagacac tcaaaatgga   2340
atggtccaag agtataaggt ttggtgtctg ggcaatgaaa ctcgatacca catcaacaaa   2400
acagtggatg gttccacctt ttccgtggtc attcccttc ttgttcctgg aatccgatac   2460
agtgtggaag tggcagccag cactgggggct gggtctgggg taaagagtga gcctcagttc   2520
```

| | |
|---|---|
| atccagctgg atgcccatgg aaaccctgtg tcacctgagg accaagtcag cctcgctcag | 2580 |
| cagatttcag atgtggtgaa gcagccggcc ttcatagcag gtattggagc agcctgttgg | 2640 |
| atcatcctca tggtcttcag catctggctt tatcgacacc gcaagaagag aaacggactt | 2700 |
| actagtacat acgcgggtat cagaaaagta acttaccaga gaggaggcga agctgtcagc | 2760 |
| agtggaggga ggcctggact tctcaacatc agtgaacctg ccgcgcagcc atggctggca | 2820 |
| gacacgtggc ctaatactgg caacaaccac aatgactgct ccatcagctg ctgcacggca | 2880 |
| ggcaatggaa acagcgacag caacctcact acctacagtc gcccagctga ttgtatagca | 2940 |
| aattataaca accaactgga taacaaacaa acaaatctga tgctccctga gtcaactgtt | 3000 |
| tatggtgatg tggaccttag taacaaaatc aatgagatga aaaccttcaa tagcccaaat | 3060 |
| ctgaaggatg gcgttttgt caatccatca gggcagccta ctccttacgc caccactcag | 3120 |
| ctcatccagt caaacctcag caacaacatg aacaatggca gcggggactc tggcgagaag | 3180 |
| cactggaaac cactgggaca gcagaaacaa gaagtggcac cagttcagta caacatcgtg | 3240 |
| gagcaaaaca agctgaacaa agattatcga gcaaatgaca cagttcctcc aactatccca | 3300 |
| tacaaccaat catacgacca gaacacagga ggatcctaca cagctcaga ccggggcagt | 3360 |
| agtacatctg ggagtcaggg gcacaagaaa ggggcaagaa cacccaaggt accaaaacag | 3420 |
| ggtggcatga actgggcaga cctgcttcct cctcccccag cacatcctcc tccacacagc | 3480 |
| aatagcgaag agtacaacat ttctgtagat gaaagctatg accaagaaat gccatgtccc | 3540 |
| gtgccaccag caaggatgta tttgcaacaa gatgaattag aagaggagga agatgaacga | 3600 |
| ggccccactc cccctgttcg gggagcagct tcttctccag ctgccgtgtc ctatagccat | 3660 |
| cagtccactg ccactctgac tccctcccca caggaagaac tccagcccat gttacaggat | 3720 |
| tgtccagagg agactggcca catgcagcac cagcccgaca ggagacggca gcctgtgagt | 3780 |
| cctcctccac caccacggcc gatctcccct ccacatacct atggctacat ttcaggaccc | 3840 |
| ctggtctcag atatggatac ggatgcgcca aagaggaag aagacgaagc cgacatggag | 3900 |
| gtagccaaga tgcaaaccag aaggcttttg ttacgtgggc ttgagcagac acctgcctcc | 3960 |
| agtgttgggg acctggagag ctctgtcacg gggtccatga tcaacggctg gggctcagcc | 4020 |
| tcagaggagg acaacatttc cagcggacgc tccagtgtta gttcttcgga cggctccttt | 4080 |
| ttcactgatg ctgactttgc ccaggcagtc gcagcagcgg cagagtatgc tggtctgaaa | 4140 |
| gtagcacgac ggcaaatgca ggatgctgct ggccgtcgac atttcatgc gtctcagtgc | 4200 |
| cctaggccca caagtcccgt gtctacgac agcaacatga gtccgccgt aatgcagaaa | 4260 |
| accagaccag ccaagaaact gaaacaccag ccaggacatc tgcgcagaga aacctacaca | 4320 |
| gatgatcttc caccacctcc tgtgccgcca cctgctataa agtcacctac tgcccaatcc | 4380 |
| aagacacagc tggaagtacg acctgtagtg gtgccaaaac tcccttctat ggatgcaaga | 4440 |
| acagacagat catcagacag aaaaggaagc agttacaagg ggagagaagt gttggatgga | 4500 |
| agacaggttg ttgacatgcg aacaaatcca ggtgatccca gagaagcaca ggaacagcaa | 4560 |
| aatgacggga aggacgtgg aaacaaggca gcaaacgag accttccacc agcaaagact | 4620 |
| catctcatcc aagaggatat tctaccttat tgtagaccta cttttccaac atcaaataat | 4680 |
| cccagagatc ccagttcctc aagctcaatg tcatcaagag gatcaggaag cagacaaaga | 4740 |
| gaacaagcaa atgtaggtcg aagaaatatt gcagaaatgc aggtacttgg aggatatgaa | 4800 |
| agaggagaag ataataatga agaattagag gaaactgaaa gctga | 4845 |

<210> SEQ ID NO 24
<211> LENGTH: 1614
<212> TYPE: PRT
<213> ORGANISM: Homo sapiens

<400> SEQUENCE: 24

```
Met Ile Ala Glu Pro Ala His Phe Tyr Leu Phe Gly Leu Ile Cys Leu
1               5                   10                  15

Cys Ser Gly Ser Arg Leu Asp Tyr Lys Asp Asp Asp Lys Arg Gln
            20                  25                  30

Glu Asp Phe Pro Pro Arg Ile Val Glu His Pro Ser Asp Leu Ile Val
        35                  40                  45

Ser Lys Gly Glu Pro Ala Thr Leu Asn Cys Lys Ala Glu Gly Arg Pro
    50                  55                  60

Thr Pro Thr Ile Glu Trp Tyr Lys Gly Gly Glu Arg Val Glu Thr Asp
65                  70                  75                  80

Lys Asp Asp Pro Arg Ser His Arg Met Leu Leu Pro Ser Gly Ser Leu
                85                  90                  95

Phe Phe Leu Arg Ile Val His Gly Arg Lys Ser Arg Pro Asp Glu Gly
            100                 105                 110

Val Tyr Val Cys Val Ala Arg Asn Tyr Leu Gly Glu Ala Val Ser His
        115                 120                 125

Asn Ala Ser Leu Glu Val Ala Ile Leu Arg Asp Asp Phe Arg Gln Asn
130                 135                 140

Pro Ser Asp Val Met Val Ala Val Gly Glu Pro Ala Val Met Glu Cys
145                 150                 155                 160

Gln Pro Pro Arg Gly His Pro Glu Pro Thr Ile Ser Trp Lys Lys Asp
                165                 170                 175

Gly Ser Pro Leu Asp Asp Lys Asp Glu Arg Ile Thr Ile Arg Gly Gly
            180                 185                 190

Lys Leu Met Ile Thr Tyr Thr Arg Lys Ser Asp Ala Gly Lys Tyr Val
        195                 200                 205

Cys Val Gly Thr Asn Met Val Gly Glu Arg Glu Ser Glu Val Ala Glu
    210                 215                 220

Leu Thr Val Leu Glu Arg Pro Ser Phe Val Lys Arg Pro Ser Asn Leu
225                 230                 235                 240

Ala Val Thr Val Asp Asp Ser Ala Glu Phe Lys Cys Glu Ala Arg Gly
                245                 250                 255

Asp Pro Val Pro Thr Val Arg Trp Arg Lys Asp Asp Gly Glu Leu Pro
            260                 265                 270

Lys Ser Arg Tyr Glu Ile Arg Asp Asp His Thr Leu Lys Ile Arg Lys
        275                 280                 285

Val Thr Ala Gly Asp Met Gly Ser Tyr Thr Cys Val Ala Glu Asn Met
    290                 295                 300

Val Gly Lys Ala Glu Ala Ser Ala Thr Leu Thr Val Gln Val Gly Ser
305                 310                 315                 320

Glu Pro Pro His Phe Val Val Lys Pro Arg Asp Gln Val Val Ala Leu
                325                 330                 335

Gly Arg Thr Val Thr Phe Gln Cys Glu Ala Thr Gly Asn Pro Gln Pro
            340                 345                 350

Ala Ile Phe Trp Arg Arg Glu Gly Ser Gln Asn Leu Leu Phe Ser Tyr
        355                 360                 365

Gln Pro Pro Gln Ser Ser Arg Phe Ser Val Ser Gln Thr Gly Asp
    370                 375                 380
```

```
Leu Thr Ile Thr Asn Val Gln Arg Ser Asp Val Gly Tyr Tyr Ile Cys
385                 390                 395                 400

Gln Thr Leu Asn Val Ala Gly Ser Ile Ile Thr Lys Ala Tyr Leu Glu
            405                 410                 415

Val Thr Asp Val Ile Ala Asp Arg Pro Pro Val Ile Arg Gln Gly
        420                 425                 430

Pro Val Asn Gln Thr Val Ala Val Asp Gly Thr Phe Val Leu Ser Cys
            435                 440                 445

Val Ala Thr Gly Ser Pro Val Pro Thr Ile Leu Trp Arg Lys Asp Gly
450                 455                 460

Val Leu Val Ser Thr Gln Asp Ser Arg Ile Lys Gln Leu Glu Asn Gly
465                 470                 475                 480

Val Leu Gln Ile Arg Tyr Ala Lys Leu Gly Asp Thr Gly Arg Tyr Thr
            485                 490                 495

Cys Ile Ala Ser Thr Pro Ser Gly Glu Ala Thr Trp Ser Ala Tyr Ile
            500                 505                 510

Glu Val Gln Glu Phe Gly Val Pro Val Gln Pro Pro Arg Pro Thr Asp
            515                 520                 525

Pro Asn Leu Ile Pro Ser Ala Pro Ser Lys Pro Glu Val Thr Asp Val
530                 535                 540

Ser Arg Asn Thr Val Thr Leu Ser Trp Gln Pro Asn Leu Asn Ser Gly
545                 550                 555                 560

Ala Thr Pro Thr Ser Tyr Ile Ile Glu Ala Phe Ser His Ala Ser Gly
            565                 570                 575

Ser Ser Trp Gln Thr Val Ala Glu Asn Val Lys Thr Glu Thr Ser Ala
            580                 585                 590

Ile Lys Gly Leu Lys Pro Asn Ala Ile Tyr Leu Phe Leu Val Arg Ala
            595                 600                 605

Ala Asn Ala Tyr Gly Ile Ser Asp Pro Ser Gln Ile Ser Asp Pro Val
610                 615                 620

Lys Thr Gln Asp Val Leu Pro Thr Ser Gln Gly Val Asp His Lys Gln
625                 630                 635                 640

Val Gln Arg Glu Leu Gly Asn Ala Val Leu His Leu His Asn Pro Thr
            645                 650                 655

Val Leu Ser Ser Ser Ile Glu Val His Trp Thr Val Asp Gln Gln
            660                 665                 670

Ser Gln Tyr Ile Gln Gly Tyr Lys Ile Leu Tyr Arg Pro Ser Gly Ala
            675                 680                 685

Asn His Gly Glu Ser Asp Trp Leu Val Phe Glu Val Arg Thr Pro Ala
690                 695                 700

Lys Asn Ser Val Val Ile Pro Asp Leu Arg Lys Gly Val Asn Tyr Glu
705                 710                 715                 720

Ile Lys Ala Arg Pro Phe Phe Asn Glu Phe Gln Gly Ala Asp Ser Glu
            725                 730                 735

Ile Lys Phe Ala Lys Thr Leu Glu Glu Ala Pro Ser Ala Pro Pro Gln
            740                 745                 750

Gly Val Thr Val Ser Lys Asn Asp Gly Asn Gly Thr Ala Ile Leu Val
            755                 760                 765

Ser Trp Gln Pro Pro Glu Asp Thr Gln Asn Gly Met Val Gln Glu
            770                 775                 780

Tyr Lys Val Trp Cys Leu Gly Asn Glu Thr Arg Tyr His Ile Asn Lys
785                 790                 795                 800

Thr Val Asp Gly Ser Thr Phe Ser Val Val Ile Pro Phe Leu Val Pro
```

```
                    805                 810                 815
Gly Ile Arg Tyr Ser Val Glu Val Ala Ala Ser Thr Gly Ala Gly Ser
                820                 825                 830

Gly Val Lys Ser Glu Pro Gln Phe Ile Gln Leu Asp Ala His Gly Asn
                835                 840                 845

Pro Val Ser Pro Glu Asp Gln Val Ser Leu Ala Gln Gln Ile Ser Asp
850                 855                 860

Val Val Lys Gln Pro Ala Phe Ile Ala Gly Ile Gly Ala Ala Cys Trp
865                 870                 875                 880

Ile Ile Leu Met Val Phe Ser Ile Trp Leu Tyr Arg His Arg Lys Lys
                885                 890                 895

Arg Asn Gly Leu Thr Ser Thr Tyr Ala Gly Ile Arg Lys Val Thr Tyr
                900                 905                 910

Gln Arg Gly Gly Glu Ala Val Ser Ser Gly Gly Arg Pro Gly Leu Leu
                915                 920                 925

Asn Ile Ser Glu Pro Ala Ala Gln Pro Trp Leu Ala Asp Thr Trp Pro
                930                 935                 940

Asn Thr Gly Asn Asn His Asn Asp Cys Ser Ile Ser Cys Cys Thr Ala
945                 950                 955                 960

Gly Asn Gly Asn Ser Asp Ser Asn Leu Thr Thr Tyr Ser Arg Pro Ala
                965                 970                 975

Asp Cys Ile Ala Asn Tyr Asn Asn Gln Leu Asp Asn Lys Gln Thr Asn
                980                 985                 990

Leu Met Leu Pro Glu Ser Thr Val Tyr Gly Asp Val Asp Leu Ser Asn
                995                 1000                1005

Lys Ile Asn Glu Met Lys Thr Phe Asn Ser Pro Asn Leu Lys Asp
        1010                1015                1020

Gly Arg Phe Val Asn Pro Ser Gly Gln Pro Thr Pro Tyr Ala Thr
        1025                1030                1035

Thr Gln Leu Ile Gln Ser Asn Leu Ser Asn Asn Met Asn Asn Gly
        1040                1045                1050

Ser Gly Asp Ser Gly Glu Lys His Trp Lys Pro Leu Gly Gln Gln
        1055                1060                1065

Lys Gln Glu Val Ala Pro Val Gln Tyr Asn Ile Val Glu Gln Asn
        1070                1075                1080

Lys Leu Asn Lys Asp Tyr Arg Ala Asn Asp Thr Val Pro Pro Thr
        1085                1090                1095

Ile Pro Tyr Asn Gln Ser Tyr Asp Gln Asn Thr Gly Gly Ser Tyr
        1100                1105                1110

Asn Ser Ser Asp Arg Gly Ser Ser Thr Ser Gly Ser Gln Gly His
        1115                1120                1125

Lys Lys Gly Ala Arg Thr Pro Lys Val Pro Lys Gln Gly Gly Met
        1130                1135                1140

Asn Trp Ala Asp Leu Leu Pro Pro Pro Ala His Pro Pro Pro
        1145                1150                1155

His Ser Asn Ser Glu Glu Tyr Asn Ile Ser Val Asp Glu Ser Tyr
        1160                1165                1170

Asp Gln Glu Met Pro Cys Pro Val Pro Pro Ala Arg Met Tyr Leu
        1175                1180                1185

Gln Gln Asp Glu Leu Glu Glu Glu Asp Glu Arg Gly Pro Thr
        1190                1195                1200

Pro Pro Val Arg Gly Ala Ala Ser Ser Pro Ala Ala Val Ser Tyr
        1205                1210                1215
```

-continued

```
Ser His Gln Ser Thr Ala Thr Leu Thr Pro Ser Pro Gln Glu Glu
1220                1225                1230

Leu Gln Pro Met Leu Gln Asp Cys Pro Glu Glu Thr Gly His Met
1235                1240                1245

Gln His Gln Pro Asp Arg Arg Arg Gln Pro Val Ser Pro Pro Pro
1250                1255                1260

Pro Pro Arg Pro Ile Ser Pro Pro His Thr Tyr Gly Tyr Ile Ser
1265                1270                1275

Gly Pro Leu Val Ser Asp Met Asp Thr Asp Ala Pro Glu Glu Glu
1280                1285                1290

Glu Asp Glu Ala Asp Met Glu Val Ala Lys Met Gln Thr Arg Arg
1295                1300                1305

Leu Leu Leu Arg Gly Leu Glu Gln Thr Pro Ala Ser Ser Val Gly
1310                1315                1320

Asp Leu Glu Ser Ser Val Thr Gly Ser Met Ile Asn Gly Trp Gly
1325                1330                1335

Ser Ala Ser Glu Glu Asp Asn Ile Ser Ser Gly Arg Ser Ser Val
1340                1345                1350

Ser Ser Ser Asp Gly Ser Phe Phe Thr Asp Ala Asp Phe Ala Gln
1355                1360                1365

Ala Val Ala Ala Ala Ala Glu Tyr Ala Gly Leu Lys Val Ala Arg
1370                1375                1380

Arg Gln Met Gln Asp Ala Ala Gly Arg Arg His Phe His Ala Ser
1385                1390                1395

Gln Cys Pro Arg Pro Thr Ser Pro Val Ser Thr Asp Ser Asn Met
1400                1405                1410

Ser Ala Ala Val Met Gln Lys Thr Arg Pro Ala Lys Lys Leu Lys
1415                1420                1425

His Gln Pro Gly His Leu Arg Arg Glu Thr Tyr Thr Asp Asp Leu
1430                1435                1440

Pro Pro Pro Pro Val Pro Pro Ala Ile Lys Ser Pro Thr Ala
1445                1450                1455

Gln Ser Lys Thr Gln Leu Glu Val Arg Pro Val Val Pro Lys
1460                1465                1470

Leu Pro Ser Met Asp Ala Arg Thr Asp Arg Ser Ser Asp Arg Lys
1475                1480                1485

Gly Ser Ser Tyr Lys Gly Arg Glu Val Leu Asp Gly Arg Gln Val
1490                1495                1500

Val Asp Met Arg Thr Asn Pro Gly Asp Pro Arg Glu Ala Gln Glu
1505                1510                1515

Gln Gln Asn Asp Gly Lys Gly Arg Gly Asn Lys Ala Ala Lys Arg
1520                1525                1530

Asp Leu Pro Pro Ala Lys Thr His Leu Ile Gln Glu Asp Ile Leu
1535                1540                1545

Pro Tyr Cys Arg Pro Thr Phe Pro Thr Ser Asn Asn Pro Arg Asp
1550                1555                1560

Pro Ser Ser Ser Ser Ser Met Ser Ser Arg Gly Ser Gly Ser Arg
1565                1570                1575

Gln Arg Glu Gln Ala Asn Val Gly Arg Arg Asn Ile Ala Glu Met
1580                1585                1590

Gln Val Leu Gly Gly Tyr Glu Arg Gly Glu Asp Asn Asn Glu Glu
1595                1600                1605
```

Leu Glu   Glu Thr Glu Ser
    1610

<210> SEQ ID NO 25
<211> LENGTH: 4605
<212> TYPE: DNA
<213> ORGANISM: Homo sapiens

<400> SEQUENCE: 25

| | | | | | | |
|---|---|---|---|---|---|---|
| atgagtctgc | tgatgtttac | acaactactg | ctctgtggat | ttttatatgt | tcgggttgat | 60 |
| ggatcgcgtc | ttcgccagga | ggactttccc | ccgcggattg | tggagcatcc | ttccgatgtc | 120 |
| atcgtctcta | agggcgagcc | cacgactctg | aactgcaagg | cggagggccg | gccaacgccc | 180 |
| accattgagt | ggtacaaaga | tggggagcga | gtggagactg | acaaggacga | tccccggtcc | 240 |
| cacaggatgc | ttctgcccag | cggatcctta | ttcttcttgc | gcatcgtgca | cgggcgcagg | 300 |
| agtaaacctg | atgaaggaag | ctacgtttgt | gttgcgagga | actatcttgg | tgaagcagtg | 360 |
| agtcgaaatg | cgtctctgga | agtggcattg | ttacgagatg | acttccgaca | aaacccaca | 420 |
| gatgttgtag | tggcagctgg | agagcctgca | atcctggagt | gccagcctcc | ccggggacac | 480 |
| ccagaaccca | ccatctactg | gaaaaaagac | aaagttcgaa | ttgatgacaa | ggaagaaaga | 540 |
| ataagtatcc | gtggtggaaa | actgatgatc | tccaatacca | ggaaaagtga | tgcagggatg | 600 |
| tatacttgtg | ttggtaccaa | tatggtggga | gaaagggaca | gtgacccagc | agagctgact | 660 |
| gtctttgaac | gacccacatt | tctcaggagg | ccaattaacc | aggtggtact | ggaggaagaa | 720 |
| gctgtagaat | tcgttgtca | agtccaagga | gatcctcaac | caactgtgag | gtggaaaaag | 780 |
| gatgatgcag | acttgccaag | aggaaggtat | gacatcaaag | acgattacac | actaagaatt | 840 |
| aaaaagacca | tgagtacaga | tgaaggcacc | tatatgtgta | ttgctgagaa | tcgggttgga | 900 |
| aaaatggaag | cctctgctac | actcaccgtc | cgagctcgcc | ctgttgctcc | cccacagttt | 960 |
| gtggttcggc | caagagatca | gattgttgct | caaggtcgaa | cagtgacatt | tccctgtgaa | 1020 |
| actaaaggaa | acccacagcc | agctgttttt | tggcagaaag | aaggcagcca | gaacctactt | 1080 |
| ttcccaaacc | aacccagca | gcccaacagt | agatgctcag | tgtcaccaac | tggagacctc | 1140 |
| acaatcacca | acattcaacg | ttccgacgcg | ggttactaca | tctgccaggc | tttaactgtg | 1200 |
| gcaggaagca | ttttagcaaa | agctcaactg | gaggttactg | atgttttgac | agatagacct | 1260 |
| ccacctataa | ttctacaagg | cccagccaac | caaacgctgg | cagtggatgg | tacagcgtta | 1320 |
| ctgaaatgta | aagccactgg | tgatcctctt | cctgtaatta | gctggttaaa | ggagggattt | 1380 |
| acttttccgg | gtagagatcc | aagagcaaca | attcaagagc | aaggcacact | gcagattaag | 1440 |
| aatttacgga | tttctgatac | tggcacttat | acttgtgtgg | ctacaagttc | aagtggagag | 1500 |
| acttcctgga | gtgcagtgct | ggatgtgaca | gagtctggag | caacaatcag | taaaaactat | 1560 |
| gatttaagtg | acctgccagg | gccaccatcc | aaaccgcagg | tcactgatgt | tactaagaac | 1620 |
| agtgtcacct | gtcctggca | gccaggtacc | cctggaaccc | ttccagcaag | tgcatatatc | 1680 |
| attgaggctt | tcagccaatc | agtgagcaac | agctggcaga | ccgtggcaaa | ccatgtaaag | 1740 |
| accacccctct | atactgtaag | aggactgcgg | cccaatacaa | tctacttatt | catggtcaga | 1800 |
| gcgatcaacc | cccaaggtct | cagtgaccca | agtcccatgt | cagatcctgt | gcgcacacaa | 1860 |
| gatatcagcc | caccagcaca | aggagtggac | cacaggcaag | tgcagaaaga | gctaggagat | 1920 |
| gtccttgtcc | gtcttcataa | tccagttgtg | ctgactccca | ccacggttca | ggtcacatgg | 1980 |
| acggttgatc | gccaaccca | gtttatccaa | ggctaccgag | tgatgtatcg | tcagactca | 2040 |

```
ggtctgcagg cgacatcttc gtggcagaat ttagatgcca aagtcccgac tgaacgaagt    2100
gctgtcttag tcaacctgaa aaaggggtg  acttatgaaa ttaaagtacg gccatatttt    2160
aatgagttcc aaggaatgga tagtgaatct aaaacggttc gtactactga agaagcccca    2220
agtgccccac cacagtctgt cactgtactg acagttggaa gctacaatag cacaagtatt    2280
agtgtttcct gggatcctcc tcctccagat caccagaatg gaattatcca agaatacaag    2340
atctggtgtc taggaaatga aacgcgattc catatcaaca aaactgtgga tgcagccatt    2400
cggtccgtaa taattggtgg attattccca ggtattcaat accgggtaga ggttgcagct    2460
agtaccagtg caggggttgg agtaaagagt gagccacagc caataataat cgggagacgc    2520
aatgaagttg tcattactga aaacaataac agcataactg agcaaatcac tgatgtggtg    2580
aagcaaccag cctttatagc tggtattggt ggtgcctgct gggtaattct gatgggtttt    2640
agcatatggt tgtattggcg aagaaagaag aggaagggac tcagtaatta tgctgttacg    2700
tttcaaagag gagatggagg actaatgagc aatggaagcc gtccaggtct tctcaatgct    2760
ggtgatccca gctatccatg gcttgctgat tcttggccag ccacgagctt gccagtaaat    2820
aatagcaaca gtggcccaaa tgagattgga aattttggcc gtggagatgt gctgccacca    2880
gttccaggcc aaggggataa aacagcaacg atgctctcag atggagccat ttatagtagc    2940
attgacttca ctaccaaaac cagttacaac agttccagcc aaataacaca ggctacccca    3000
tatgccacga cacagatctt gcattccaac agcatacatg aattggctgt cgatctgcct    3060
gatccacaat ggaaaagctc aattcagcaa aaaacagatc tgatgggatt tggttattct    3120
ctacctgatc agaacaaagg taacaatggt gggaaaggtg aaaaaagaa  gaaaaataaa    3180 aactcttcta aaccacagaa aaacaatgga tccacttggg ccaatgtccc tctacctccc    3240
cccccagtcc agccccttcc tggcacggag ctgaacact  atgcagtgga caacaagaa     3300 aatggctatg acagtgatag ctggtgccca ccattgccag tacaaactta cttacaccaa    3360
ggtctggaag atgaactgga agaagatgat gatagggtcc caacacctcc tgttcgaggc    3420
gtggcttctt ctcctgctat ctcctttgga cagcagtcca ctgcaactct tactccatcc    3480
ccacgggaag agatgcaacc catgctgcag gctcacctgg atgagttgac aagagcctat    3540
cagtttgata tagcaaaaca aacatggcac attcaaagca ataatcaacc tccacagcct    3600
ccagttccac cgttaggtta tgtgtctgga gccttgattt ctgatttgga aacggatgtt    3660
gcagatgatg atgccgacga cgaagaggaa gctttagaaa tccccaggcc cctgagagca    3720
ctggaccaga ctcctggatc cagcatggac aatctagaca gctctgtgac aggttcaatg    3780
gtaaatggat ggggctctgc atctgatgag gatcgtaact ttctagtca  tagatctagt    3840 gtaggtagct cctcagatgg ctctatcttt gccagcggca gttttgcaca agcactggtg    3900
gcagcagcag ataaagctgg ttttaggctg gatggaacca gccttacaag aacaggaaaa    3960
gcctttacct cctctcaaag acctcgacct accagcccat tttctactga cagtaacacc    4020
agtgcagccc tgagtcaaag tcagaggcct cggcccacta aaaacacaa  gggagggcgg    4080 atggaccaac aaccagcatt gcctcatcga agggaaggaa tgacagatga tcttccacca    4140
ccaccagatc ccccgccagg tcagggttta aggcagcaaa taggcccgag ccagcaggct    4200
ggtaacgtgg aaaactcagc agagagaaaa ggaagctctc tagagagaca acatgcatcc    4260
agcttagaag acacaaagag ctcattggat tgtccagcta gaacctccct agagtggcag    4320
cgacaaaccc aggaatggat aagctccaca gaacgacaag aagatatacg gaaagcccca    4380
cacaaacaag gtgtcggatc agaggaggcc ttggtgccct atagcaagcc cagtttccca    4440
```

```
tctccaggtg gccacagctc atcaggaaca gcttcttcta agggatccac tggacctagg    4500
aaaaccgagg tgttgagagc aggccaccag cgcaatgcca gcgaccttct tgacatagga    4560
tatatgggct ccaacagtca aggacagttt acaggtgaat tatag                    4605
```

<210> SEQ ID NO 26
<211> LENGTH: 1534
<212> TYPE: PRT
<213> ORGANISM: Homo sapiens

<400> SEQUENCE: 26

```
Met Ser Leu Leu Met Phe Thr Gln Leu Leu Cys Gly Phe Leu Tyr
1               5                   10                  15

Val Arg Val Asp Gly Ser Arg Leu Arg Gln Glu Asp Phe Pro Pro Arg
            20                  25                  30

Ile Val Glu His Pro Ser Asp Val Ile Val Ser Lys Gly Glu Pro Thr
            35                  40                  45

Thr Leu Asn Cys Lys Ala Glu Gly Arg Pro Thr Pro Thr Ile Glu Trp
    50                  55                  60

Tyr Lys Asp Gly Glu Arg Val Glu Thr Asp Lys Asp Asp Pro Arg Ser
65                  70                  75                  80

His Arg Met Leu Leu Pro Ser Gly Ser Leu Phe Phe Leu Arg Ile Val
                85                  90                  95

His Gly Arg Arg Ser Lys Pro Asp Glu Gly Ser Tyr Val Cys Val Ala
            100                 105                 110

Arg Asn Tyr Leu Gly Glu Ala Val Ser Arg Asn Ala Ser Leu Glu Val
            115                 120                 125

Ala Leu Leu Arg Asp Asp Phe Arg Gln Asn Pro Thr Asp Val Val Val
    130                 135                 140

Ala Ala Gly Glu Pro Ala Ile Leu Glu Cys Gln Pro Pro Arg Gly His
145                 150                 155                 160

Pro Glu Pro Thr Ile Tyr Trp Lys Lys Asp Lys Val Arg Ile Asp Asp
                165                 170                 175

Lys Glu Glu Arg Ile Ser Ile Arg Gly Gly Lys Leu Met Ile Ser Asn
            180                 185                 190

Thr Arg Lys Ser Asp Ala Gly Met Tyr Thr Cys Val Gly Thr Asn Met
            195                 200                 205

Val Gly Glu Arg Asp Ser Asp Pro Ala Glu Leu Thr Val Phe Glu Arg
    210                 215                 220

Pro Thr Phe Leu Arg Arg Pro Ile Asn Gln Val Val Leu Glu Glu Glu
225                 230                 235                 240

Ala Val Glu Phe Arg Cys Gln Val Gln Gly Asp Pro Gln Pro Thr Val
                245                 250                 255

Arg Trp Lys Lys Asp Asp Ala Asp Leu Pro Arg Gly Arg Tyr Asp Ile
            260                 265                 270

Lys Asp Asp Tyr Thr Leu Arg Ile Lys Lys Thr Met Ser Thr Asp Glu
            275                 280                 285

Gly Thr Tyr Met Cys Ile Ala Glu Asn Arg Val Gly Lys Met Glu Ala
    290                 295                 300

Ser Ala Thr Leu Thr Val Arg Ala Arg Pro Ala Pro Pro Gln Phe
305                 310                 315                 320

Val Val Arg Pro Arg Asp Gln Ile Val Ala Gln Gly Arg Thr Val Thr
                325                 330                 335

Phe Pro Cys Glu Thr Lys Gly Asn Pro Gln Pro Ala Val Phe Trp Gln
```

```
                    340                 345                 350
Lys Glu Gly Ser Gln Asn Leu Leu Phe Pro Asn Gln Pro Gln Gln Pro
            355                 360                 365

Asn Ser Arg Cys Ser Val Ser Pro Thr Gly Asp Leu Thr Ile Thr Asn
        370                 375                 380

Ile Gln Arg Ser Asp Ala Gly Tyr Tyr Ile Cys Gln Ala Leu Thr Val
385                 390                 395                 400

Ala Gly Ser Ile Leu Ala Lys Ala Gln Leu Glu Val Thr Asp Val Leu
                405                 410                 415

Thr Asp Arg Pro Pro Ile Ile Leu Gln Gly Pro Ala Asn Gln Thr
            420                 425                 430

Leu Ala Val Asp Gly Thr Ala Leu Leu Lys Cys Lys Ala Thr Gly Asp
        435                 440                 445

Pro Leu Pro Val Ile Ser Trp Leu Lys Glu Gly Phe Thr Phe Pro Gly
    450                 455                 460

Arg Asp Pro Arg Ala Thr Ile Gln Glu Gln Gly Thr Leu Gln Ile Lys
465                 470                 475                 480

Asn Leu Arg Ile Ser Asp Thr Gly Thr Tyr Thr Cys Val Ala Thr Ser
                485                 490                 495

Ser Ser Gly Glu Thr Ser Trp Ser Ala Val Leu Asp Val Thr Glu Ser
            500                 505                 510

Gly Ala Thr Ile Ser Lys Asn Tyr Asp Leu Ser Asp Leu Pro Gly Pro
        515                 520                 525

Pro Ser Lys Pro Gln Val Thr Asp Val Thr Lys Asn Ser Val Thr Leu
    530                 535                 540

Ser Trp Gln Pro Gly Thr Pro Gly Thr Leu Pro Ala Ser Ala Tyr Ile
545                 550                 555                 560

Ile Glu Ala Phe Ser Gln Ser Val Ser Asn Ser Trp Gln Thr Val Ala
                565                 570                 575

Asn His Val Lys Thr Thr Leu Tyr Thr Val Arg Gly Leu Arg Pro Asn
            580                 585                 590

Thr Ile Tyr Leu Phe Met Val Arg Ala Ile Asn Pro Gln Gly Leu Ser
        595                 600                 605

Asp Pro Ser Pro Met Ser Asp Pro Val Arg Thr Gln Asp Ile Ser Pro
    610                 615                 620

Pro Ala Gln Gly Val Asp His Arg Gln Val Gln Lys Glu Leu Gly Asp
625                 630                 635                 640

Val Leu Val Arg Leu His Asn Pro Val Val Leu Thr Pro Thr Thr Val
                645                 650                 655

Gln Val Thr Trp Thr Val Asp Arg Gln Pro Gln Phe Ile Gln Gly Tyr
            660                 665                 670

Arg Val Met Tyr Arg Gln Thr Ser Gly Leu Gln Ala Thr Ser Ser Trp
        675                 680                 685

Gln Asn Leu Asp Ala Lys Val Pro Thr Glu Arg Ser Ala Val Leu Val
    690                 695                 700

Asn Leu Lys Lys Gly Val Thr Tyr Glu Ile Lys Val Arg Pro Tyr Phe
705                 710                 715                 720

Asn Glu Phe Gln Gly Met Asp Ser Glu Ser Lys Thr Val Arg Thr Thr
                725                 730                 735

Glu Glu Ala Pro Ser Ala Pro Pro Gln Ser Val Thr Val Leu Thr Val
            740                 745                 750

Gly Ser Tyr Asn Ser Thr Ser Ile Ser Val Ser Trp Asp Pro Pro
        755                 760                 765
```

-continued

Pro Asp His Gln Asn Gly Ile Ile Gln Glu Tyr Lys Ile Trp Cys Leu
770                 775                 780
Gly Asn Glu Thr Arg Phe His Ile Asn Lys Thr Val Asp Ala Ala Ile
785                 790                 795                 800
Arg Ser Val Ile Ile Gly Gly Leu Phe Pro Gly Ile Gln Tyr Arg Val
                805                 810                 815
Glu Val Ala Ala Ser Thr Ser Ala Gly Val Gly Val Lys Ser Glu Pro
                820                 825                 830
Gln Pro Ile Ile Ile Gly Arg Arg Asn Glu Val Val Ile Thr Glu Asn
                835                 840                 845
Asn Asn Ser Ile Thr Glu Gln Ile Thr Asp Val Val Lys Gln Pro Ala
                850                 855                 860
Phe Ile Ala Gly Ile Gly Gly Ala Cys Trp Val Ile Leu Met Gly Phe
865                 870                 875                 880
Ser Ile Trp Leu Tyr Trp Arg Arg Lys Lys Arg Lys Gly Leu Ser Asn
                885                 890                 895
Tyr Ala Val Thr Phe Gln Arg Gly Asp Gly Gly Leu Met Ser Asn Gly
                900                 905                 910
Ser Arg Pro Gly Leu Leu Asn Ala Gly Asp Pro Ser Tyr Pro Trp Leu
                915                 920                 925
Ala Asp Ser Trp Pro Ala Thr Ser Leu Pro Val Asn Asn Ser Asn Ser
                930                 935                 940
Gly Pro Asn Glu Ile Gly Asn Phe Gly Arg Gly Asp Val Leu Pro Pro
945                 950                 955                 960
Val Pro Gly Gln Gly Asp Lys Thr Ala Thr Met Leu Ser Asp Gly Ala
                965                 970                 975
Ile Tyr Ser Ser Ile Asp Phe Thr Thr Lys Thr Ser Tyr Asn Ser Ser
                980                 985                 990
Ser Gln Ile Thr Gln Ala Thr Pro Tyr Ala Thr Thr Gln Ile Leu His
                995                 1000                1005
Ser Asn Ser Ile His Glu Leu Ala Val Asp Leu Pro Asp Pro Gln
        1010            1015                1020
Trp Lys Ser Ser Ile Gln Gln Lys Thr Asp Leu Met Gly Phe Gly
        1025            1030                1035
Tyr Ser Leu Pro Asp Gln Asn Lys Gly Asn Asn Gly Gly Lys Gly
        1040            1045                1050
Gly Lys Lys Lys Lys Asn Lys Asn Ser Ser Lys Pro Gln Lys Asn
        1055            1060                1065
Asn Gly Ser Thr Trp Ala Asn Val Pro Leu Pro Pro Pro Pro Val
        1070            1075                1080
Gln Pro Leu Pro Gly Thr Glu Leu Glu His Tyr Ala Val Glu Gln
        1085            1090                1095
Gln Glu Asn Gly Tyr Asp Ser Asp Ser Trp Cys Pro Pro Leu Pro
        1100            1105                1110
Val Gln Thr Tyr Leu His Gln Gly Leu Glu Asp Glu Leu Glu Glu
        1115            1120                1125
Asp Asp Asp Arg Val Pro Thr Pro Pro Val Arg Gly Val Ala Ser
        1130            1135                1140
Ser Pro Ala Ile Ser Phe Gly Gln Gln Ser Thr Ala Thr Leu Thr
        1145            1150                1155
Pro Ser Pro Arg Glu Glu Met Gln Pro Met Leu Gln Ala His Leu
        1160            1165                1170

-continued

```
Asp Glu Leu Thr Arg Ala Tyr Gln Phe Asp Ile Ala Lys Gln Thr
1175                1180                1185

Trp His Ile Gln Ser Asn Asn Gln Pro Pro Gln Pro Pro Val Pro
1190                1195                1200

Pro Leu Gly Tyr Val Ser Gly Ala Leu Ile Ser Asp Leu Glu Thr
1205                1210                1215

Asp Val Ala Asp Asp Ala Asp Asp Glu Glu Glu Ala Leu Glu
1220                1225                1230

Ile Pro Arg Pro Leu Arg Ala Leu Asp Gln Thr Pro Gly Ser Ser
1235                1240                1245

Met Asp Asn Leu Asp Ser Ser Val Thr Gly Ser Met Val Asn Gly
1250                1255                1260

Trp Gly Ser Ala Ser Asp Glu Asp Arg Asn Phe Ser Ser His Arg
1265                1270                1275

Ser Ser Val Gly Ser Ser Ser Asp Gly Ser Ile Phe Ala Ser Gly
1280                1285                1290

Ser Phe Ala Gln Ala Leu Val Ala Ala Ala Asp Lys Ala Gly Phe
1295                1300                1305

Arg Leu Asp Gly Thr Ser Leu Thr Arg Thr Gly Lys Ala Phe Thr
1310                1315                1320

Ser Ser Gln Arg Pro Arg Pro Thr Ser Pro Phe Ser Thr Asp Ser
1325                1330                1335

Asn Thr Ser Ala Ala Leu Ser Gln Ser Gln Arg Pro Arg Pro Thr
1340                1345                1350

Lys Lys His Lys Gly Gly Arg Met Asp Gln Gln Pro Ala Leu Pro
1355                1360                1365

His Arg Arg Glu Gly Met Thr Asp Asp Leu Pro Pro Pro Pro Asp
1370                1375                1380

Pro Pro Pro Gly Gln Gly Leu Arg Gln Gln Ile Gly Pro Ser Gln
1385                1390                1395

Gln Ala Gly Asn Val Glu Asn Ser Ala Glu Arg Lys Gly Ser Ser
1400                1405                1410

Leu Glu Arg Gln His Ala Ser Ser Leu Glu Asp Thr Lys Ser Ser
1415                1420                1425

Leu Asp Cys Pro Ala Arg Thr Ser Leu Glu Trp Gln Arg Gln Thr
1430                1435                1440

Gln Glu Trp Ile Ser Ser Thr Glu Arg Gln Glu Asp Ile Arg Lys
1445                1450                1455

Ala Pro His Lys Gln Gly Val Gly Ser Glu Glu Ala Leu Val Pro
1460                1465                1470

Tyr Ser Lys Pro Ser Phe Pro Ser Pro Gly Gly His Ser Ser Ser
1475                1480                1485

Gly Thr Ala Ser Ser Lys Gly Ser Thr Gly Pro Arg Lys Thr Glu
1490                1495                1500

Val Leu Arg Ala Gly His Gln Arg Asn Ala Ser Asp Leu Leu Asp
1505                1510                1515

Ile Gly Tyr Met Gly Ser Asn Ser Gln Gly Gln Phe Thr Gly Glu
1520                1525                1530

Leu
```

<210> SEQ ID NO 27
<211> LENGTH: 4161
<212> TYPE: DNA
<213> ORGANISM: Homo sapiens

<400> SEQUENCE: 27

```
atgctgcgct acctgctgaa aacgctgctg cagatgaact tgttcgcgga ctctctggcc    60
ggggacatct ccaactccag cgagctgctc ttgggcttca actcctcgct ggcggcgctc   120
aaccacaccc tgctgcctcc cggcgatccc tctctcaacg ggtcaagggt aggaccggag   180
gacgctatgc cccgcatcgt ggagcagccg ccagatctgc tggtctcccg aggcgagccc   240
gccacgttgc cctgccgcgc tgaaggccga ccccgaccca acattgagtg gtacaagaac   300
ggggcgcgtg tggccactgt gcgggaggat ccgcgtgcgc accgctgctg ctgcccagc   360
ggcgccctct tcttcccgcg catcgtgcac gggcgccgcg cgcggccgga cgaaggtgtc   420
tacacttgcg tggctcgcaa ctacctgggg gcagcagcga gcagaaacgc ctcgctggaa   480
gtggcagtcc tccgtgatga tttccggcag tctcctggaa acgtggtggt ggcagtgggg   540
gagccagcag tactggaatg cgtgcccccc cgcggccacc cggagccttc cgtgtcctgg   600
aggaaggacg tgcaagact  caaggaagag gaaggaagga tcacgatccg tggagggaag   660
ctgatgatgt cacatacact caagagcgat gcaggcatgt atgtgtgcgt agcctccaac   720
atggcgggag aacgggagag tgcggcagct gaagtcatgg tactggagcg tccctcattc   780
ctgcgcagac cagtgaatca ggtggtcctg gctgatgccc ctgtgacttt cctatgtgag   840
gtgaagggg  atcccccacc tcgtctacgc tggcgcaagg aggatgggga actgccaca   900
ggcaggtatg agatccggag tgaccacagc ctttggattg gcatgtgag  tgccgaagat   960
gagggaacgt acacctgtgt ggcggagaac agtgtgggcc gcgctgaagc atctggctcc  1020
ctcagtgttc acgtcccacc ccagttggtg acccagcccc aggaccagat ggcagctcct  1080
ggagagagcg tggctttcca gtgcgagacc aaaggaaacc ccccacctgc catcttctgg  1140
cagaaggagg ggagtcaggt cctgcttttc cccagtcagt cacttcagcc gacggggcgc  1200
ttctcagtgt ctccaagagg ccaacttaac atcaccgcgg tgcagcgtgg ggatgctggg  1260
tactacgtgt gccaggctgt cagtgtggct ggcagcatcc tggccaaggc cctgctggag  1320
ataaaaggag cctctttgga tgggctgcct cctgtcatcc tccagggacc agccaatcag  1380
acgctggtgc ttggctcctc cgtgtggctg ccctgcagag tgactgggaa ccctcaaccc  1440
agtgtccgat ggaagaagga tgggcagtgg ctgcagggg  atgacctcca gttcaagaca  1500
atggccaacg gtaccctgta catcgccaat gtgcaggaga tggacatggg cttctacagc  1560
tgcgtggcca agagttccac agggggaagcc acatggagcg gctggcttaa gatgcgggaa  1620
gactggggag tatcaccaga ccccctaca  gaacccagtt cccctccggg ggctccctct  1680
cagccagtgg tcactgagat caccaagaac agcattaccc tgacctggaa gcccaaccca  1740
caaactgggg ctgcagtcac gtcttatgtg atagaggcct tcagcccagc agctggcaac  1800
acatggcgta ctgtggcaga tggcgtgcag ctggagacac acacagtcag cggtctgcag  1860
cccaatacca tctacctgtt tctggttcga gcagtgggag cctggggcct cagtgagccc  1920
agccccgtct ctgagcctgt ccgtacacag gatagcagcc cctctaggcc agtggaggac  1980
ccatggagag ccagcaggg  actggcggaa gtggctgtgc cctgcagga  gcccatagtc  2040
ctgggacccc ggaccctgca ggtgtcctgg actgtggatg cccagtcca  gctggtgcaa  2100
ggtttccggg tgtcttggag ggtagcaggc cctgagggag aagctggac  aatgttggac  2160
ctacagtccc caagccagca agtactgtg  ctaagaggac tccctccagg gacccaaatc  2220
cagatcaagg tgcaagccca aggccaggag gggctggggg ctgaaagcct ctctgtgacc  2280
```

```
aggagcattc ctgaggaggc ccccagtggc cccccacagg gagtggcggt ggccttgggg    2340
ggtgatggca acagcagtat cactgtgtcc tgggaacctc cactcccctc ccagcaaaat    2400
ggggtcatca cggaatacca gatctggtgc ctgggcaatg agagccgctt tcacctcaat    2460
cgatctgcag caggctgggc acgctccgca atgctccgag actggtgcc cggtctcctc     2520 tatcgaaccc tggtcgcggc ggccaccagc gcaggcgtgg gcgtgcccag tgccccagtg    2580
ctggtgcagc tgccgtcccc gccggacctg gagcccgggc tggaggtggg cgcggggctg    2640
gcggtgcggc tggcgagggt gctgcgggag cccgccttcc tcgcgggcag cggcgcagcc    2700
tgcggggcgc tgcttctcgg gctctgcgcc gccctctact ggcgccggaa acagcgcaaa    2760
gagctcagcc actacacggc ctcttttgcc tacacaccgg cagtgtcctt cccgcactca    2820
gagggcctct ctggagccag ttccaggcca cccatgggcc ttggccccgc cccctactca    2880
tggctggcag attcgtggcc ccacccatct cgaagcccct cggcccagga acccagggga    2940
agctgctgcc ctagcaatcc tgaccccgga cacagatatt acaacgaagc gggaatctcc    3000
ctgtatctag ctcagacggc caggggcacg gccgcccctg gcgagggtcc tgtctatagc    3060
accattgacc cagcggggga ggagctgcag accttccatg ggggcttccc ccaacatccc    3120
tcaggagatc tgggtccctg gagccagtac gctcctccag agtggagcca ggggacagt    3180 ggagccaagg gaggcaaagt gaagcttctg gggaaacctg tgcagatgcc ctctctgaac    3240
tggccagaag ccctgccccc acctcctcct tcttgtgaac tgagctgcct agaagggccg    3300
gaggaggagc tggagggcag ctcagagcca gaggagtggt gcccgccaat gcctgagaga    3360
agtcacctga cggagcccag ctccagtgga gggtgcctgg tcaccccatc ccgaagggaa    3420
accccctctc ccacaccttc ctatggacag cagtccacag ccactcttac accctcacct    3480 cctgacccctc cccagccccc aactgacatg ccccatctcc atcagatgcc caggagggtg    3540 cccccttggggc cgagttcccc tctcagtgta tcccagccca tgctgggcat ccgtgaagcg    3600
aggcctgctg gcttgggtgc tggccctgca gcctcacccc acctcagccc cagtcctgcc    3660
cctagcacag ccagcagtgc cccaggcaga acctggcagg ggaatgggga gatgactccc    3720
ccacttcaag gaccccgtgc tcgattccgg aagaaaccca aggctcttcc ctacaggagg    3780
gagaacagtc ctggggactt gcccccacca cccttgccac cgccagagga agaggcgagc    3840
tgggccctag agctgagggc agcaggcagc atgtcctccc tggagcggga gcgcagtggg    3900
gagaggaaag cggtccaggc cgtgcccctg gcagcccagc gggtgctcca cccagatgaa    3960
gaggcctggc tcccatacag cagaccaagc ttcctgtccc ggggcagggg caccagcaca    4020
tgttccacgg ccggcagcaa ctcttccagg ggctccagca gctctagggg ctcccggggc    4080
cctggccgga gccggagtcg gagtcagagc cggagccaga gccaaaggcc aggacagaaa    4140
cgccgagagg aaccaagatg a                                              4161
```

<210> SEQ ID NO 28
<211> LENGTH: 1386
<212> TYPE: PRT
<213> ORGANISM: Homo sapiens

<400> SEQUENCE: 28

Met Leu Arg Tyr Leu Leu Lys Thr Leu Leu Gln Met Asn Leu Phe Ala
1               5                   10                  15

Asp Ser Leu Ala Gly Asp Ile Ser Asn Ser Ser Glu Leu Leu Leu Gly
            20                  25                  30

Phe Asn Ser Ser Leu Ala Ala Leu Asn His Thr Leu Leu Pro Pro Gly

-continued

```
             35                  40                  45
Asp Pro Ser Leu Asn Gly Ser Arg Val Gly Pro Glu Asp Ala Met Pro
         50                  55                  60
Arg Ile Val Glu Gln Pro Pro Asp Leu Leu Val Ser Arg Gly Glu Pro
 65                  70                  75                  80
Ala Thr Leu Pro Cys Arg Ala Glu Gly Arg Pro Arg Pro Asn Ile Glu
                 85                  90                  95
Trp Tyr Lys Asn Gly Ala Arg Val Ala Thr Val Arg Glu Asp Pro Arg
            100                 105                 110
Ala His Arg Leu Leu Leu Pro Ser Gly Ala Leu Phe Phe Pro Arg Ile
        115                 120                 125
Val His Gly Arg Arg Ala Arg Pro Asp Glu Gly Val Tyr Thr Cys Val
    130                 135                 140
Ala Arg Asn Tyr Leu Gly Ala Ala Ser Arg Asn Ala Ser Leu Glu
145                 150                 155                 160
Val Ala Val Leu Arg Asp Asp Phe Arg Gln Ser Pro Gly Asn Val Val
                165                 170                 175
Val Ala Val Gly Glu Pro Ala Val Leu Glu Cys Val Pro Pro Arg Gly
            180                 185                 190
His Pro Glu Pro Ser Val Ser Trp Arg Lys Asp Gly Ala Arg Leu Lys
        195                 200                 205
Glu Glu Glu Gly Arg Ile Thr Ile Arg Gly Gly Lys Leu Met Met Ser
    210                 215                 220
His Thr Leu Lys Ser Asp Ala Gly Met Tyr Val Cys Val Ala Ser Asn
225                 230                 235                 240
Met Ala Gly Glu Arg Glu Ser Ala Ala Ala Glu Val Met Val Leu Glu
                245                 250                 255
Arg Pro Ser Phe Leu Arg Arg Pro Val Asn Gln Val Val Leu Ala Asp
            260                 265                 270
Ala Pro Val Thr Phe Leu Cys Glu Val Lys Gly Asp Pro Pro Pro Arg
        275                 280                 285
Leu Arg Trp Arg Lys Glu Asp Gly Glu Leu Pro Thr Gly Arg Tyr Glu
    290                 295                 300
Ile Arg Ser Asp His Ser Leu Trp Ile Gly His Val Ser Ala Glu Asp
305                 310                 315                 320
Glu Gly Thr Tyr Thr Cys Val Ala Glu Asn Ser Val Gly Arg Ala Glu
                325                 330                 335
Ala Ser Gly Ser Leu Ser Val His Val Pro Pro Gln Leu Val Thr Gln
            340                 345                 350
Pro Gln Asp Gln Met Ala Ala Pro Gly Glu Ser Val Ala Phe Gln Cys
        355                 360                 365
Glu Thr Lys Gly Asn Pro Pro Pro Ala Ile Phe Trp Gln Lys Glu Gly
    370                 375                 380
Ser Gln Val Leu Leu Phe Pro Ser Gln Ser Leu Gln Pro Thr Gly Arg
385                 390                 395                 400
Phe Ser Val Ser Pro Arg Gly Gln Leu Asn Ile Thr Ala Val Gln Arg
                405                 410                 415
Gly Asp Ala Gly Tyr Tyr Val Cys Gln Ala Val Ser Val Ala Gly Ser
            420                 425                 430
Ile Leu Ala Lys Ala Leu Leu Glu Ile Lys Gly Ala Ser Leu Asp Gly
        435                 440                 445
Leu Pro Pro Val Ile Leu Gln Gly Pro Ala Asn Gln Thr Leu Val Leu
    450                 455                 460
```

```
Gly Ser Ser Val Trp Leu Pro Cys Arg Val Thr Gly Asn Pro Gln Pro
465                 470                 475                 480

Ser Val Arg Trp Lys Lys Asp Gly Gln Trp Leu Gln Gly Asp Asp Leu
                485                 490                 495

Gln Phe Lys Thr Met Ala Asn Gly Thr Leu Tyr Ile Ala Asn Val Gln
            500                 505                 510

Glu Met Asp Met Gly Phe Tyr Ser Cys Val Ala Lys Ser Ser Thr Gly
            515                 520                 525

Glu Ala Thr Trp Ser Gly Trp Leu Lys Met Arg Glu Asp Trp Gly Val
            530                 535                 540

Ser Pro Asp Pro Pro Thr Glu Pro Ser Ser Pro Pro Gly Ala Pro Ser
545                 550                 555                 560

Gln Pro Val Val Thr Glu Ile Thr Lys Asn Ser Ile Thr Leu Thr Trp
                565                 570                 575

Lys Pro Asn Pro Gln Thr Gly Ala Ala Val Thr Ser Tyr Val Ile Glu
            580                 585                 590

Ala Phe Ser Pro Ala Ala Gly Asn Thr Trp Arg Thr Val Ala Asp Gly
            595                 600                 605

Val Gln Leu Glu Thr His Thr Val Ser Gly Leu Gln Pro Asn Thr Ile
610                 615                 620

Tyr Leu Phe Leu Val Arg Ala Val Gly Ala Trp Gly Leu Ser Glu Pro
625                 630                 635                 640

Ser Pro Val Ser Glu Pro Val Arg Thr Gln Asp Ser Ser Pro Ser Arg
                645                 650                 655

Pro Val Glu Asp Pro Trp Arg Gly Gln Gln Gly Leu Ala Glu Val Ala
            660                 665                 670

Val Arg Leu Gln Glu Pro Ile Val Leu Gly Pro Arg Thr Leu Gln Val
            675                 680                 685

Ser Trp Thr Val Asp Gly Pro Val Gln Leu Val Gln Gly Phe Arg Val
            690                 695                 700

Ser Trp Arg Val Ala Gly Pro Glu Gly Gly Ser Trp Thr Met Leu Asp
705                 710                 715                 720

Leu Gln Ser Pro Ser Gln Gln Ser Thr Val Leu Arg Gly Leu Pro Pro
                725                 730                 735

Gly Thr Gln Ile Gln Ile Lys Val Gln Ala Gln Gly Gln Glu Gly Leu
            740                 745                 750

Gly Ala Glu Ser Leu Ser Val Thr Arg Ser Ile Pro Glu Glu Ala Pro
            755                 760                 765

Ser Gly Pro Pro Gln Gly Val Ala Val Ala Leu Gly Gly Asp Gly Asn
770                 775                 780

Ser Ser Ile Thr Val Ser Trp Glu Pro Pro Leu Pro Ser Gln Gln Asn
785                 790                 795                 800

Gly Val Ile Thr Glu Tyr Gln Ile Trp Cys Leu Gly Asn Glu Ser Arg
                805                 810                 815

Phe His Leu Asn Arg Ser Ala Ala Gly Trp Ala Arg Ser Ala Met Leu
            820                 825                 830

Arg Gly Leu Val Pro Gly Leu Leu Tyr Arg Thr Leu Val Ala Ala Ala
            835                 840                 845

Thr Ser Ala Gly Val Gly Val Pro Ser Ala Pro Val Leu Val Gln Leu
850                 855                 860

Pro Ser Pro Pro Asp Leu Glu Pro Gly Leu Glu Val Gly Ala Gly Leu
865                 870                 875                 880
```

-continued

Ala Val Arg Leu Ala Arg Val Leu Arg Glu Pro Ala Phe Leu Ala Gly
            885                 890                 895

Ser Gly Ala Ala Cys Gly Ala Leu Leu Leu Gly Leu Cys Ala Ala Leu
        900                 905                 910

Tyr Trp Arg Arg Lys Gln Arg Lys Glu Leu Ser His Tyr Thr Ala Ser
        915                 920                 925

Phe Ala Tyr Thr Pro Ala Val Ser Phe Pro His Ser Glu Gly Leu Ser
    930                 935                 940

Gly Ala Ser Ser Arg Pro Pro Met Gly Leu Gly Pro Ala Pro Tyr Ser
945                 950                 955                 960

Trp Leu Ala Asp Ser Trp Pro His Pro Ser Arg Ser Pro Ser Ala Gln
            965                 970                 975

Glu Pro Arg Gly Ser Cys Cys Pro Ser Asn Pro Asp Pro Asp Asp Arg
            980                 985                 990

Tyr Tyr Asn Glu Ala Gly Ile Ser Leu Tyr Leu Ala Gln Thr Ala Arg
        995                 1000                1005

Gly Thr Ala Ala Pro Gly Glu Gly Pro Val Tyr Ser Thr Ile Asp
    1010                1015                1020

Pro Ala Gly Glu Glu Leu Gln Thr Phe His Gly Gly Phe Pro Gln
    1025                1030                1035

His Pro Ser Gly Asp Leu Gly Pro Trp Ser Gln Tyr Ala Pro Pro
    1040                1045                1050

Glu Trp Ser Gln Gly Asp Ser Gly Ala Lys Gly Lys Val Lys
    1055                1060                1065

Leu Leu Gly Lys Pro Val Gln Met Pro Ser Leu Asn Trp Pro Glu
    1070                1075                1080

Ala Leu Pro Pro Pro Pro Ser Cys Glu Leu Ser Cys Leu Glu
    1085                1090                1095

Gly Pro Glu Glu Glu Leu Glu Gly Ser Ser Glu Pro Glu Glu Trp
    1100                1105                1110

Cys Pro Pro Met Pro Glu Arg Ser His Leu Thr Glu Pro Ser Ser
    1115                1120                1125

Ser Gly Gly Cys Leu Val Thr Pro Ser Arg Arg Glu Thr Pro Ser
    1130                1135                1140

Pro Thr Pro Ser Tyr Gly Gln Gln Ser Thr Ala Thr Leu Thr Pro
    1145                1150                1155

Ser Pro Pro Asp Pro Pro Gln Pro Pro Thr Asp Met Pro His Leu
    1160                1165                1170

His Gln Met Pro Arg Arg Val Pro Leu Gly Pro Ser Ser Pro Leu
    1175                1180                1185

Ser Val Ser Gln Pro Met Leu Gly Ile Arg Glu Ala Arg Pro Ala
    1190                1195                1200

Gly Leu Gly Ala Gly Pro Ala Ala Ser Pro His Leu Ser Pro Ser
    1205                1210                1215

Pro Ala Pro Ser Thr Ala Ser Ser Ala Pro Gly Arg Thr Trp Gln
    1220                1225                1230

Gly Asn Gly Glu Met Thr Pro Pro Leu Gln Gly Pro Arg Ala Arg
    1235                1240                1245

Phe Arg Lys Lys Pro Lys Ala Leu Pro Tyr Arg Arg Glu Asn Ser
    1250                1255                1260

Pro Gly Asp Leu Pro Pro Pro Leu Pro Pro Pro Glu Glu Glu
    1265                1270                1275

Ala Ser Trp Ala Leu Glu Leu Arg Ala Ala Gly Ser Met Ser Ser

```
                 1280                1285                1290
Leu Glu Arg Glu Arg Ser Gly Glu Arg Lys Ala Val Gln Ala Val
    1295                1300                1305

Pro Leu Ala Ala Gln Arg Val Leu His Pro Asp Glu Glu Ala Trp
    1310                1315                1320

Leu Pro Tyr Ser Arg Pro Ser Phe Leu Ser Arg Gly Gln Gly Thr
    1325                1330                1335

Ser Thr Cys Ser Thr Ala Gly Ser Asn Ser Ser Arg Gly Ser Ser
    1340                1345                1350

Ser Ser Arg Gly Ser Arg Gly Pro Gly Arg Ser Arg Ser Arg Ser
    1355                1360                1365

Gln Ser Arg Ser Gln Ser Gln Arg Pro Gly Gln Lys Arg Arg Glu
    1370                1375                1380

Glu Pro Arg
    1385

<210> SEQ ID NO 29
<211> LENGTH: 195
<212> TYPE: DNA
<213> ORGANISM: Artificial Sequence
<220> FEATURE:
<223> OTHER INFORMATION: IL-8 promoter region

<400> SEQUENCE: 29
gataaggaac aaataggaag tgtgatgact caggtttgcc ctgaggggat gggccatcag    60
ttgcaaatcg tggaatttcc tctgacataa tgaaaagatg agggtgcata agttctctag   120
tagggtgatg atataaaaag ccaccggagc actccataag gcacaaactt tcagagacag   180
cagagcacac aagct                                                   195

<210> SEQ ID NO 30
<211> LENGTH: 354
<212> TYPE: DNA
<213> ORGANISM: Mus musculus

<400> SEQUENCE: 30
gaagtgcagc tggtggagtc tgggggaggc ttagtgaagc ctggagggtc cctgaaactc    60
tcctgtgcag cctctggatt cactttcagt acctatgcca tgtcttgggt tcgccagact   120
ccggagaaga ggctggagtg ggtcgcaacc attagtaatg gtggtactta cacctactat   180
ccagacagtg tgaagggtcg attcaccatc tccagagaca tgccagaaca cccctgtac   240 ctgcaaatga gcagtctgag gtctgaggac acggccatgt atttctgtgc aagactaatc   300
tactatgatt accttgacta ctggggccac ggcaccactc tcacagtctc ctca         354

<210> SEQ ID NO 31
<211> LENGTH: 118
<212> TYPE: PRT
<213> ORGANISM: Mus musculus

<400> SEQUENCE: 31

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Glu Lys Arg Leu Glu Trp Val
        35                  40                  45

Ala Thr Ile Ser Asn Gly Gly Thr Tyr Thr Tyr Tyr Pro Asp Ser Val
```

```
                50                  55                  60
Lys Gly Arg Phe Thr Ile Ser Arg Asp Asn Ala Glu Asn Thr Leu Tyr
 65                  70                  75                  80

Leu Gln Met Ser Ser Leu Arg Ser Glu Asp Thr Ala Met Tyr Phe Cys
                        85                  90                  95

Ala Arg Leu Ile Tyr Tyr Asp Tyr Leu Asp Tyr Trp Gly His Gly Thr
                100                 105                 110

Thr Leu Thr Val Ser Ser
            115

<210> SEQ ID NO 32
<211> LENGTH: 342
<212> TYPE: DNA
<213> ORGANISM: Mus musculus

<400> SEQUENCE: 32
gatgctgtga tgacccaaac tccactctcc ctgcctgtca gtcttggaga tcaagcctcc      60
atctcttgca ggtctagtca gagccttgaa aacagtaatg gaaacaccta tttgaactgg     120
tacttccaga aaccaggcca gtctccacag ctcctgatct acagggtttc caaccgattt     180
tctggggtcc tagacaggtt cagtggtagt ggatcaggga cagatttcac actgaaaatc     240
agcagagtgg aggctgaaga tttcggagtt tatttctgcc tccaagttac tcatgtcccg     300
tggacgttcg gtggaggcac caagctggaa atcaaacggg ct                        342

<210> SEQ ID NO 33
<211> LENGTH: 114
<212> TYPE: PRT
<213> ORGANISM: Mus musculus

<400> SEQUENCE: 33

Asp Ala Val Met Thr Gln Thr Pro Leu Ser Leu Pro Val Ser Leu Gly
  1               5                  10                  15

Asp Gln Ala Ser Ile Ser Cys Arg Ser Ser Gln Ser Leu Glu Asn Ser
                 20                  25                  30

Asn Gly Asn Thr Tyr Leu Asn Trp Tyr Phe Gln Lys Pro Gly Gln Ser
             35                  40                  45

Pro Gln Leu Leu Ile Tyr Arg Val Ser Asn Arg Phe Ser Gly Val Leu
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Phe Gly Val Tyr Phe Cys Leu Gln Val
                 85                  90                  95

Thr His Val Pro Trp Thr Phe Gly Gly Gly Thr Lys Leu Glu Ile Lys
            100                 105                 110

Arg Ala

<210> SEQ ID NO 34
<211> LENGTH: 449
<212> TYPE: DNA
<213> ORGANISM: Homo sapiens

<400> SEQUENCE: 34
gcctccggac tctagagcca ccatggtgct gcagacccag gtgttcatct ccctgctgct      60
gtggatctcc ggcgcgtacg gcgatatcgt gatgattaaa cgtacggtgg ccgccccctc     120
cgtgttcatc ttcccccccct ccgacgagca gctgaagtcc ggcaccgcct ccgtggtgtg    180
```

-continued

| | |
|---|---|
| cctgctgaat aacttctacc ccagagaggc caaggtgcag tggaaggtgg acaacgccct | 240 |
| gcagtccggg aactcccagg agagcgtgac cgagcaggac agcaaggaca gcacctacag | 300 |
| cctgagcagc accctgaccc tgagcaaagc cgactacgag aagcacaagg tgtacgcctg | 360 |
| cgaggtgacc caccagggcc tgagctcccc cgtcaccaag agcttcaaca ggggggagtg | 420 |
| ttagggcccc gtttaaacgg gggaggcta | 449 |

<210> SEQ ID NO 35
<211> LENGTH: 1132
<212> TYPE: DNA
<213> ORGANISM: Artificial Sequence
<220> FEATURE:
<223> OTHER INFORMATION: human H-chain signal and IgG1 constant DNA

<400> SEQUENCE: 35

| | |
|---|---|
| gcctccggac tctagagcca ccatgaaaca cctgtggttc ttcctcctgc tggtggcagc | 60 |
| tcccagatgg gtgctgagcc aggtgcaatt gtgcaggcgg ttagctcagc ctccaccaag | 120 |
| ggcccaagcg tcttcccct ggcaccctcc tccaagagca cctctggcgg cacagccgcc | 180 |
| ctgggctgcc tggtcaagga ctacttcccc gaacccgtga ccgtgagctg gaactcaggc | 240 |
| gccctgacca gcggcgtgca caccttcccc gctgtcctgc agtcctcagg actctactcc | 300 |
| ctcagcagcg tggtgaccgt gccctccagc agcttgggca cccagaccta catctgcaac | 360 |
| gtgaatcaca agcccagcaa caccaaggtg acaagagag ttgagcccaa atcttgtgac | 420 |
| aaaactcaca catgcccacc ctgcccagca cctgaactcc tggggggacc ctcagtcttc | 480 |
| ctcttccccc caaaacccaa ggacaccctc atgatctccc ggacccctga ggtcacatgc | 540 |
| gtggtggtgg acgtgagcca cgaagaccct gaggtcaagt tcaactggta cgtggacggc | 600 |
| gtggaggtgc ataatgccaa gacaaagccc cgggaggagc agtacaacag cacgtaccgg | 660 |
| gtggtcagcg tcctcaccgt cctgcaccag gactggctga atggcaagga gtacaagtgc | 720 |
| aaggtctcca acaaagccct cccagccccc atcgagaaaa ccatctccaa agccaaaggc | 780 |
| cagccccggg aaccacaggt gtacaccctg cccccatccc gggaggagat gaccaagaac | 840 |
| caggtcagcc tgacctgcct ggtcaaaggc ttctatccca gcgacatcgc cgtggagtgg | 900 |
| gagagcaatg gccagcccga gaacaactac aagaccaccc ctcccgtgct ggactccgac | 960 |
| ggctccttct tcctctacag caagctcacc gtggacaaga gcaggtggca gcagggcaac | 1020 |
| gtcttctcat gctccgtgat gcatgaggct ctgcacaacc actacaccca gaagagcctc | 1080 |
| tccctgtctc ccggcaaatg agatatcggg cccgtttaaa cgggggaggc ta | 1132 |

<210> SEQ ID NO 36
<211> LENGTH: 1118
<212> TYPE: DNA
<213> ORGANISM: Artificial Sequence
<220> FEATURE:
<223> OTHER INFORMATION: human H-chain signal and IgG2 constant DNA

<400> SEQUENCE: 36

| | |
|---|---|
| gcctccggac tctagagcca ccatgaaaca cctgtggttc ttcctcctgc tggtggcagc | 60 |
| tcccagatgg gtgctgagcc aggtgcaatt gtgcaggcgg ttagctcagc cagcaccaag | 120 |
| ggcccttccg tgttccctct ggccccttgt agccgttcca ccagcgagtc caccgccgcc | 180 |
| cttggctgtc tggtgaagga ctacttccct gagcctgtga ccgtgagctg gaactccgga | 240 |
| gcccttacca gcggcgtgca caccttccct gccgtgctgc agtccagcgg cctttactcc | 300 |
| ctgagctccg tggtgaccgt gcctagctcc aacttcggca cccaaaccta cacctgtaac | 360 |

```
gtggaccaca agcctagcaa caccaaggtg gacaagaccg tggagcgtaa gtgttgtgtg      420
gagtgtcctc cttgtcctgc ccctcctgtg gccggacctt ccgtgttcct tttccctcct      480
aagcctaagg acaccctgat gatcagccgt accctgagg tgacctgtgt ggtggtggac       540
gtgtcccacg aggaccctga ggtgcagttc aactggtacg tggacggcgt ggaggtgcac      600
aacgccaaga ccaagcctcg tgaggagcaa ttcaacagca ccttccgtgt ggtgtccgtg      660
cttaccgtgg tgcaccaaga ctggctgaac ggcaaggagt acaagtgtaa ggtgagcaac      720
aagggacttc ctgcccctat cgagaagacc atctccaaga ccaagggcca acctcgtgag      780
cctcaagtgt acacccttcc tcctagccgt gaggagatga ccaagaacca agtgtccctt      840
acctgtctgg tgaagggctt ctaccctagc gacatcgccg tggagtggga gtccaacgga      900
caacctgaga caactacaa gaccacccct cctatgcttg acagcgacgg ctccttcttc        960
ctgtacagca agctgaccgt ggacaagtcc cgttggcaac aaggcaacgt gttcagctgt      1020
tccgtgatgc acgaggccct gcacaaccac tacacccaaa agagcctttc cctgagccct      1080
ggaaagtgat atcgggcccg tttaaacggg ggaggcta                              1118

<210> SEQ ID NO 37
<211> LENGTH: 717
<212> TYPE: DNA
<213> ORGANISM: Artificial Sequence
<220> FEATURE:
<223> OTHER INFORMATION: cMAb1 L chain na

<400> SEQUENCE: 37
atggtgctgc agacccaggt gttcatctcc ctgctgctgt ggatctccgg cgcgtacggc       60
gatgctgtga tgacccaaac tccactctcc ctgcctgtca gtcttggaga tcaagcctcc      120
atctcttgca ggtctagtca gagccttgaa aacagtaatg gaaacaccta tttgaactgg      180
tacttccaga aaccaggcca gtctccacag ctcctgatct acagggtttc caaccgattt      240
tctggggtcc tagacaggtt cagtggtagt ggatcaggga cagatttcac actgaaaatc      300
agcagagtgg aggctgaaga tttcggagtt tatttctgcc tccaagttac tcatgtcccg      360
tggacgttcg gtggaggcac caagctggaa atcaaacggg ctgtggccgc ccctccgtg       420 ttcatcttcc cccctccga cgagcagctg aagtccggca ccgcctccgt ggtgtgcctg      480
ctgaataact tctaccccag agaggccaag gtgcagtgga aggtggacaa cgccctgcag      540
tccgggaact cccaggagag cgtgaccgag caggacagca aggacagcac ctacagcctg      600
agcagcaccc tgaccctgag caaagccgac tacgagaagc acaaggtgta cgcctgcgag      660
gtgacccacc agggcctgag ctccccccgtc accaagagct caacaggggg ggagtgt        717

<210> SEQ ID NO 38
<211> LENGTH: 239
<212> TYPE: PRT
<213> ORGANISM: Artificial Sequence
<220> FEATURE:
<223> OTHER INFORMATION: cMAb1 L chain aa

<400> SEQUENCE: 38

Met Val Leu Gln Thr Gln Val Phe Ile Ser Leu Leu Leu Trp Ile Ser
  1               5                  10                  15

Gly Ala Tyr Gly Asp Ala Val Met Thr Gln Thr Pro Leu Ser Leu Pro
                 20                  25                  30

Val Ser Leu Gly Asp Gln Ala Ser Ile Ser Cys Arg Ser Ser Gln Ser
         35                  40                  45
```

```
Leu Glu Asn Ser Asn Gly Asn Thr Tyr Leu Asn Trp Tyr Phe Gln Lys
         50                  55                  60

Pro Gly Gln Ser Pro Gln Leu Leu Ile Tyr Arg Val Ser Asn Arg Phe
 65                  70                  75                  80

Ser Gly Val Leu Asp Arg Phe Ser Gly Ser Gly Ser Gly Thr Asp Phe
                 85                  90                  95

Thr Leu Lys Ile Ser Arg Val Glu Ala Glu Asp Phe Gly Val Tyr Phe
             100                 105                 110

Cys Leu Gln Val Thr His Val Pro Trp Thr Phe Gly Gly Gly Thr Lys
         115                 120                 125

Leu Glu Ile Lys Arg Ala Val Ala Ala Pro Ser Val Phe Ile Phe Pro
         130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                 165                 170                 175

Asn Ala Leu Gln Ser Gly Asn Ser Gln Glu Ser Val Thr Glu Gln Asp
             180                 185                 190

Ser Lys Asp Ser Thr Tyr Ser Leu Ser Ser Thr Leu Thr Leu Ser Lys
         195                 200                 205

Ala Asp Tyr Glu Lys His Lys Val Tyr Ala Cys Glu Val Thr His Gln
         210                 215                 220

Gly Leu Ser Ser Pro Val Thr Lys Ser Phe Asn Arg Gly Glu Cys
225                 230                 235

<210> SEQ ID NO 39
<211> LENGTH: 1401
<212> TYPE: DNA
<213> ORGANISM: Artificial Sequence
<220> FEATURE:
<223> OTHER INFORMATION: cMAb1-1 H chain na

<400> SEQUENCE: 39
atgaaacacc tgtggttctt cctcctgctg gtggcagctc ccagatgggt gctgagcgaa      60
gtgcagctgg tggagtctgg gggaggctta gtgaagcctg agggtccct gaaactctcc     120 tgtgcagcct ctggattcac tttcagtacc tatgccatgt cttgggttcg ccagactccg     180
gagaagaggc tggagtgggt cgcaaccatt agtaatggtg gtacttacac ctactatcca     240
gacagtgtga aggtgcgatt caccatctcc agagacaatg ccgagaacac cctgtacctg     300
caaatgagca gtctgaggtc tgaggacacg gccatgtatt tctgtgcaag actaatctac     360
tatgattacc ttgactactg gggccacggc accactctca cagtcagctc agcctccacc     420
aagggcccaa gcgtcttccc cctggcaccc tcctccaaga gcacctctgg cggcacagcc     480
gccctgggct gcctggtcaa ggactacttc cccgaacccg tgaccgtgag ctggaactca     540
ggcgccctga ccagcggcgt gcacaccttc ccgctgtcc tgcagtcctc aggactctac     600
tccctcagca gcgtggtgac cgtgccctcc agcagcttgg gcacccagac ctacatctgc     660
aacgtgaatc acaagcccag caacaccaag gtggacaaga gagttgagcc caaatcttgt     720
gacaaaactc acacatgccc accctgccca gcacctgaac tcctgggggg accctcagtc     780
ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccccgggagg agcagtacaa cagcacgtac     960
```

```
cgggtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
ggccagcccc gggaaccaca ggtgtacacc ctgcccccat cccgggagga gatgaccaag    1140
aaccaggtca gcctgacctg cctggtcaaa ggcttctatc ccagcgacat cgccgtggag    1200
tgggagagca atggccagcc cgagaacaac tacaagacca cccctcccgt gctggactcc    1260
gacggctcct tcttcctcta cagcaagctc accgtggaca agagcaggtg gcagcagggc    1320
aacgtcttct catgctccgt gatgcatgag gctctgcaca accactacac ccagaagagc    1380
ctctccctgt ctcccggcaa a                                              1401
```

<210> SEQ ID NO 40
<211> LENGTH: 467
<212> TYPE: PRT
<213> ORGANISM: Artificial Sequence
<220> FEATURE:
<223> OTHER INFORMATION: cMAb1-1 H chain aa

<400> SEQUENCE: 40

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Thr Tyr Ala Met Ser Trp Val Arg Gln Thr Pro Glu Lys Arg Leu
    50                  55                  60

Glu Trp Val Ala Thr Ile Ser Asn Gly Gly Thr Tyr Thr Tyr Tyr Pro
65                  70                  75                  80

Asp Ser Val Lys Gly Arg Phe Thr Ile Ser Arg Asp Asn Ala Glu Asn
                85                  90                  95

Thr Leu Tyr Leu Gln Met Ser Ser Leu Arg Ser Glu Asp Thr Ala Met
            100                 105                 110

Tyr Phe Cys Ala Arg Leu Ile Tyr Tyr Asp Tyr Leu Asp Tyr Trp Gly
        115                 120                 125

His Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285
```

```
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
                340                 345                 350
Glu Lys Thr Ile Ser Lys Ala Lys Gly Gln Pro Arg Glu Pro Gln Val
            355                 360                 365
Tyr Thr Leu Pro Pro Ser Arg Glu Glu Met Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
                420                 425                 430
Asp Lys Ser Arg Trp Gln Gln Gly Asn Val Phe Ser Cys Ser Val Met
            435                 440                 445
His Glu Ala Leu His Asn His Tyr Thr Gln Lys Ser Leu Ser Leu Ser
    450                 455                 460
Pro Gly Lys
465

<210> SEQ ID NO 41
<211> LENGTH: 1389
<212> TYPE: DNA
<213> ORGANISM: Artificial Sequence
<220> FEATURE:
<223> OTHER INFORMATION: cMAb1-2 H chain na

<400> SEQUENCE: 41
atgaaacacc tgtggttctt cctcctgctg gtggcagctc ccagatgggt gctgagcgaa      60
gtgcagctgg tggagtctgg gggaggctta gtgaagcctg agggtccct gaaactctcc      120 tgtgcagcct ctggattcac tttcagtacc tatgccatgt cttgggttcg ccagactccg     180
gagaagaggc tggagtgggt cgcaaccatt agtaatggtg gtacttacac ctactatcca     240
gacagtgtga agggtcgatt caccatctcc agagacaatg ccgagaacac cctgtacctg     300
caaatgagca gtctgaggtc tgaggacacg gccatgtatt tctgtgcaag actaatctac     360
tatgattacc ttgactactg gggccacggc accactctca cagtcagctc agccagcacc     420
aagggcccat ccgtgttccc tctggcccct tgtagccgtt ccaccagcga gtccaccgcc     480
gcccttggct gtctggtgaa ggactacttc cctgagcctg tgaccgtgag ctggaactcc     540 ggagcccta ccagcggcgt gcacaccttc cctgccgtgc tgcagtccag cggcctttac     600
tccctgagct ccgtggtgac cgtgcctagc tccaacttcg gcacccaaac ctacacctgt     660
aacgtggacc acaagcctag caacaccaag gtggacaaga ccgtggagcg taagtgttgt     720
gtggagtgtc ctccttgtcc tgcccctcct gtggccggac cttccgtgtt cctttttccct     780 cctaagccta aggacaccct gatgatcagc cgtacccctg aggtgacctg tgtggtggtg     840
gacgtgtccc acgaggaccc tgaggtgcag ttcaactggt acgtgacgg cgtggaggtg     900 cacaacgcca agaccaagcc tcgtgaggag caattcaaca gcaccttccg tgtggtgtcc     960
```

```
gtgcttaccg tggtgcacca agactggctg aacggcaagg agtacaagtg taaggtgagc   1020
aacaagggac ttcctgcccc tatcgagaag accatctcca agaccaaggg ccaacctcgt   1080
gagcctcaag tgtacaccct tcctcctagc cgtgaggaga tgaccaagaa ccaagtgtcc   1140
cttacctgtc tggtgaaggg cttctaccct agcgacatcg ccgtggagtg ggagtccaac   1200
ggacaacctg agaacaacta caagaccacc cctcctatgc ttgacagcga cggctccttc   1260
ttcctgtaca gcaagctgac cgtggacaag tcccgttggc aacaaggcaa cgtgttcagc   1320
tgttccgtga tgcacgaggc cctgcacaac cactacaccc aaaagagcct ttccctgagc   1380
cctggaaag                                                            1389

<210> SEQ ID NO 42
<211> LENGTH: 463
<212> TYPE: PRT
<213> ORGANISM: Artificial Sequence
<220> FEATURE:
<223> OTHER INFORMATION: cMAb1-2 H chain aa

<400> SEQUENCE: 42

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Thr Tyr Ala Met Ser Trp Val Arg Gln Thr Pro Glu Lys Arg Leu
    50                  55                  60

Glu Trp Val Ala Thr Ile Ser Asn Gly Gly Thr Tyr Thr Tyr Tyr Pro
65                  70                  75                  80

Asp Ser Val Lys Gly Arg Phe Thr Ile Ser Arg Asp Asn Ala Glu Asn
                85                  90                  95

Thr Leu Tyr Leu Gln Met Ser Ser Leu Arg Ser Glu Asp Thr Ala Met
            100                 105                 110

Tyr Phe Cys Ala Arg Leu Ile Tyr Tyr Asp Tyr Leu Asp Tyr Trp Gly
        115                 120                 125

His Gly Thr Thr Leu Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285
```

Val Gln Phe Asn Trp Tyr Val Asp Gly Val Glu Val His Asn Ala Lys
            290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 43
<211> LENGTH: 15
<212> TYPE: DNA
<213> ORGANISM: Mus musculus

<400> SEQUENCE: 43
acctatgcca tgtct                                                    15

<210> SEQ ID NO 44
<211> LENGTH: 5
<212> TYPE: PRT
<213> ORGANISM: Mus musculus

<400> SEQUENCE: 44

Thr Tyr Ala Met Ser
1               5

<210> SEQ ID NO 45
<211> LENGTH: 51
<212> TYPE: DNA
<213> ORGANISM: Mus musculus

<400> SEQUENCE: 45
accattagta atggtggtac ttacacctac tatccagaca gtgtgaaggg t            51

<210> SEQ ID NO 46
<211> LENGTH: 17
<212> TYPE: PRT
<213> ORGANISM: Mus musculus

<400> SEQUENCE: 46

Thr Ile Ser Asn Gly Gly Thr Tyr Thr Tyr Tyr Pro Asp Ser Val Lys
1               5                   10                  15

Gly

```
<210> SEQ ID NO 47
<211> LENGTH: 27
<212> TYPE: DNA
<213> ORGANISM: Mus musculus

<400> SEQUENCE: 47
ctaatctact atgattacct tgactac                                              27

<210> SEQ ID NO 48
<211> LENGTH: 9
<212> TYPE: PRT
<213> ORGANISM: Mus musculus

<400> SEQUENCE: 48

Leu Ile Tyr Tyr Asp Tyr Leu Asp Tyr
1               5

<210> SEQ ID NO 49
<211> LENGTH: 48
<212> TYPE: DNA
<213> ORGANISM: Mus musculus

<400> SEQUENCE: 49
aggtctagtc agagccttga aaacagtaat ggaaacacct atttgaac                       48

<210> SEQ ID NO 50
<211> LENGTH: 16
<212> TYPE: PRT
<213> ORGANISM: Mus musculus

<400> SEQUENCE: 50

Arg Ser Ser Gln Ser Leu Glu Asn Ser Asn Gly Asn Thr Tyr Leu Asn
1               5                   10                  15

<210> SEQ ID NO 51
<211> LENGTH: 21
<212> TYPE: DNA
<213> ORGANISM: Mus musculus

<400> SEQUENCE: 51
agggtttcca accgattttc t                                                    21

<210> SEQ ID NO 52
<211> LENGTH: 7
<212> TYPE: PRT
<213> ORGANISM: Mus musculus

<400> SEQUENCE: 52

Arg Val Ser Asn Arg Phe Ser
1               5

<210> SEQ ID NO 53
<211> LENGTH: 27
<212> TYPE: DNA
<213> ORGANISM: Mus musculus

<400> SEQUENCE: 53
ctccaagtta ctcatgtccc gtggacg                                              27

<210> SEQ ID NO 54
<211> LENGTH: 9
<212> TYPE: PRT
<213> ORGANISM: Mus musculus

<400> SEQUENCE: 54
```

Leu Gln Val Thr His Val Pro Trp Thr
1               5

<210> SEQ ID NO 55
<211> LENGTH: 1389
<212> TYPE: DNA
<213> ORGANISM: Artificial Sequence
<220> FEATURE:
<223> OTHER INFORMATION: hMAb1-T1H

<400> SEQUENCE: 55

| | | | | | |
|---|---|---|---|---|---|
| atgaaacacc | tgtggttctt | cctcctgctg | gtggcagctc | ccagatgggt | gctgagcgag | 60 |
| gtgcagctgg | tggaaagcgg | cggaggcctg | gtgcagcctg | gcggctctct | gagactgagc | 120 |
| tgtgccgcca | gcggcttcac | cttcagcacc | tacgccatga | gctgggtccg | acaggcccct | 180 |
| ggcaagggac | tggaatgggt | ggcaaccatc | agcaacggcg | gcacctacac | ctactacccc | 240 |
| gacagcgtga | agggccggtt | caccatcagc | cgggacaacg | ccaagaacac | cctgtacctg | 300 |
| cagatgaaca | gcctgcgggc | cgaggacacc | gccgtgtact | actgcgccag | actgatctac | 360 |
| tacgactacc | tggactactg | gggccagggc | accctggtca | ccgtcagctc | agccagcacc | 420 |
| aagggcccdt | ccgtgttccc | tctggcccct | gtagccgtt | ccaccagcga | gtccaccgcc | 480 |
| gcccttggct | gtctggtgaa | ggactacttc | cctgagcctg | tgaccgtgag | ctggaactcc | 540 |
| ggagcccdtta | ccagcggcgt | gcacaccttc | cctgccgtgc | tgcagtccag | cggccttttac | 600 |
| tccctgagct | ccgtggtgac | cgtgcctagc | tccaacttcg | gcacccaaac | ctacacctgt | 660 |
| aacgtggacc | acaagcctag | caacaccaag | gtggacaaga | ccgtggagcg | taagtgttgt | 720 |
| gtggagtgtc | ctccttgtcc | tgcccctcct | gtggccggac | cttccgtgtt | ccttttccct | 780 |
| cctaagccta | aggacaccct | gatgatcagc | cgtaccccdg | aggtgacctg | tgtggtggtg | 840 |
| gacgtgtccc | acgaggaccc | tgaggtgcag | ttcaactggt | acgtggacgg | cgtggaggtg | 900 |
| cacaacgcca | agaccaagcc | tcgtgaggag | caattcaaca | gcaccttccg | tgtggtgtcc | 960 |
| gtgcttaccg | tggtgcacca | agactggctg | aacggcaagg | agtacaagtg | taaggtgagc | 1020 |
| aacaagggac | ttcctgcccc | tatcgagaag | accatctcca | agaccaaggg | ccaacctcgt | 1080 |
| gagcctcaag | tgtacaccct | tcctcctagc | cgtgaggaga | tgaccaagaa | ccaagtgtcc | 1140 |
| cttacctgtc | tggtgaaggg | cttctaccct | agcgacatcg | ccgtggagtg | ggagtccaac | 1200 |
| ggacaacctg | agaacaacta | caagaccacc | cctcctatgc | ttgacagcga | cggctccttc | 1260 |
| ttcctgtaca | gcaagctgac | cgtggacaag | tcccgttggc | aacaaggcaa | cgtgttcagc | 1320 |
| tgttccgtga | tgcacgaggc | cctgcacaac | cactacaccc | aaaagagcct | ttccctgagc | 1380 |
| cctggaaag | | | | | | 1389 |

<210> SEQ ID NO 56
<211> LENGTH: 463
<212> TYPE: PRT
<213> ORGANISM: Artificial Sequence
<220> FEATURE:
<223> OTHER INFORMATION: hMAb1-T1H aa

<400> SEQUENCE: 56

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe

-continued

```
            35                  40                  45
Ser Thr Tyr Ala Met Ser Trp Val Arg Gln Ala Pro Gly Lys Gly Leu
 50                  55                  60

Glu Trp Val Ala Thr Ile Ser Asn Gly Gly Thr Tyr Thr Tyr Tyr Pro
 65                  70                  75                  80

Asp Ser Val Lys Gly Arg Phe Thr Ile Ser Arg Asp Asn Ala Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Leu Ile Tyr Tyr Asp Tyr Leu Asp Tyr Trp Gly
            115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
    195                 200                 205

Pro Ser Ser Asn Phe Gly Thr Gln Thr Tyr Thr Cys Asn Val Asp His
210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
    275                 280                 285

Val Gln Phe Asn Trp Tyr Val Asp Gly Val Glu Val His Asn Ala Lys
290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
    355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
    435                 440                 445

His Asn His Tyr Thr Gln Lys Ser Leu Ser Leu Ser Pro Gly Lys
450                 455                 460
```

<210> SEQ ID NO 57
<211> LENGTH: 1389
<212> TYPE: DNA
<213> ORGANISM: Artificial Sequence
<220> FEATURE:
<223> OTHER INFORMATION: hMAb1-T2H na

<400> SEQUENCE: 57

| | |
|---|---|
| atgaaacacc tgtggttctt cctcctgctg gtggcagctc ccagatgggt gctgagcgag | 60 |
| gtgcagctgg tggaaagcgg cggaggcctg gtgcagcctg gcggctctct gagactgagc | 120 |
| tgtgccgcca gcggcttcac cttcagcacc tacgccatga gctgggtccg acaggcccct | 180 |
| ggcaagggac tggaatgggt ggcaaccatc agccaaggcg gcacctacac ctactacccc | 240 |
| gacagcgtga aggccggtt caccatcagc cgggacaacg ccaagaacac cctgtacctg | 300 |
| cagatgaaca gcctgcgggc cgaggacacc gccgtgtact actgcgccag actgatctac | 360 |
| tacgactacc tggactactg gggccagggc accctggtca ccgtcagctc agccagcacc | 420 |
| aagggccctt ccgtgttccc tctggcccct gtagccgtt ccaccagcga gtccaccgcc | 480 |
| gcccttggct gtctggtgaa ggactacttc cctgagcctg tgaccgtgag ctggaactcc | 540 |
| ggagcccta ccagcggcgt gcacaccttc cctgccgtgc tgcagtccag cggcctttac | 600 |
| tccctgagct ccgtggtgac cgtgcctagc tccaacttcg gcacccaaac ctacacctgt | 660 |
| aacgtggacc acaagcctag caacaccaag gtggacaaga ccgtggagcg taagtgttgt | 720 |
| gtggagtgtc ctccttgtcc tgcccctcct gtggccggac cttccgtgtt ccttttccct | 780 |
| cctaagccta aggacaccct gatgatcagc cgtacccctg aggtgacctg tgtggtggtg | 840 |
| gacgtgtccc acgaggaccc tgaggtgcag ttcaactggt acgtggacgg cgtggaggtg | 900 |
| cacaacgcca agaccaagcc tcgtgaggag caattcaaca gcaccttccg tgtggtgtcc | 960 |
| gtgcttaccg tggtgcacca agactggctg aacggcaagg agtacaagtg taaggtgagc | 1020 |
| aacaagggac ttcctgcccc tatcgagaag accatctcca gaccaagggg ccaacctcgt | 1080 |
| gagcctcaag tgtacaccct tcctcctagc cgtgaggaga tgaccaagaa ccaagtgtcc | 1140 |
| cttacctgtc tggtgaaggg cttctaccct agcgacatcg ccgtggagtg ggagtccaac | 1200 |
| ggacaacctg agaacaacta caagaccacc cctcctatgc ttgacagcga cggctccttc | 1260 |
| ttcctgtaca gcaagctgac cgtggacaag tcccgttggc aacaaggcaa cgtgttcagc | 1320 |
| tgttccgtga tgcacgaggc cctgcacaac cactacaccc aaaagagcct tccctgagc | 1380 |
| cctggaaag | 1389 |

<210> SEQ ID NO 58
<211> LENGTH: 463
<212> TYPE: PRT
<213> ORGANISM: Artificial Sequence
<220> FEATURE:
<223> OTHER INFORMATION: hMAb1-T2H aa

<400> SEQUENCE: 58

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Thr Tyr Ala Met Ser Trp Val Arg Gln Ala Pro Gly Lys Gly Leu

```
            50                  55                  60
Glu Trp Val Ala Thr Ile Ser Gln Gly Gly Thr Tyr Thr Tyr Tyr Pro
 65                  70                  75                  80

Asp Ser Val Lys Gly Arg Phe Thr Ile Ser Arg Asp Asn Ala Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Leu Ile Tyr Tyr Asp Tyr Leu Asp Tyr Trp Gly
            115                 120                 125

Gln Gly Thr Leu Val Thr Val Ser Ser Ala Ser Thr Lys Gly Pro Ser
        130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Asn Phe Gly Thr Gln Thr Tyr Thr Cys Asn Val Asp His
            210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Asp Val Ser His Glu Asp Pro Glu
            275                 280                 285

Val Gln Phe Asn Trp Tyr Val Asp Gly Val Glu Val His Asn Ala Lys
        290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
        450                 455                 460

<210> SEQ ID NO 59
```

<211> LENGTH: 1389
<212> TYPE: DNA
<213> ORGANISM: Artificial Sequence
<220> FEATURE:
<223> OTHER INFORMATION: hMAb1-T3H na

<400> SEQUENCE: 59

```
atgaaacacc tgtggttctt cctcctgctg gtggcagctc ccagatgggt gctgagcgag      60
gtgcagctgg tggaaagcgg cggaggcctg gtgcagcctg gcggctctct gagactgagc     120
tgtgccgcca gcggcttcac cttcagcacc tacgccatga gctgggtccg acaggcccct     180
ggcaagcggc tggaatgggt ggcaaccatc agcaacggcg gcacctacac ctactacccc     240
gacagcgtga agggccggtt caccatcagc cgggacaacg ccaagaacac cctgtacctg     300
cagatgaaca gcctgcgggc cgaggacacc gccgtgtact actgcgccag actgatctac     360
tacgactacc tggactactg gggccagggc accctggtca ccgtcagctc agccagcacc     420
aagggccctt ccgtgttccc tctggcccct gtagccgtt ccaccagcga gtccaccgcc     480
gcccttggct gtctggtgaa ggactactc cctgagcctg tgaccgtgag ctggaactcc     540
ggagcccttac cagcggcgt gcacaccttc cctgccgtgc tgcagtccag cggcctttac     600
tccctgagct ccgtggtgac cgtgcctagc tccaacttcg gcacccaaac ctacacctgt     660
aacgtggacc acaagcctag caacaccaag gtggacaaga ccgtggagcg taagtgttgt     720
gtggagtgtc ctccttgtcc tgcccctcct gtggccggac cttccgtgtt cttttcccct     780
cctaagccta aggacaccct gatgatcagc cgtacccctg aggtgacctg tgtggtggtg     840
gacgtgtccc acgaggaccc tgaggtgcag ttcaactggt acgtggacgg cgtggaggtg     900
cacaacgcca agaccaagcc tcgtgaggag caattcaaca gcaccttccg tgtggtgtcc     960
gtgcttaccg tggtgcacca agactggctg aacggcaagg agtacaagtg taaggtgagc    1020
aacaagggac ttcctgcccc tatcgagaag accatctcca agaccaaggg ccaacctcgt    1080
gagcctcaag tgtacaccct tcctcctagc cgtgaggaga tgaccaagaa ccaagtgtcc    1140
cttacctgtc tggtgaaggg cttctaccct agcgacatcg ccgtggagtg ggagtccaac    1200
ggacaacctg agaacaacta caagaccacc cctcctatgc ttgacagcga cggctccttc    1260
ttcctgtaca gcaagctgac cgtggacaag tcccgttggc aacaaggcaa cgtgttcagc    1320
tgttccgtga tgcacgaggc cctgcacaac cactacaccc aaaagagcct ttccctgagc    1380
cctggaaag                                                          1389
```

<210> SEQ ID NO 60
<211> LENGTH: 463
<212> TYPE: PRT
<213> ORGANISM: Artificial Sequence
<220> FEATURE:
<223> OTHER INFORMATION: hMAb1-T3H aa

<400> SEQUENCE: 60

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Thr Tyr Ala Met Ser Trp Val Arg Gln Ala Pro Gly Lys Arg Leu
    50                  55                  60

Glu Trp Val Ala Thr Ile Ser Asn Gly Gly Thr Tyr Thr Tyr Tyr Pro

```
                65                  70                  75                  80
Asp Ser Val Lys Gly Arg Phe Thr Ile Ser Arg Asp Asn Ala Lys Asn
                85                  90                  95

Thr Leu Tyr Leu Gln Met Asn Ser Leu Arg Ala Glu Asp Thr Ala Val
               100                 105                 110

Tyr Tyr Cys Ala Arg Leu Ile Tyr Asp Tyr Leu Asp Tyr Trp Gly
           115                 120                 125

Gln Gly Thr Leu Val Thr Val Ser Ser Ala Ser Thr Lys Gly Pro Ser
           130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
               165                 170                 175

Ser Trp Asn Ser Gly Ala Leu Thr Ser Gly Val His Thr Phe Pro Ala
               180                 185                 190

Val Leu Gln Ser Ser Gly Leu Tyr Ser Leu Ser Ser Val Val Thr Val
           195                 200                 205

Pro Ser Ser Asn Phe Gly Thr Gln Thr Tyr Thr Cys Asn Val Asp His
           210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
               245                 250                 255

Phe Leu Phe Pro Pro Lys Pro Lys Asp Thr Leu Met Ile Ser Arg Thr
               260                 265                 270

Pro Glu Val Thr Cys Val Val Val Asp Val Ser His Glu Asp Pro Glu
           275                 280                 285

Val Gln Phe Asn Trp Tyr Val Asp Gly Val Glu Val His Asn Ala Lys
           290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
               325                 330                 335

Cys Lys Val Ser Asn Lys Gly Leu Pro Ala Pro Ile Glu Lys Thr Ile
               340                 345                 350

Ser Lys Thr Lys Gly Gln Pro Arg Glu Pro Gln Val Tyr Thr Leu Pro
           355                 360                 365

Pro Ser Arg Glu Glu Met Thr Lys Asn Gln Val Ser Leu Thr Cys Leu
           370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
               405                 410                 415

Asp Gly Ser Phe Phe Leu Tyr Ser Lys Leu Thr Val Asp Lys Ser Arg
               420                 425                 430

Trp Gln Gln Gly Asn Val Phe Ser Cys Ser Val Met His Glu Ala Leu
           435                 440                 445

His Asn His Tyr Thr Gln Lys Ser Leu Ser Leu Ser Pro Gly Lys
           450                 455                 460

<210> SEQ ID NO 61
<211> LENGTH: 1389
<212> TYPE: DNA
<213> ORGANISM: Artificial Sequence
```

<220> FEATURE:
<223> OTHER INFORMATION: hMAb1-T4H na

<400> SEQUENCE: 61

```
atgaaacacc tgtggttctt cctcctgctg gtggcagctc ccagatgggt gctgagcgag      60
gtgcagctgg tggaaagcgg cggaggcctg gtgcagcctg gcggctctct gagactgagc     120
tgtgccgcca gcggcttcac cttcagcacc tacgccatga gctgggtccg acaggcccct     180
ggcaagcggc tggaatgggt ggcaaccatc agccaaggcg gcacctacac ctactacccc     240
gacagcgtga agggccggtt caccatcagc cggacaacg ccaagaacac cctgtacctg      300
cagatgaaca gcctgcgggc cgaggacacc gccgtgtact actgcgccag actgatctac     360
tacgactacc tggactactg gggccagggc accctggtca ccgtcagctc agccagcacc     420
aagggcccct ccgtgttccc tctggcccct gtagccgtt ccaccagcga gtccaccgcc      480
gcccttggct gtctggtgaa ggactacttc cctgagcctg tgaccgtgag ctggaactcc     540
ggagcccctta ccagcggcgt gcacaccttc cctgccgtgc tgcagtccag cggcctttac    600
tccctgagct ccgtggtgac cgtgcctagc tccaacttcg cacccaaac ctacacctgt      660
aacgtggacc acaagcctag caacaccaag gtggacaaga ccgtggagcg taagtgttgt     720
gtggagtgtc ctccttgtcc tgcccctcct gtggccggac cttccgtgtt ccttttccct    780
cctaagccta aggacaccct gatgatcagc cgtacccctg aggtgacctg tgtggtggtg   840
gacgtgtccc acgaggaccc tgaggtgcag ttcaactggt acgtggacgg cgtggaggtg   900
cacaacgcca agaccaagcc tcgtgaggag caattcaaca gcaccttccg tgtggtgtcc    960
gtgcttaccg tggtgcacca agactggctg aacggcaagg agtacaagtg taaggtgagc   1020
aacaagggac ttcctgcccc tatcgagaag accatctcca agaccaaggg ccaacctcgt   1080
gagcctcaag tgtacaccct tcctcctagc cgtgaggaga tgaccaagaa ccaagtgtcc   1140
cttacctgtc tggtgaaggg cttctaccct agcgacatcg ccgtggagtg ggagtccaac   1200
ggacaacctg agaacaacta caagaccacc cctcctatgc ttgacagcga cggctccttc   1260
ttcctgtaca gcaagctgac cgtggacaag tcccgttggc aacaggcaa cgtgttcagc   1320
tgttccgtga tgcacgaggc cctgcacaac cactacaccc aaaagagcct ttccctgagc   1380
cctggaaag                                                            1389
```

<210> SEQ ID NO 62
<211> LENGTH: 463
<212> TYPE: PRT
<213> ORGANISM: Artificial Sequence
<220> FEATURE:
<223> OTHER INFORMATION: hMAb1-T4H aa

<400> SEQUENCE: 62

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Thr Tyr Ala Met Ser Trp Val Arg Gln Ala Pro Gly Lys Arg Leu
    50                  55                  60

Glu Trp Val Ala Thr Ile Ser Gln Gly Gly Thr Tyr Thr Tyr Tyr Pro
65                  70                  75                  80

Asp Ser Val Lys Gly Arg Phe Thr Ile Ser Arg Asp Asn Ala Lys Asn

```
                    85                  90                  95
Thr Leu Tyr Leu Gln Met Asn Ser Leu Arg Ala Glu Asp Thr Ala Val
                100                 105                 110
Tyr Tyr Cys Ala Arg Leu Ile Tyr Tyr Asp Tyr Leu Asp Tyr Trp Gly
                115                 120                 125
Gln Gly Thr Leu Val Thr Val Ser Ser Ala Ser Thr Lys Gly Pro Ser
            130                 135                 140
Val Phe Pro Leu Ala Pro Cys Ser Arg Ser Thr Ser Glu Ser Thr Ala
145                 150                 155                 160
Ala Leu Gly Cys Leu Val Lys Asp Tyr Phe Pro Glu Pro Val Thr Val
                165                 170                 175
Ser Trp Asn Ser Gly Ala Leu Thr Ser Gly Val His Thr Phe Pro Ala
                180                 185                 190
Val Leu Gln Ser Ser Gly Leu Tyr Ser Leu Ser Ser Val Val Thr Val
                195                 200                 205
Pro Ser Ser Asn Phe Gly Thr Gln Thr Tyr Thr Cys Asn Val Asp His
            210                 215                 220
Lys Pro Ser Asn Thr Lys Val Asp Lys Thr Val Glu Arg Lys Cys Cys
225                 230                 235                 240
Val Glu Cys Pro Pro Cys Pro Ala Pro Pro Val Ala Gly Pro Ser Val
                245                 250                 255
Phe Leu Phe Pro Pro Lys Pro Lys Asp Thr Leu Met Ile Ser Arg Thr
                260                 265                 270
Pro Glu Val Thr Cys Val Val Val Asp Val Ser His Glu Asp Pro Glu
            275                 280                 285
Val Gln Phe Asn Trp Tyr Val Asp Gly Val Glu Val His Asn Ala Lys
        290                 295                 300
Thr Lys Pro Arg Glu Glu Gln Phe Asn Ser Thr Phe Arg Val Val Ser
305                 310                 315                 320
Val Leu Thr Val Val His Gln Asp Trp Leu Asn Gly Lys Glu Tyr Lys
                325                 330                 335
Cys Lys Val Ser Asn Lys Gly Leu Pro Ala Pro Ile Glu Lys Thr Ile
            340                 345                 350
Ser Lys Thr Lys Gly Gln Pro Arg Glu Pro Gln Val Tyr Thr Leu Pro
        355                 360                 365
Pro Ser Arg Glu Glu Met Thr Lys Asn Gln Val Ser Leu Thr Cys Leu
    370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Met Leu Asp Ser
                405                 410                 415
Asp Gly Ser Phe Phe Leu Tyr Ser Lys Leu Thr Val Asp Lys Ser Arg
            420                 425                 430
Trp Gln Gln Gly Asn Val Phe Ser Cys Ser Val Met His Glu Ala Leu
        435                 440                 445
His Asn His Tyr Thr Gln Lys Ser Leu Ser Leu Ser Pro Gly Lys
    450                 455                 460

<210> SEQ ID NO 63
<211> LENGTH: 717
<212> TYPE: DNA
<213> ORGANISM: Artificial Sequence
<220> FEATURE:
<223> OTHER INFORMATION: hMAb1-T1L na
```

<400> SEQUENCE: 63

```
atggtgctgc agacccaggt gttcatctcc ctgctgctgt ggatctccgg cgcgtacggc      60
gacatcgtga tgacccagag ccccctgagc ctgcccgtga cactgggcga gcctgccagc     120
atcagctgca gaagcagcca gagcctggaa aacagcaacg gcaacaccta cctgaactgg     180
tatctgcaga agcccggcca gtcccccag ctgctgatct accgggtgtc caaccggttc      240
agcggcgtgc ccgacagatt cagcggcagc ggctccggca ccgacttcac cctgaagatc     300
agccgggtgg aagccgagga cgtgggcgtg tactactgtc tgcaggtcac acacgtgccc     360
tggaccttcg gccctggcac caaggtggac atcaagcgta cggtggccgc ccctccgtg      420
ttcatcttcc cccctccga cgagcagctg aagtccggca ccgcctccgt ggtgtgcctg      480
ctgaataact tctacccag agaggccaag gtgcagtgga aggtggacaa cgccctgcag      540
tccgggaact cccaggagag cgtgaccgag caggacagca aggacagcac ctacagcctg     600
agcagcaccc tgaccctgag caaagccgac tacgagaagc acaaggtgta cgcctgcgag     660
gtgacccacc agggcctgag ctccccccgtc accaagagct tcaacagggg ggagtgt      717
```

<210> SEQ ID NO 64
<211> LENGTH: 239
<212> TYPE: PRT
<213> ORGANISM: Artificial Sequence
<220> FEATURE:
<223> OTHER INFORMATION: hMAb1-T1L aa

<400> SEQUENCE: 64

```
Met Val Leu Gln Thr Gln Val Phe Ile Ser Leu Leu Trp Ile Ser
1               5                   10                  15

Gly Ala Tyr Gly Asp Ile Val Met Thr Gln Ser Pro Leu Ser Leu Pro
            20                  25                  30

Val Thr Leu Gly Glu Pro Ala Ser Ile Ser Cys Arg Ser Ser Gln Ser
        35                  40                  45

Leu Glu Asn Ser Asn Gly Asn Thr Tyr Leu Asn Trp Tyr Leu Gln Lys
    50                  55                  60

Pro Gly Gln Ser Pro Gln Leu Leu Ile Tyr Arg Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Leu Gln Val Thr His Val Pro Trp Thr Phe Gly Pro Gly Thr Lys
        115                 120                 125

Val Asp Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
```

<210> SEQ ID NO 65
<211> LENGTH: 717
<212> TYPE: DNA
<213> ORGANISM: Artificial Sequence
<220> FEATURE:
<223> OTHER INFORMATION: hMAb1-T2L na

<400> SEQUENCE: 65

```
atggtgctgc agacccaggt gttcatctcc ctgctgctgt ggatctccgg cgcgtacggc      60
gacatcgtga tgacccagag ccccctgagc ctgcccgtga cactgggcga gcctgccagc     120
atcagctgca gaagcagcca gagcctggaa acgagaacag agaacctgta cctgaactgg     180
tatctgcaga gcccggcca gtccccccag ctgctgatct accgggtgtc caaccggttc     240
agcggcgtgc ccgacagatt cagcggcagc ggctccggca ccgacttcac cctgaagatc     300
agccgggtgg aagccgagga cgtgggcgtg tactactgtc tgcaggtcac acacgtgccc     360
tggaccttcg gccctggcac caaggtggac atcaagcgta cggtggccgc ccctccgtg      420
ttcatcttcc cccctccga cgagcagctg aagtccggca cgcctccgt ggtgtgcctg      480
ctgaataact tctaccccag agaggccaag gtgcagtgga aggtggacaa cgccctgcag     540
tccgggaact cccaggagag cgtgaccgag caggacagca aggacagcac ctacagcctg     600
agcagcaccc tgaccctgag caaagccgac tacgagaagc acaaggtgta cgcctgcgag     660
gtgacccacc agggcctgag ctccccgtc accaagagct tcaacagggg ggagtgt       717
```

<210> SEQ ID NO 66
<211> LENGTH: 239
<212> TYPE: PRT
<213> ORGANISM: Artificial Sequence
<220> FEATURE:
<223> OTHER INFORMATION: hMAb1-T2L aa

<400> SEQUENCE: 66

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Leu Ser Leu Pro
            20                  25                  30

Val Thr Leu Gly Glu Pro Ala Ser Ile Ser Cys Arg Ser Ser Gln Ser
        35                  40                  45

Leu Glu Asn Glu Asn Lys Asn Leu Tyr Leu Asn Trp Tyr Leu Gln Lys
    50                  55                  60

Pro Gly Gln Ser Pro Gln Leu Leu Ile Tyr Arg Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Leu Gln Val Thr His Val Pro Trp Thr Phe Gly Pro Gly Thr Lys
        115                 120                 125

Val Asp Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175
```

```
Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 67
<211> LENGTH: 5
<212> TYPE: PRT
<213> ORGANISM: Mus musculus

<400> SEQUENCE: 67

```
Thr Tyr Ala Met Ser
1               5
```

<210> SEQ ID NO 68
<211> LENGTH: 17
<212> TYPE: PRT
<213> ORGANISM: Artificial Sequence
<220> FEATURE:
<223> OTHER INFORMATION: CDRH2-2

<400> SEQUENCE: 68

```
Thr Ile Ser Gln Gly Gly Thr Tyr Thr Tyr Tyr Pro Asp Ser Val Lys
1               5                   10                  15

Gly
```

<210> SEQ ID NO 69
<211> LENGTH: 9
<212> TYPE: PRT
<213> ORGANISM: Mus musculus

<400> SEQUENCE: 69

```
Leu Ile Tyr Tyr Asp Tyr Leu Asp Tyr
1               5
```

<210> SEQ ID NO 70
<211> LENGTH: 16
<212> TYPE: PRT
<213> ORGANISM: Artificial Sequence
<220> FEATURE:
<223> OTHER INFORMATION: CDRL1-2

<400> SEQUENCE: 70

```
Arg Ser Ser Gln Ser Leu Glu Asn Glu Asn Lys Asn Leu Tyr Leu Asn
1               5                   10                  15
```

<210> SEQ ID NO 71
<211> LENGTH: 7
<212> TYPE: PRT
<213> ORGANISM: Mus musculus

<400> SEQUENCE: 71

```
Arg Val Ser Asn Arg Phe Ser
1               5
```

<210> SEQ ID NO 72
<211> LENGTH: 9
<212> TYPE: PRT
<213> ORGANISM: Mus musculus

<210> SEQ ID NO 72

<400> SEQUENCE: 72

Leu Gln Val Thr His Val Pro Trp Thr
1               5

<210> SEQ ID NO 73
<211> LENGTH: 39
<212> TYPE: DNA
<213> ORGANISM: Artificial Sequence
<220> FEATURE:
<223> OTHER INFORMATION: primer 1F

<400> SEQUENCE: 73
aaaggtacca ccatgggctc tggaggagac agcctcctg                              39

<210> SEQ ID NO 74
<211> LENGTH: 39
<212> TYPE: DNA
<213> ORGANISM: Artificial Sequence
<220> FEATURE:
<223> OTHER INFORMATION: primer 1R

<400> SEQUENCE: 74
aaagatatcc tgctccaggg tccagggacc atgctcact                              39

<210> SEQ ID NO 75
<211> LENGTH: 144
<212> TYPE: DNA
<213> ORGANISM: Artificial Sequence
<220> FEATURE:
<223> OTHER INFORMATION: primer2F

<400> SEQUENCE: 75
ggtaccgcca tgggctctgg aggagacagc ctcctcggcg gcagaggttc cctgcctctg       60
ctgctcctgc tcatcatggg aggcatggct gattacaagg atgacgacga taagcaggac      120
tccccgcccc agatcctagt ccac                                             144

<210> SEQ ID NO 76
<211> LENGTH: 37
<212> TYPE: DNA
<213> ORGANISM: Artificial Sequence
<220> FEATURE:
<223> OTHER INFORMATION: primer 2R

<400> SEQUENCE: 76
gctagcggag taatctacag gagaagcacc agccttg                               37

<210> SEQ ID NO 77
<211> LENGTH: 142
<212> TYPE: DNA
<213> ORGANISM: Artificial Sequence
<220> FEATURE:
<223> OTHER INFORMATION: primer 3F

<400> SEQUENCE: 77
ggtaccgcca tgggctctgg aggagacagc ctcctcggcg gcagaggttc cctgcctctg       60
ctgctcctgc tcatcatggg aggcatggct gattacaagg atgacgacga taagcctggc      120
cctgccagga tgagctgcca ag                                               142

<210> SEQ ID NO 78
<211> LENGTH: 144
<212> TYPE: DNA
<213> ORGANISM: Artificial Sequence
<220> FEATURE:

```
<223> OTHER INFORMATION: primer 4F

<400> SEQUENCE: 78
ggtaccgcca tgggctctgg aggagacagc ctcctcggcg gcagaggttc cctgcctctg      60
ctgctcctgc tcatcatggg aggcatggct gattacaagg atgacgacga taaggtggct    120
gtcctccggg aggatttcca gatc                                            144

<210> SEQ ID NO 79
<211> LENGTH: 142
<212> TYPE: DNA
<213> ORGANISM: Artificial Sequence
<220> FEATURE:
<223> OTHER INFORMATION: primer 5F

<400> SEQUENCE: 79
ggtaccgcca tgggctctgg aggagacagc ctcctcggcg gcagaggttc cctgcctctg      60
ctgctcctgc tcatcatggg aggcatggct gattacaagg atgacgacga taagaccaac    120
agcgcaggac atagggagag cc                                              142

<210> SEQ ID NO 80
<211> LENGTH: 143
<212> TYPE: DNA
<213> ORGANISM: Artificial Sequence
<220> FEATURE:
<223> OTHER INFORMATION: primer 6F

<400> SEQUENCE: 80
ggtaccgcca tgggctctgg aggagacagc ctcctcggcg gcagaggttc cctgcctctg      60
ctgctcctgc tcatcatggg aggcatggct gattacaagg atgacgacga taagatccag    120
gagccccagg actacacgga gcc                                             143

<210> SEQ ID NO 81
<211> LENGTH: 144
<212> TYPE: DNA
<213> ORGANISM: Artificial Sequence
<220> FEATURE:
<223> OTHER INFORMATION: primer 7F

<400> SEQUENCE: 81
ggtaccgcca tgggctctgg aggagacagc ctcctcggcg gcagaggttc cctgcctctg      60
ctgctcctgc tcatcatggg aggcatggct gattacaagg atgacgacga taagaggctg    120
ccggaaaaag tgcccagtgc ccca                                            144

<210> SEQ ID NO 82
<211> LENGTH: 47
<212> TYPE: DNA
<213> ORGANISM: Artificial Sequence
<220> FEATURE:
<223> OTHER INFORMATION: primer 8F

<400> SEQUENCE: 82
cagatatacc agtgaggatg cctgaatcct aaaacacagg atggatc                    47

<210> SEQ ID NO 83
<211> LENGTH: 47
<212> TYPE: DNA
<213> ORGANISM: Artificial Sequence
<220> FEATURE:
<223> OTHER INFORMATION: primer 8R

<400> SEQUENCE: 83
```
gatccatcct gtgttttagg attcaggcat cctcactggt atatctg                47

<210> SEQ ID NO 84
<211> LENGTH: 42
<212> TYPE: DNA
<213> ORGANISM: Artificial Sequence
<220> FEATURE:
<223> OTHER INFORMATION: primer 9F

<400> SEQUENCE: 84
ggtaccgcca tgggacaagg agaggagccg agagcagcca tg                    42

<210> SEQ ID NO 85
<211> LENGTH: 40
<212> TYPE: DNA
<213> ORGANISM: Artificial Sequence
<220> FEATURE:
<223> OTHER INFORMATION: primer 9R

<400> SEQUENCE: 85
gcggccgcgg aggaatcacc agccttgggc acagcaccag                       40

<210> SEQ ID NO 86
<211> LENGTH: 39
<212> TYPE: DNA
<213> ORGANISM: Artificial Sequence
<220> FEATURE:
<223> OTHER INFORMATION: primer 10F

<400> SEQUENCE: 86
ggtaccgcca tgggacaagg agaggagctg agagcagcc                        39

<210> SEQ ID NO 87
<211> LENGTH: 38
<212> TYPE: DNA
<213> ORGANISM: Artificial Sequence
<220> FEATURE:
<223> OTHER INFORMATION: primer 10R

<400> SEQUENCE: 87
gcggccgcgg aggaatcacc agccttgggc acaacacc                         38

<210> SEQ ID NO 88
<211> LENGTH: 37
<212> TYPE: DNA
<213> ORGANISM: Artificial Sequence
<220> FEATURE:
<223> OTHER INFORMATION: primer 11F

<400> SEQUENCE: 88
ggtaccgcca tgggctctgg aggagaaagc ctccggg                          37

<210> SEQ ID NO 89
<211> LENGTH: 31
<212> TYPE: DNA
<213> ORGANISM: Artificial Sequence
<220> FEATURE:
<223> OTHER INFORMATION: primer 11R

<400> SEQUENCE: 89
ggagtaatct acaggagaag caccagcctt g                                31

<210> SEQ ID NO 90
<211> LENGTH: 35
<212> TYPE: DNA

```
<213> ORGANISM: Artificial Sequence
<220> FEATURE:
<223> OTHER INFORMATION: primer 12F

<400> SEQUENCE: 90
ggatccgcca tgggctctgg aggagaaagc ctccg                          35

<210> SEQ ID NO 91
<211> LENGTH: 42
<212> TYPE: DNA
<213> ORGANISM: Artificial Sequence
<220> FEATURE:
<223> OTHER INFORMATION: primer 12R

<400> SEQUENCE: 91
gcggccgctc aggagtaatc tacaggagaa gcaccagcct tg                  42

<210> SEQ ID NO 92
<211> LENGTH: 144
<212> TYPE: DNA
<213> ORGANISM: Artificial Sequence
<220> FEATURE:
<223> OTHER INFORMATION: primer for pCI-cynoROBO4-1 or pCI-cynoROBO4-2

<400> SEQUENCE: 92
ggtaccgcca tgggctctgg aggagaaagc ctccgaggct cccgggcttc cggcctctg    60 ctgctcctgc tcatcatggg aggcatggct gattacaagg atgacgacga taagcaggac  120
tccccgcccc agatcctagt ccac                                         144

<210> SEQ ID NO 93
<211> LENGTH: 64
<212> TYPE: DNA
<213> ORGANISM: Artificial Sequence
<220> FEATURE:
<223> OTHER INFORMATION: primer 13F

<400> SEQUENCE: 93
ggggacaagt ttgtacaaaa aagcaggctt caccatgatt gcggagcccg ctcactttta    60
cctg                                                                64

<210> SEQ ID NO 94
<211> LENGTH: 54
<212> TYPE: DNA
<213> ORGANISM: Artificial Sequence
<220> FEATURE:
<223> OTHER INFORMATION: primer 13R

<400> SEQUENCE: 94
ggggaccact ttgtacaaga aagctgggtc gctttcagtt tcctctaatt cttc          54

<210> SEQ ID NO 95
<211> LENGTH: 129
<212> TYPE: DNA
<213> ORGANISM: Artificial Sequence
<220> FEATURE:
<223> OTHER INFORMATION: primer 14F

<400> SEQUENCE: 95
gcggccgcat gattgcggag cccgctcact tttacctgtt tggattaata tgtctctgtt    60
caggctcccg tcttgattac aaggatgacg acgataagcg tcaggaagat tttccacctc   120
gcattgttg                                                          129
```

<210> SEQ ID NO 96
<211> LENGTH: 33
<212> TYPE: DNA
<213> ORGANISM: Artificial Sequence
<220> FEATURE:
<223> OTHER INFORMATION: primer 14R

<400> SEQUENCE: 96
gctagctcag ctttcagttt cctctaattc ttc                33

<210> SEQ ID NO 97
<211> LENGTH: 38
<212> TYPE: DNA
<213> ORGANISM: Artificial Sequence
<220> FEATURE:
<223> OTHER INFORMATION: primer 15F

<400> SEQUENCE: 97
gcggccgcat gagtctgctg atgtttacac aactactg           38

<210> SEQ ID NO 98
<211> LENGTH: 40
<212> TYPE: DNA
<213> ORGANISM: Artificial Sequence
<220> FEATURE:
<223> OTHER INFORMATION: primer 15R

<400> SEQUENCE: 98
gctagcctat aattcacctg taaactgtcc ttgactgttg          40

<210> SEQ ID NO 99
<211> LENGTH: 38
<212> TYPE: DNA
<213> ORGANISM: Artificial Sequence
<220> FEATURE:
<223> OTHER INFORMATION: primer 16F

<400> SEQUENCE: 99
gcggccgcat gctgcgctac ctgctgaaaa cgctgctg           38

<210> SEQ ID NO 100
<211> LENGTH: 36
<212> TYPE: DNA
<213> ORGANISM: Artificial Sequence
<220> FEATURE:
<223> OTHER INFORMATION: primer 16R

<400> SEQUENCE: 100
gctagctcat cttggttcct ctcggcgttt ctgtcc             36

<210> SEQ ID NO 101
<211> LENGTH: 26
<212> TYPE: DNA
<213> ORGANISM: Artificial Sequence
<220> FEATURE:
<223> OTHER INFORMATION: primer 17F

<400> SEQUENCE: 101
ggtaccgata aggaacaaat aggaag                        26

<210> SEQ ID NO 102
<211> LENGTH: 26
<212> TYPE: DNA
<213> ORGANISM: Artificial Sequence
<220> FEATURE:
<223> OTHER INFORMATION: primer 17R

```
<400> SEQUENCE: 102
gagctcagct tgtgtgctct gctgtc                                        26

<210> SEQ ID NO 103
<211> LENGTH: 20
<212> TYPE: PRT
<213> ORGANISM: Mus musculus

<400> SEQUENCE: 103

Glu Val Gln Leu Val Glu Ser Gly Gly Gly Leu Val Lys Pro Gly Gly
1               5                   10                  15

Ser Leu Lys Leu
            20

<210> SEQ ID NO 104
<211> LENGTH: 15
<212> TYPE: PRT
<213> ORGANISM: Mus musculus

<400> SEQUENCE: 104

Asp Ala Val Met Thr Gln Thr Pro Leu Ser Leu Pro Val Ser Leu
1               5                   10                  15

<210> SEQ ID NO 105
<211> LENGTH: 18
<212> TYPE: DNA
<213> ORGANISM: Artificial Sequence
<220> FEATURE:
<223> OTHER INFORMATION: primer LYHF6

<400> SEQUENCE: 105
cctcaccatg aactttgg                                                 18

<210> SEQ ID NO 106
<211> LENGTH: 32
<212> TYPE: DNA
<213> ORGANISM: Artificial Sequence
<220> FEATURE:
<223> OTHER INFORMATION: primer G1EVR1

<400> SEQUENCE: 106
aagatatctt atttaccagg agagtgggag ag                                 32

<210> SEQ ID NO 107
<211> LENGTH: 26
<212> TYPE: DNA
<213> ORGANISM: Artificial Sequence
<220> FEATURE:
<223> OTHER INFORMATION: primer MK19EIF1

<400> SEQUENCE: 107
aagaattcat gaagttgcct gttagg                                        26

<210> SEQ ID NO 108
<211> LENGTH: 32
<212> TYPE: DNA
<213> ORGANISM: Artificial Sequence
<220> FEATURE:
<223> OTHER INFORMATION: primer KEVR1

<400> SEQUENCE: 108
aagatatctt aacactcatt cctgttgaag ct                                 32

<210> SEQ ID NO 109
```

```
<211> LENGTH: 30
<212> TYPE: DNA
<213> ORGANISM: Artificial Sequence
<220> FEATURE:
<223> OTHER INFORMATION: primer 3. 3-F1

<400> SEQUENCE: 109
tataccgtcg acctctagct agagcttggc                                    30

<210> SEQ ID NO 110
<211> LENGTH: 30
<212> TYPE: DNA
<213> ORGANISM: Artificial Sequence
<220> FEATURE:
<223> OTHER INFORMATION: primer 3. 3-R1

<400> SEQUENCE: 110
gctatggcag ggcctgccgc cccgacgttg                                    30

<210> SEQ ID NO 111
<211> LENGTH: 47
<212> TYPE: DNA
<213> ORGANISM: Artificial Sequence
<220> FEATURE:
<223> OTHER INFORMATION: primer MAb1 LF

<400> SEQUENCE: 111
tctccggcgc gtacggcgat gctgtgatga cccaaactcc actctcc                 47

<210> SEQ ID NO 112
<211> LENGTH: 45
<212> TYPE: DNA
<213> ORGANISM: Artificial Sequence
<220> FEATURE:
<223> OTHER INFORMATION: primer MAb1 LR

<400> SEQUENCE: 112 ggaggggcg gccacagccc gtttgatttc cagcttggtg cctcc                    45

<210> SEQ ID NO 113
<211> LENGTH: 44
<212> TYPE: DNA
<213> ORGANISM: Artificial Sequence
<220> FEATURE:
<223> OTHER INFORMATION: primer MAb1 HF

<400> SEQUENCE: 113
cagatgggtg ctgagcgaag tgcagctggt ggagtctggg ggag                    44

<210> SEQ ID NO 114
<211> LENGTH: 45
<212> TYPE: DNA
<213> ORGANISM: Artificial Sequence
<220> FEATURE:
<223> OTHER INFORMATION: primer MAb1 H1R

<400> SEQUENCE: 114
ttggtggagg ctgagctgac tgtgagagtg gtgccgtggc cccag                   45

<210> SEQ ID NO 115
<211> LENGTH: 45
<212> TYPE: DNA
<213> ORGANISM: Artificial Sequence
<220> FEATURE:
<223> OTHER INFORMATION: primer MAb1 2R

<400> SEQUENCE: 115
```
ttggtgctgg ctgagctgac tgtgagagtg gtgccgtggc cccag                45

<210> SEQ ID NO 116
<211> LENGTH: 38
<212> TYPE: DNA
<213> ORGANISM: Artificial Sequence
<220> FEATURE:
<223> OTHER INFORMATION: primer H-N53Q-F

<400> SEQUENCE: 116
gggtggcaac catcagccaa ggcggcacct acacctac                        38

<210> SEQ ID NO 117
<211> LENGTH: 38
<212> TYPE: DNA
<213> ORGANISM: Artificial Sequence
<220> FEATURE:
<223> OTHER INFORMATION: primer H-N53Q-R

<400> SEQUENCE: 117
gtaggtgtag gtgccgcctt ggctgatggt tgccaccc                        38

<210> SEQ ID NO 118
<211> LENGTH: 46
<212> TYPE: DNA
<213> ORGANISM: Artificial Sequence
<220> FEATURE:
<223> OTHER INFORMATION: primer L inf-F

<400> SEQUENCE: 118
gcctccggac tctagagcca ccatggtgct gcagacccag gtgttc                46

<210> SEQ ID NO 119
<211> LENGTH: 50
<212> TYPE: DNA
<213> ORGANISM: Artificial Sequence
<220> FEATURE:
<223> OTHER INFORMATION: primer L-EKL-R

<400> SEQUENCE: 119
caggtacagg ttcttgttct cgttttccag gctctggctg cttctgcagc            50

<210> SEQ ID NO 120
<211> LENGTH: 49
<212> TYPE: DNA
<213> ORGANISM: Artificial Sequence
<220> FEATURE:
<223> OTHER INFORMATION: primer L-EKL-F

<400> SEQUENCE: 120
gaaaacgaga caagaacct gtacctgaac tggtatctgc agaagcccg              49

<210> SEQ ID NO 121
<211> LENGTH: 41
<212> TYPE: DNA
<213> ORGANISM: Artificial Sequence
<220> FEATURE:
<223> OTHER INFORMATION: primer L inf-R

<400> SEQUENCE: 121
tagcctcccc cgtttaaacg ggcccctaac actccccct g                     41